(12) United States Patent
Kordikowski et al.

(10) Patent No.: US 11,932,630 B2
(45) Date of Patent: Mar. 19, 2024

(54) HETEROARYL AMINOPROPANOL DERIVATIVES

(71) Applicant: NOVARTIS AG, Basel (CH)

(72) Inventors: Andreas Kordikowski, Binningen (CH); Yugang Liu, Warren, NJ (US); Rainer Martin Lüönd, Therwil (CH); Christian Markert, Riehen (CH); Wolfgang Miltz, Allschwil (CH); Till Roehn, Zurich (CH); Carsten Spanka, Lörrach (DE); Gebhard Thoma, Lörrach (DE); Tian Xie, Shanghai (CN)

(*) Notice: Subject to any disclaimer, the term of this patent is extended or adjusted under 35 U.S.C. 154(b) by 15 days.

(21) Appl. No.: 17/716,423

(22) Filed: Apr. 8, 2022

(65) Prior Publication Data

US 2022/0348566 A1    Nov. 3, 2022

Related U.S. Application Data

(60) Provisional application No. 63/311,231, filed on Feb. 17, 2022.

(30) Foreign Application Priority Data

Apr. 16, 2021   (WO) ............... PCT/CN2021/087655

(51) Int. Cl.
| | |
|---|---|
| C07D 413/10 | (2006.01) |
| A61K 31/41 | (2006.01) |
| A61K 31/4245 | (2006.01) |
| A61K 31/436 | (2006.01) |
| A61K 31/4439 | (2006.01) |
| A61K 45/06 | (2006.01) |
| C07D 257/04 | (2006.01) |
| C07D 401/12 | (2006.01) |
| C07D 401/14 | (2006.01) |
| C07D 413/14 | (2006.01) |
| C07D 471/04 | (2006.01) |

(52) U.S. Cl.
CPC ............ *C07D 413/10* (2013.01); *A61K 31/41* (2013.01); *A61K 31/4245* (2013.01); *A61K 31/436* (2013.01); *A61K 31/4439* (2013.01); *A61K 45/06* (2013.01); *C07D 257/04* (2013.01); *C07D 401/12* (2013.01); *C07D 401/14* (2013.01); *C07D 413/14* (2013.01); *C07D 471/04* (2013.01)

(58) Field of Classification Search
CPC .. C07D 413/10; C07D 257/04; C07D 401/12; C07D 401/14; C07D 413/14; A61K 31/41; A61K 31/4245; A61K 31/436; A61K 31/4439; A61K 45/06
USPC ....................................................... 514/302
See application file for complete search history.

(56) References Cited

U.S. PATENT DOCUMENTS

| | | |
|---|---|---|
| 2004/0186418 A1 | 9/2004 | Karashima |
| 2008/0033024 A1 | 2/2008 | Sandanayaka et al. |

FOREIGN PATENT DOCUMENTS

| | | |
|---|---|---|
| CN | 105829286 A | 8/2016 |
| EP | 3669872 A1 | 6/2020 |
| WO | 2020073949 A1 | 11/2007 |
| WO | 2010062829 A1 | 6/2010 |
| WO | 2011158108 A2 | 12/2011 |
| WO | 2015009609 A1 | 1/2015 |
| WO | 2015092740 A1 | 6/2015 |
| WO | 2016118638 A1 | 7/2016 |
| WO | 2017175185 A1 | 10/2017 |
| WO | 2018175746 A1 | 9/2018 |
| WO | 2020026108 A1 | 2/2020 |
| WO | 2020073949 A1 | 4/2020 |
| WO | 2020144604 A1 | 7/2020 |

OTHER PUBLICATIONS

Yinhui, Qin et al., "Design, synthesis and antibacterial evaluation of novel 15-membered 11a-azahomoclarithromycin derivatives with the 1, 2, 3-triazole side chain", European Journal of Medicinal Chemistry, vol. 180, pp. 321-339, 2019.
C Markert et al., Discovery of LYS006, a Potent and Highly Selective Inhibitor of Leukotriene A4 Hydrolase, Journal of Medicinal Chemistry, 2021, 1889-1903, 64.
(Continued)

*Primary Examiner* — Kahsay Habte
(74) *Attorney, Agent, or Firm* — Sophie Binet Cross

(57) ABSTRACT

The present invention provides a compound of formula (I) or a pharmaceutically acceptable salt thereof,

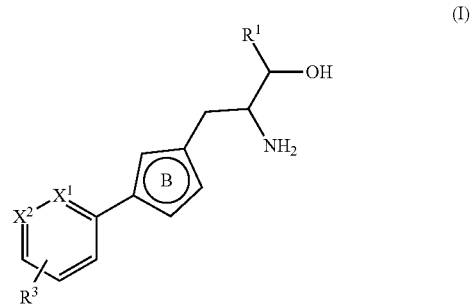

a method for manufacturing the compounds of the invention, and its therapeutic uses. The present invention further provides a combination of pharmacologically active agents and a pharmaceutical composition.

20 Claims, 18 Drawing Sheets

(56) References Cited

OTHER PUBLICATIONS

Gu et al., Discover potential inhibitors of 5-LOX and LTA4H from Rhei Radix et Rhizoma, Notopterygii Rhizoma et Radix and Genitana Macrophyllae Radix based on molecular simulation methods, China Journal of Chinese Materia Medica, 2017, 4494-4502, 42-23.

Patrick Appiah-Kub and Mahmoud Soliman, Hybrid Receptor-Bound/MM-GBSA-Per-residue Energy-Based Pharmacophore Modelling: Enhanced Approach for Identification of Selective LTA4H Inhibitors as Potential Anti-Inflammatory Drugs, Cell Biochem Biophys, 2017, 35-48, 75.

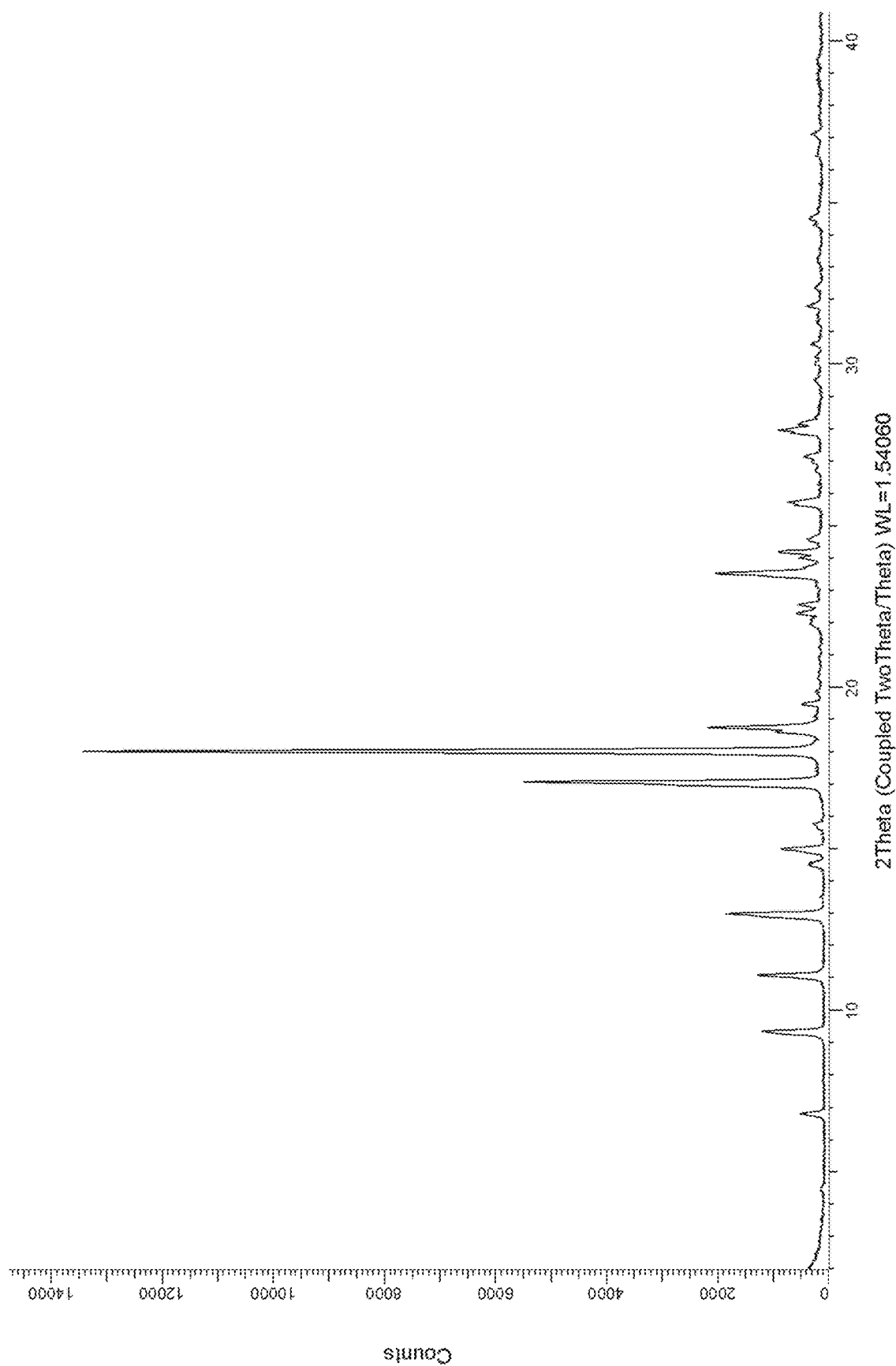

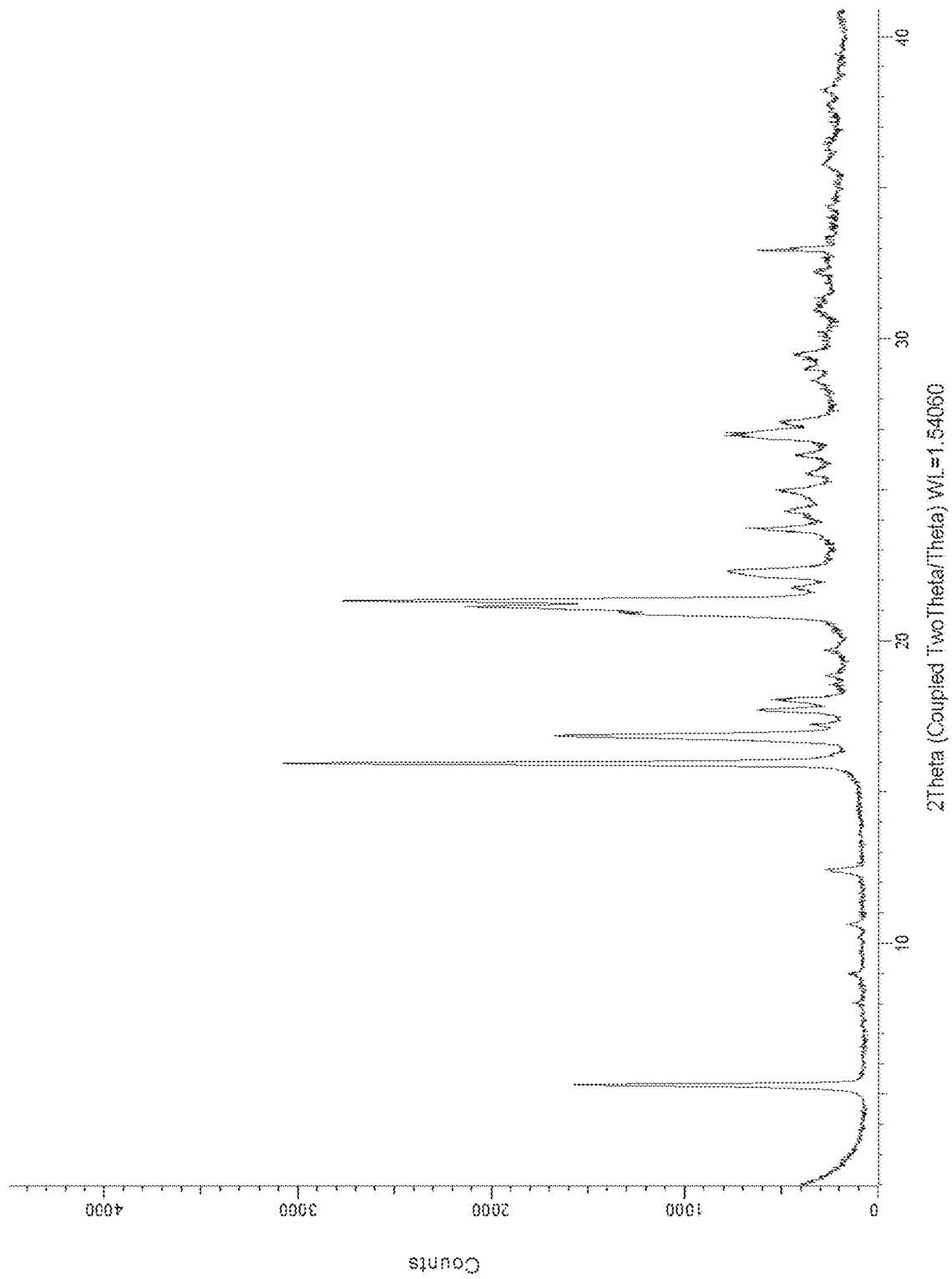

HETEROARYL AMINOPROPANOL DERIVATIVES

CROSS-REFERENCE TO RELATED APPLICATIONS

This application is a U.S. application which claims priority to PCT application No. PCT/CN2021/087,655, filed on Apr. 16, 2021 and to US provisional Patent application No. 63/311,231, filed on Feb. 17, 2022; the content of which is incorporated herein by reference in their entirety.

FIELD OF THE INVENTION

The present invention relates to compounds of formula (I) or pharmaceutically acceptable salts thereof, and to their use in inhibiting LTA4H. Hence the compounds of the invention may be useful in the treatment of diseases and/or disorders related to LTA4H. Such diseases and/or disorders include for example Inflammatory and autoimmune disorders and pulmonary and respiratory tract inflammation. The present invention further relates to pharmaceutical compositions comprising said novel heteroaryl aminopropanol derivatives of formula (I), methods of using said compounds in the treatment of various diseases and disorders, and processes for preparing the said novel compounds.

BACKGROUND OF THE INVENTION

Leukotriene A4 hydrolase (LTA4H) catalyzes the hydrolysis of LTA4 to produce LTB4. LTB4 stimulates an array of pro-inflammatory responses for example where leukocyte chemotaxis or cytokine release may be implicated. Inhibition of LTA4H furthermore elevates biosynthesis of anti-inflammatory, pro-resolving lipoxin A4 which can promote resolution of chronic inflammation. LTA4H inhibition may therefore be of benefit in diseases where chronic, non-resolving inflammation might be a critical component of the pathology and appear to include a broad range of autoinflammatory and autoimmune diseases.

SUMMARY OF THE INVENTION

The invention provides compounds, pharmaceutically acceptable salts thereof, pharmaceutical compositions thereof and combinations thereof, which compounds are LTA4H inhibitors. The invention further provides methods of treating diseases and/or disorders mediated by LTA4H, comprising administering to a subject in need thereof an effective amount of LTA4H inhibitors Various embodiments of the invention are described herein. Within certain aspects, provided herein is a compound of formula (I) or a pharmaceutically acceptable salt thereof:

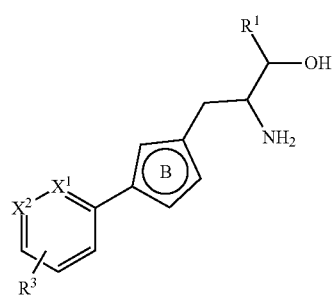

or a pharmaceutically acceptable salt thereof, wherein:
Ring B is a 5-membered ring heteroaryl;
$R^1$ is H or $C_{1-4}$alkyl;
$X^1$ is N or CH;
$X^2$ is N or $CR^2$, wherein $R^2$ is H or $C_{1-4}$alkyl;
$R^3$ is:

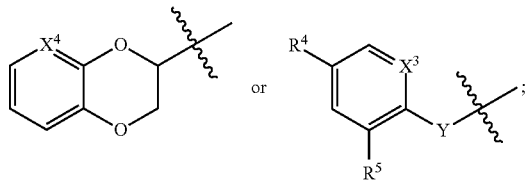

V is N or CH;
$X^4$ is N or CH;
Y is O, $NR^a$ or $CH_2$; and $R^a$ is H or $C_{1-4}$alkyl;
$R^4$ is selected from the group consisting of is selected from halo, halo$C_{1-4}$alkoxy, $C_{1-4}$alkoxy, halo$C_{1-4}$alkyl, $C_{1-4}$alkyl, 5-membered heteroaryl and $C_{1-5}$cycloalkyl; and
$R^5$ is H or halo.

In another aspect, the invention provides a pharmaceutical composition comprising a compound of the present invention and one or more pharmaceutically acceptable carriers.

In another aspect, the invention provides a combination, in particular a pharmaceutical combination, comprising a compound of the present invention and one or more therapeutically active agents.

Figure 1A:
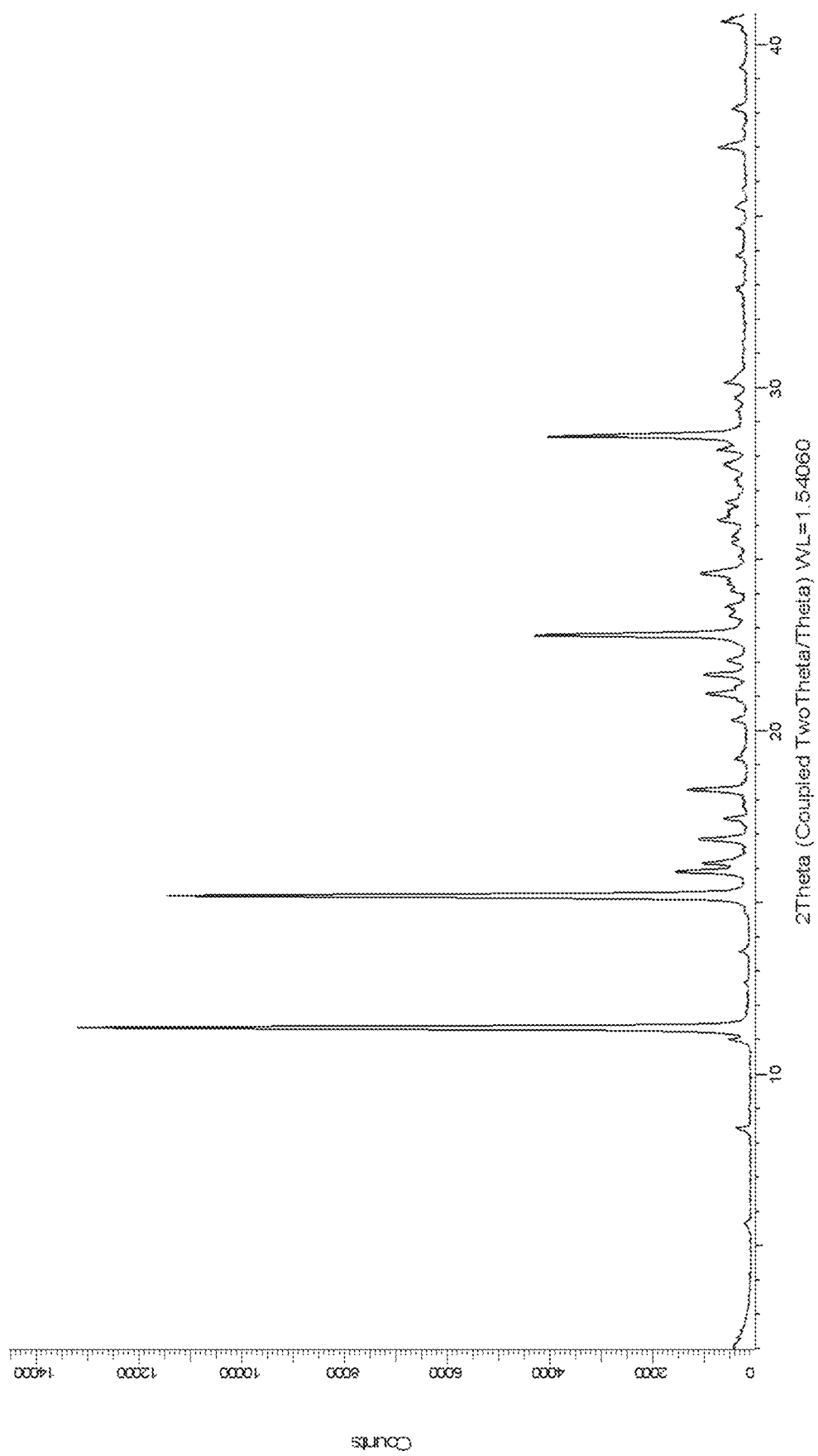
FIG. 1A provides an illustrative XRPD spectrum for compound of example 41, designated herein as Form C FIG. 1B provides an illustrative DSC for compound of example 41, designated herein as Form C.

More detailed listings of the XRPD peaks for any one of forms A to F are set forth in Tables below, in which the % relative intensity (I/b x 100) is also provided. It should be understood that in the X-ray powder diffraction spectra or pattern that there is inherent variability in the values measured in degrees 2θ (°2θ) as a result of, for example, instrumental variation (including differences between instruments). As such, it should be understood that there is a variability of up to t 0.2 °2θ in XRPD peak measurements and yet such peak values would still be considered to be representative of a particular solid state form of the crystalline materials described herein. It should also be understood that other measured values from XRPD experiments and DSC/TGA experiments, such as relative intensity and water content, can vary as a result of, for example, sample preparation and/or storage and/or environmental conditions, and yet the measured values will still be considered to be representative of a particular solid state form of the crystalline materials described herein.

DETAILED DESCRIPTION OF THE INVENTION

The invention therefore provides a compound of formula (I):

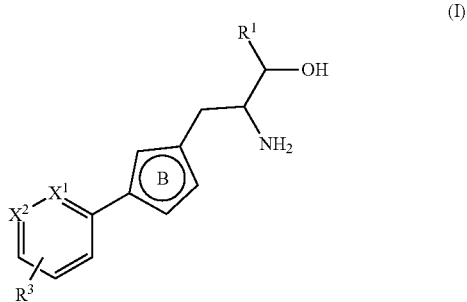

or a pharmaceutically acceptable salt thereof, wherein:
Ring B is a 5-membered ring heteroaryl;
$R^1$ is H or $C_{1-4}$alkyl;
$X^1$ is N or CH;
$X^2$ is N or $CR^2$, wherein $R^2$ is H or $C_{1-4}$alkyl;
$R^3$ is:

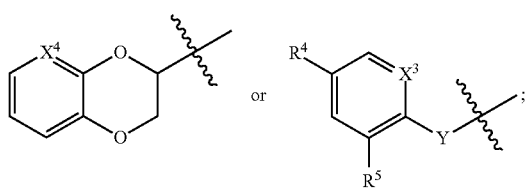

$X^3$ is N or CH;
$X^4$ is N or CH;
Y is O, $NR^a$ or $CH_2$; and $R^a$ is H or $C_{1-4}$alkyl;
$R^4$ is selected from the group consisting of is selected from halo, halo$C_{1-4}$alkoxy, $C_{1-4}$alkoxy, halo$C_{1-4}$alkyl, $C_{1-4}$alkyl, 5-membered heteroaryl and $C_{1-5}$cycloalkyl; and
$R^5$ is H or halo.

Unless specified otherwise, the term "compounds of the present invention" or "compound of the present invention" refers to compounds of formula (I) and subformulae thereof (i.e. Formulae (IA), (IB), (II) to (V)), and exemplified compounds, and salts thereof, as well as all stereoisomers (including diastereoisomers and enantiomers), rotamers, tautomers and isotopically labeled compounds (including deuterium substitutions), as well as inherently formed moieties.

Definitions

As used herein, the term "$C_1$-$C_4$ alkyl" refers to a fully saturated branched or unbranched hydrocarbon moiety having up to 4 carbon atoms. Unless otherwise provided, it refers to hydrocarbon moieties having 1 to 4 carbon atoms. Representative examples of alkyl include, but are not limited to, methyl, ethyl, n-propyl, iso-propyl, n-butyl, sec-butyl, iso-butyl, tert-butyl and the like.

As used herein, the term "$C_1$-$C_4$ alkoxy" refers to alkyl-O—, wherein alkyl is defined herein above. Representative examples of alkoxy include, but are not limited to, methoxy, ethoxy, propoxy, 2-propoxy, butoxy, tert butoxy and the like. Typically, alkoxy groups have about 1 to 4 carbon atoms or 1 to 2 carbon atoms.

As used herein, the term "halo$C_1$-$C_4$alkyl refers to $C_1$-$C_4$ alkyl as defined above which is substituted by one or more halogens. Examples include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "halo$C_1$-$C_4$alkoxy" refers to $C_{1-4}$alkoxy as defined above which is substituted with one or more halogens.

As used herein, the term "$C_3$-$C_5$cycloalkyl" refers to saturated monocyclic hydrocarbon groups of 3-5 carbon atoms. Cycloalkyl may also be referred to as a carbocyclic ring and vice versa additionally referring to the number of carbon atoms present. Unless otherwise provided, cycloalkyl refers to cyclic hydrocarbon groups having between 3 and 5 ring carbon atoms or between 3 and 4 ring carbon atoms. Exemplary monocyclic hydrocarbon groups include, but are not limited to, cyclopropyl, cyclobutyl and cyclopentyl.

As used herein, the term "halogen" or "halo" refers to fluoro, chloro, bromo, and iodo.

As used herein, the term "5-membered heteroaryl" refers to a 5 membered monocyclic aromatic ring system, having 1 to 4 heteroatoms selected from O, N or S. Typical heteroaryl groups include for example 2-, 4-, or 5-imidazolyl; 3-, 4-, or 5-pyrazolyl; 2-, 4-, or 5-thiazoyl; 3-, 4-, or 5-isothiazolyl; 2-, 4-, or 5-oxazolyl; or 3-, 4-, or 5-isoxazolyl.

As used herein, the term "tautomer" is used to designate 2 molecules with the same molecular formula but different connectivity, which can interconvert in a rapid equilibrium. For example certain heteroaryl group exists in various tautomeric forms. A representative example of tautomers are compounds of Formula (I) wherein $R^3$ is a pyrazolyl group:

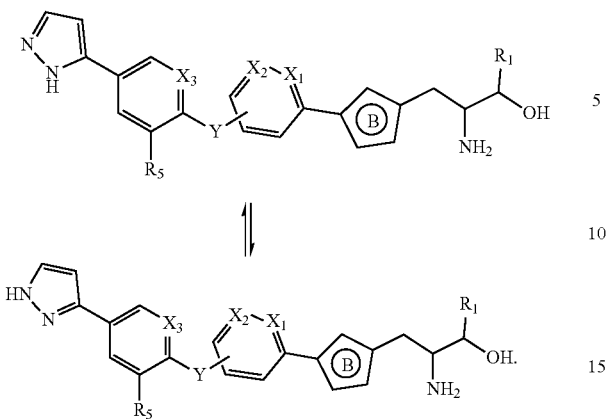
Other specific examples of tautomers are:
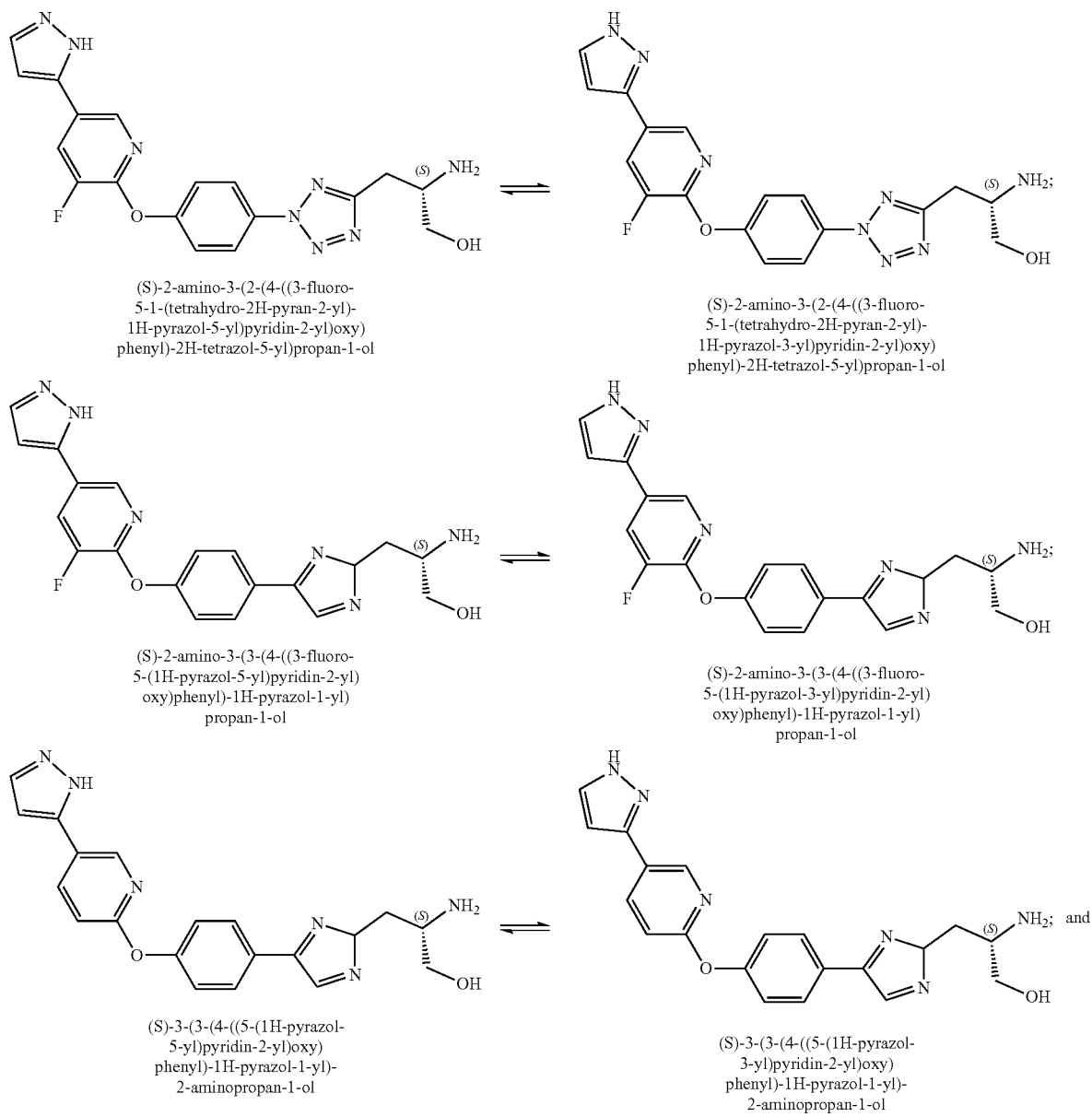

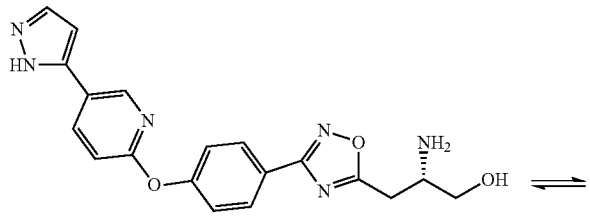

(S)-3-(3-(4-((5-1H-Pyrazol-
5-yl)pyridin-2-yl)oxy)
phenyl)-1,2,4-oxadiazol-
5-yl)-2-aminopropan-1-ol

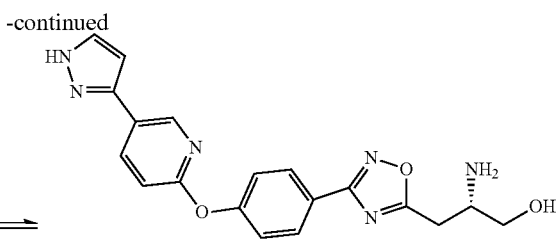

(S)-3-(3-(4-((5-1H-Pyrazol-
3-yl)pyridin-2-yl)oxy)
phenyl)-1,2,4-oxadiazol-
5-yl)-2-aminopropan-1-ol As used herein, the terms "about" and "substantially" indicate with respect to features such as endotherms, endothermic peak, exotherms, baseline shifts, etc., that their values can vary. With reference to X-ray diffraction peak positions, "about" or "substantially" means that typical peak position and intensity variability are taken into account. For example, one skilled in the art will appreciate that the peak positions (2θ) will show some inter-apparatus variability, typically as much as 0.2°. Occasionally, the variability could be higher than 0.2° depending on apparatus calibration differences. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only. For DSC, variation in the temperatures observed will depend upon the rate of temperature change as well as sample preparation technique and the particular instrument employed. Thus, the endotherm/melting point values reported herein relating to DSC/TGA thermograms can vary t 5° C. (and still be considered to be characteristic of the particular crystalline form described herein). When used in the context of other features, such as, for example, percent by weight (% by weight), reaction temperatures, the term "about" indicates a variance of t 5%.

Various enumerated embodiments of the invention are described herein. It will be recognized that features specified in each embodiment may be combined with other specified features to provide further embodiments of the present invention.

In embodiment 1, the invention relates to a compound of Formula (I):

(I)

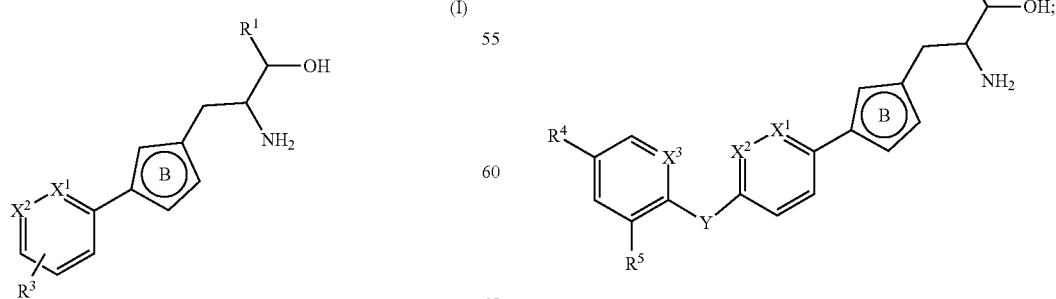

or a pharmaceutically acceptable salt thereof,
wherein:
Ring B is a 5-membered ring heteroaryl;
$R^1$ is H or $C_{1-4}$alkyl;
$X^1$ is N or CH;
$X^2$ is N or $CR^2$, wherein $R^2$ is H or $C_{1-4}$alkyl;
$R^3$ is:

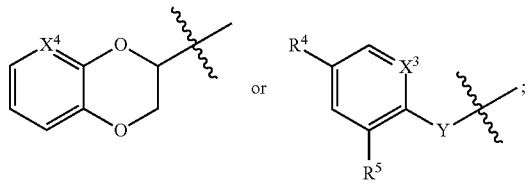

$X^3$ is N or CH;
$X^1$ Is N or CH;
Y is O, $NR^a$ or $CH_2$; and $R^1$ is H or $C_{1-4}$alkyl;
$R^4$ is selected from the group consisting of is selected from halo, halo$C_{1-4}$alkoxy, $C_{1-4}$alkoxy, halo$C_{1-4}$alkyl, $C_{1-4}$alkyl, 5-membered heteroaryl and $C_{1-5}$cycloalkyl; and
$R^5$ is H or halo.

In one aspect of this embodiment, $R^3$ is attached at the meta or para position from the point of attachment to the ring B.

In embodiment 2, the invention relates to a compound of Formula (I) having formula (IA):

(IA)

or a pharmaceutically acceptable salt thereof, wherein $R^1$, $X^1$, $X^2$, $X^3$, Y, $R^4$ and $R^5$ are as previously defined.

In embodiment 3, the invention relates to a compound of Formula (I) having Formula (IB):

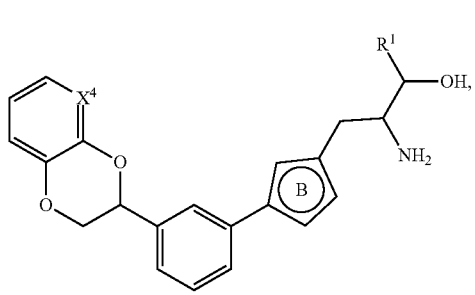
(IB)

or a pharmaceutically acceptable salt thereof, wherein Ring B, R¹ and X⁴ are as previously defined.

In one aspect of this embodiment, X⁴ is N. in another aspect of this embodiment X⁴ is CH.

In embodiment 4, the invention relates to a compound of Formula (I) having formula (IC):

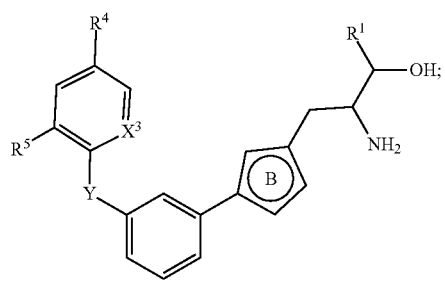
(IB)

or a pharmaceutically acceptable salt thereof, wherein R¹, R⁴, R⁵, X³, Y are as previously defined.

In embodiment 5, the invention relates to a compound of formula (I), (IA), (IB) or (IC) according to embodiment 1, 2, 3 or 4 having Formula (II):

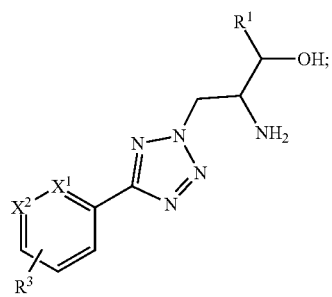
(II)

or a pharmaceutically acceptable salt thereof wherein all variables are as previously defined in embodiment 1, 2, 3 or 4.

In embodiment 6, the invention relates to a compound of Formula (I), IA), (IB) according to embodiment 1, 2, 3 or 4, having Formula (III):

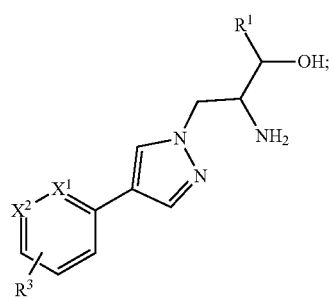
(III)

or a pharmaceutically acceptable salt thereof wherein all variables are as previously defined in embodiment 1, 2 or 3.

In embodiment 7, the invention relates to a compound of Formula (I), (IA), (IB) or (IC) according to embodiment 1, 2, 3 or 4 having Formula (IV):

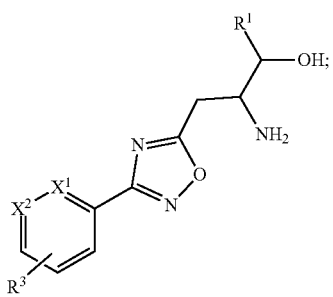
Formula (IV)

or a pharmaceutically acceptable salt thereof, wherein all variables are as previously defined in embodiment 1, 2, 3 or 4.

In embodiment 8, the invention relates to a compound of Formula (I), (IA), (IB) or (IC) according to embodiment 1, 2, 3 or 4 having Formula (V):

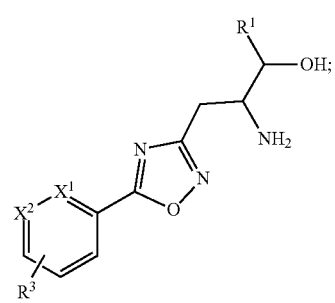
(V)

or a pharmaceutically acceptable salt thereof, wherein all variables are as previously defined in embodiment 1, 2, 3 or 4.

In embodiment 9, the invention relates to a compound of Formula (I), (IA), (IB) or (IC) according to embodiment 1, 2, 3 or 4 having Formula (VI):

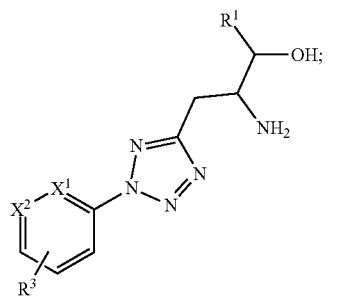

(VI)

or a pharmaceutically acceptable salt thereof, wherein all variables are as previously defined in embodiment 1, 2, 3 or 4.

In embodiment 10, the invention relates to a compound according to any of embodiments 1,2 and 5-9 wherein $X^1$ is CH; or a pharmaceutically acceptable salt thereof. In one aspect of this embodiment, $X^2$ is N. In another aspect of this embodiment $X^2$ is CH or C—$C_{1-4}$alkyl, preferably CH or C—$CH_3$.

In embodiment 10a, the invention relates to a compound according to any of embodiments, 1, 2 and 5-9 wherein $X^1$ is N and $X^2$ is CH; or a pharmaceutically acceptable salt thereof.

In embodiment 11, the invention relates to a compound according to any of embodiments 1, 2 to 10, and 10a wherein $R^1$ is H; or a pharmaceutically acceptable salt thereof.

In embodiment 11a, the invention relates to a compound according to any of embodiments 1 to 10 and 10a wherein $R^1$ is methyl; or a pharmaceutically acceptable salt thereof.

In embodiment 12, the invention relates to a compound according to any of embodiments 1, 2, 4 to 11, 11a wherein $X^3$ is N and Y is O, or a pharmaceutically acceptable salt thereof.

In embodiment 12a, the invention relates to a compound according to any of embodiments 1, 2, 4 to 11, 11a wherein $X^3$ is CH and Y is O; or a pharmaceutically acceptable salt thereof. In embodiment 13, the invention relates to a compound according to any of embodiments 1, 2, 4 to 11, 11a, 12 and 12a wherein $R^5$ is H or halo and $R^4$ is selected from halo, halo$C_{1-4}$alkoxy, $C_{1-4}$alkoxy, halo$C_{1-4}$alkyl, $C_{1-4}$alkyl, 5-membered heteroaryl and $C_{3-5}$cycloalkyl; or a pharmaceutically acceptable salt thereof.

In embodiment 14, the invention relates to a compound according to embodiment 13 wherein $R^4$ is selected from cyclopropyl, Cl, Br, —$OCH_3$, —$OCHF_2$, $CF_3$, pyrazolyl, oxazolyl, and $R^5$ is H or F; or a pharmaceutically acceptable salt thereof.

In embodiment 15, the invention relates to a compound according to embodiment 1 wherein the compound is selected from:

(S)-2-amino-3-(3-(3-((S)-2,3-dihydrobenzo[b][1,4]dioxin-2-yl)phenyl)-1,2,4-oxadiazol-5-yl)propan-1-ol;
(S)-2-amino-3-(3-(3-((5-chloropyridin-2-yl)oxy)phenyl)-1,2,4-oxadiazol-5-yl)propan-1-ol;
(S)-2-amino-3-(3-(3-((5-(difluoromethoxy)pyridin-2-yl)oxy)phenyl)-1,2,4-oxadiazol-5-yl)propan-1-ol;
(S)-2-amino-3-(3-(4-((5-(trifluoromethyl)pyridin-2-yl)oxy)phenyl)-1,2,4-oxadiazol-5-yl)propan-1-ol;
(S)-2-amino-3-(3-(4-((5-(difluoromethoxy)pyridin-2-yl)oxy)phenyl)-1,2,4-oxadiazol-5-yl)propan-1-ol;
Ethyl (S)-2-amino-3-(5-(4-((5-chloropyridin-2-yl)oxy)phenyl)-1,2,4-oxadiazol-3-yl)propanoate;
tert-butyl ((2S)-1-(3-(4-((3-fluoro-5-(1-(tetrahydro-2H-pyran-2-yl)-1H-pyrazol-5-yl)pyridin-2-yl)oxy)phenyl)-1,2,4-oxadiazol-5-yl)-3-hydroxypropan-2-yl)carbamate;
(R)-2-amino-3-(3-(4-((5-chloro-3-fluoropyridin-2-yl)oxy)phenyl)-1,2,4-oxadiazol-5-yl)propan-1-ol;
tert-butyl (S)-(1-(3-(3-((5-(1H-pyrazol-5-yl)pyridin-2-yl)oxy)phenyl)-1,2,4-oxadiazol-5-yl)-3-hydroxypropan-2-yl)carbamate;
(S)-2-amino-3 (3-(3-((5-(trifluoromethyl)pyridin-2-yl)oxy)phenyl)-1,2,4-oxadiazol-5-yl)propan-1-ol;
(S)-2-amino-3-(3-(3-((R)-2,3-dihydro-[1,4]dioxino[2,3-b]pyridin-3-yl)phenyl)-1,2,4-oxadiazol-5-yl)propan-1-ol;
(S)-2-amino-3-(3-(4-((5-chloro-3-fluoropyridin-2-yl)oxy)phenyl)-1,2,4-oxadiazol-5-yl)propan-1-ol;
(S)-3-(3-(4-((5-(1H-Pyrazol-5-yl)pyridin-2-yl)oxy)phenyl)-1,2,4-oxadiazol-5-yl)-2-aminopropan-1-ol;
(S)-2-amino-3-(5-(3-((R)-2,3-dihydro-[1,4]dioxin[2,3-b]pyridin-3-yl)phenyl)-2H-tetrazol-2-yl)propan-1-ol;
(S)-2-amino-3-(3-(3-((R)-2,3-dihydrobenzo[b][1,4]dioxin-2-yl)phenyl)-1,2,4-oxadiazol-5-yl)propan-1-ol;
(S)-2-amino-3-(3-(4-((5-chloropyridin-2-yl)oxy)phenyl)-1,2,4-oxadiazol-5-yl)propan-1-oi;
(S)-2-amino-3-(3-(4-(((R)-1-phenylpropan-2-yl)oxy)phenyl)-1,2,4-oxadiazol-5-yl)propan-1-ol;
(3S)-3-amino-4-(3-(4-((5-bromo-3-fluoropyridin-2-yl)oxy)phenyl)-1,2,4-oxadiazol-5-yl)butan-2-ol;
(R)-3-(5-(4-((5-(1H-pyrazol-3-yl)pyridin-2-yl)oxy)phenyl)-2H-tetrazol-2-yl)-2-aminopropan-1-ol;
(R)-3-(5-(4-((5-(1H-pyrazol-3-yl)pyridin-2-yl)oxy)phenyl)-2H-tetrazol-2-yl)-2-aminopropan-1-ol;
(S)-2-amino-3-(3-(5-((3 fluoro-5-(1H-pyrazol-5-yl)pyridin-2-yl)oxy)pyridin-2-yl)-1H-pyrazol-1-1)propan-1-ol;
(S)-2-amino-3-(5-(5-((3fluoro-5-(1H-pyrazol-5-yl)pyridin-2-yl)oxy)pyridin-2-yl)-2H-tetrazol-2-yl)propan-1-ol;
(S)-2-amino-3-(3-(5-((5-chloro-3-fluoropyridin-2-yl)oxy)pyridin-2-yl)-1H-pyrazol-1-yl)propan-1-ol; (S)-2-amino-3-(3-(3-((5-chloro-3-fluoropyridin-2-yl)oxy)phenyl)-1H-pyrazol-1-yl)propan-1-ol;
(S)-2-amino-3-(4-(4-((5-chloro-3-fluoropyridin-2-yl)oxy)phenyl)-1H-pyrazol-1-yl)propan-1-ol;
(S)-2-Amino-3-(3-(4-((5-chloro-3-fluoropyridin-2-yl)oxy)phenyl)-1H-pyrazol-1-yl)propan-1-ol;
(S)-2-Amino-3-(5-(4-(4-chlorophenoxy)phenyl)-2H-tetrazol-2-yl)propan-1-ol;
(S)-2-Amino-3-(5-(4-((5-cyclopropylpyridin-2-yl)oxy)phenyl)-2H-tetrazol-2-yl)propan-1-ol;
(S)-2-Amino-3-(5-(4-((5-chloro-3-fluoropyridin-2-yl)oxy)phenyl)-2H-tetrazol-2-yl)propan-1-ol;
(R)-2-Amino-3-(5-(4-((5-chloro-3-fluoropyridin-2-yl)oxy)phenyl)-2H-tetrazol-2-yl)propan-1-ol;
(R)-2-Amino-3-(5 (4-((5-chloropyridin-2-yl)oxy)phenyl)-2H-tetrazol-2-yl)propan-1-ol;
(S)-2-Amino-3-(5-(4-((3-fluoro-5-(1H-pyrazol-5-yl)pyridin-2-yl)oxy)phenyl)-2H-tetrazol-2-yl)propan-1-ol;
(S)-2-Amino-3 (5-(4-((5-bromopyridin-2-yl)oxy)phenyl)-2H-tetrazol-2-yl)propan-1-ol;
(S)-2 Amino-3-(5-(4-((5-chloropyridin-2-yl)oxy)phenyl)-2H-tetrazol-2-yl)propan-1-ol;

(S)-2Amino-3-(5-(6-(4-chlorophenoxy)pyridin-3-yl)-2H-tetrazol-2-yl)propan-1-ol;

(S)-3-(3-(4-((5-(1H-pyrazol-5-yl)pyridin-2-yl)oxy)phenyl)-1H-pyrazol-1-yl)-2-aminopropan-1-ol;

(S)-2-amino-3-(3-(4-((3-fluoro-5-(1H-pyrazol-3-yl)pyridin-2-yloxy)phenyl)-1H-pyrazol-1-yl)propan-1-ol;

(2S)-2-amino-3-[5-(4-[[3-fluoro-5-(1,3-oxazol-2-yl)pyridin-2-yl]oxy]phenyl)-2H-1,2,3,4-tetrazol-2-yl]propan-1-ol;

(S)-2Amino-3-(2-(4-((5-chloro-3-fluoropyridin-2-yl)oxy)phenyl)-2H-tetrazol-5-yl)propan-1-ol;

(R)-2Amino-3-(2-(4-((5-chloro-3-fluoropyridin-2-yl)oxy)phenyl)-2H-tetrazol-5-yl)propan-1-ol; and (2S)-2-amino-3-(2-(4-((3-fluoro-5-(1-(tetrahydro-2H-pyran-2-yl)-1H-pyrazol-5-yl)pyridin-2-yl)oxy)phenyl)-2H-tetrazol-5-yl)propan-1-ol; or a pharmaceutically acceptable salt thereof.

In embodiment 15a, the invention relates to a compound of formula (I), or a pharmaceutically acceptable salt thereof, according to embodiment 13, wherein the compound is selected from 2-amino-3-(3-(4-((3-fluoro-5-(1H-pyrazol-5-yl)pyridin-2-yl)oxy)phenyl)-1H-pyrazol-1-yl)propan-1-ol; (S)-2-amino-3-(3-(4-((3-fluoro-5-(1H-pyrazol-3-yl)pyridin-2-yl)oxy)phenyl)-1H-pyrazol-1-yl)propan-1-ol and (R)-2-amino-3-(3-(4-((3-fluoro-5-(1H-pyrazol-5-yl)pyridin-2-yl)oxy)phenyl)-1H-pyrazol-1-yl)propan-1-ol; or tautomer thereof and/or a pharmaceutically acceptable salt thereof.

In embodiment 15b, the invention relates to a compound of formula (I), or a pharmaceutically acceptable salt thereof, according to embodiment 13, wherein the compound is (S)-2-amino-3-(3-(4-((3-fluoro-5-(1H-pyrazol-5-yl)pyridin-2-yl)oxy)phenyl)-1H-pyrazol-1-yl)propan-1-ol also represented as:

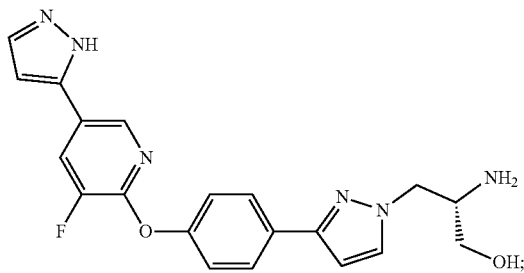 [SMILES: N[C@H](CO)Cn1ccc(-c2ccc(Oc3ncc(-c4ccn[nH]4)cc3F)cc2)n1]

or a pharmaceutically acceptable salt thereof. As previously stated, compound of embodiment 15b also exists in its tautomeric form:

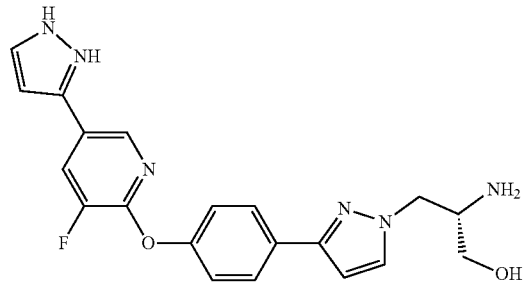 [SMILES: N[C@H](CO)Cn1ccc(-c2ccc(Oc3ncc(-c4cc[nH]n4)cc3F)cc2)n1]

((S)-2-amino-3-(3-(4-((3-fluoro-5-(1H-pyrazol-3-yl)pyridin-2-yl)oxy)phenyl)-1H-pyrazol-1-yl)propan-1-ol).

In embodiment 15c, the Invention relates to a compound of formula (I), according to embodiment 13, wherein the compound is selected from (R)-2-amino-3-(3-(4-((5-chloro-3-fluoropyridin-2-yl)oxy)phenyl)-1,2,4-oxadiazol-5-yl)propan-1-ol, (S)-2-amino-3-(3-(3-((R)-2,3-dihydro-[1,4]dioxino[2,3-b]pyridin-3-yl)phenyl)-1,2,4-oxadiazol-5-yl)propan-1-ol, (S)-2-amino-3-(5-(3-((R)-2,3-dihydro-[1,4]dioxino[2,3-b]pyridin-3-yl)phenyl)-2H-tetrazol-2-yl)propan-1-ol, and (S)-2-Amino-(5-(4-((3-fluoro-5-(1H-pyrazol-5-yl)pyridin-2-yl)oxy)phenyl)-2H-tetrazol-2-yl)propan-1-ol; or a pharmaceutically acceptable salt thereof.

In another aspect of the invention, the compounds of Formula (I), or any sub-formulae described herein, according to any one of the preceding embodiments, are not substrate of the organic anion transporter OAT3.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto. When both a basic group and an acid group are present in the same molecule, the compounds of the present invention may also form internal salts, e.g., zwitterionic molecules.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In one embodiment, the present invention provides a compound of formula (I), or a pharmaceutically acceptable salt thereof, according to any one of embodiments 1 to 15, which is in a salt form selected from acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate.

In another aspect, the present invention provides compounds of the present invention in fumarate, maleate, adipate, tartrate, glutamate and hipurrate salt form.

In one embodiment, the present invention provides (S)-2-amino-3-(3-(4-((3-fluoro-5-(1H-pyrazol-5-yl)pyridin-2-yl)oxy)phenyl)-1H-pyrazol-1-yl)propan-1-ol in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, Isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another embodiment, the present invention provides (S)-2-amino-3-(3-(4-((3-fluoro-5-(1H-pyrazol-5-yl)pyridin-2-yl)oxy)phenyl)-1H-pyrazol-1-yl)propan-1-ol in fumarate, maleate, adipate, tartrate, glutamate and hipurrate salt form.

In yet another embodiment, the present invention provides (S)-2-amino-3-(3-(4-((3-fluoro-5-(1H-pyrazol-5-yl) pyridin-2-yl)oxy)phenyl)-1H-pyrazol-1-yl)propan-1-ol in hipurrate salt form.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

Practitioners should provide, at minimum, a relatively narrow subgenus around an identified development compound and indicate that at least one site (more preferably, multiple sites) In the generic structure may be a deuterium atom. An example of what it recommended follows below:

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present invention. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. Accordingly it should be understood that the invention includes compounds that incorporate one or more of any of the aforementioned isotopes, including for example, radioactive Isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$. or labeled compound may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagents in place of the non-labeled reagent previously employed.

Further Definitions

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "a therapeutically effective amount" refers to the amount of the compound of the present invention that, when administered to a subject, is effective to (1) at least partially alleviate, prevent and/or ameliorate a condition, or a disorder or a disease (i) mediated by the LTA4H or (ii) associated with LTA4H activity, or (iii) characterized by activity (normal or abnormal) of the LTA4H; or (2) reduce or inhibit the activity of the LTA4H. In another embodiment, the term "a therapeutically effective amount" refers to the amount of the compound of the present invention that, when administered to a cell, or a tissue, or a non cellular biological material, or a medium, is effective to at least partially reducing or inhibiting the activity of the LTA4H.

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is In need of a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

The compounds of the present invention, including salts, hydrates and solvates thereof, may under the appropriate conditions, be isolated in one or more crystalline forms.

Figure 1B:
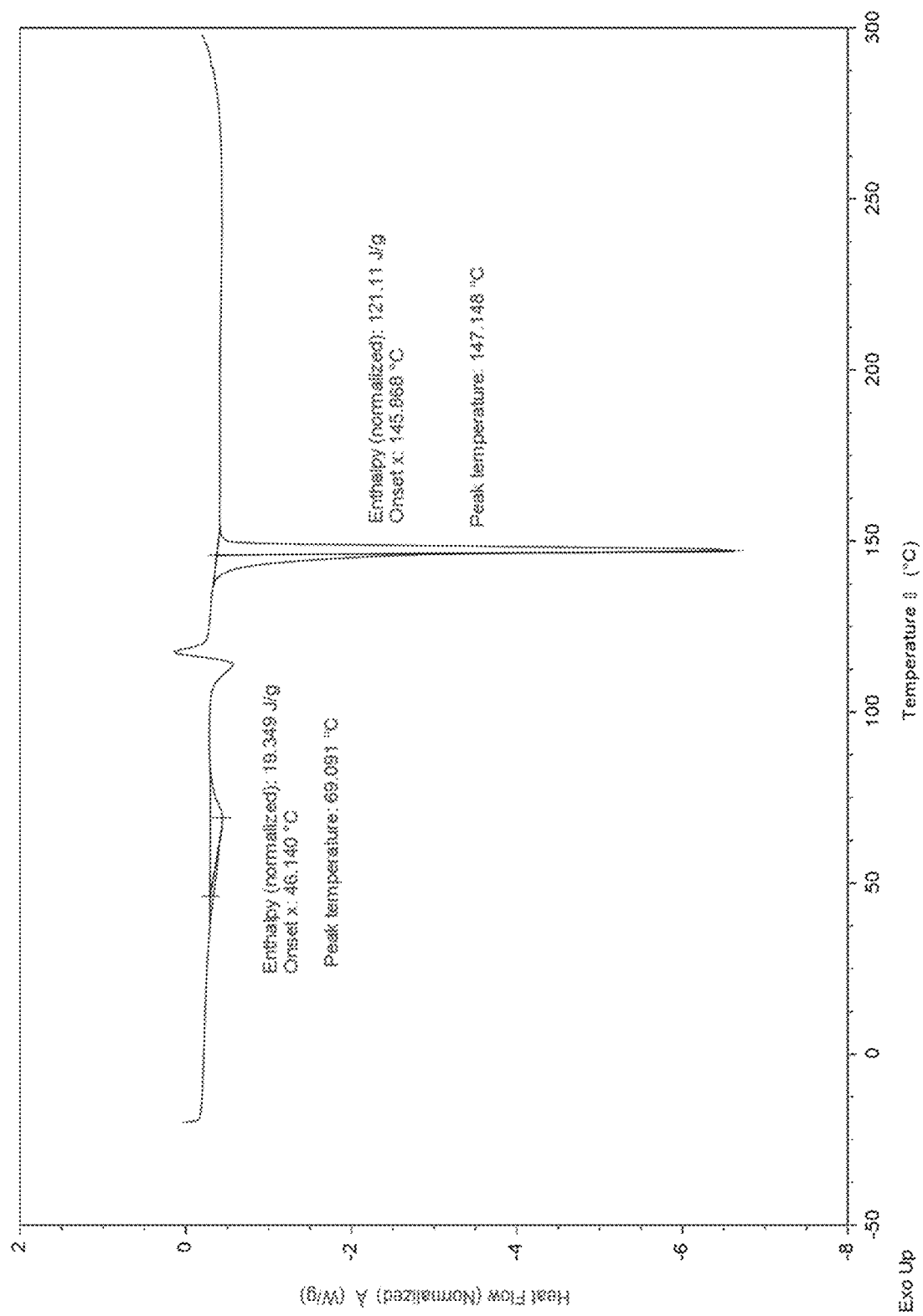
FIG. 1C provides an Illustrative TGA for compound of example 41, designated herein as Form C.
Figure 1C:
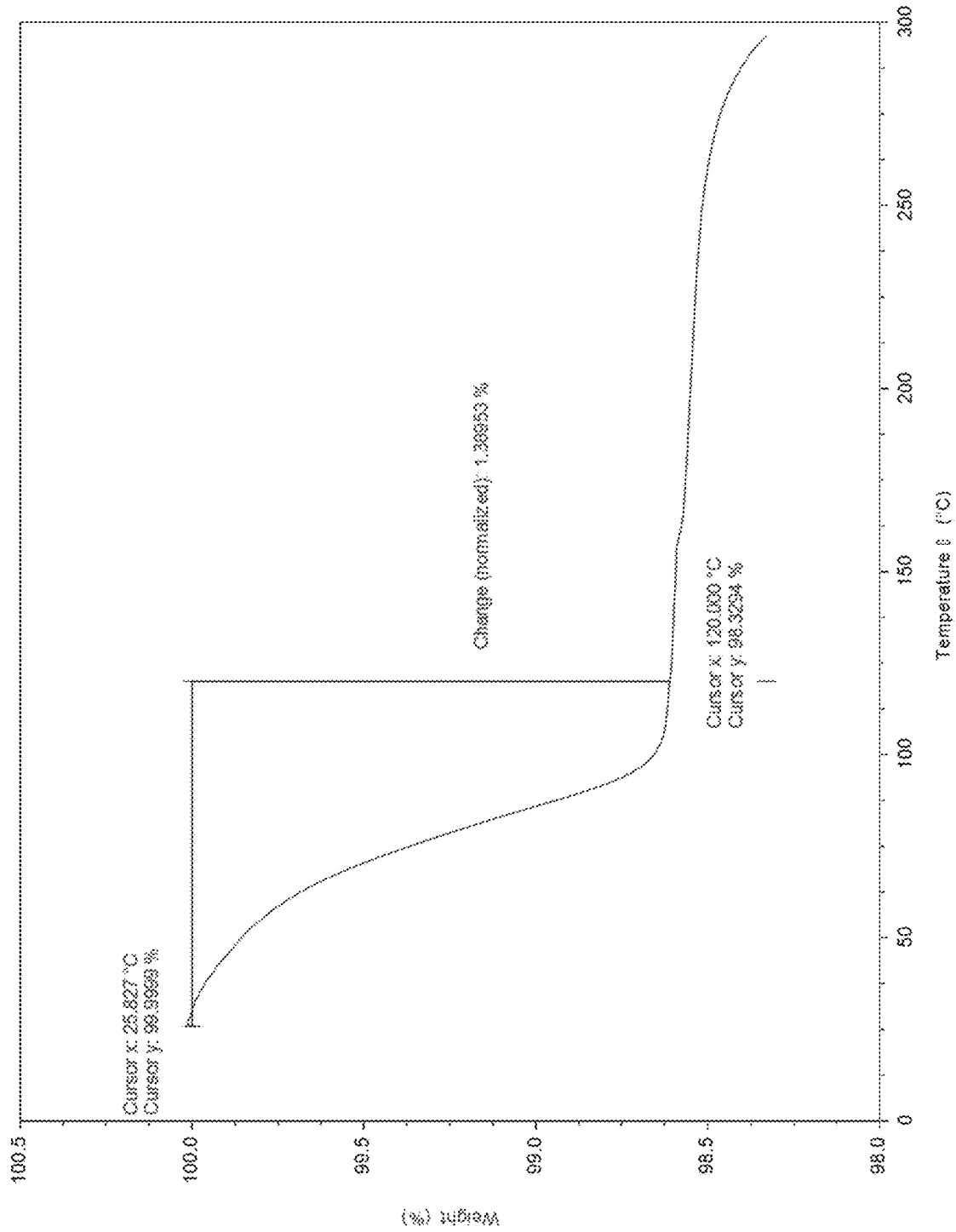

In one embodiment, the invention provide crystalline form C of (S)-2-amino-3-(3-(4-((3-fluoro-5-(1H-pyrazol-5-yl)pyridin-2-yl)oxy)phenyl)-1H-pyrazol-1-yl)propan-1-ol in its free base as characterized in FIGS. 1A, 1B and 1C and example 41. The crystalline Form C is characterized by one or more of the following characteristics:

(i) an x-ray powder diffraction pattern comprising representative peaks in terms of 2θ at 11.4±0.2 °2θ, 15.2±0.2 °2θ, 22.8±0.2 °2θ and 28.6±0.2 °2θ, measured at a temperature of about 25° C. and an x-ray wavelength, X, of 1.5406 Å;

(ii) an x-ray powder diffraction pattern comprising four or more 2θ values selected from the group consisting of 11.4±0.2 °2θ, 15.2±0.2 °2θ, 15.9±0.2 °2θ, 16.9±0.2 °2θ, 18.3±0.2 °2θ, 22.8±0.2 °2θ, 24.6±0.2 °2θ, and 28.6±0.2 °2θ, measured at a temperature of about 25° C. and an x-ray wavelength, λ, of 1.5406 Å;

(iii) an x-ray powder diffraction pattern comprising five or more 2θ values selected from the group consisting of 11.4±0.2 °2θ, 15.2±0.2 °2θ, 15.9±0.2 °2θ, 16.9±0.2°2θ, 18.3±0.2 °2θ, 22.8±0.2 °2θ, 24.6±0.2 °2θ, and 28.6±0.2 °2θ, measured at a temperature of about 25° C. and an x-ray wavelength, X, of 1.5406 Å;

iv) an x-ray diffraction spectrum substantially the same as the x-ray powder diffraction spectrum shown in FIG. 1A;

v) a differential scanning calorimetry (DSC) thermogram substantially the same as that shown in shown in FIG. 1B; i.e. with a dehydration endotherm at about 45° C. with an enthalpy of 19 J/g followed by a small melting endotherm and an immediate exothermic recrystallization event at about 110° C. when heated from 30 to 300° C. at a rate of 10K/min; vi) a thermo gravimetric analysis (TGA) diagram substantially the same as that shown in shown in FIG. 1C, i.e. with a loss on drying at about 1.4% when heated from 30 to 300° C. at a rate of 10K/min.

Figure 2A:
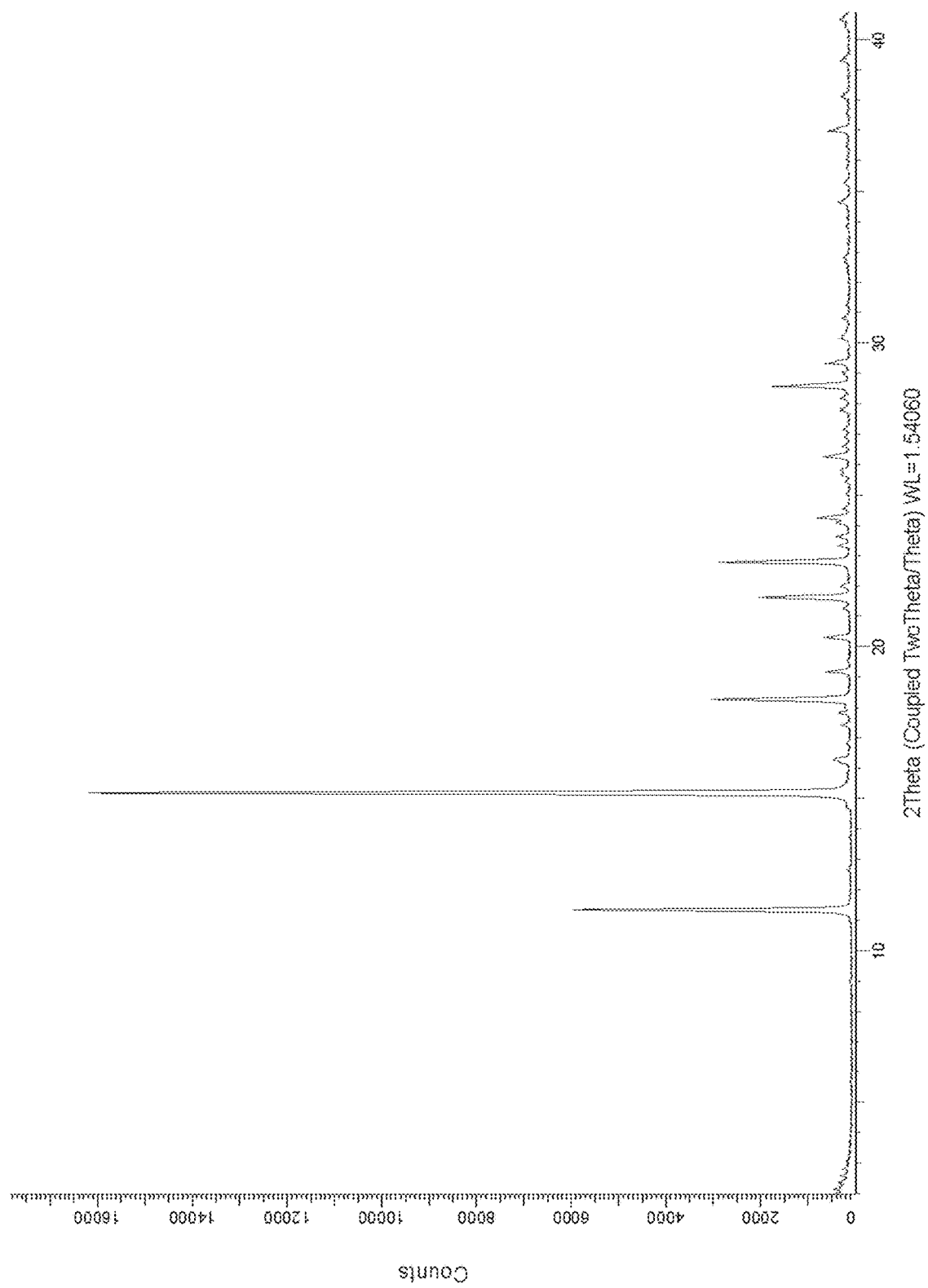
FIG. 2A provides an illustrative XRPD spectrum for compound of example 42, designated herein as Form D.
Figure 2B:
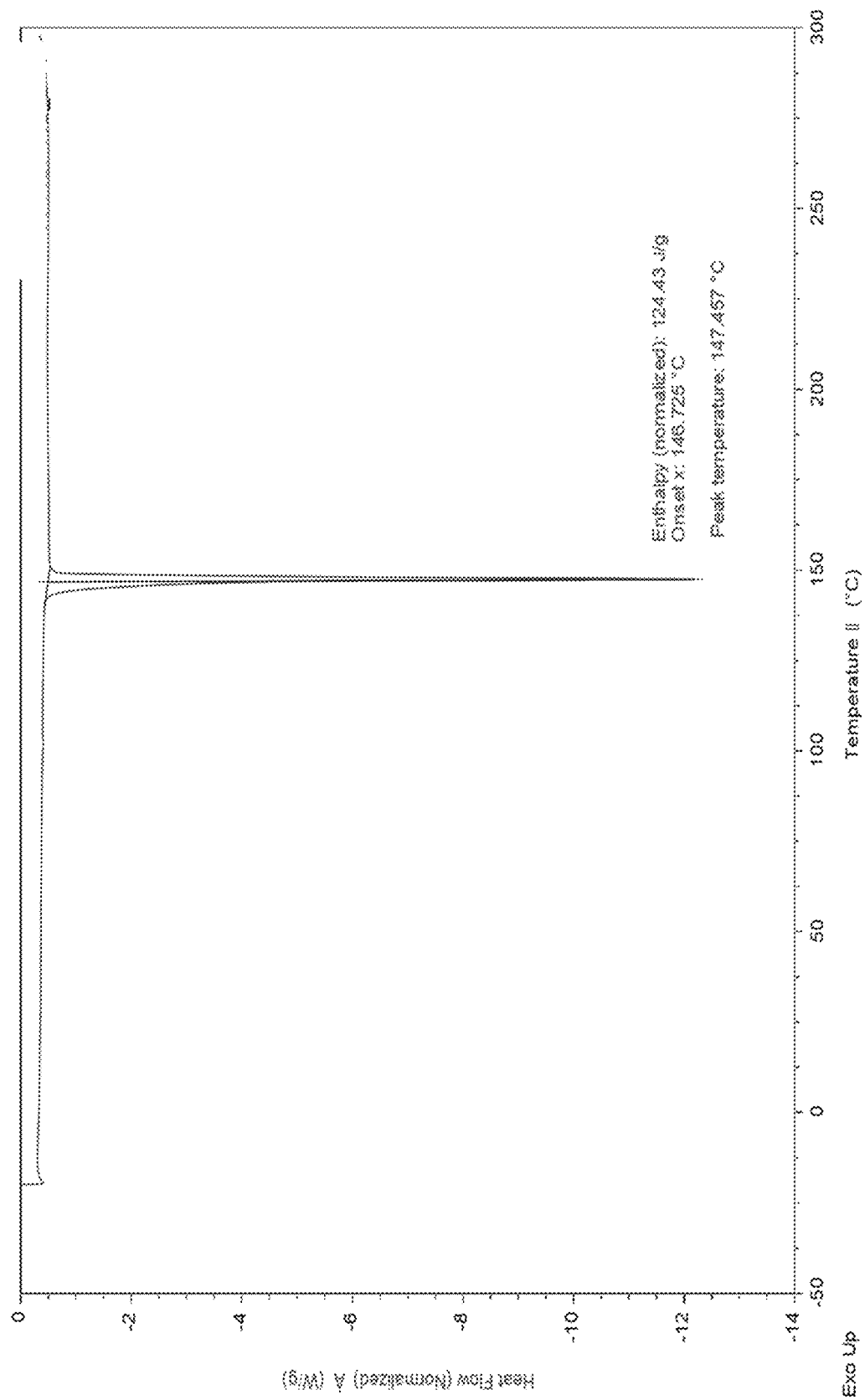
FIG. 2B provides an illustrative DSC for compound of example 42, designated herein as Form D.
Figure 2C:
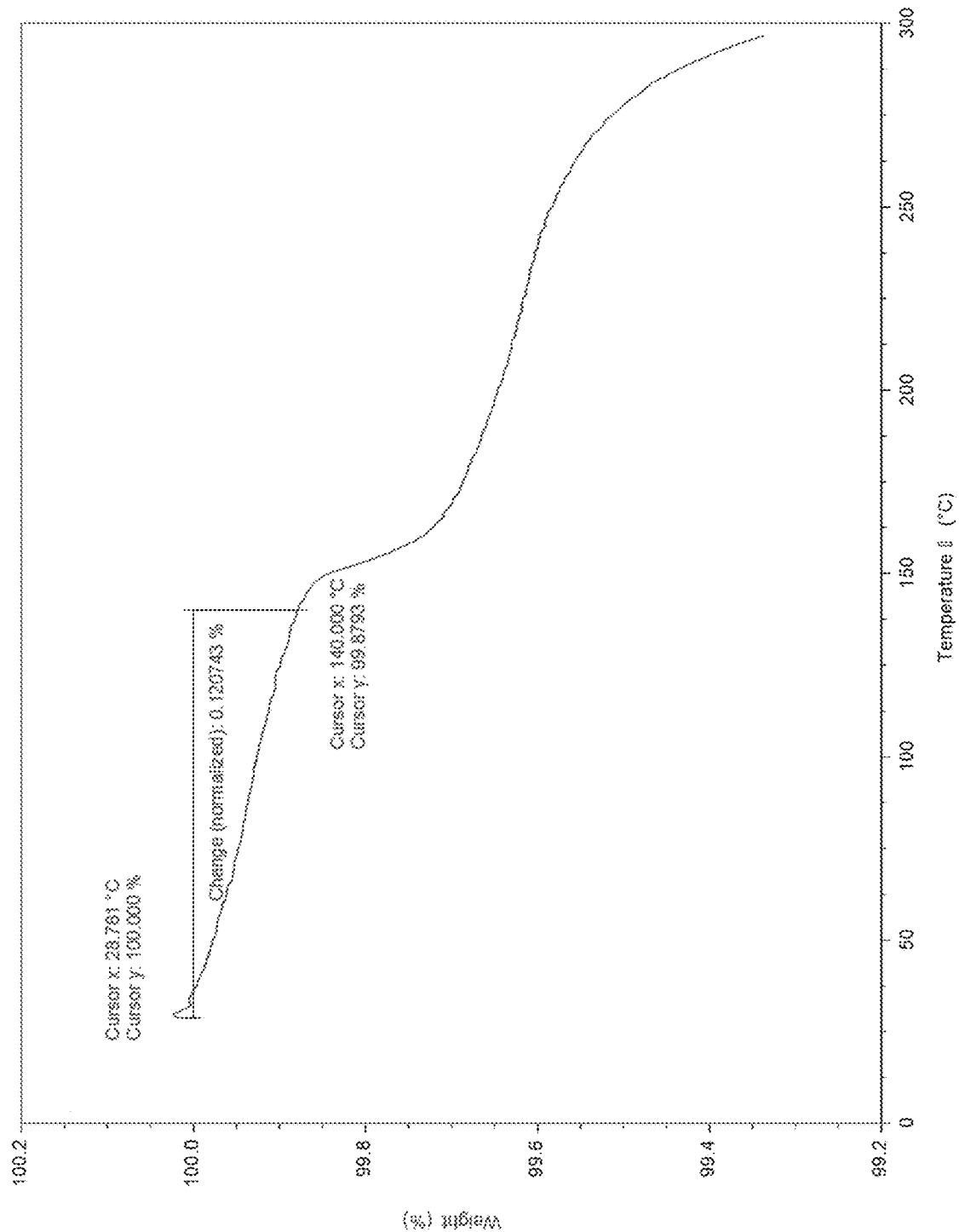
FIG. 2C provides an illustrative TGA for compound of example 42, designated herein as Form D.

In one embodiment, the invention provide crystalline form D of (S)-2-amino-3-(3-(4-((3-fluoro-5 (1H-pyrazol-5-yl)pyridin-2-yl)oxy)phenyl)-1H-pyrazol-1-yl)propan-1-ol in its free base as characterized in FIGS. 2A, 2B and 2C and example 42. The crystalline Form D is characterized by one or more of the following characteristics:

(i) an x-ray powder diffraction pattern comprising representative peaks in terms of 2θ at 11.3±0.2°2θ, 18.3±0.2 °2θ, 24.2±0.2 °2θ and 28.6±0.2 °2θ, measured at a temperature of about 25° C. and an x-ray wavelength, X, of 1.5406 Å;

(ii) an x-ray powder diffraction pattern comprising four or more 2θ values selected from the group consisting of 11.3±0.2 °2θ, 15.2±0.2 °2θ, 18.3±0.2 °2θ, 19.2±0.2 °2θ, 20.3±0.2 °2θ, 21.6±0.2 °2θ, 22.8±0.2 °2θ, 24.2±0.2 °2θ and 28.6±0.2 °2θ, measured at a temperature of about 25° C. and an x-ray wavelength, X, of 1.5406 Å;

(iii) an x-ray powder diffraction pattern comprising five or more 2θ values selected from the group consisting of 11.3±0.2 °2θ, 15.2±0.2 °2θ, 18.3±0.2 °2θ, 19.2±0.2°2θ, 20.3±0.2 °2θ, 21.6±0.2 °2θ, 22.8±0.2 °2θ, 24.2±0.2 °2θ and 28.6±0.2 °2θ, measured at a temperature of about 25° C. and an x-ray wavelength, X, of 1.5406 Å;

iv) an x-ray diffraction spectrum substantially the same as the x-ray powder diffraction spectrum shown in FIG. 2A;

v) a differential scanning calorimetry (DSC) thermogram substantially the same as that shown in shown in FIG. 2B; i.e. melting endotherm at about 146° C. with an enthalpy of about 121 J/g when heated from 30 to 300° C. at a rate of 10K/min;

vi) a thermo gravimetric analysis (TGA) diagram substantially the same as that shown in shown in FIG. 2C, i.e. with a loss on drying at about 0.15% at about 140° C.; when heated from 30 to 300° C. at a rate of 10K/min.

Figure 5A:
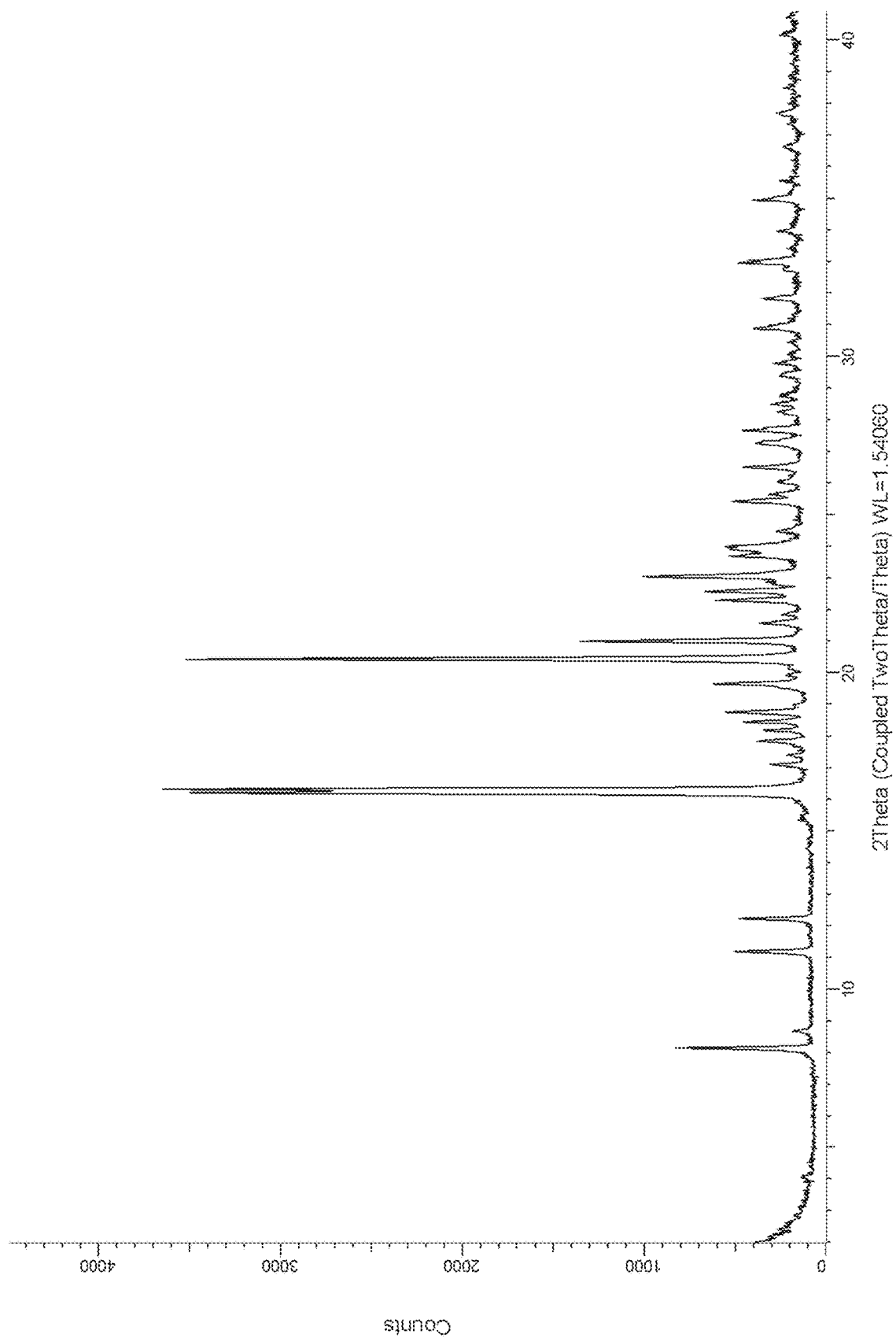
FIG. 5A provides an illustrative XRPD spectrum for compound of example 45, designated herein as Form A FIG. 5B provides an illustrative DSC for compound of example 45, designated herein as Form A.
Figure 5B:
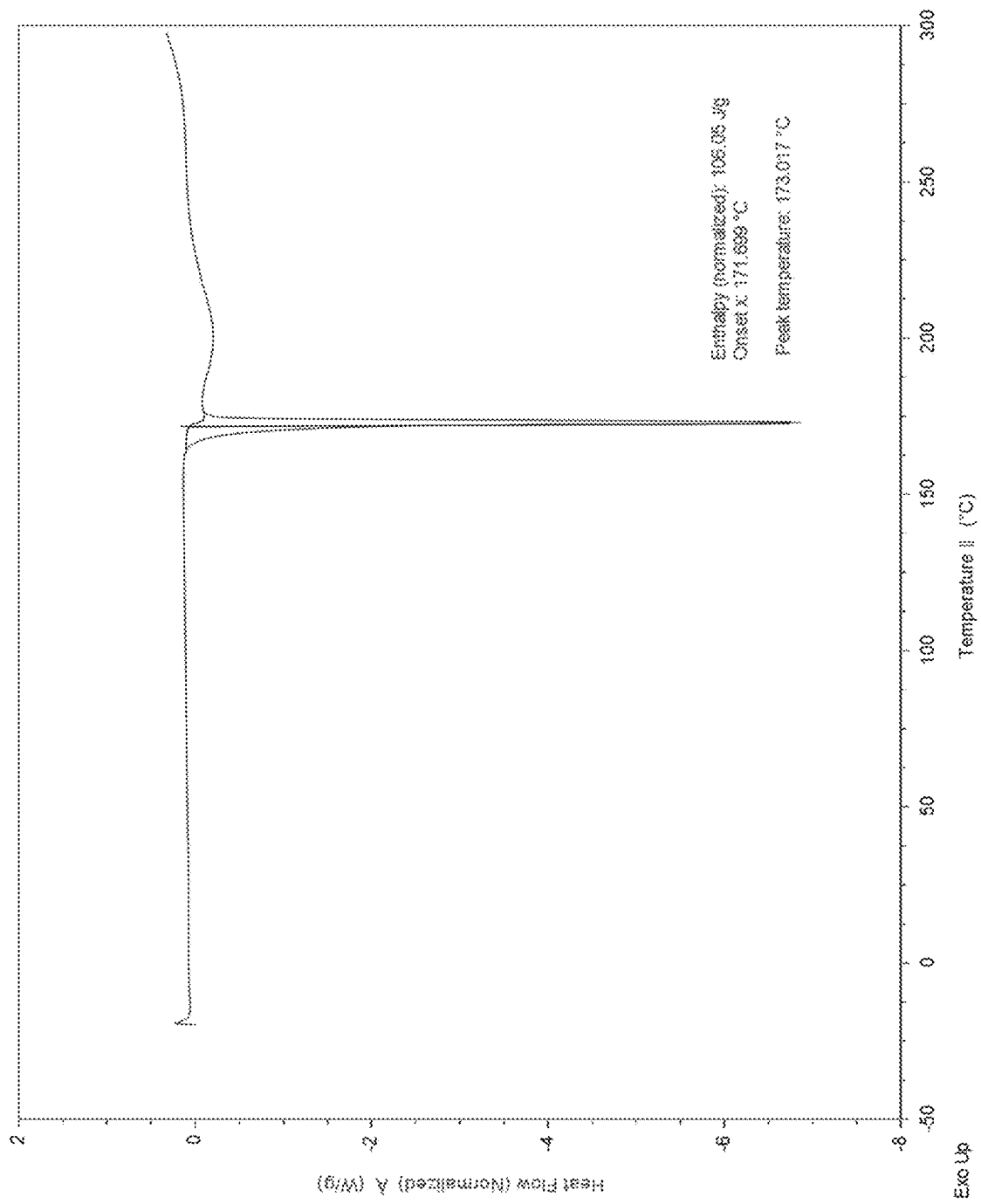
FIG. 5C provides an illustrative TGA for compound of example 45, designated herein as Form A.
Figure 5C:
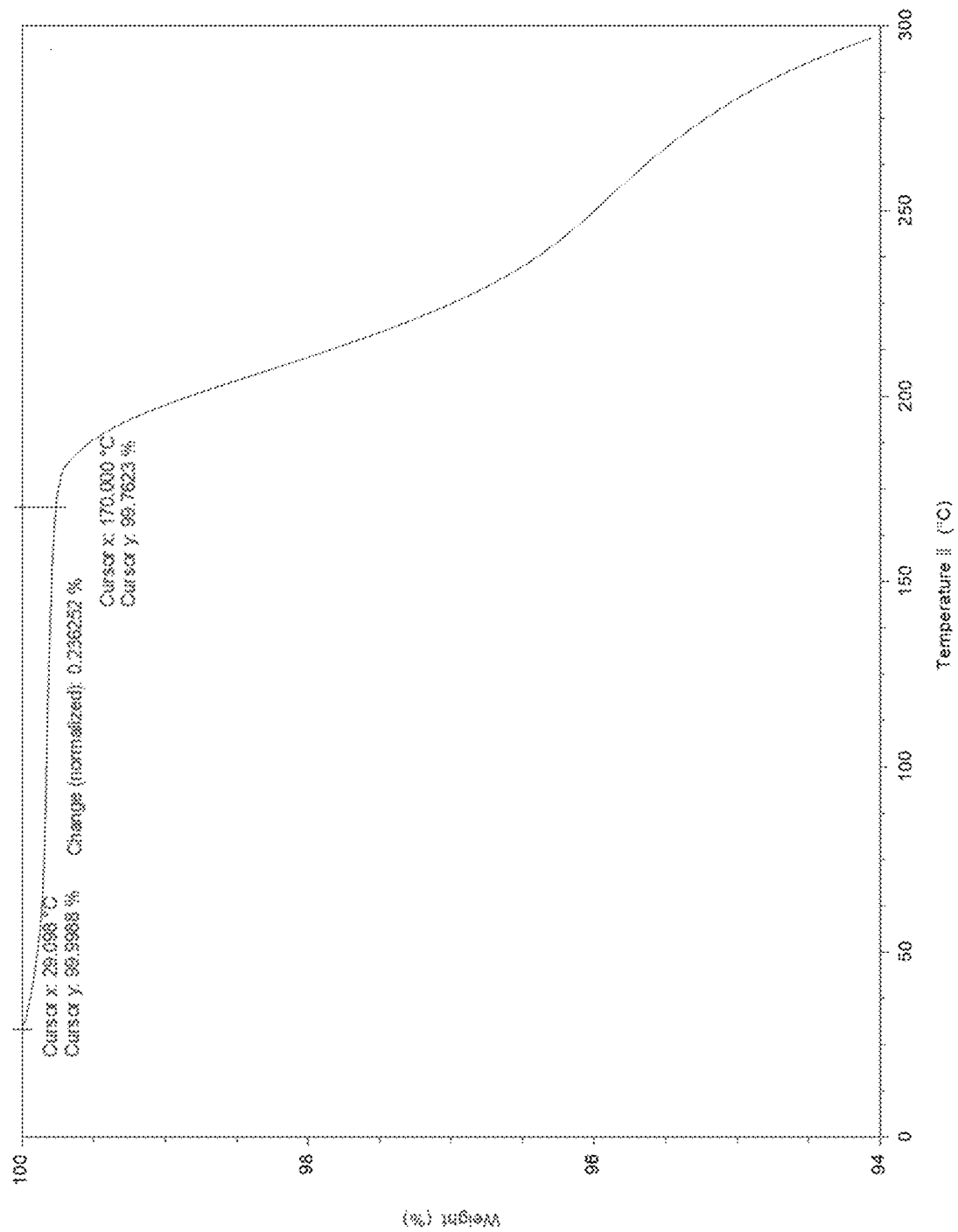

In another embodiment, the invention provides a crystalline form A of (S)-2-amino-3-(3-(4-((3-fluoro-5-(1H-pyrazol-5-yl)pyridin-2-yl)oxy)phenyl)-1H-pyrazol-1-yl)propan-1-ol hippurate salt as characterized in FIGS. 5A, 5B and 5C and example 45. (i) an x-ray powder diffraction pattern comprising representative peaks in terms of 8.1±0.2 °2θ, 16.2±0.2 °2θ, 16.3±0.2 °2θ, 20.4±0.2 °2θ, 21.0±0.2 °2θ, and 23.1±0.2 °2θ, measured at a temperature of about 25° C. and an x-ray wavelength, X, of 1.5406 Å;

(ii) an x-ray powder diffraction pattern comprising four or more 2θ values selected from the group consisting of 8.1±0.2 °2θ, 11.2±0.2°2θ, 12.2±0.2°2θ, 16.2±0.2 °2θ, 16.3±0.2 °2θ, 18.8±0.2 °2θ, 19.7±0.2 °2θ, 20.4±0.2 °2θ, 21.0±0.2 °2θ, 22.3±0.2 °2θ, 22.6±0.2°2θ, and 23.1±0.2 °2θ, measured at a temperature of about 25° C. and an x-ray wavelength, 1, of 1.5406 Å;

(iii) an x-ray powder diffraction pattern comprising five or more 2θ values selected from the group consisting of 8.1±0.2 °2θ, 11.2±0.2 °2θ, 12.2±0.2 °2θ, 16.2±0.2 °2θ, 16.3±0.2 °2θ, 18.8±0.2 °2θ, 19.7±0.2 °2θ, 20.4±0.2 °2θ, 21.0±0.2 °2θ, 22.3±0.2 °2θ, 22.6±0.2 °2θ, and 23.1±0.2 °2θ, measured at a temperature of about 25° C. and an x-ray wavelength, X, of 1.5406 Å;

iv) an x-ray diffraction spectrum substantially the same as the x-ray powder diffraction spectrum shown in FIG. 5A;

v) a differential scanning calorimetry (DSC) thermogram substantially the same as that shown in shown in FIG. 5B; i.e. melting endotherm at about 172° C. with an enthalpy of about 106 J/g when heated from 30 to 300° C. at a rate of 10K/min;

vi) a thermo gravimetric analysis (TGA) diagram substantially the same as that shown in shown in FIG. 5C, i.e. with a loss on drying at about 0.2% at about 170° C. when heated from 30 to 300° C. at a rate of 10K/min.

Figure 4B:
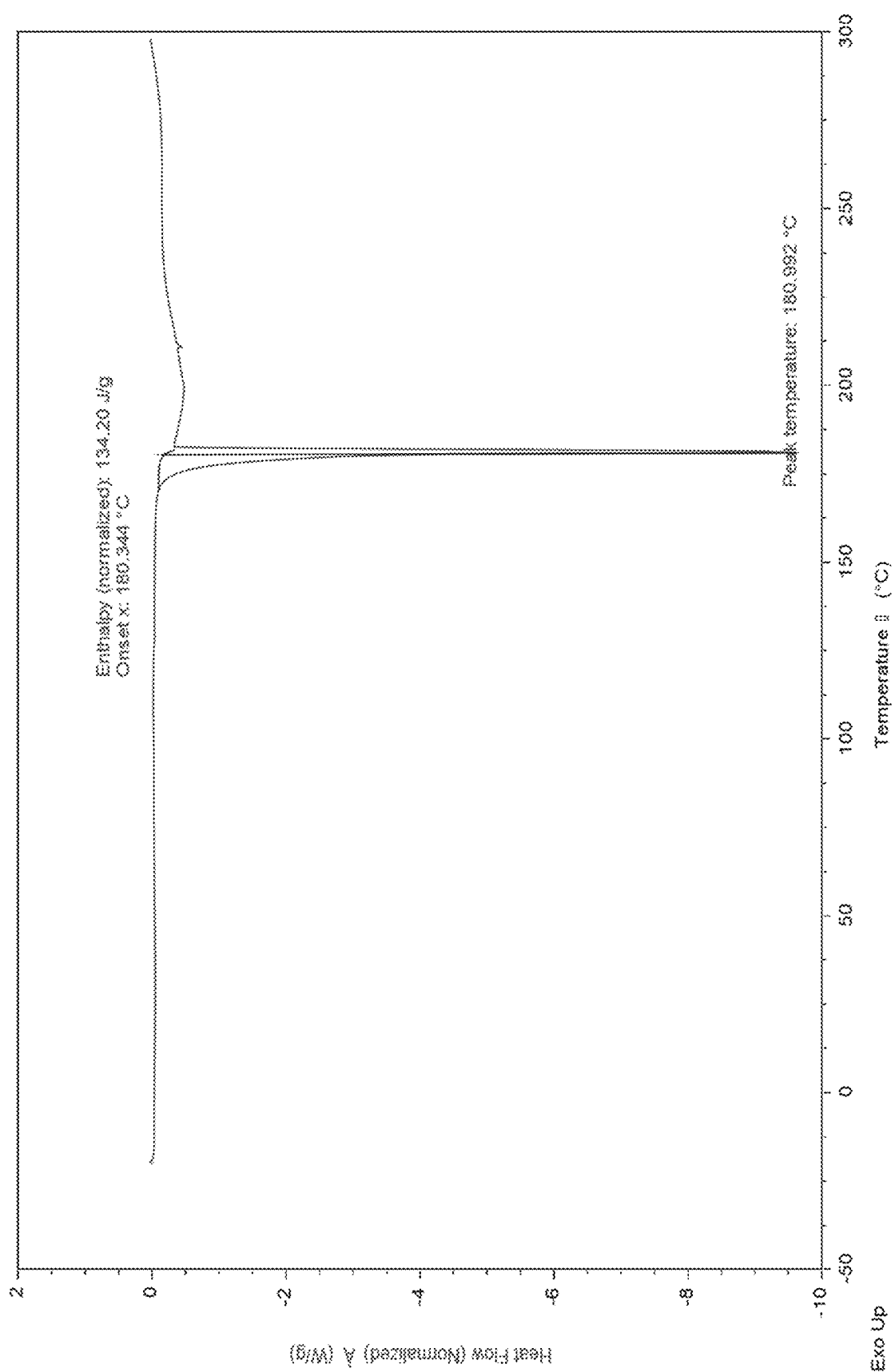
FIG. 4A provides an illustrative XRPD spectrum for compound of example 44, designated herein as Form B FIG. 4B provides an illustrative DSC for compound of example 44, designated herein as Form B.
FIG. 4C provides an illustrative TGA for compound of example 44, designated herein as Form B.
Figure 4C:
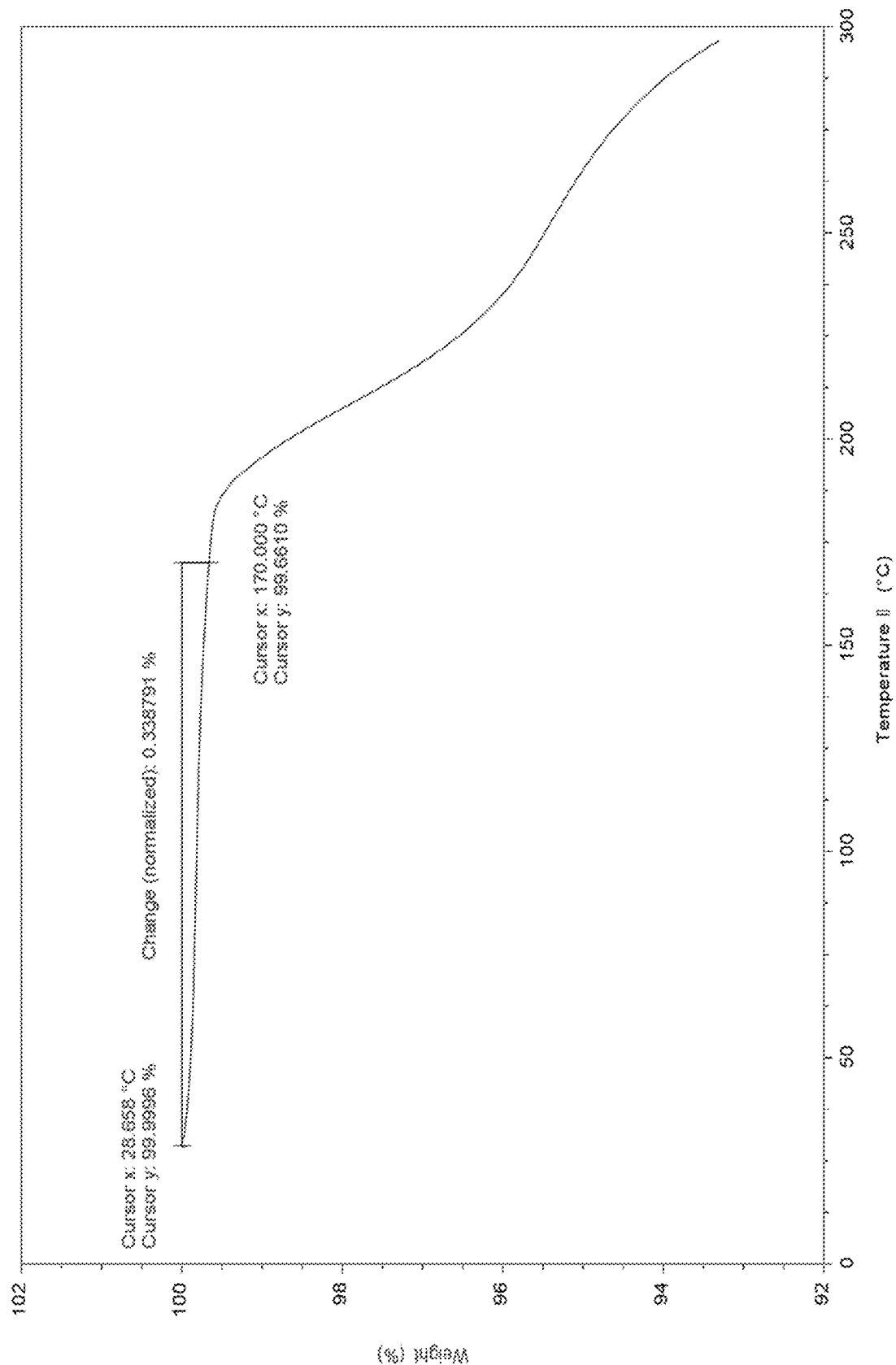

In another embodiment, the invention provides a crystalline form B of (S)-2-amino-3-(3-(4-((3-fluoro-5-(1H-pyrazol-5-yl)pyridin-2-yl)oxy)phenyl)-1H-pyrazol-1-yl)propan-1-ol hippurate salt as characterized in FIGS. 4A, 4B and 4C and example 44. The crystalline Form B is characterized by one or more of the following characteristics:

(I) an x-ray powder diffraction pattern comprising representative peaks in terms of 2θ at 13.0 t 0.2 °2θ, 17.1 t 0.2 °2θ, 18.0 t 0.2 °2θ, 18.8 t 0.2 °2θ and 23.5 t 0.2 °2θ, measured at a temperature of about 25° C. and an x-ray wavelength, X, of 1.5406 Å;

(ii) an x-ray powder diffraction pattern comprising four or more 2θ values selected from the group consisting of 9.3 t 0.2 °2θ, 11.1 t 0.2 °2θ, 13.0 t 0.2 °2θ, 17.1 t 0.2 °2θ, 18.0 t 0.2 °2θ, 18.8 t 0.2 °2θ, 23.5 t 0.2 °2θ, and 24.2±0.2 °2θ, measured at a temperature of about 25° C. and an x-ray wavelength,) of 1.5406 Å;

(iii) an x-ray powder diffraction pattern comprising five or more 2θ values selected from the group consisting of 9.3 t 0.2 °2θ, 11.1 t 0.2°2θ, 13.0 t 0.2°2θ, 17.1 t 0.2°2θ, 18.0 t 0.2 °2θ, 18.8 t 0.2 °2θ, 23.5 t 0.2 °2θ, and 24.2 t 0.2 °2θ, measured at a temperature of about 251 C and an x-ray wavelength, X, of 1.5406 Å;

iv) an x-ray diffraction spectrum substantially the same as the x-ray powder diffraction spectrum shown in FIG. 4A;

v) a differential scanning calorimetry (DSC) thermogram substantially the same as that shown in shown in FIG. 4B; i.e. melting endotherm at about 180'C with an enthalpy of about 134 J/g when heated from 30 to 300° C. at a rate of 10K/min;

vi) a thermo gravimetric analysis (TGA) diagram substantially the same as that shown in shown in FIG. 4C, i.e. with a loss on drying at about 0.3% at about 170° C. when heated from 30 to 300° C. at a rate of 10K/min.

Figure 3A:
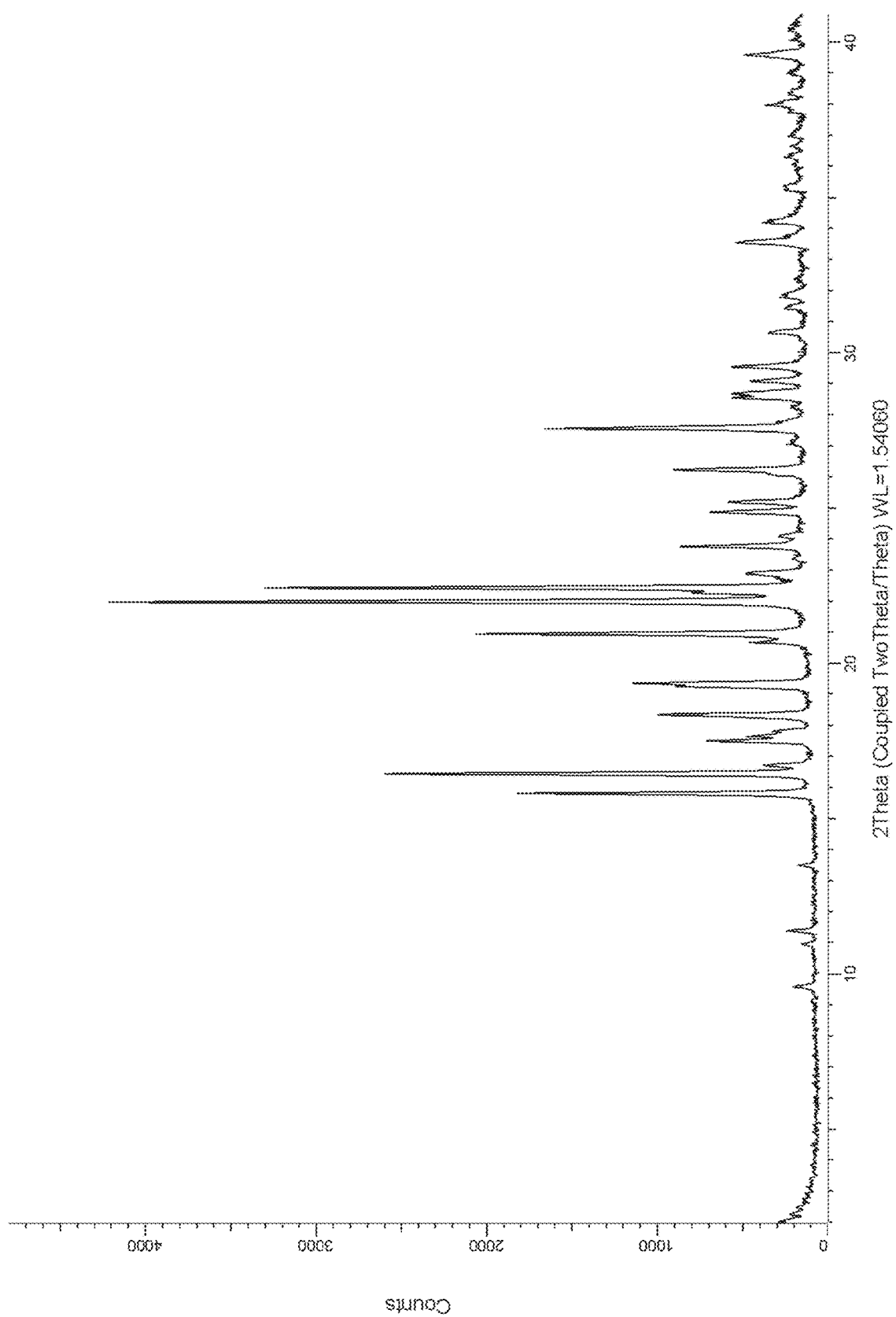
FIG. 3A provides an illustrative XRPD spectrum for compound of example 43, designated herein as Form E FIG. 3B provides an illustrative DSC for compound of example 43, designated herein as Form E.
Figure 3B:
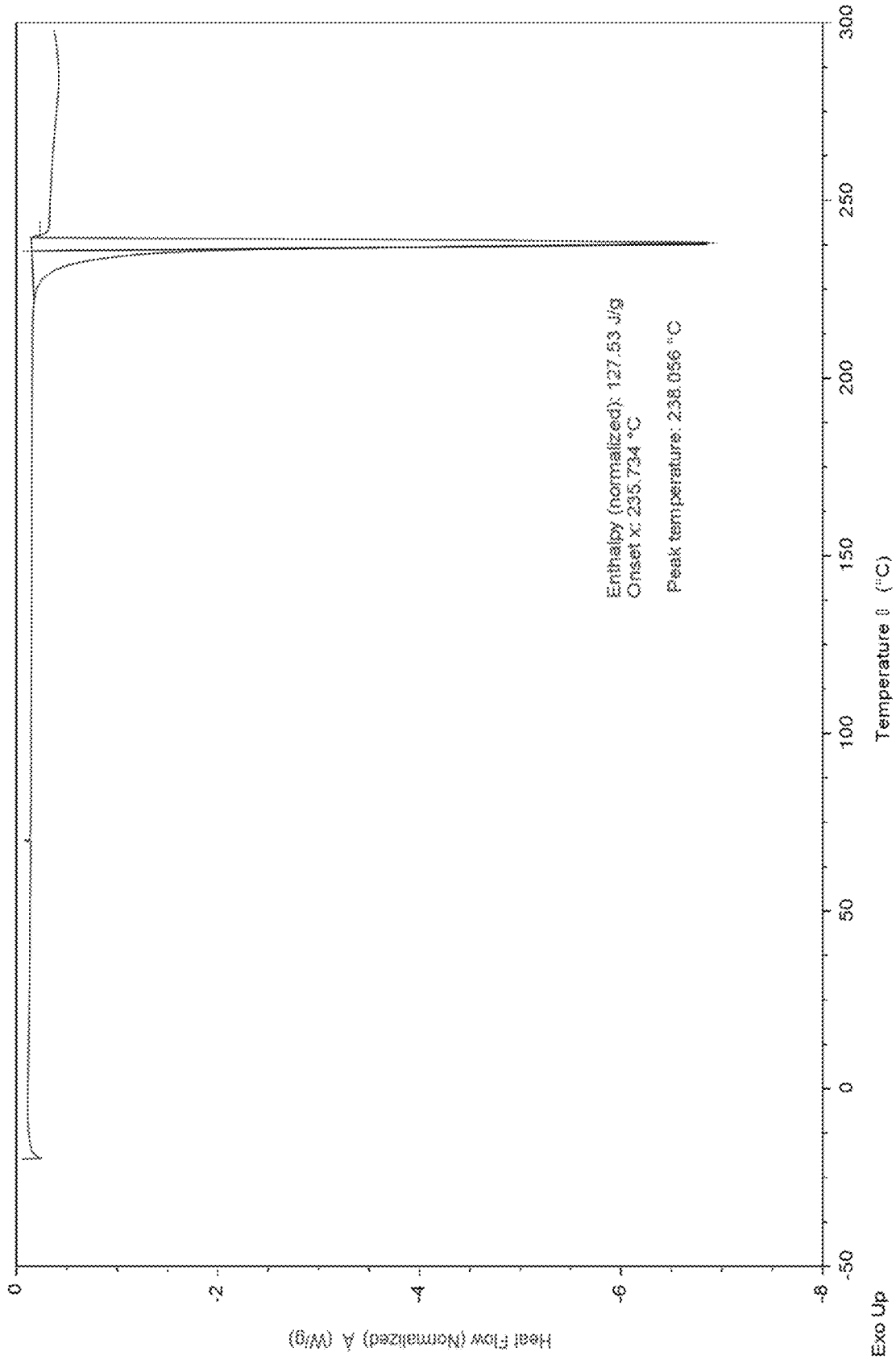
FIG. 3C provides an illustrative TGA for compound of example 43, designated herein as Form E.
Figure 3C:
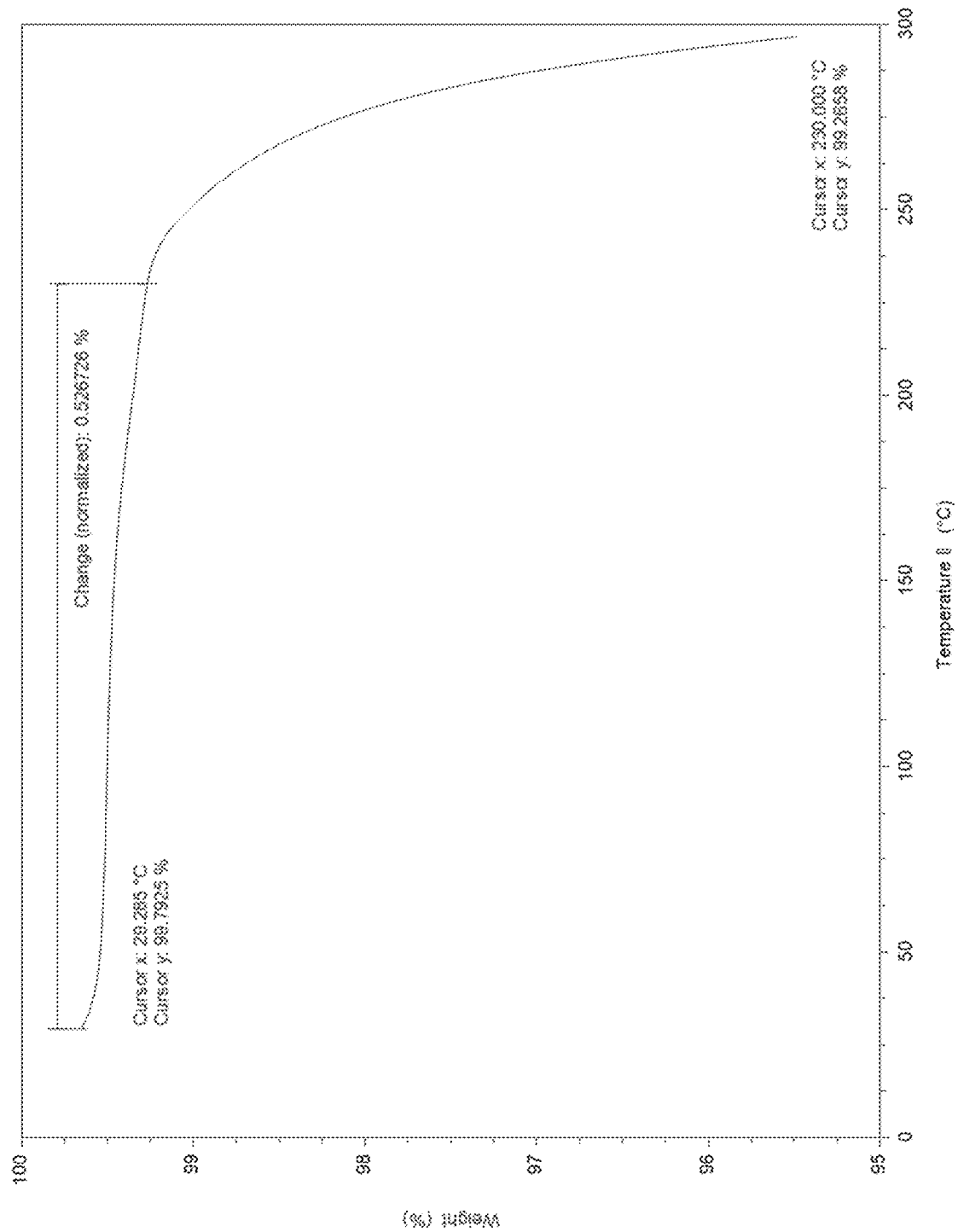

In another embodiment, the invention provides a crystalline form E of (S)-2-amino-3-(3-(4-((3-fluoro-5-(1H-pyrazol-5-yl)pyridin-2-yl)oxy)phenyl)-1H-pyrazol-1-yl)propan-1-ol hydrochloric salt as characterized in FIGS. 3A, 3B and 3C and example 43. The crystalline Form E is characterized by one or more of the following characteristics:

(i) an x-ray powder diffraction pattern comprising representative peaks in terms of 2θ at 15.8 t 0.2 °2θ, 16.4 t 0.2 °2θ, 21.0 t 0.2 °2θ, 22.0 t 0.2 °2θ, 22.0 t 0.2 °2θ and 27.6 t 0.2 °2θ, measured at a temperature of about 25° C. and an x-ray wavelength, X, of 1.5406 Å; (ii) an x-ray powder diffraction pattern comprising four or more 2θ values selected from the group consisting of 15.8 t 0.2 °2θ, 16.4 t 0.2 °2θ, 18.3 t 0.2 °2θ, 19.3 t 0.2 °2θ, 21.0 t 0.2 °2θ, 22.0 t 0.2°2θ, 22.4 t 0.2 °2θ, 23.8±0.2 °2θ, 26.2 t 0.2 °2θ, and 27.6 t 0.2 °2θ, measured at a temperature of about 25° C. and an x-ray wavelength, λ, of 1.5406 Å;

(iii) an x-ray powder diffraction pattern comprising five or more 2θ values selected from the group consisting of 15.8 t 0.2 °2θ, 16.4 t 0.2 °2θ, 18.3 t 0.2 °2θ, 19.3 t 0.2 °2θ, 21.0 t 0.2 °2θ, 22.0±0.2 °2θ, 22.4±0.2 °2θ, 23.8±0.2°2θ, 26.2±0.2 °2θ, and 27.6±0.2 °2θ, measured at a temperature of about 25° C. and an x-ray wavelength, X, of 1.5406 Å;

iv) an x-ray diffraction spectrum substantially the same as the x-ray powder diffraction spectrum shown in FIG. 3A;

v) a differential scanning calorimetry (DSC) thermogram substantially the same as that shown in shown in FIG. 3B; i.e. melting endotherm at about 236'C with an enthalpy of about 127 J/g when heated from 30 to 300° C. at a rate of 10K/min;

vi) a thermo gravimetric analysis (TGA) diagram substantially the same as that shown in shown in FIG. 3C, i.e. with a loss on drying at about 0.5% at about 230° C. when heated from 30 to 300° C. at a rate of 10K/min.

Figure 6B:
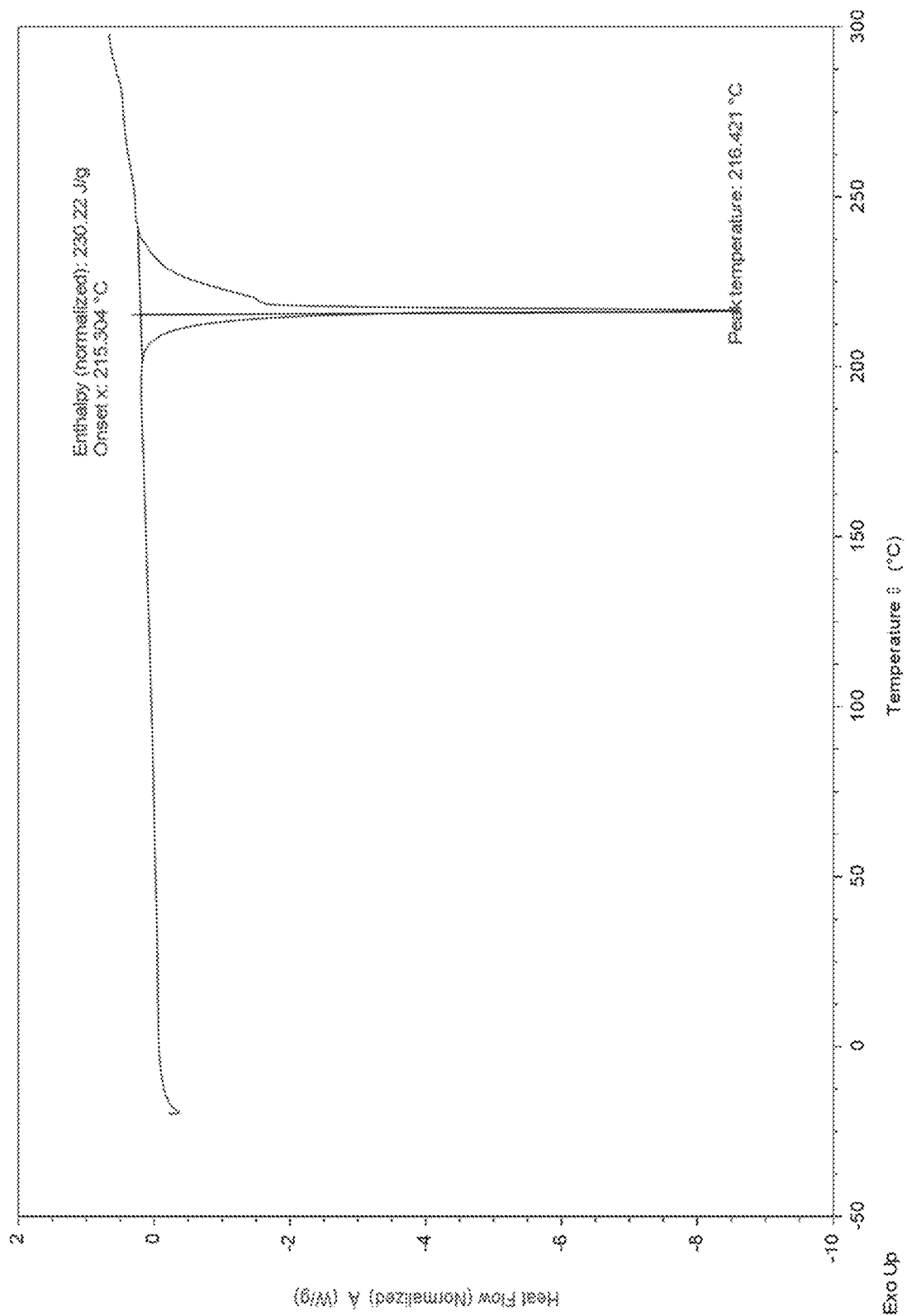
FIG. 6A provides an illustrative XRPD spectrum for compound of example 46, designated herein as Form F FIG. 6B provides an illustrative DSC for compound of example 46, designated herein as Form F.
FIG. 6C provides an illustrative TGA for compound of example 46, designated herein as Form F.
Figure 6C:
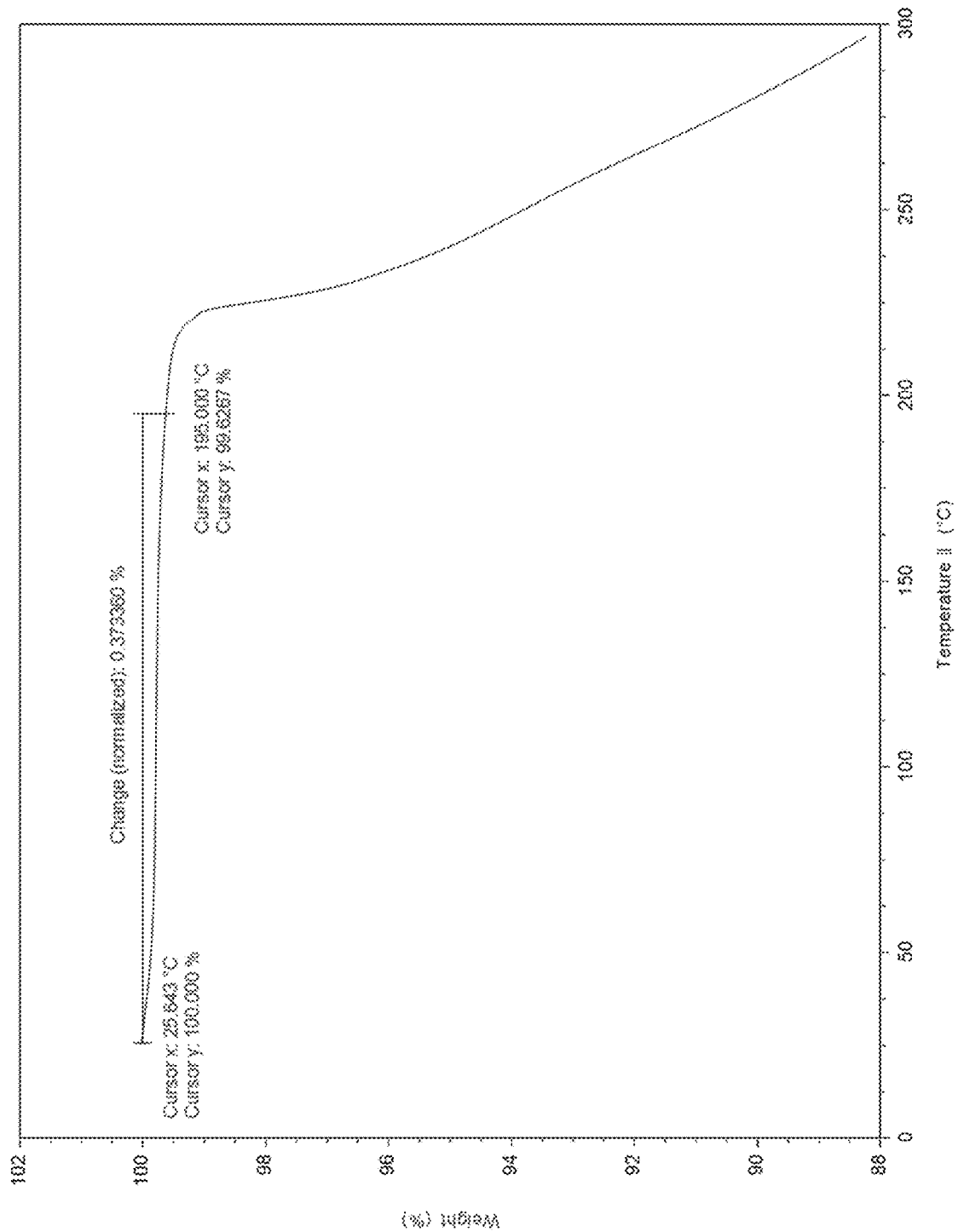

In yet another embodiment, the invention provides a crystalline form F of (S)-2-amino-3-(3-(4-((3-fluoro-5-(1H-pyrazol-5-yl)pyridin-2-yl)oxy)phenyl)-1H-pyrazol-1-yl) propan-1-01 hydrochloric salt as characterized in FIGS. 6A, 6B and 6C and example 46. The crystalline Form F is characterized by one or more of the following characteristics:

(i) an x-ray powder diffraction pattern comprising representative peaks in terms of 2θ at 5.3±0.2 °2θ, 15.9±0.2 °2θ, 16.8±0.2 °2θ, 17.7±0.2 °2θ, 21.0±0.2 °2θ, 21.3±0.2 °2θ, 22.3±0.2 °2θ, and 23.7±0.2 °2θ, measured at a temperature of about 25° C. and an x-ray wavelength, X, of 1.5406 Å;

(ii) an x-ray powder diffraction pattern comprising four or more 2θ values selected from the group consisting of 5.3±0.2 °2θ, 11.4±0.2 °2θ, 15.9±0.2 °2θ, 16.8±0.2 °2θ, 17.2±0.2 °2θ, 17.7±0.2°29, 18.0±0.2 °2θ, 21.0±0.2 °2θ, 21.3±0.2 °2θ, 22.3±0.2 °2θ, 23.7±0.2 °2θ, and 26.8±0.2 °2θ, measured at a temperature of about 25° C. and an x-ray wavelength, X, of 1.5406 Å;

(iii) an x-ray powder diffraction pattern comprising five or more 2θ values selected from the group consisting of 5.3±0.2 °2θ, 11.4±0.2 °2θ, 15.9±0.2 °2θ, 16.8±0.2 °2θ, 17.2±0.2 °2θ, 17.7±0.2 °2θ, 18.0±0.2 °2θ, 21.0±0.2 °2θ, 21.3±0.2 °2θ, 22.3±0.2 °2θ, 23.7±0.2 °2θ, and 26.8±0.2 °2θ, measured at a temperature of about 25° C. and an x-ray wavelength, X, of 1.5406 Å;

iv) an x-ray diffraction spectrum substantially the same as the x-ray powder diffraction spectrum shown in FIG. 6A;

v) a differential scanning calorimetry (DSC) thermogram substantially the same as that shown in shown in FIG. 6B; i.e. melting at bout 215° C. with an enthalpy with decomposition, when heated from 30 to 300° C. at a rate of 10K/min;

vi) a thermo gravimetric analysis (TGA) diagram substantially the same as that shown in shown in FIG. 6C, i.e. with a loss on drying at about 0.4% at about 195° C., when heated from 30 to 300° C. at a rate of 10K/min.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I), (IA), (IB) or (IC) and any of formulae (II) to (VI) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of any one of formulas (I), (IA), (IB), (IC) and Formulae (II) to (VI).

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Synthetic Schemes

Compounds of Formula (II) can be prepared according to general scheme A or B:

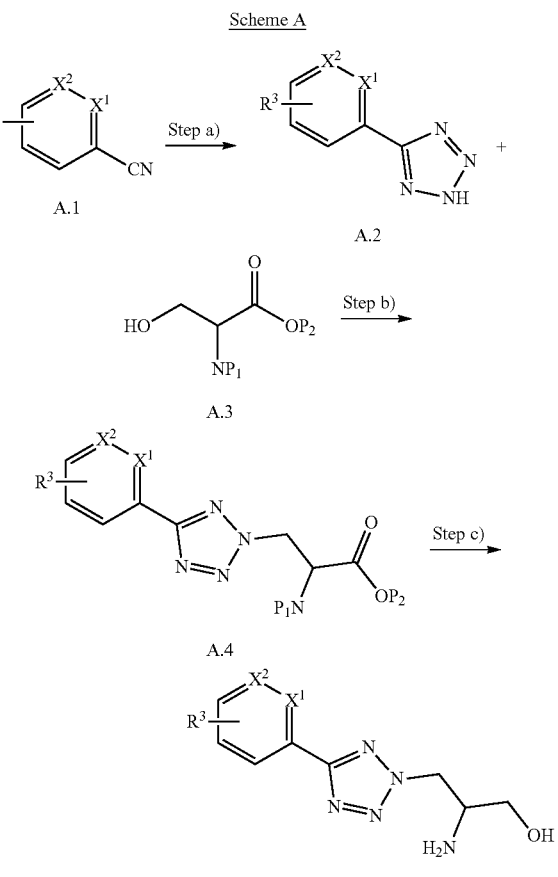

Scheme A

Compound of Formula (II)

The cyano group of a suited building block A.1 can be treated with an azide in the presence of an organotin oxide to yield a tetrazol A.2, which can be reacted with a protected serine derivative A.3 to give intermediate A.4. Sequential or simultaneous deprotection can furnish a compound of formula (II).

Scheme B

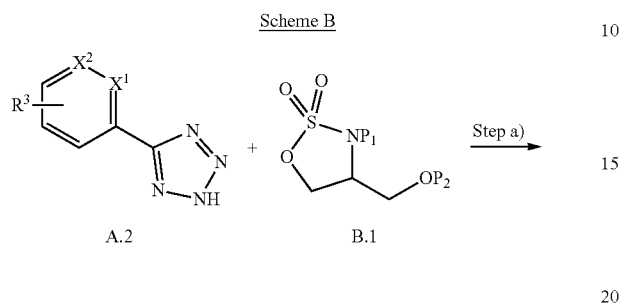

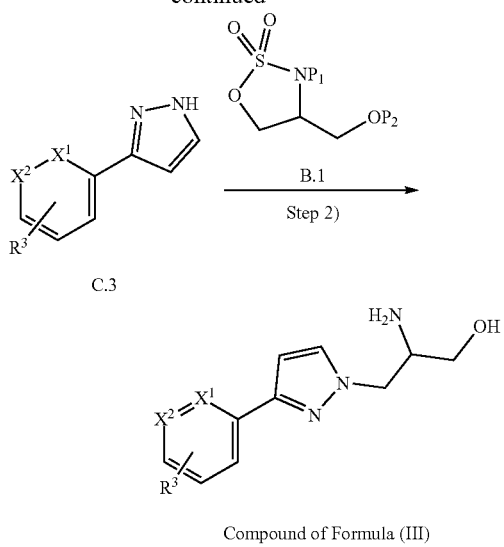

Alternatively, a tetrazol A.2 can be reacted with a protected 4-(hydroxymethyl)-1,2,3-oxathiazolidine 2,2-dioxide B.1 in the presence of a base to yield intermediate B.2, which can be deprotected to give a compound of formula (II).

Compounds of Formula (III) can be prepared according to general scheme C:

Scheme C

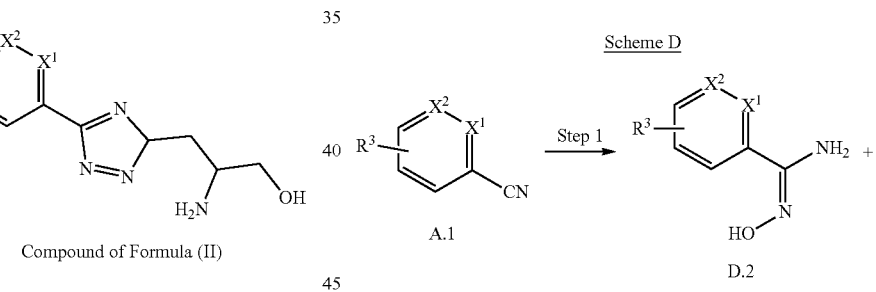

A suited building block C.1 can be reacted in the presence of a cytalyst with a boron reagent C.2, which can be protected or unprotected to yield intermediate C.3. Alternatively, the corresponding boronic ester can be used instead of the acid. Treatment with a protected building B.1 and subsequent removal of the protecting groups can furnish compounds of formula (III).

Compounds of Formula (IV) can be prepared according to general scheme D:

Scheme D

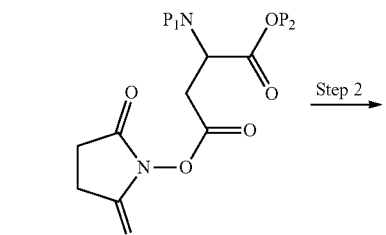

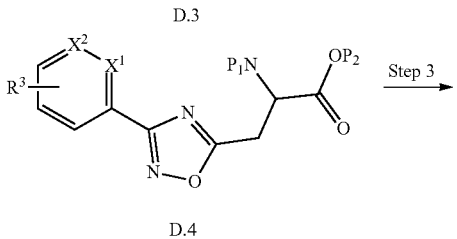

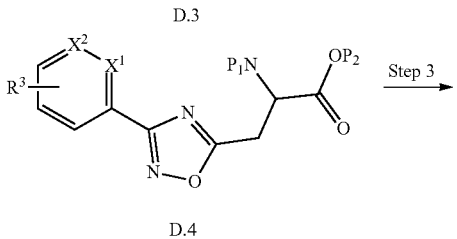

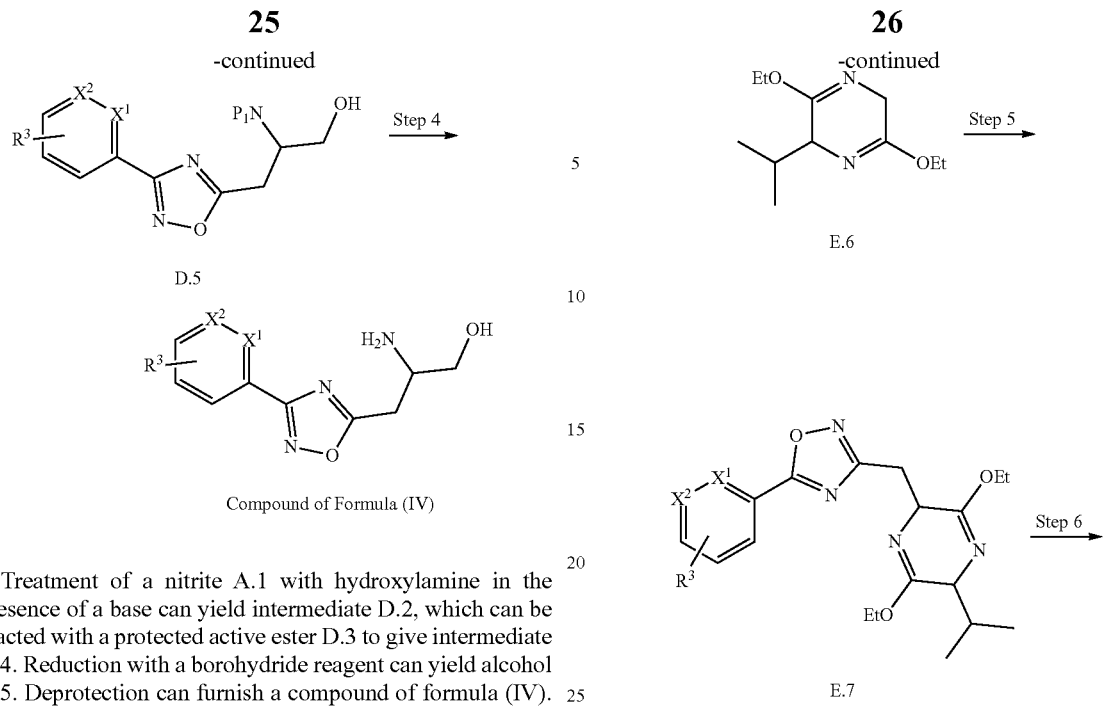

Treatment of a nitrite A.1 with hydroxylamine in the presence of a base can yield intermediate D.2, which can be reacted with a protected active ester D.3 to give intermediate D.4. Reduction with a borohydride reagent can yield alcohol D.5. Deprotection can furnish a compound of formula (IV).

Compounds of Formula (V) can be prepared according to Scheme E:

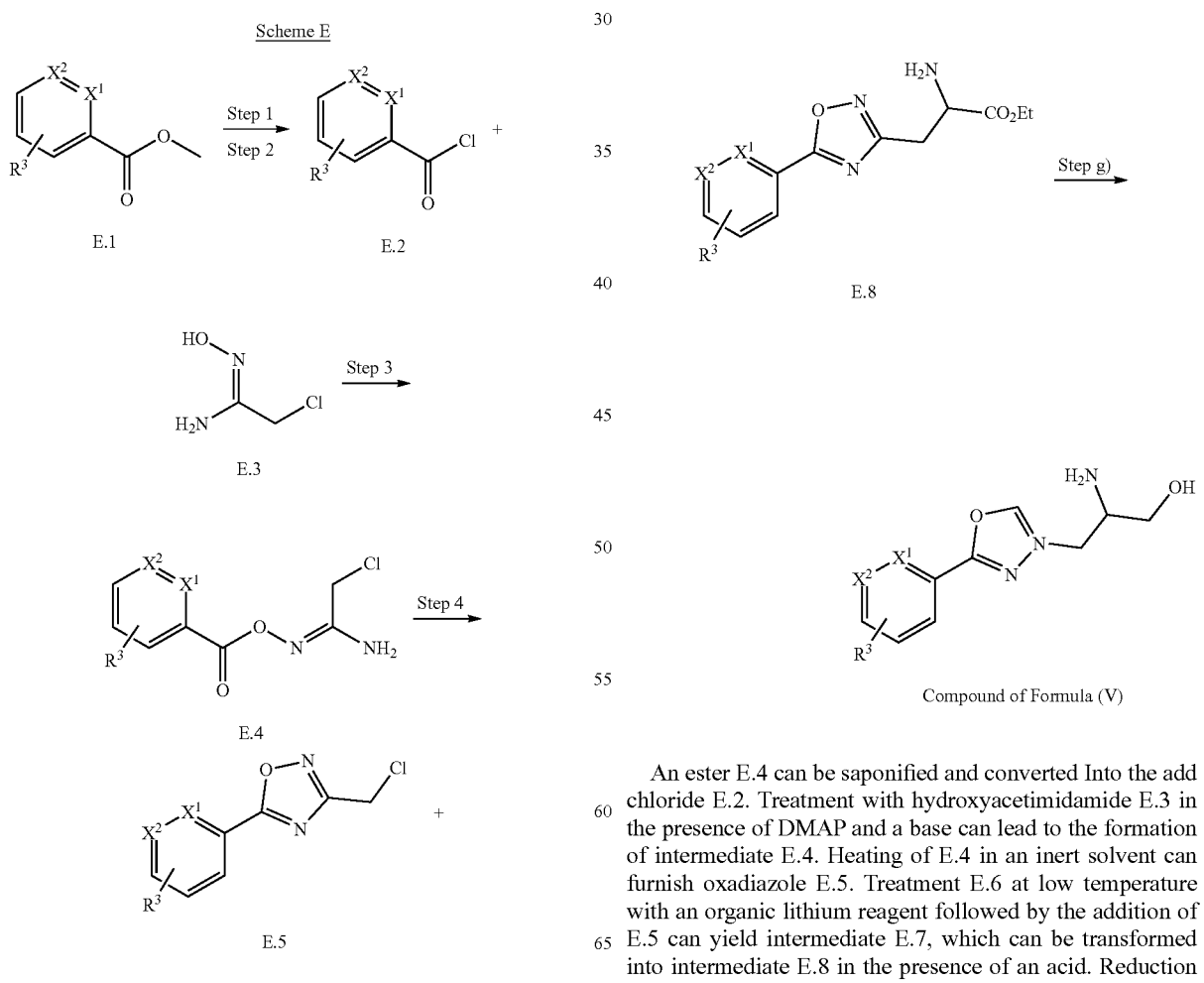

An ester E.4 can be saponified and converted Into the add chloride E.2. Treatment with hydroxyacetimidamide E.3 in the presence of DMAP and a base can lead to the formation of intermediate E.4. Heating of E.4 in an inert solvent can furnish oxadiazole E.5. Treatment E.6 at low temperature with an organic lithium reagent followed by the addition of E.5 can yield intermediate E.7, which can be transformed into intermediate E.8 in the presence of an acid. Reduction of the acid can afford a compound of formula (V).

Compounds of Formula (VI) can be prepared according to general scheme F:

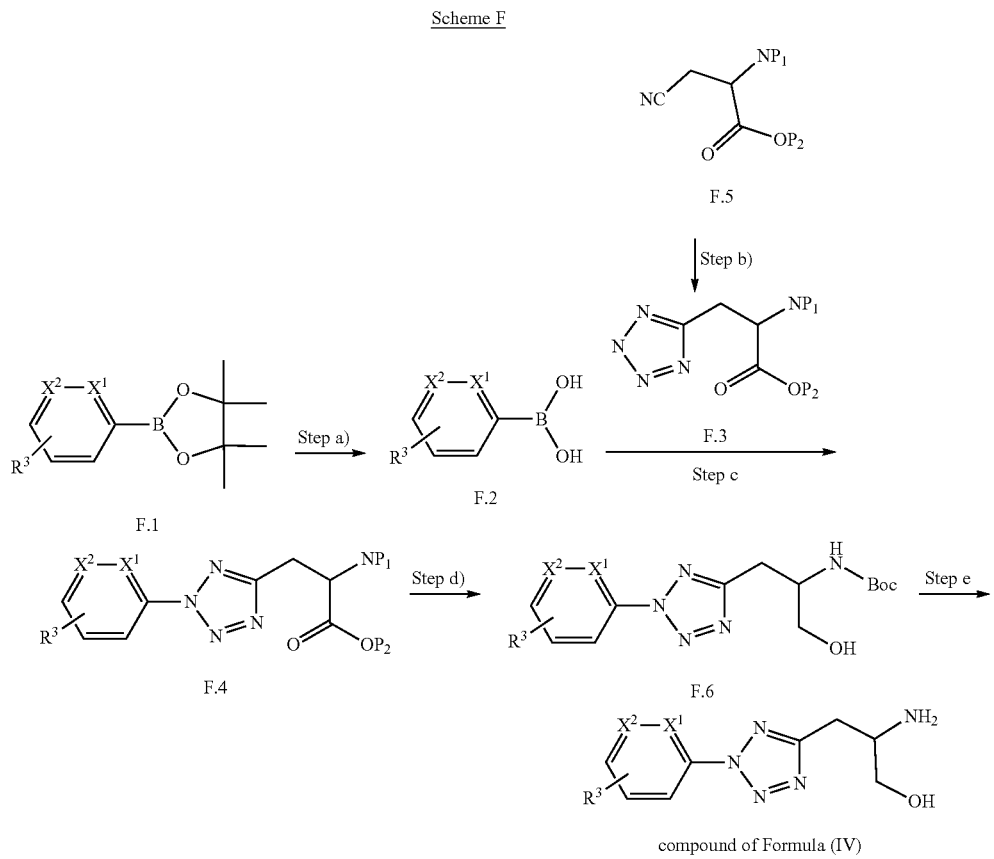

Scheme F compound of Formula (IV)

A dioxaborolane F.1 can be treated with NaIO₄ to yield boronic acid F.2. The reaction with tetrazol F.3 in the presence of a Cu catalyst, O₂ and a base can yield intermediate F.6. Tetrazol F.3 can be prepared from protected nitrile F.5 by the reaction with an azide. Reduction with a borohydride reagent can yield alcohol F.6. Deprotection can afford a compound of formula (VI) Additional schemes G-I for the syntheses of Intermediates A 1 in Schemes A and D.

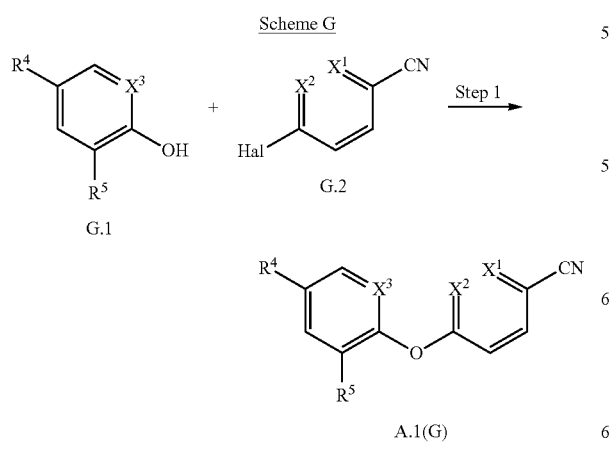

Scheme G

The reaction of G.1 with aromatic halide G.2 in the presence of a base can yield an intermediate A.1(G).

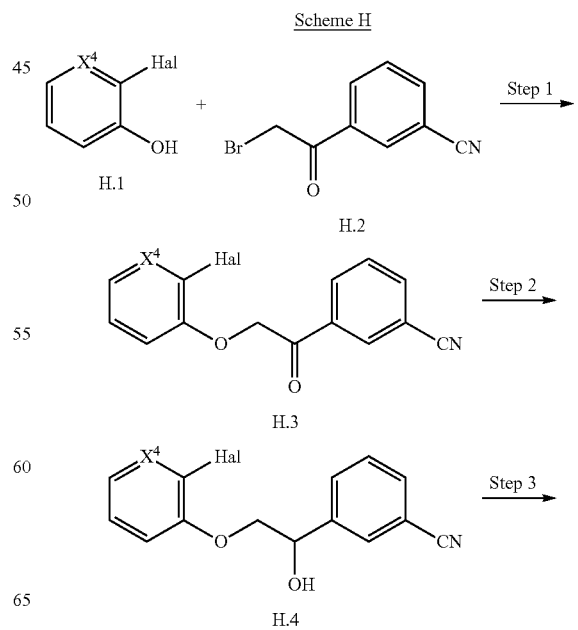

Scheme H

-continued

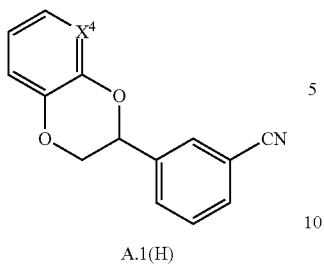

A.1(H)

The reaction of a compound H.1 with a bromide H.2 in the presence of a base can yield a compound H.3. Reduction of with a Rh catalyst can afford H.4. In the presence of a chiral ligand enantomerically pure H.4 can be obtained. Treatment with a Cu catalyst at elevated temperature can yield a compound A.1(H).

Scheme I

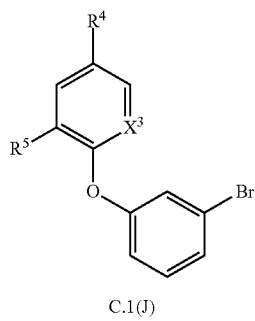

C.1(J)

The reaction of a halide J.1 with a phenol J.2 in the presence of a base can yield an intermediate C.1(J).

Scheme K

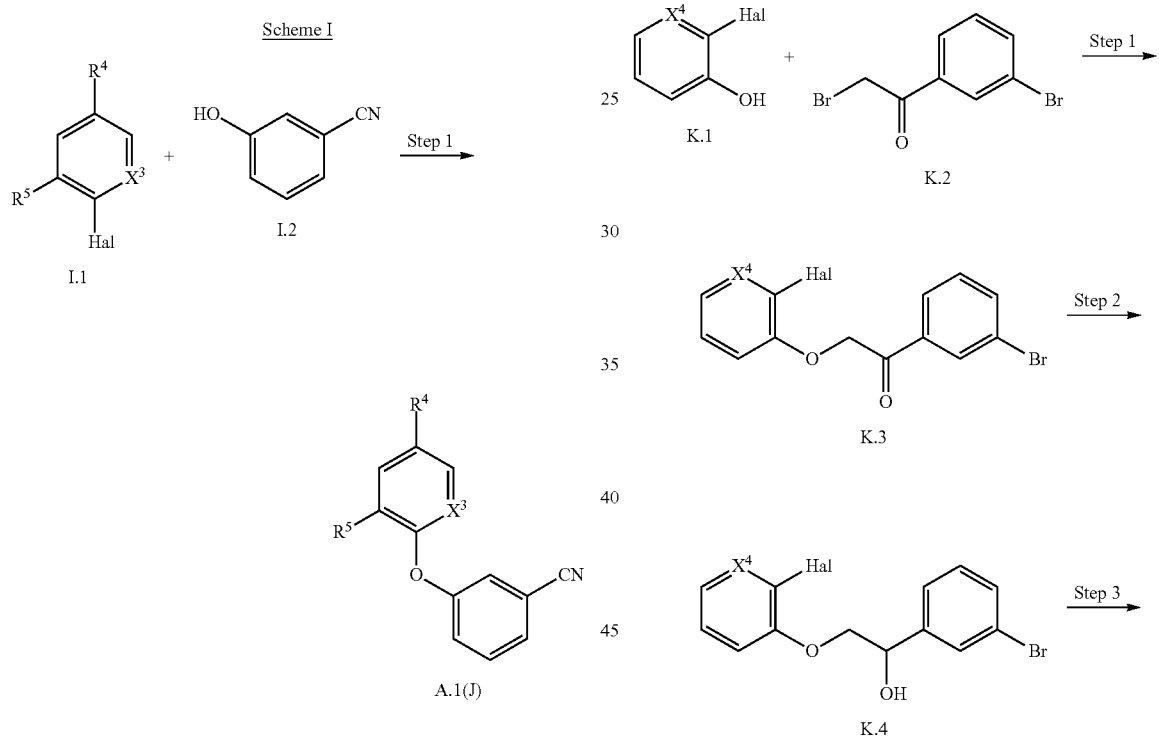

A.1(J)

The reaction of a halide 1.1 with a phenol 1.2 in the presence of a base can yield an intermediate A.1(I).

Additional schemes J-L for the syntheses of intermediates C.1 in scheme C:

Scheme J

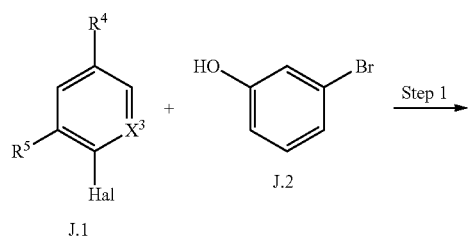

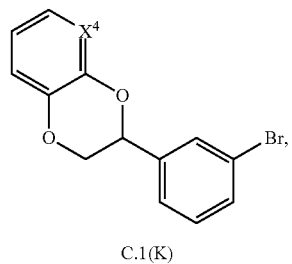

C.1(K)

The reaction of a compound K.1 with a bromide K.2 in the presence of a base can yield a compound K.3. Reduction of with a Rh catalyst can afford K.4. In the presence of a chiral ligand enantomerically pure K.4 can be obtained. Treatment with a Cu catalyst at elevated temperature can yield a compound C.1(K).

Scheme L

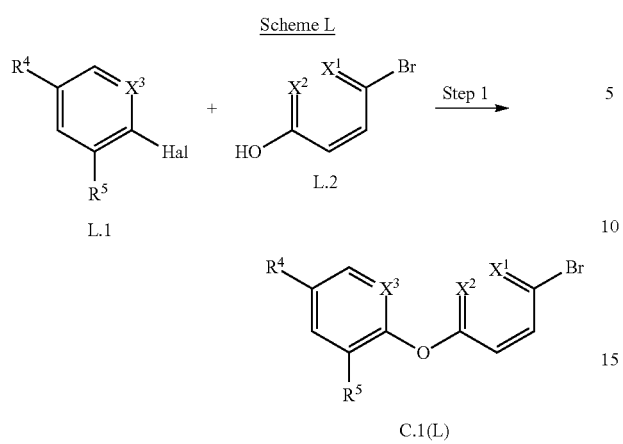

The reaction of a halide L.1 with a phenol L.2 in the presence of a base can yield an Intermediate C.1(L).

Additional schemes M-O for the syntheses of intermediates E.1 for scheme E

Scheme M

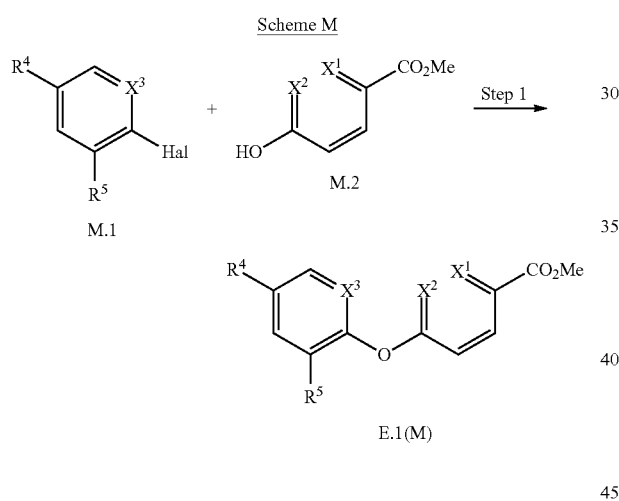

The reaction of a halide M.1 with a phenol M.2 in the presence of a base can yield an intermediate E.1(M).

Scheme N

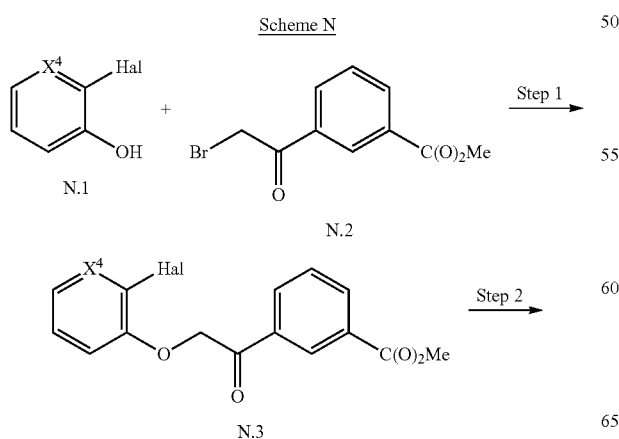

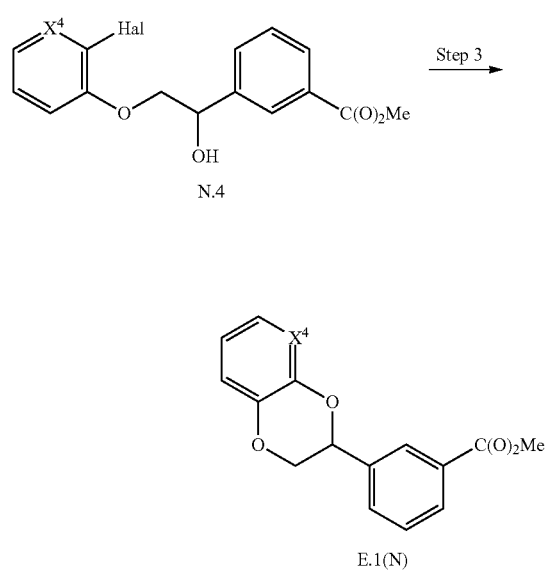

The reaction of a compound N.1 with a bromide N.2 in the presence of a base can yield a compound N.3. Reduction of with a Rh catalyst can afford N.4. In the presence of a chiral ligand enantiomerically pure N.4 can be obtained. Treatment with a Cu catalyst at elevated temperature can yield a compound E.1(N).

Scheme O

The reaction of a halide O.1 with a phenol O.2 in the presence of a base can yield an intermediate E.1(O).

Additional schemes P-R for the syntheses of intermediates F.1 in scheme F

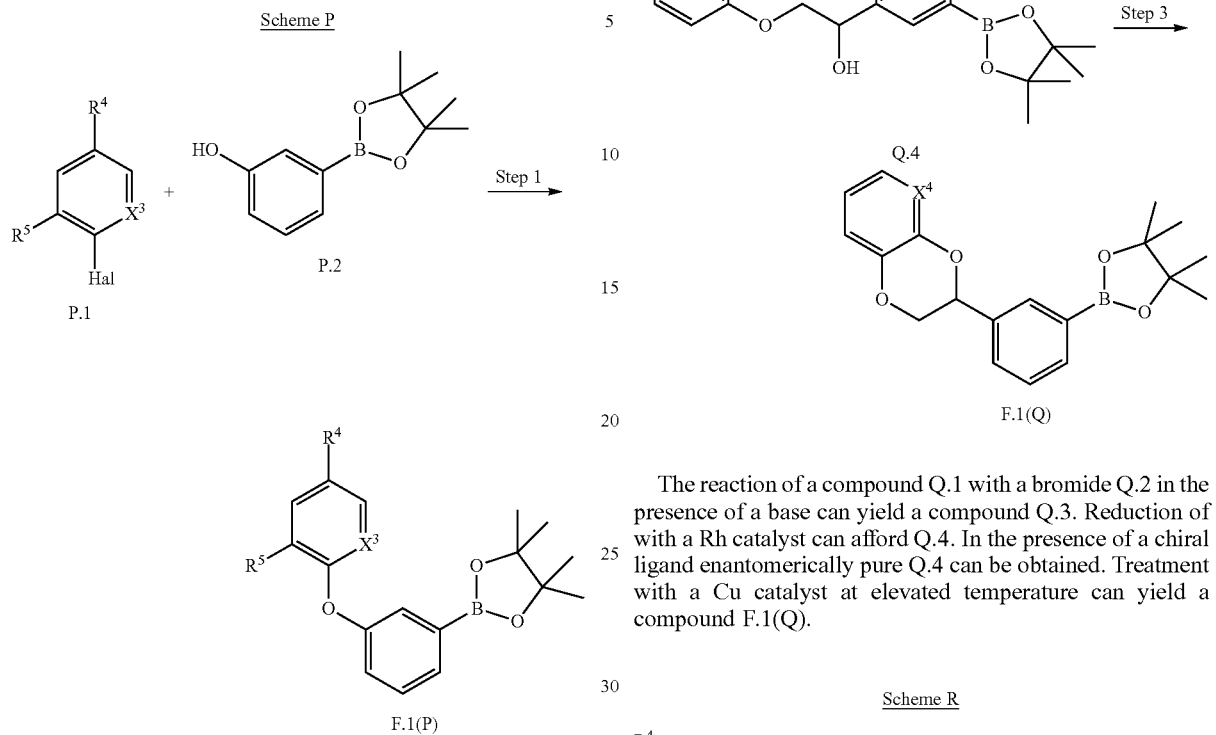

The reaction of a halide P.1 with a phenol P.2 in the presence of a base can yield an intermediate F.1(P).

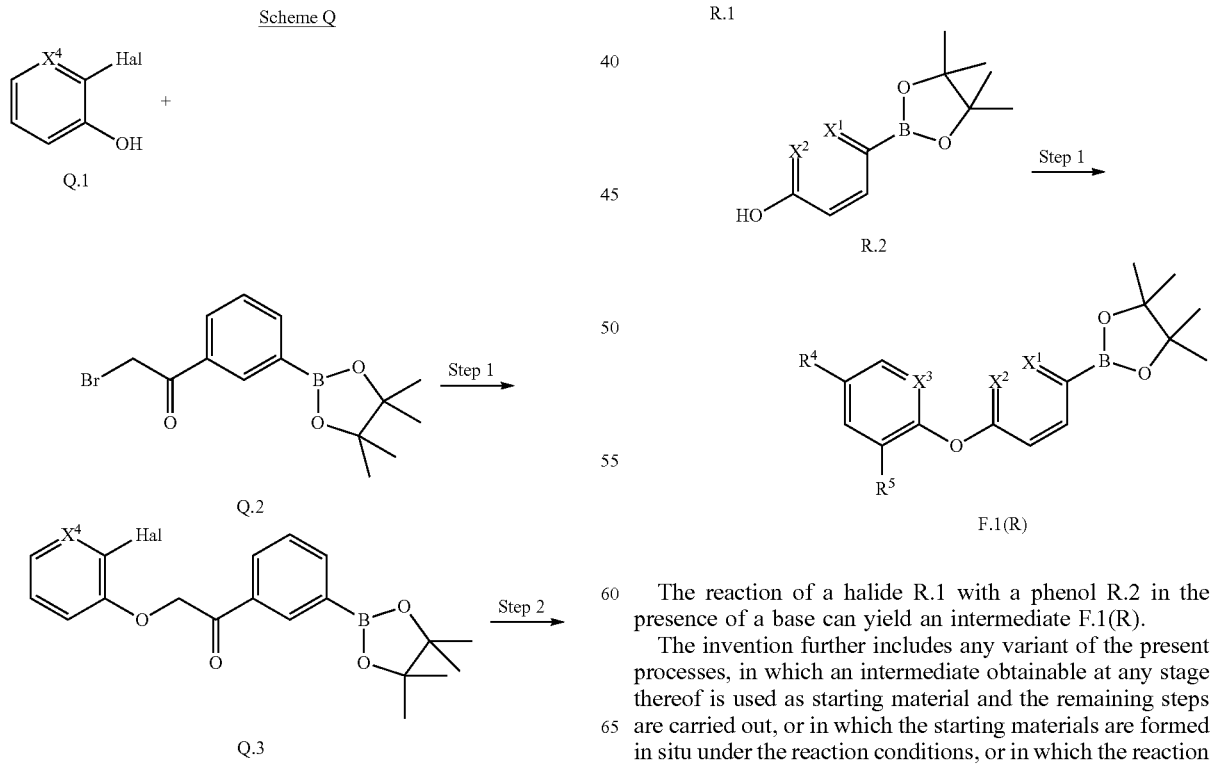

The reaction of a compound Q.1 with a bromide Q.2 in the presence of a base can yield a compound Q.3. Reduction of with a Rh catalyst can afford Q.4. In the presence of a chiral ligand enantiomerically pure Q.4 can be obtained. Treatment with a Cu catalyst at elevated temperature can yield a compound F.1(Q).

The reaction of a halide R.1 with a phenol R.2 in the presence of a base can yield an intermediate F.1(R).

The invention further includes any variant of the present processes, in which an intermediate obtainable at any stage thereof is used as starting material and the remaining steps are carried out, or in which the starting materials are formed in situ under the reaction conditions, or in which the reaction components are used in the form of their salts or optically pure material. Compounds of the present invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or poyvinylpyrrolidone; if desired d) disintegrants, e.g., starches, agar, alginic acid or its sodium salt, or effervescent mixtures; and e) absorbents, colorants, flavors and sweeteners.

The compounds of the present invention in free form or in pharmaceutically acceptable salt form, exhibit valuable pharmacological properties, e.g. LTA4H modulating properties, e.g. as indicated in vitro and in vivo tests as provided in the next sections, and are therefore indicated for therapy or for use as research chemicals, e.g. as tool compounds.

Compounds of the present invention may be useful in the treatment of an indication selected from: is selected from: acute or chronic inflammation, anaphylactic reactions, allergic reactions, atopic dermatitis, psoriasis, acute respiratory distress syndrome, immune complex-mediated pulmonary injury and chronic obstructive pulmonary disease, inflammatory bowel diseases (including ulcerative colitis, Crohn's disease and post-surgical trauma), gastrointestinal ulcers, non-alcoholic fatty liver disease (NAFLD), non-alcoholic steatohepatitis (NASH), neutrophilic dermatoses (including but not limited to Pyoderma gangrenosum, Sweet's syndrome, acne and neutrophilic urticaria), immune-complex-mediated glomerulonephritis, Hidradenitis suppurative, autoimmune diseases (including insulin-dependent diabetes mellitus, multiple sclerosis, rheumatoid arthritis, osteoarthritis and systemic lupus erythematosus), vasculitides (including but not limited to cutaneous vasculitis, Behcets disease and Henoch Schonlein Purpura), cardiovascular disorders (including, but not limited to hypertension, atherosclerosis, aneurysm, critical leg ischemia, peripheral arterial occlusive disease, pulmonary artery hypertension and Reynaud's syndrome), sepsis, inflammatory and neuropathic pain including arthritic pain, periodontal disease including gingivitis, ear infections, migraine, benign prostatic hyperplasia, Sjogren-Larsson Syndrome and cancers (including, but not limited to, leukemias and lymphomas, prostate cancer, breast cancer, lung cancer, malignant melanoma, renal carcinoma, head and neck tumors and colorectal cancer).

Thus, as a further aspect, the present invention provides the use of a compound of any of Formulae (I) to (V), or a pharmaceutically acceptable salt thereof, or the use of a compound of any of examples 1 to 46 in therapy. In a further embodiment, the therapy is selected from a disease which may be treated by inhibition of LTA4H activity. In another embodiment, the disease is selected from the afore-mentioned list, suitably ulcerative colitis, acne, Hidradenitis suppurative, asthma, e.g. neutrophilic asthma, psoriasis, and neutrophilic inflammatory conditions such as non-alcoholic fatty liver disease (NAFLD) and non-alcoholic steatohepatitis (NASH).

As a further aspect, the present invention provides a compound of Formula (I) selected from 2-amino-3-(3-(4-((3-fluoro-5-(1H-pyrazol-5-yl)pyridin-2-yl)oxy)phenyl)-1H-pyrazol-1-yl)propan-1-ol; (S)-2-amino-3-(3-(4-((3-fluoro-5-(1H-pyrazol-5-yl)pyridin-2-yl)oxy)phenyl)-1H-pyrazol-1-yl)propan-1-ol and (R)-2-amino-3-(3-(4-((3 fluoro-5-(1H-pyrazol-5-yl)pyridin-2-yl)oxy)phenyl)-1H-pyrazol-1-yl)propan-1-ol; or a pharmaceutically acceptable salt thereof, for use in therapy. In a further aspect of this embodiment, the therapy is selected from a disease which may be treated by inhibition of LTA4H. In another aspect of this embodiment, the disease is selected from the afore-mentioned list, suitably ulcerative colitis, acne, Hidradenitis suppurative, asthma, e.g. neutrophilic asthma, psoriasis, and neutrophilic inflammatory conditions such as non-alcoholic fatty liver disease (NAFLD) and non-alcoholic steatohepatitis (NASH).

Thus, as a further aspect, the present invention provides a compound of Formula (I) which is (S)-2-amino-3-(3-(4-((3-fluoro-5-(1H-pyrazol-5-yl)pyridin-2-yl)oxy)phenyl)-1H-pyrazol-1-yl)propan-1-ol, or a pharmaceutically acceptable salt thereof, for use in therapy. In a further aspect of this embodiment, the therapy is selected from a disease which may be treated by inhibition of LTA4H. in another aspect of this embodiment, the disease is selected from the afore-mentioned list, suitably ulcerative colitis, acne, Hidradenitis suppurative, asthma, e.g. neutrophilic asthma, psoriasis, and neutrophilic inflammatory conditions such as non-alcoholic fatty liver disease (NAFLD) and non-alcoholic steatohepatitis (NASH).

As a further aspect, the present invention provides a compound of Formula (I) is selected from (R)-2-amino-3-(3-(4-((5-chloro-3-fluoropyridin-2-yl)oxy)phenyl)-1,2,4-oxadiazol-5-yl)propan-1-ol, (S)-2-amino-3-(3-(3-((R)-2,3-dihydro-[1,4]dioxin[2,3-b]pyridin-3-yl)phenyl)-1,2,4-oxadiazol-5-yl)propan-1-ol, (S)-2-amino-3-(5-(3-((R)-2,3-dihydro-(1,4)dioxino[2,3-b]pyridin-3-yl)phenyl)-2H-tetrazol-2-yl)propan-1-ol, and (S)-2-Amino-3-(5-(4-((3-fluoro-5-(1H-pyrazol-5-yl)pyridin-2-yl)oxy)phenyl)-2H-tetrazol-2-yl)propan-1-ol; or a pharmaceutically acceptable salt thereof for use in therapy. In a further aspect of this embodiment, the therapy is selected from a disease which may be treated by inhibition of LTA4H. in another aspect of this embodiment, the disease is selected from the afore-mentioned list, suitably ulcerative colitis, acne, Hidradenitis suppurative, asthma, e.g. neutrophilic asthma, psoriasis, and neutrophilic inflammatory conditions such as non-alcoholic fatty liver disease (NAFLD) and non-alcoholic steatohepatitis (NASH).

In another aspect, the invention provides a method of treating a disease which is treated by inhibition of LTA4H comprising administration of a therapeutically acceptable amount of a compound of the present invention (e.g. a compound of any of Formulae (I) to (V) or any of the specific compounds of examples 1 to 46, or pharmaceutically acceptable salt thereof). In a further embodiment, the disease is selected from the afore-mentioned list, suitably ulcerative colitis, acne, Hidradenitis suppurative, asthma, e.g. neutrophilic asthma, psoriasis, and neutrophilic inflammatory conditions such as non-alcoholic fatty liver disease (NAFLD) and non alcoholic steatohepatitis (NASH).

Thus, as a further aspect, the present invention provides the use of a compound of the present invention (e.g. a compound of any of Formulae (I) to (V) or any of the specific compounds of examples 1 to 46, or pharmaceutically acceptable salt thereof) for the manufacture of a medicament. In a further embodiment, the medicament is for treatment of a disease which may be treated by inhibition of LTA4H. In another embodiment, the disease is selected from the afore-mentioned list, suitably ulcerative colitis, acne, Hidradenitis suppurative, asthma, e.g. neutrophilic asthma, psoriasis, and neutrophilic inflammatory conditions such as non-alcoholic fatty liver disease (NAFLD) and non-alcoholic steatohepatitis (NASH).

The pharmaceutical composition or combination of the present invention may, for example, be in unit dosage of about 1-1000 mg of active ingredient(s) for a subject of about 50-70 kg.

Combinations:

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient The latter also applies to cocktail therapy, e.g. the administration of three or more therapeutic agent.

By "combination", there is meant either a fixed combination in one dosage unit form, or a combined administration where a compound of the present invention and a combination partner may be administered independently at the same time or separately within time intervals that especially allow that the combination partners show a cooperative, e.g. synergistic effect. The single components may be packaged together in a kit or separately. One or both of the components (e.g., powders or liquids) may be reconstituted or diluted to a desired dose prior to administration.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the present invention.

In one embodiment, the invention provides a product comprising a compound of the present invention and at least one other therapeutic agent as a combined preparation for simultaneous, separate or sequential use in therapy. In one embodiment, the therapy is the treatment of a disease or condition mediated by [LTA4H. Products provided as a combined preparation include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical composition comprising a compound of the present invention and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

Accordingly, the invention provides the use of a compound of the present invention for treating a disease or condition mediated by LTA4H, wherein the medicament is prepared for administration with another therapeutic agent. The invention also provides the use of another therapeutic agent for treating a disease or condition mediated by LTA4H, wherein the medicament is administered with a compound of the present invention.

The invention also provides a compound of the present invention for use in a method of treating a disease or condition mediated by LTA4H, wherein the compound of the present invention is prepared for administration with another therapeutic agent. The invention also provides another therapeutic agent for use in a method of treating a disease or condition mediated by LTA4H, wherein the other therapeutic agent is prepared for administration with a compound of the present invention. The invention also provides a compound of the present invention for use in a method of treating a disease or condition mediated by LT14H, wherein the compound of the present invention is administered with another therapeutic agent. The invention also provides another therapeutic agent for use in a method of treating a disease or condition mediated by LTA4H, wherein the other therapeutic agent is administered with a compound of the present invention.

The invention also provides the use of a compound of the present invention for treating a disease or condition mediated by LTA4H, wherein the patient has previously (e.g. within 24 hours) been treated with another therapeutic agent. The invention also provides the use of another therapeutic agent for treating a disease or condition mediated by LTA4H, wherein the patient has previously (e.g. within 24 hours) been treated with compound of the present invention.

In one embodiment, the other therapeutic agent is selected from: a COX inhibitor, a Cysteinyl-Leukotriene Receptor antagonist (including Montelukast, Pranlukast, Zafirlukast), a leukotriene $C_4$ synthase (LTC4S) inhibitor, a NLRP3 inhibitor, a statin, sulfasalazine, Mesalamine, a calcineurin inhibitor, e.g. cyclosporin A or FK 506; a mTOR inhibitor, e.g. rapamycin, 40-O-(2-hydroxyethyl)-repamycin, biolimus-7 or biolimus-9; an ascomycin having immunosuppressive properties, e.g. ABT-281, ASM981; corticosteroids; cyclophosphamide; azathioprene; methotrexate; leflunomide; mizoribine; mycophenolic acid or salt; mycophenolate mofetil; IL-1beta inhibitor.

Specific individual combinations which may provide particular treatment benefits include NLRP3 inhibitors or LTC4S inhibitors.

In one embodiment, the instant invention relates to a combination of a compound according to any one of Formulae (I) to (V) or a pharmaceutically acceptable salt thereof with a NLRP3 inhibitor.

Examples of NLRP3 inhibitors for use in said combination are those described in PCT patent applications: WO/2020/234715, WO/2020/021447, WO/2017/184624, WO/2017/184623, WO/2017/184604, WO/2019/023147, WO/2019/023145, WO/2020/010140, WO/2019/079119, WO/2020/010143, WO/2020/102096, WO/2020/010118, WO/2020/086732, WO/2020/086728, WO12020/102576, WO12020/102574, WO/2020/102100, WO/2020/102098, WO/2020/154321 and WO/2020/154499.

More particularly NLRP3 inhibitors for use in said combination are selected from the group consisting of:

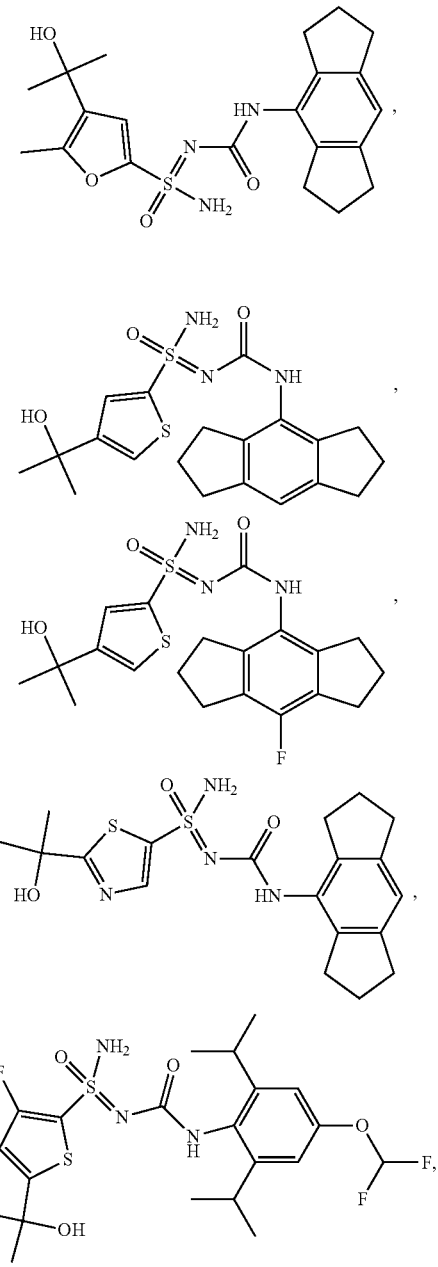

-continued
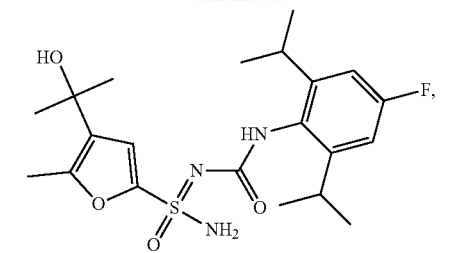
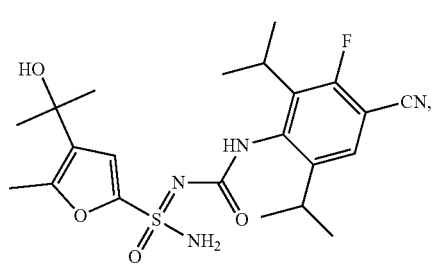
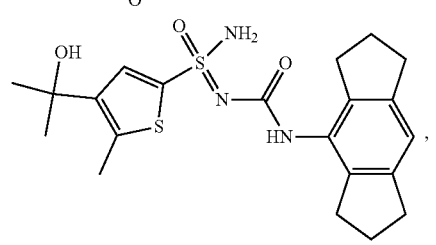
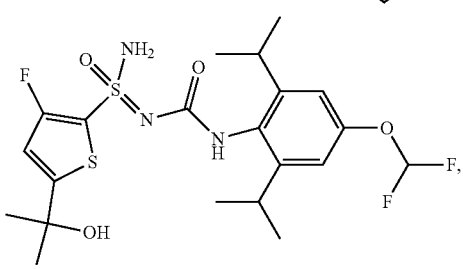
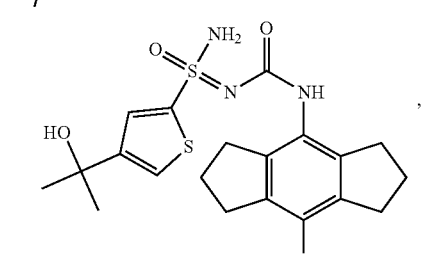
or a pharmaceutically acceptable salt thereof, preferably from the group consisting of:
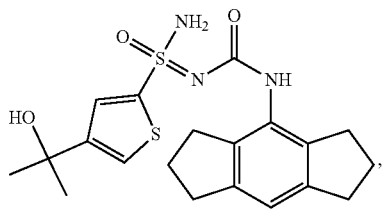
-continued
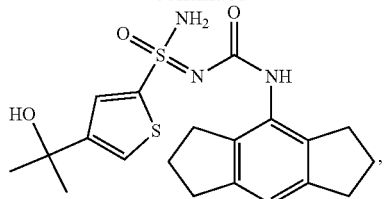
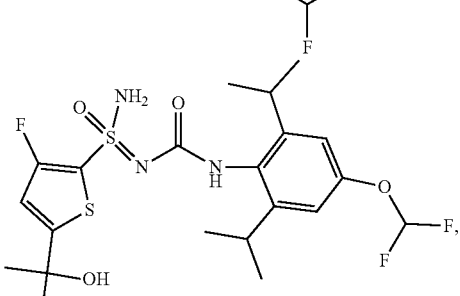
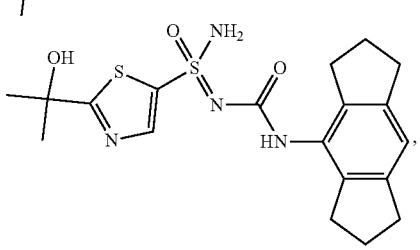
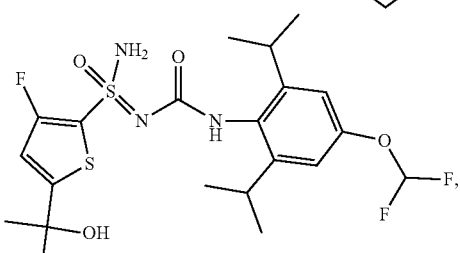
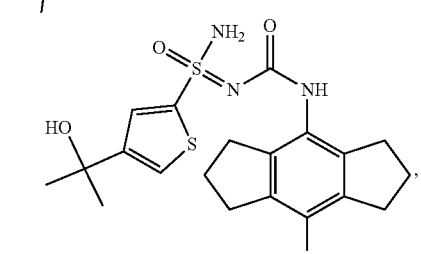
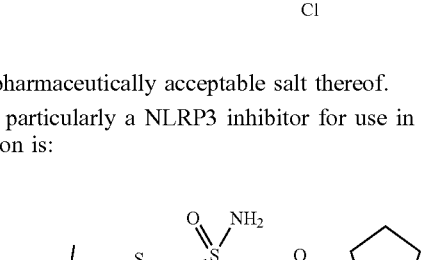
or a pharmaceutically acceptable salt thereof.
More particularly a NLRP3 inhibitor for use in said combination is:
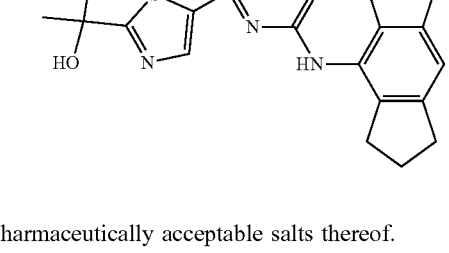
or pharmaceutically acceptable salts thereof.

In another embodiment, the NLRP3 inhibitor for use in said combination is selected from the compounds specifically disclosed in WO2020/234715. In one aspect of this embodiment the NLRP3 inhibitor is selected from 3-methyl-2-(5-methyl-6-((1-methylpiperidin-3-yl)amino)pyridazin-3-yl)-5-(trifluoromethyl) phenol, (S)-3-methyl-2-(5-methyl-6-((1-methylpiperidin-3-yl)amino)pyridazin-3-yl)-5-(trifluoromethyl)phenol, and (R)-3-methyl-2-(5-methyl-6-((1-methylpiperidin-3-yl)amino)pyridazin-3-yl)-5-(trifluoromethyl)phenol, or a pharmaceutically acceptable salt thereof, preferably (R)-3-methyl-2-(5-methyl-6-((1-methylpiperidin-3-yl)amino)pyridazin-3-yl)-5-(trifluoromethyl)phenol or a pharmaceutically acceptable salt thereof. In another aspect of this embodiment, the NLRP3 inhibitor disclosed in WO2020/234715 is selected from 2-(4-methyl-6-((1-methylpiperidin-3-yl)amino)pyridazin-3-yl)-5-(trifluoromethyl)phenol, (S)-2-(4-methyl-6-((1-methylpiperidin-3-yl)amino)pyridazin-3-yl)-5-(trifluoromethyl)phenol, and (R)-2-(4-methyl-6-((1-methylpiperidin-3-yl)amino)pyridazin-3-yl)-5-(trifluoromethyl)phenol, or a pharmaceutically acceptable salt thereof, preferably (R)-2-(4-methyl-6-((1-methylpiperidin-3-yl)amino)pyridazin-3-yl)-5-(trifluoromethyl)phenol, or a pharmaceutically acceptable salt thereof. In yet another aspect of this embodiment, the NLRP3 inhibitor disclosed in WO2020/234715 is selected from 2-(6-((3-hydroxycyclohexyl)amino)pyridazin-3-yl)-3-methyl-5-(trifluoromethyl)phenol, 2-(6-(((1S,3R)-3-hydroxycyclohexyl)amino)pyridazin-3-yl)-3-methyl-5-(trifluoromethyl)phenol, 2-(6-(((1R,3R)-3-hydroxycyclohexyl)amino)pyridazin-3-yl)-3-methyl-5-(trifluoromethyl)phenol, 2-(6-(((1S,3S)-3-hydroxycyclohexyl)amino)pyridazin-3-yl)-3-methyl-5-(trifluoromethyl)phenol, or a pharmaceutically acceptable salt thereof, preferably the compound is 2-(6-(((1R,3S)-3-hydroxycyclohexyl)amino)pyridazin-3-yl)-3-methyl-5-(trifluoromethyl)phenol, or a pharmaceutically acceptable salt thereof.

In one embodiment, the instant invention relates to a combination of a compound according to any one of Formula (I) to (V) or a pharmaceutically acceptable salt thereof with a NLRP3 inhibitor as described above for use in the treatment of HS or NASH.

In one embodiment, the instant invention relates to a combination of the any one of the compounds of Formula (I) to (V) or a pharmaceutically acceptable salt thereof with a LTC4S inhibitor.

Examples of LTC4S inhibitors for use in said combination are one of examples 1 to 120 described in PCT patent application WO20221034529, which is hereby incorporated by reference.

More particularly LTC4S inhibitors for use in said combination are selected from the group consisting of: 1-(3,4-difluorophenyl)-9-(6-(2,2,2-trifluoroethoxy)pyrimidin-4-yl)-1,9-diazaspiro[5.5]undecan-2-one; 9-(2-amino-6-(4-(trifluoromethyl)-1H-pyrazol-1-yl)pyrimidin-4-yl)-1-(3,4-difluorophenyl)-1,9-diazaspiro[5.5]undecane-2-one; (R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one; (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one; 9-(2-amino-6-(trifluoromethyl)pyrimidin-4-yl)-1-(3,4-difluorophenyl)-1,9-diazaspiro(5.5)undecan-2-one and 9-(2-amino-6-(1,1-difluoroethyl)pyrimidin-4-yl)-1-(3,4-difluorophenyl)-1,9-diazaspiro(5.5)undecan-2-one; or a pharmaceutically acceptable salt thereof.

In one embodiment, the instant invention relates to a combination of the any one of the compounds of Formula (I) to (V) or a pharmaceutically acceptable salt thereof with a LTC4S inhibitor for use in the treatment of asthma or atopic dermatitis.

In one embodiment of the invention, there is provided a product comprising (S)-2-amino-3-(3-(4-((3-fluoro-5-(1H-pyrazol-5-yl)pyridin-2-yl)oxy)phenyl)-1H-pyrazol-1-yl)propan-1-ol, or a pharmaceutically acceptable salt thereof and a NLRP3 inhibitor as defined above as a combined preparation for simultaneous, separate or sequential use in therapy.

In another embodiment of the invention, there is provided a product (S)-2-amino-3-(3-(4-((3-fluoro-5-(1H-pyrazol-5-yl)pyridin-2-yl)oxy)phenyl)-1H-pyrazol-1-yl)propan-1-ol, or a pharmaceutically acceptable salt thereof and LTC4S inhibitor as defined above as a combined preparation for simultaneous, separate or sequential use in therapy.

In one embodiment of the invention, there is provided a pharmaceutical composition comprising (S)-2-amino-3-(3-(4-((3-fluoro-5-(1H-pyrazol-5-yl)pyridin-2-yl)oxy)phenyl)-1H-pyrazol-1-yl)propan-1-ol, or a pharmaceutically acceptable salt thereof, a NLRP3 inhibitor as defined above and a pharmaceutically acceptable carrier.

In a further embodiment of the invention, there is provided a pharmaceutical composition comprising (S)-2-amino-3-(3-(4-((3-fluoro-5-(1H-pyrazol-5-yl)pyridin-2-yl)oxy)phenyl)-1H-pyrazol-1-yl)propan-1-ol, or a pharmaceutically acceptable salt thereof, a LTC4S inhibitor and a pharmaceutically acceptable carrier.

Biological Assays and Date

A compound of formula (I) or a pharmaceutically acceptable salt thereof, exhibit valuable pharmacological properties, e.g. properties susceptible to LTA4H, e.g. as indicated in tests as provided in the next sections and are therefore indicated for therapy related to LTA4H.

a) Human LTA4H Enzyme Assay:

Leukotriene M hydrolase (LTA4H) catalyzes the vinylogous hydrolysis of the epoxide, leukotriene A4 (LTA4) into the pro-inflammatory mediator LTB4. LTA4H is also able to catalyze the hydrolysis of di- and tripeptide substrates, as well as the chromogenic 7-amino-4-methylcoumarin (AMC) derivatives of amino acids. The AMC derivative of Arginine (Arg-AMC) can be used as a surrogate substrate for LTA4H and enables the measurement of enzyme activity and compound $IC_{50}$ values by monitoring the fluorescence intensity upon AMC release.

For compound testing, compounds are delivered as 10 mM stock solutions in 90% DMSO (10% water) in matrix tubes. From this, a 1:5 dilution series is prepared with a starting concentration of 10 mM going down to 0.64 µM. For the enzymatic assay 0.5 µL of compound solution is transferred to each well and 24.5 NL of assay buffer (50 mM Tris buffer, pH 7.5, 150 mM NaCl, 10 mM $CaCl_2$)) is added to the well followed by 25 µL of enzyme solution (36 nM human LTA4H in assay buffer). The enzyme compound mixture is incubated at room temperature for 15 min prior to the addition of 50 µL substrate solution. A final substrate concentration of 600 µM, which is around the KM value of Arg-AMC, at a final enzyme concentration of 9 nM is chosen. Upon addition of the substrate, the plate is immediately placed in a fluorescence reader and the fluorescence is measured every 10 minutes for 60 minutes using the filter setting λ excitation=380 nm and A emission=460 nm. AMC at varying concentrations (0.00128-100 µM) in assay buffer is used as a standard curve. Raw data is converted to rate (moles per minute) using the AMC calibration curve calculated from the AMC standards. The data is analyzed in GraphPad Prism (GraphPad software Inc.) using non-linear regression to determine IC$_{50}$ values of LTA4H inhibitors.

Due to the assay setup, the maximally detectable potency of compounds is at around 2-3 nM. Therefore compounds with a potency that may theoretically result in IC$_{50}$ values lower than 2 nM are given as 2 nM (=lower cutoff of assay). The potencies of the tested compounds are shown in table 1 (mean values of at least 3 measurements were provided).

b) Human Whole Blood Assay:

Compounds are tested in a human whole blood assay (hWB) to test their ability to inhibit LTB4 biosynthesis in a human cellular system. To this end, fresh blood is collected in heparinized vacutainers by venipuncture from volunteers. Blood is diluted 1:3 with RPM (Roswell Park Memorial Institute) medium and aliquots of 200 µL are transferred to 96-well round bottom cell culture plates. For compound testing, compounds are delivered as 10 mM stock solutions in 90% DMSO in matrix tubes. From this, a four-fold serial dilution is prepared with a starting concentration of 250 µM going down to 2.45 µM. 4 µL of compound dilution or vehicle is added to 200 µL of blood and incubated for 4 hours at 37° C. in a humidified incubator. Then blood is stimulated with 10 µg/ml calcium ionophore A23187 (Sigma) or equal volume DMSO (control) and incubated for an additional 15 min at 37° C. in a humidified incubator. Incubation is terminated by centrifugation at 300 g for 10 min at 22° C. Plasma supernatant is taken and transferred to a 96 well plate for eicosanoid determination by ELISA (Assay designs) according to the manufacturer's protocol after 1:20 dilution in assay buffer. The data is analyzed in GraphPad Prism (GraphPad software Inc.) using non-linear regression to determine IC$_{50}$ values of LTA4H inhibitors. The potencies of the tested compounds are shown in table 1.

TABLE 1

| | ArgAMC IC$_{50}$ (nM) | hWB IC$_{50}$ (nM) |
|---|---|---|
| | nM | nM |
| Example 01 | 0.6 | 91 |
| Example 02 | 2.1 | 72 |
| Example 03 | 1.5 | 100 |
| Example 04 | 11.8 | 327 |
| Example 05 | 28.3 | 1850 |
| Example 06 | 9.4 | 510 |
| Example 07 | 1.8 | 117 |
| Example 08 | 1.4 | 54 |
| Example 09 | 2.5 | 74 |
| Example 10 | 6.3 | 141 |
| Example 11 | 1.0 | 44 |
| Example 12 | 3.6 | 115 |
| Example 13 | 2.5 | 51 |
| Example 14 | 2.3 | 39 |
| Example 15 | 2.9 | 79 |
| Example 16 | 2.4 | 229 |
| Example 17 | 16.7 | 297 |
| Example 18 | 6.1 | 343 |
| Example 19 | 4.9 | 65 |
| Example 20 | 3.2 | 75 |
| Example 21 | 3.1 | 123 |
| Example 22 | 2.7 | 89 |
| Example 23 | 37.6 | 753 |
| Example 24 | 2.0 | 379 |
| Example 25 | 160.2 | n.t. |
| Example 26 | 2.6 | 89 |
| Example 27 | 3.3 | 214 |
| Example 28 | 6.2 | 504 |
| Example 29 | 1.5 | 162 |
| Example 30 | 1.3 | 69 |
| Example 31 | 4.5 | 179 |
| Example 32 | 2.9 | 45 |
| Example 33 | 2.4 | 290 |

TABLE 1-continued

| | ArgAMC IC$_{50}$ (nM) | hWB IC$_{50}$ (nM) |
|---|---|---|
| Example 34 | 4.0 | 800 |
| Example 35 | 15.8 | n.t. |
| Example 36 | 2.9 | 60 |
| Example 37 | 2.6 | 47 |
| Example 38 | 7.4 | 515 |
| Example 39 | 2.2 | 63 |
| Example 40 | 2.6 | 62 |

Preparation of Compounds

Compounds of the present invention can be prepared as described in the following Examples.

Abbreviations:
Boc: tert-Butyloxycarbonyl
CAN: Ceric ammonium nitrate
DCM: Dichloromethane
DIAD: (E)-Di-tert-butyl diazene-1,2-dicarboxylate
DMAP: 4-(Dimethylamino)-pyridine
DMF: Dimethylformamide
DMSO: Dimethyl sulfoxide
Hal: Halogene
HPLC: High-performance liquid chromatography
MTBE: Methyl tert-butyl ether
NMR: Nuclear magnetic resonance
PdCl$_2$(dtbpf): 1,1'-Bis (di-t-butylphosphino)ferrocene palladium dichloride
rt: Room temperature
SFC: Supercritical fluid chromatography
TBDMSCl: tert-Butyldimethylsilyl chloride
THF: Tetrahydrofuran
TMEDA: Tetramethylethylenediamine
TMS: Trimethylsilyl
UPLC: Ultra-performance liquid chromatography Analytical details NMR Spectroscopy NMR spectra were obtained using Bruker Ultrashield™ 400 (400 MHz) spectrometers. All $^1$H NMR spectra are reported in δ units (ppm) and were recorded in e.g. CDCl$_3$, DMSO-d6 or CD$_3$OD and referenced to the solvent peaks.

Analytical Liquid Chromatography

Waters Acquity UPLC/MS systems (Waters, Milford, MA) equipped with a binary solvent manager, a sample manager, a column manager, a photodiode array detector (PDA) and a Waters ZQ2000 MS detector. UV absorption was monitored at λ=210-450 nM. The MS detector was operated in continuously positive/negative ESI alternating mode with full scan from 120-1200 Da in 0.3 seconds. Mass spectra were acquired and stored in centroid mode. MS based confirmation of molecular weight was based on the formation of the pseudo-molecular ions [M+H]$^+$ in positive mode.

Method A: Column: Acquity UPLC HSS T3, 1.8 µm, 2.1×50 mm at 60'C, Eluent A: H$_2$O+0.05% HCOOH+3.75 mM ammonium acetate, B: ACN+0.04% HCOOH, Gradient: 5-98% B in 1.4 min, 98% B for 0.4 min, 98→5% B in 0.1 min, 5% B for 0.1 min; flow: 1.0 mL/min.

Method B: Column: Acquity UPLC HSS T3, 1.8 µm, 2.1×50 mm at 60° C., Eluent A: H$_2$O+0.05% HCOOH+3.75 mM ammonium acetate, B: ACN+0.04% HCOOH, Gradient: 5-98% B in 9.4 min, 98% B for 0.4 min, 98→5% B in 0.1 min, 5% B for 0.1 min; flow: 1.0 mL/min.

Method C: Column: Acquity CORTECS C18+, 2.7 µm, 2.1×50 mm at 80° C., Eluent A: H$_2$O+0.05% HCOOH+ 4.76% iPrOH+3.75 mM ammonium acetate, B: iPrOH+

0.05% HCOOH, Gradient: initial 1% B, 1-(50% B in 1.4 min, 50-.98% B in 0.3 min; 0.1 min 98% B; flow: 1.0 mL/min.

Preparative Methods:

Flash chromatography: Teledyne ISCO, CombiFlash Rf. Column: pre-packed RediSep Rf cartridges. Samples were typically adsorbed on ISOLUTE™.

SFC: Waters Preparative SFC-100-MS; Detection: Waters 2998 Photodiode Array Detector and Waters MS Single Quadrupole Detection; Modifier. Methanol; ABPR: 120bar, Column temperature: 40° C.; Flow rate: 100 g/min.

Prep HPLC: Waters Autopurification-MS System; Detection: Waters 2998 Photodiode Array Detector and Waters MS Single Quadrupole Detection; Column temperature: RT; Eluent A: water, Eluent B: acetonitrile, both containing 0.1% TFA or 0.1% NH$_4$OH.

All reagents, starting materials and intermediates utilized in these examples were available from commercial sources or were readily prepared by methods known to those skilled in the art.

Syntheses of intermediates: Intermediate A

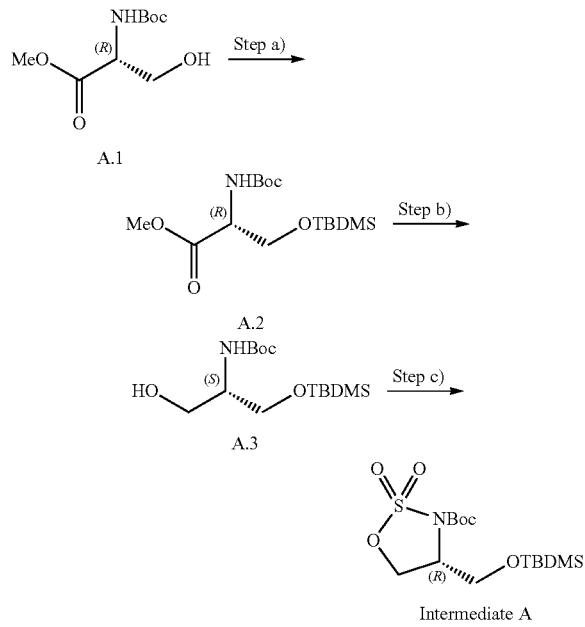

Step a) Methyl N-(tert-butoxycarbonyl)-O-(tert-butyldimethylsilyl)-D-serinate (A.2). To a solution of A.1 (5.0 g, 22.8 mmol) and imidazole (2.33 g, 34.2 mmol) in CH$_2$Cl$_2$ (75 mL) was added a solution of TBDMSCl (4.70 g, 29.6 mmol) in CH$_2$Cl$_2$ (25 mL) within 20 min with ice cooling under argon. The resulting colorless suspension was stirred for additional 40 min. with ice cooling. The still cold reaction mixture was diluted with water and extracted with MTBE. The combined organic phases were washed with brine and dried over Na$_2$SO$_4$. Evaporation gave compound A.2 as yellowish oil (8.44 g, quant.), which was used without further purification in the next step. TLC: R$_f$=0.73 (cyclohexane/ethyl acetate 7:3, KMnO$_4$-staining); $^1$H NMR (CDCl$_3$): δ=5.31 (1H, br d), 4.33 (1H, ddd), 4.02 (1H, dd) 3.80 (1H, dd), 3.72 (3H, s), 1.44 (9H, s), 0.84 (9H, s), 0.01 (3H, s), 0.00 (3H, s).

Step b) tert-Butyl (S)-(1-((tert-butyldimethylsilyl)oxy)-3-hydroxypropan-2-yl)carbamate (A.3). To a solution of A.2 (7.16 g, 21.5 mmol) in THF (70 mL) was added LiBH$_4$ (0.94 g, 42.9 mmol) with Ice cooling under argon. During the addition, a weak effervescence could be observed. Stirring was continued over night at 25'C. Then, the reaction mixture was poured onto half saturated NH$_4$Cl solution (250 mL) and extracted with MTBE. The combined organic layers were washed brine and dried over Na$_2$SO$_4$. Evaporation to dryness gave compound A.3 as a colorless oil (6.30 g, 96%), which was used without further purification in the next step. TLC: R$_f$=0.17 (cyclohexane/ethyl acetate 8:2, KMnO$_4$-staining); $^1$H NMR (CDCl$_3$): δ=5.06 (1H, br s), 3.70-3.89 (3H, m), 3.49-3.65 (2H, m)1.38 (9H, s), 0.82 (9H, s), 0.02 (3H, s), 0.00 (3H, s).

Step c) tert-Butyl (R)-4-(((tert-butyldimethylsilyl)oxy) methyl)-1,2,3-oxathiazolidine-3-carboxylate 2,2-dioxide (A). Under argon imidazole (8.42 g, 124 mmol) was suspended in CH$_2$Cl$_{1-2}$ (100 mL) and cooled to 0° C. Within 10 min a solution of SOCl$_2$ (2.70 mL, 37.1 mmol) in CH$_2$Cl$_2$ (25 mL) was added maintaining the internal temperature below 5° C. The thick colorless suspension formed was stirred for 1 hour at 25° C. Then, the internal temperature was lowered to –10° C. and a solution of A.3 (6.30 g, 20.6 mmol) was added dropwise in 10 min. The cold bath was removed and stirring was continued for 1.5 h. Then, water (150 mL) was added and the mixture was extracted with CH$_2$Cl$_2$. The combined organic extracts were washed with 10% aqueous citric acid and brine and dried over Na$_2$SO$_4$. The solvent was removed and the yellowish oil (6.82 g, 94%, diastereomeric sulfoxide-mixture) was taken up in acetonitrile (150 mL). Then, RuCl$_3$·H$_2$O (93 mg, 0.4 mmol, 2 mol %) was added, followed by dropwise addition of a solution of NaIO$_4$ (6.62 g, 30.1 mmol) in water (75 mL) maintaining the internal temperature below 5° C. with Ice cooling. After stirring at 0° C. for additional 45 min ethyl acetate (150 ml) and Hyflow (25 g) were added to the yellow-brown suspension. All solids were filtered off and the aqueous layer of the filtrate was extracted with ethyl acetate/MTBE 3:1 (100 mL). The combined organic layers were washed with brine, 5% aqueous sodium thiosulfate and again with brine. Drying over Na$_2$SO$_4$ and evaporation of the solvent gave a solid contaminated yellowish oil. The solids could be removed by trituration with cyclohexane. Flash chromatography on silica (gradient: cyclohexane/ethyl acetate) gave compound A as a colorless oil, which solidified upon standing (3.88 g, 51%). TLC: R$_f$=0.41 (cyclohexane/ethyl acetate 85:15, KMnO$_4$-staining); [α]$_D^{23}$: −25° (c=1, CH$_2$Cl$_2$); $^1$H NMR (CDCl$_3$): δ=4.47-4.57 (2H, m), 4.18 (1H, m), 3.78 (1H, dd), 3.69 (1H, t), 1.47 (9H, s), 0.81 (9H, s), 0.01 (3H, s), 0.00 (3H, s).

Intermediate B

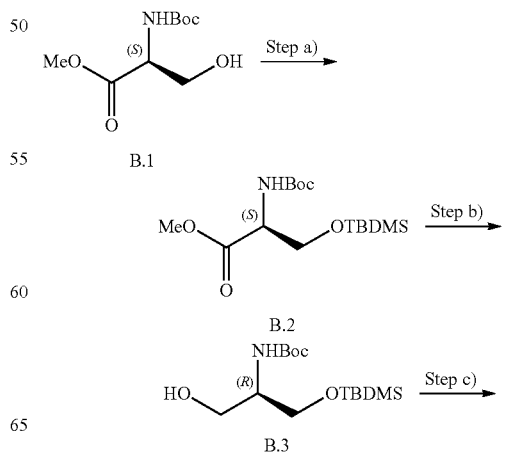

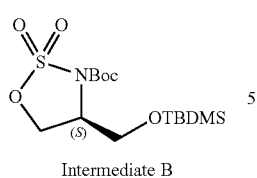

Intermediate B

Intermediate B was prepared by similar procedures used for the synthesis of Intermediate A replacing A.1 by its S-enantiomer B.1. $[\alpha]_D^{23}$: +20.2' (c=1, $CH_2Cl_2$); $^1H$ NMR ($CDCl_3$): δ=4.48 4.58 (2H, m), 4.18 (1H, m), 3.78 (1H, dd), 3.69 (1H, t), 1.47 (9H, s), 0.81 (9H, s), 0.00 (6H, s).

SYNTHESES OF EXAMPLES

Example 1 (S)-2-amino-3-(3-(3-((S)-2,3-dihydrobenzo[b][1,4]dioxin-2-yl)phenyl)-1,2,4-oxadiazol-5-yl)propan-1-ol

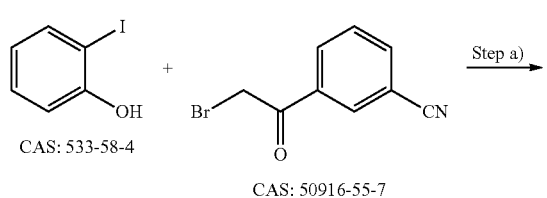

CAS: 533-58-4

CAS: 50916-55-7

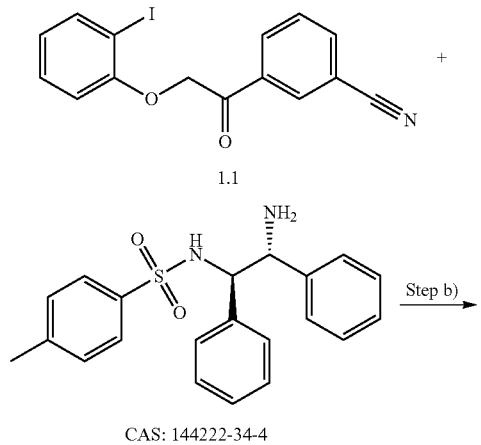

CAS: 144222-34-4

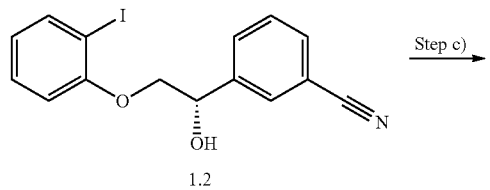

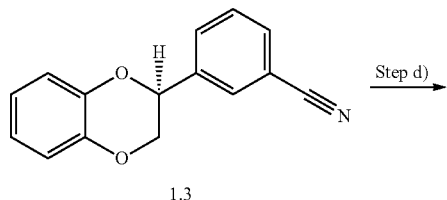

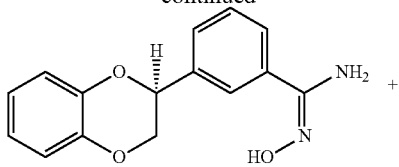

1.4

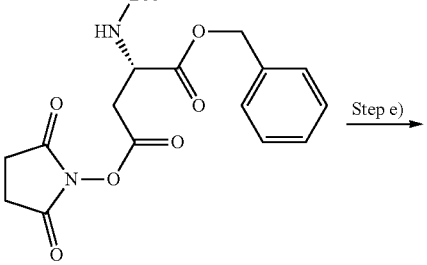

CAS: 140171-25-1

Example 1

Step a) 3-(2-(2-iodophenoxy)acetyl)benzonitrile (1.1). According to WO2013/134226: To a 250 mL one-necked flask equipped with a magnetic stir bar was added 2-iodophenol (10.51 g, 46.8 mmol), acetonitril (16.5 ml) and potassium carbonate (7.12 g, 51.5 mmol). The pinky suspension was stirred for 1.5 hr at rt. 3-(2-bromoacetyl)benzonitrile (12.15 g, 51.5 mmol) dissolved in acetonitrile (33 ml) was added dropwise over 10 min. The reaction mixture was stirred at rt over night. Additional potassium carbonate (380 mg) and 3-(2-bromoacetyl)benzonitrile (600 mg) was added. After 2 hr the reaction mixture was cooled to 15° C. and quenched with 2M hydrochloric acid (30 ml). Water (100 ml) was added and the reaction mixture was extracted with ethyl acetate (200 ml). The organic layer was washed with water (2×100 ml) and brine (100 ml), dried over sodium sulfate, filtered and concentrated in vacuo to give (1.1) as a beige raisin (19.24 g, quantitative). UPLC retention time 1.15 min (Method A). $^1$H NMR (DMSO-d6): δ=5.71 (s, 2H), 6.77 (t, J=7.52 Hz, 1H), 7.00 (d, J=8.19 Hz, 1H), 7.31 (t, J=7.64 Hz, 1H), 7.76-7.86 (m, 2H), 8.17 (d, J=7.70 Hz, 1H), 8.27 (d, J=7.95 Hz, 1H), 8.52 (s, 1H). MS/ESI+364.3 [M+H]$^+$.381.1 [M+NH.]$^+$.

Step b) (S)-3-(1-hydroxy-2-(2-iodophenoxy)ethyl)benzonitrile (1.2). According to WO2013/134226 p 79 Å-8: To a 500 mL 3-necked flask equipped with a magnetic stir bar and a thermometer was added 3-(2-(2-iodophenoxy)acetyl)benzonitrile (1.1) (19.2 g, 46.5 mmol) followed by acetonitril (86 ml). Argon was bubbled through the slightly cloudy mixture for 5 min. N-((1R,2R)-2-amino-1,2-diphenylethyl)-4-methylbenzenesulfonamide (0.239 g, 0.651 mmol), Cp*RhCl$_2$ dimer (CAS: 12354-85-7) (0.173 g, 0.279 mmol) and triethylamine (15.48 ml, 112 mmol) were added at rt. and stirred for 1.5 hr. The reaction mixture was cooled to 0° C. and formic acid (6.25 ml, 163 mmol) was added dropwise over 10 min below 15° C. After 30 min at 10° C. the reaction mixture was cooled to 0° C. and quenched with water (200 ml) under strong stirring. The mixture was extracted twice with ethyl acetate and the organic layers were washed with water and brine, dried over sodium sulfate, filtered and concentrated in vacuo to give (1.2) (19.76 g crude). Chromatography on silica (gradient: heptane/ethyl acetate) afforded (1.2) as a colorless raisin (13.86 g, 77%). UPLC retention time 1.08 min (Method A). $^1$H NMR (DMSO-d6): 15=4.09 (dd, J=9.78, 5.50 Hz, 1H), 4.18 (dd, J=9.66, 5.75 Hz, 1H), 5.03 (t, J=5.20 Hz, 1H), 5.89 (s, 1H) 6.73 (t, J=7.46 Hz, 1H), 7.00 (d, J=8.31 Hz, 1H), 7.32 (t, J=7.76 Hz, 1H), 7.52-7.62 (m, 1H), 7.70-7.78 (m, 2H), 7.87 (d, J=7.70 Hz, 1H), 7.96 (s, 1H). MS/ESI+ 383.1 [M+NH$_4^+$]$^+$.

Step c) (S)-3-(2,3-dihydrobenzo[b][1,4]dioxin-2-yl)benzonitrile (1.3). To a 500 mL 2-necked flask equipped with a magnetic stir bar and a reflux condensor was added (S)-3-(1-hydroxy-2-(2-lodophenoxy)ethyl)benzonitrile (1.2) (8.76 g, 21.59 mmol) followed by DMF (72 ml). Cesium carbonate (14.07 g, 43.2 mmol), Cu(I)Iodide (0.411 g, 2.159 mmol) and N,N-dimethylglycine hydrochloride were added and the mixture was stirred at 135° C. for 4 hr under argon. The cold reaction mixture was diluted with water and extracted with ethyl acetate. The organic phase was washed twice with sat aq. ammonium chloride solution. The aqueous phase was backextracted with ethyl acetate and the combined organic layers were washed with water and brine, dried over sodium sulfate, filtered and concentrated in vacuo to give (1.3) (6.28 g crude). Chromatography on silica (gradient heptane/ethyl acetate) afforded (1.3) as a milky raisin (3.55 g, 66%). UPLC retention time 1.13 min (Method A). $^1$H NMR (DMSO-d6): δ=4.15 (dd, J=11.49, 8.07 Hz, 1H), 4.49 (dd, J=11.49, 2.20 Hz, 1H), 5.31-5.40 (m, 1H), 6.85-6.97 (m, 3H), 6.97-7.05 (m, 1H), 7.62-7.71 (m, 1H), 7.88 (d. J=7.70 Hz, 1H), 7.85 (d, J=8.07 Hz, 1H), 7.97 (s, 1H). MS/ESI+255.2 [M+NH$_4^+$]$^+$, MS/ESI-236.3 [M−H]$^-$.

Step d) (S,E)-3-(2,3-dihydrobenzo[b][1,4]dioxin-2-yl)-N'-hydroxybenzimidamide (1.4). To a 100 mL 2-necked flask equipped with a magnetic stir bar and a reflux condensor was added (S)-3-(2,3-dihydrobenzo[b][1,4]dioxin-2-yl)benzonitrile (1.3) (1.2 g, 5.06 mmol) and ethanol (17 ml). 50% hydroxylamine solution in water (1.19 ml, 20.23 mmol) was added dropwise and the reaction mixture was refluxed for 1 hr to give a clear solution. The mixture was concentrated in vacuo to yield crude (1.4) (1.39 g, 99%) which was used without further purification in the next step. A small probe (60 mg) was triturated in dichloromethane/ pentane to give 38 mg of a white powder. UPLC retention time 0.79 min (Method A). $^1$H NMR (DMSO-d6): δ=4.11 (dd, J=11.43, 8.38 Hz, 1H), 4.45 (dd, J=11.49, 2.45 Hz, 1H), 5.27 (dd, J=8.31, 2.20 Hz, 1H), 5.84 (s, 2H), 6.85-7.02 (m, 3H), 7.40-7.52 (m, 2H), 7.69 (d, J=7.70 Hz, 1H), 7.80 (s, 1H), 9.66 (s, 1H). MS/ESI+271.2 [M+H]$^+$.

Step e) benzyl (S)-2-((tert-butoxycarbonyl)amino)-3-(3-(3-((S)-2,3-dihydrobenzo[b][1,4]-dioxin-2-yl)phenyl)-1,2,4-oxadiazol-5-yl)propanoate (1.5). A 100 mL 2-necked flask equipped with a magnetic stir bar and a reflux condensor was charged with (S,E)-3-(2,3-dihydrobenzo[b][1,4]dioxin-2-yl)-N'-hydroxybenzimidamide (1.4) (505 mg, 1.87 mmol) and 2-Me-THF (18.7 ml) followed by Boc-Asp(OSu)-OBzl [CAS 140171-25-1] (1179 mg, 2.81 mmol from Bachem). The reaction mixture was stirred at 87° C. for 4 d. The solvent was evaporated on a rotavap yielding 2.05 g crude product. Chromatography on silica (gradient: cyclohexane/ ethyl acetate) afforded (1.5) (1122 mg, 100%). UPLC retention time 1.38 min (Method A). $^1$H NMR (DMSO-d6): δ=ppm 1.27-1.37 (m, 9H), 3.43 (dd, J=15.71, 8.74 Hz, 1H), 3.55 (dd, J=15.65, 5.99 Hz, 1H), 4.12 (dd, J=11.49, 8.31 Hz, 1H), 4.50 (dd, J=11.55, 2.38 Hz, 1H), 4.67 (d, J=6.11 Hz, 1H), 5.16 (s, 2H), 5.40 (dd, J=8.19, 2.08 Hz, 1H), 6.87-6.97 (m, 3H), 6.99-7.04 (m, 1H), 7.27-7.38 (m, 5H), 7.57-7.67 (m, 2H), 7.69-7.74 (m, 1H), 8.00 (d, J=7.70 Hz, 1H), 8.11 (s, 1H). MS/ESI+558.3 [M+H]$^+$.

Step f) tert-butyl ((S)-1-(3-(3-((S)-2,3-dihydrobenzo[b] [1,4]dioxin-2-yl)phenyl)-1,2,4-oxadiazol-5-yl)-3-hydroxypropan-2-yl)carbamate (1.6). A 100 mL one-necked flask equipped with a magnetic stir bar was charged with benzyl (S)-2-((tert-butoxycarbonyl)amino)-3-(3-(3-((S)-2,3-dihydrobenzo[b][1,4]-dioxin-2-yl)phenyl)-1,2,4-oxadiazol-5-yl) propanoate (1.5) (723 mg, 1.206 mmol) and THF (16 ml). At 0° C. lithium borohydride (105 mg, 4.82 mmol) was added and the cooling bath was removed after 10 min. The reaction mixture was quenched adding 3 spoons of (solute HM-N (Biotage 9800-1000) after 30 min. The solvent was evaporated on a rotavap and the remaining product adsorbed onto (solute was purified using a Redisep RP-C18 (86 g) column applying a water/acetonitrile gradient yielding tert-butyl ((S)-1-(3-(3-((S)-2,3-dihydrobenzo[b][1,4]dioxin-2-yl)phenyl)-1,2,4-oxadiazol-5-yl)-3-hydroxypropan-2-yl)carbamate (1.6) (303 mg, 54.3%). UPLC retention time 1.17 min (Method A). $^1$H NMR (DMSO-d6): δ =ppm 1.29 (s, 9H), 2.99 (dd, J=14.79, 9.17 Hz, 1H), 3.27 (dd, J=14.79, 4.52 Hz, 1H), 3.33-3.53 (m, 2H), 3.92 (br. s., 1H), 4.11 (dd, J=11.49, 8.31 Hz, 1H), 4.50 (dd, J=11.49, 2.45 Hz, 1H), 4.92 (t, J=5.62 Hz, 1H), 5.40 (dd, J=8.19, 2.08 Hz, 1H), 6.81-7.06 (m, 5H), 7.63 (t, J=7.64 Hz, 1H), 7.71 (d, J=7.83 Hz, 1H), 8.01 (d, J=7.70 Hz, 1H), 8.12 (s, 1H). MS/ESI+454.3 [M+H]$^+$.

Step g) (S)-2-amino-3-(3-(3-((S)-2,3-dihydrobenzo[b][1, 4]dioxin-2-yl)phenyl)-1,2,4-oxadiazol-5-yl)propan-1-ol (Example 1) A 100 mL one-necked flask equipped with a magnetic stir bar was charged with tert-butyl ((S)-1-(3-(3-((S)-2,3-dihydrobenzo[b][1,4]dioxin-2-yl)phenyl)-1,2,4-oxadiazol-5-yl)-3-hydroxypropan-2-yl)carbamate (1.6) (275 mg, 0.606 mmol) and dichloromethane (6 ml). TFA (0.934 ml, 12.13 mmol) was added and the mixture was stirred at rt for 2 hr. The reaction mixture was concentrated in vacuo and the remaining oil dissolved in ethyl acetate, washed thrice with sat. aq. sodium bicarbonate solution, little water and brine. The crude product (245 mg) was purified using a Redisep RP-C$_{18}$ (43 g) column applying a water/acetonitrile gradient yielding 70 mg. The sticky solid was lyophilised and finely triturated with isopropyl ether to give (S)-2-amino-3-(3-(3-((S)-2,3-dihydrobenzo[b][1,4]dioxin-2-yl)

phenyl)-1,2,4-oxadiazol-5-yl)propan-1-ol (Example 1) as a white powder (56 mg, 26%). UPLC retention time 0.77 min (Method A). ¹H NMR (DMSO-d6): δ=ppm 2.09 (br. s., 3H), 3.06-3.28 (m, 2H), 3.57-3.68 (m, 2H), 3.75-3.82 (m, 1H), 4.07 (dd, J=11.43, 8.86 Hz, 1H), 4.42 (dd, J=11.43, 2.38 Hz, 1H), 5.22 (dd, J=8.86, 2.14 Hz, 1H), 6.89-7.06 (m, 4H), 7.52-7.65 (m, 2H), 8.10 (d, J=7.46 Hz, 1H), 8.16 (s, 1H). MS/ESI+354.2 [M+H]⁺.

Example 2 (S)-2-amino-3-(3-(3-((5-chloropyridin-2-yloxy)phenyl)-1,2,4-oxadiazol-5-yl)propan-1-ol

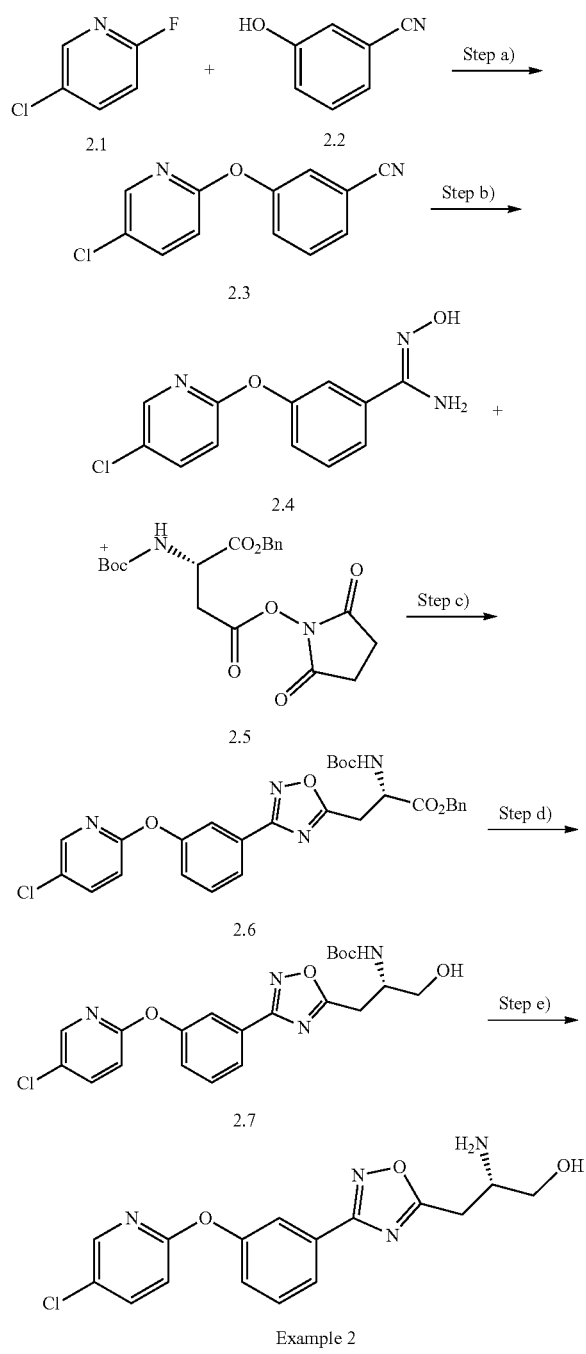

Step a) 3-((5-chloropyridin-2-yl)oxy)benzonitrile (2.3). To a 100 mL one-necked round bottom flask equipped with a magnetic stir bar and a reflux condenser was added 3-cyanophenol (Sigma-Aldrich) (2.2) (1.036 g, 8.70 mmol), 5-chloro-2-fluoropyridine (Apollo Scientific Ltd.) (2.1) (1.04 g, 7.91 mmol), $K_2CO_3$ (3.28 g, 23.72 mmol) and DMF (40.0 ml). The suspension was stirred for 113 hours at 100° C. The reaction mixture was cooled to rt and water/EtOAc were added. The aqueous phase was extracted twice with EtOAc. The organic layers were washed with brine, combined and dried over $Na_2SO_4$. Concentrating in vacuo afforded a brown oil. Purification by column chromatography (ISCO CombiFlash Rf, absorbed on silica gel, EtOAc in cyclohexane 0-10%) afforded 3-((5-chloropyridin-2-yl)oxy) benzonitrile (2.3) as white solid (1.55 g, 85%). UPLC retention time 1.07 min (Method A). ¹H NMR (400 MHz, CDCl₃) δ=ppm 8.11 (d, J=2.5 Hz, 1H), 7.71 (dd, J=8.7, 2.6 Hz, 1H), 7.54-7.47 (m, 2H), 7.45 (s, 1H), 7.42-7.36 (m, 1H), 6.96 (d, J=8.7 Hz, 1H). MS/ESI+231.2 [M+H]⁺.

Step b) (Z)-3-((5-chloropyridin-2-yl)oxy)-N'-hydroxybenzimidamide (2.4). To a 50 mL one-necked pear shaped flask equipped with a magnetic stir bar was added 3-((5-chloropyridin-2-yl)oxy)benzonitrile (2.3) (1.00 g, 4.34 mmol), hydroxylamine hydrochloride (1.506 g, 21.68 mmol), NaHCO₃(1.821 g, 21.68 mmol) and ethanol (20.0 ml)/Water (10.0 ml). The white suspension was heated to 85° C. and stirred for 65 minutes. The reaction mixture was cooled to rt. EtOH was removed in vacuo. To the remaining white suspension was added water and EtOAc. The aqueous phase was extracted twice with EtOAc. The organic layers were washed with brine, combined and dried over $Na_2SO_4$. Analysis by LC-MS and 1H NMR revealed high purity of the workup product (Z)-3-((5-chloropyridin-2-yl)oxy)-N'-hydroxybenzimidamide (2.4) (1.1 g, 95%)

UPLC retention time 0.71 min (Method A). ¹H NMR (400 MHz, DMSO-d6) δ=ppm 9.68 (s, 1H), 8.21 (d, J=2.6 Hz, 1H), 7.97 (dd, J=8.8, 2.7 Hz, 1H), 7.55 (d, J=8.0 Hz, 1H), 7.44-7.39 (m, 2H), 7.15 (dd, J=7.8, 2.0 Hz, 1H), 7.12 (d, J=8.8 Hz, 1H), 5.82 (s, 2H). MS/ESI+264.3 [M+H]⁺.

Step c) benzyl (S)-2-((tert-butoxycarbonyl)amino)-3-(3-(3-((5-chloropyridin-2-yl)oxy) phenyl)-1,2,4-oxadiazol-5-yl)propanoate (2.6). To a 20 mL microwave vial equipped with a magnetic stir bar was added product (Z)-3-((5-chloropyridin-2-yl)oxy)-N'-hydroxybenzimid-amide (2.4) (450 mg, 1.707 mmol), Boc-Asp(OSu)-OBzl [CAS 140171-25-1] (2.5) (789 mg, 1.877 mmol) and THF (10.0 ml). The colorless solution was heated to 120° C. and stirred for 19 hours. A yellow solution was obtained. THF was removed in vacuo. Purification by column chromatography (ISCO CombiFlash Rf, absorbed on silica, EtOAc in cyclohexane 0-18%) afforded benzyl (S)-2-((tert-butoxycarbonyl) amino)-3-(3-(3-((5-chloropyridin-2-yl)oxy) phenyl)-1,2,4-oxadiazol-5-yl)propanoate (2.6) (871 mg, 93%). UPLC retention time 1.41 min (Method A). ¹H NMR (400 MHz, CDCl₃) δ=ppm 8.11 (d, J=2.5 Hz, 1H), 7.85 (d, J=7.8 Hz, 1H), 7.77 (S, 1H), 7.66 (dd, J=8.7, 2.6 Hz, 1H), 7.49 (t, J=8.0 Hz, 1H), 7.28-7.24 (m, 6H), 6.93 (d, J=8.7 Hz, 1H), 5.54 (d, J=7.3 Hz, 1H), 5.23-5.11 (m, 2H), 4.90-4.83 (m, 1H), 3.49 (qd, J=16.1, 4.9 Hz, 2H), 1.42 (s, 9H). MS/ESI+551.4 [M+H]⁺.

Step d) tert-butyl (S)-(1-(3-(3-((5-chloropyridin-2-yl) oxy)phenyl)-1,2,4-oxadiazol-5-yl)-3-hydroxypropan-2-yl) carbamate (2.7). To a 25 mL two-necked round bottom flask equipped with a magnetic stir bar, rubber septum and gas inlet was added benzyl (S)-2-((tert-butoxycarbo-nyl) amino)-3-(3-(3-((5-chloropyridin-2-yl)oxy) phenyl)-1,2,4-oxadiazol-5-yl)propanoate (2.6) (506 mg, 0.918 mmol). The flask was evacuated and backfilled with Ar five times. Anhydrous THF (Volume: 10.0 mL) was added and the colorless solution was cooled to 0° C. LiBH4 (100 mg, 4.59 mmol) was added in one portion and the reaction mixture was stirred for 70 minutes.

The reaction was quenched with MeOH (3 ml). Sat. aq. NH₄Cl solution and EtOAc were added. The aqueous phase was extracted twice with EtOAc and the organic layers were washed wit brine, combined and dried over Na₂SO₄. Purification by column chromatography (ISCO CombiFlash Rf, absorbed on silica gel, EtOAc in cyclohexane 20-50%) afforded tert-butyl (S)-(1-(3-(3-((5-chloropyridin-2-yl)oxy) phenyl)-1,2,4-oxadiazol-5-yl)-3-hydroxypropan-2-yl)carbamate (2.7) (317 mg, 77%). UPLC retention time 1.13 min (Method A). ¹H NMR (400 MHz, CDCl₃) δ=ppm 8.08 (d, J=2.6 Hz, 1H), 7.88 (d, J=7.8 Hz, 1H), 7.81-7.77 (m, 1H), 7.63 (dd, J=8.7, 2.7 Hz, 1H), 7.47 (t, J=8.0 Hz, 1H), 7.28-7.21 (m, 1H), 6.90 (d, J=8.7 Hz, 1H), 5.37 (d, J=8.5 Hz, 1H), 4.14 (s, 1H), 3.78-3.64 (m, 2H), 3.35 (s, 1H), 3.22 (d, J=5.8 Hz, 2H), 1.37 (5, 9H). MS/ESI+447.3 [M+H]⁺.

Step e) (S)-2-amino-3-(3-(3-((5-chloropyridin-2-yl)oxy) phenyl)-1,2,4-oxadiazol-5-yl)propan-1-ol (Example 2). To a 25 mL one-necked round bottom flask equipped with a magnetic stir bar was added tert-butyl (S)-(1-(3-(3-((5-chloropyridin-2-yl)oxy)phenyl)-1,2,4-oxadiazol-5-yl)-3-hydroxypropan-2-yl)carbamate (2.7) (316 mg, 0.707 mmol), dioxane (4.0 ml) and aq. HCl (4.0 ml, 8.00 mmol). The cloudy solution was stirred for 5 days at rt. The solvent was removed In vacuo. Approx. 0.2M aq. NaOH solution (10 ml) was added and a white solid precipitated. EtOAc was added. The aqueous phase was extracted twice with EtOAc. The organic layers were washed with brine, combined and dried over Na₂SO₄. Purification by column chromatography (ISCO CombiFlash Rf, absorbed on silica gel, MeOH in CH₂Cl₂ 0-8.5%) afforded light, white crystals (S)-2-amino-3-(3-(3 ((5-chloropyridin-2-yl)oxy)phenyl)-1,2,4-oxadiazol-5-yl)propan-1-ol (Example 2) (202 mg, 82%). UPLC retention time 0.71 min (Method A). ¹H NMR (400 MHz, CDCl₃) δ=ppm 8.11 (d, J=2.6 Hz, 1H), 7.92 (d, J=7.8 Hz, 1H), 7.85-7.80 (m, 1H), 7.66 (dd, J=8.7, 2.7 Hz, 1H), 7.50 (t, J=8.0 Hz, 1H), 7.30-7.23 (m, 1H), 6.92 (d, J=8.7 Hz, 1H), 3.67 (dd, J=10.6, 4.4 Hz, 1H), 3.53 (dd, J=10.6, 6.2 Hz, 1H), 3.49-3.41 (m, 1H), 3.11 (dd, J=15.6, 4.7 Hz, 1H), 2.97 (dd, J=15.6, 8.2 Hz, 1H), 2.07 (s br, 3H). MS/ESI+347.3 [M+H]⁺.

Example 3 (S)-2-amino-3-(3-(3-((5-(difluoromethoxy)pyridin-2-yl)oxy)phenyl)-1,2,4-oxadiazol-5-yl)propan-1-ol

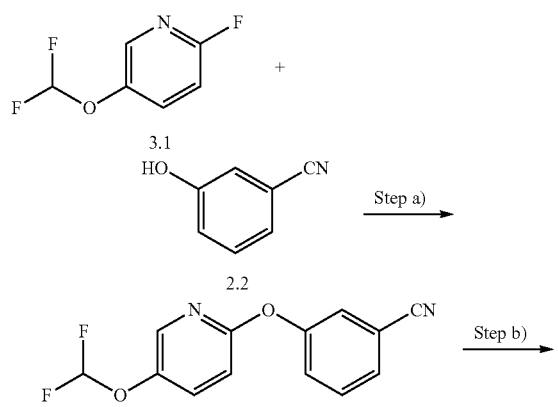

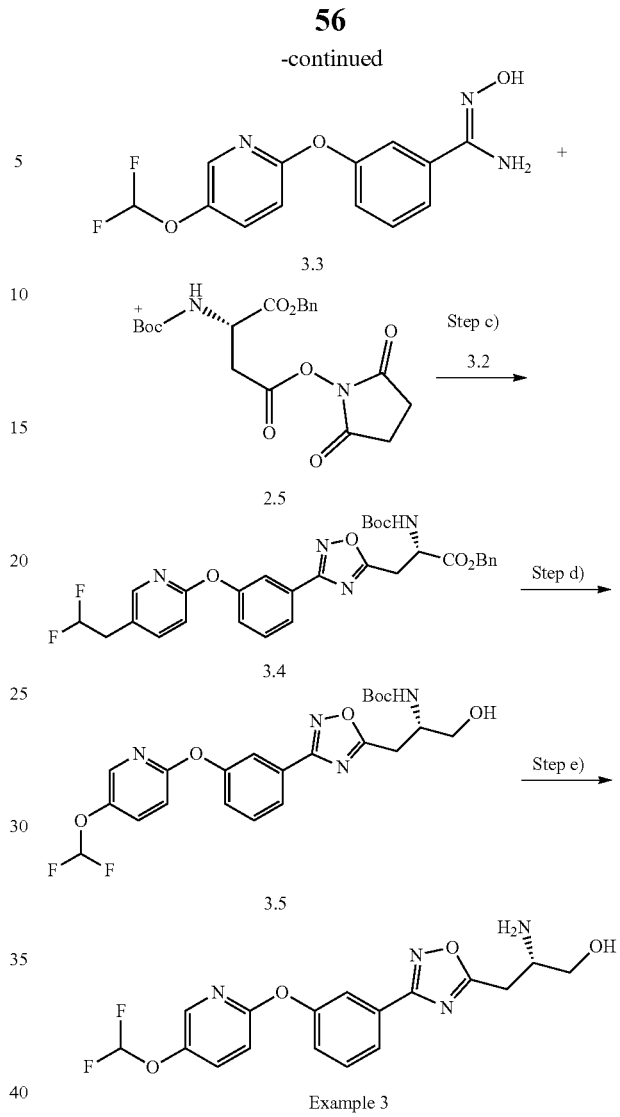

Example 3

Step a) 3-((5-(difluoromethoxy)pyridin-2-yl)oxy)benzonitrile (3.2). To a 100 mL one-necked pear shaped flask equipped with a magnetic stir bar and a reflux condenser was added 5-(difluoromethoxy)-2-fluoropyridine (3.1) (0.938 g, 5.75 mmol), 3-cyanophenol (Sigma-Aldrich) (2.2) (0.754 g, 6.33 mmol), potassium carbonate (2.385 g, 17.25 mmol) and DMF (30.0 ml). The suspension was then stirred for 7 days at 90'C. The reaction mixture was cooled to rt. Water/EtOAc were added and the aqueous phase was extracted twice with EtOAc. The organic layers were washed with brine, combined and dried over Na₂SO₄. Purification by column chromatography (ISCO CombiFlash Rf, absorbed on silica gel, EtOAc in cyclohexane 0-16%) afforded 3-((5-(difluoromethoxy)pyridin-2-yl)oxy)benzonitrile (3.2) as a colorless oil (1.02 g, 67.6%). UPLC retention time 1.04 min (Method A). ¹H NMR (400 MHz, CDCl₃) δ=ppm 8.03 (d, J=2.7 Hz, 1H), 7.58 (dd, J=8.8, 2.9 Hz, 1H), 7.52-7.48 (m, 2H), 7.47-7.44 (m, 1H), 7.43-7.37 (m, 1H), 7.01 (d, J=8.9 Hz, 1H), 6.50 (t, J=72.6 Hz, 1H). MS/ESI+263.2 [M+H]⁺.

Step b) (Z)-3-((5-(difluoromethoxy)pyridin-2-yl)oxy)-N'-hydroxybenzimidamide (3.3). To a 50 mL one-necked round bottom flask equipped with a magnetic stir bar and a condenser (air) was added 3-((5-(difluoromethoxy)pyridin-2-yl)oxy)benzonitrile (3.2) (545 mg, 2.078 mmol), hydroxylamine hydrochloride (722 mg, 10.39 mmol), NaHCO$_3$ (873 mg, 10.39 mmol) and ethanol (6.0 ml)/Water (3.0 ml). The suspension was stirred for 1 hour at 85° C. EtOH was removed in vacuo. EtOAc and water were added. The aqeuous phase was extracted twice with EtOAc. The organic layers were washed with brine, combined and dried over Na$_2$SO$_4$. Purification by column chromatography (ISCO CombiFlash Rf, absorbed on silica gel, EtOAc in cyclohexane 20-45%) afforded (Z)-3-((5-(difluoromethoxy)pyridin-2-yl)oxy)-N'-hydroxybenz-imidamide (3.3) (564 mg, 92%). UPLC retention time 0.69 min (Method A). $^1$H NMR (400 MHz, CDCl$_3$) δ=ppm 8.22 (s br, 1H), 8.04 (d, J=2.8 Hz, 1H), 7.52 (dd, J=8.9, 2.9 Hz, 1H), 7.48-7.45 (m, 1H), 7.45-7.39 (m, 2H), 7.19 (ddd, J=7.7, 2.3, 1.4 Hz, 1H), 6.94 (d, J=8.9 Hz, 1H), 6.47 (t, J=72.9 Hz, 1H), 4.87 (s, 2H). MS/ESI+296.5 [M+H]$^+$.

Step c) benzyl (S)-2-((tert-butoxycarbonyl)amino)-3-(3-(3-((5-(difluoromethoxy)pyridin-2-yl)oxy)phenyl)-1,2,4-oxadiazol-5-yl)propanoate (3.4). To a 20 mL microwave vial equipped with a magnetic stir bar was added (Z)-3-((5-(difluoromethoxy)pyridin-2-yl)oxy)-N'-hydroxybenz-imidamide (3.3) (546 mg, 1.849 mmol) in THF (10 ml) and Boc-Asp(OSu)-OBzl [CAS 140171-25-1] (2.5) (855 mg, 2.034 mmol). The vial was sealed and the colorless solution was stirred for 66 hours at 100'C. The solvent was removed in vacuo. Purification by column chromatography (ISCO CombiFlash Rf, absorbed on silica gel, EtOAc in cyclohexane 0-20%) afforded a colorless sticky oil benzyl (S)-2-((tert-butoxycarbonyl)amino)-3-(3-(3-((5-(difluoromethoxy)pyridin-2-yl)oxy)phenyl)-1,2,4-oxadiazol-5-yl) propanoate (3.4) (945 mg, 88%). UPLC retention time 1.35 min (Method A). $^1$H NMR (400 MHz, CDCl$_3$) δ=ppm 8.03 (d, J=2.7 Hz, 1H), 7.85 (d, J=7.8 Hz, 1H), 7.78 (d, J=1.8 Hz, 1H), 7.53 (dd, J=8.9, 2.9 Hz, 1H), 7.49 (t, J=8.0 Hz, 1H), 7.31-7.22 (m, 6H), 6.98 (d, J=8.9 Hz, 1H), 6.47 (t, J=72.9 Hz, 1H), 5.54 (d, J=7.5 Hz, 1H), 5.23-5.10 (m, 2H), 4.86 (d, J=6.9 Hz, 1H), 3.49 (qd, J=16.1, 4.9 Hz, 2H), 1.41 (s, 9H). MS/ESI+583.5 [M+H]$^+$.

Step d) tert-butyl (S)-(1-(3-(3-((5-(difluoromethoxy)pyridin-2-yl)oxy)phenyl)-1,2,4-oxadiazol-5-yl)-3-hydroxypropan-2-yl)carbamate (3.5). To a 25 mL two-necked round bottom flask equipped with a magnetic stir bar, gas inlet and rubber septum was added benzyl (S)-2-((tert-butoxycarbonyl)amino)-3-(3-(3-((5-(difluoromethoxy)pyridin-2-yl)oxy) phenyl)-1,2,4-oxadiazol-5-yl)propanoate (3.4) (514 mg, 0.882 mmol). The flask was evacuated and backfilled with Ar four times. Anhydrous THF (9.0 ml) was added and the colorless solution was cooled to 0° C. Then, LiBH4 (96 mg, 4.41 mmol) was added and the reaction mixture was stirred for 1 hour. MeOH was added and volatiles were removed in vacuo. Purification by column chromatography (ISCO CombiFlash Rf, absorbed on silica gel, EtOAc In cyclohexane 20-50%) afforded tert-butyl (S)-(1-(3-(3-((5-(difluoromethoxy)pyridin-2-yl)oxy)phenyl-1,2,4-oxadiazol-5-yl)-3-hydroxypropan-2-yl)carbamate (3.5) (292 mg, 69.2%). UPLC retention time 1.09 min (Method A). $^1$H NMR (400 MHz, CDCl$_3$) δ=ppm 8.05 (d, J=2.7 Hz, 1H), 7.92 (d, J=7.8 Hz, 1H), 7.84 (s, 1H), 7.57-7.49 (m, 2H), 7.32-7.27 (m, 1H), 6.98 (d, J=8.9 Hz, 1H), 6.48 (t, J=72.9 Hz, 1H), 5.19 (s br, 1H), 4.22-4.14 (m, 1H), 3.85-3.73 (m, 2H), 3.28 (d, J=5.8 Hz, 2H), 1.42 (s, 9H). MS/ESI+479.4 [M+H]$^+$.

Step e) (S)-2-amino-3-(3-(3-((5-(difluoromethoxy)pyridin-2-yl)oxy)phenyl)-1,2,4-oxadiazol-5-yl)propan-1-ol (Example 3). To a 25 mL one-necked pear shaped flask equipped with a magnetic stir bar was added tert-butyl (S)-(1-(3-(3-((5-(difluoromethoxy)pyridin-2-yl)oxy) phenyl-1,2,4-oxadiazol-5-yl)-3-hydroxypropan-2-yl)carbamate (3.5) (283 mg, 0.591 mmol), dioxane (6.0 ml) and aq. HCl (6.0 ml, 12.00 mmol). The cloudy solution was stirred for 2 days at rt. 2M aq. NaOH solution (6.0 ml) was added and volatiles were removed In vacuo. To the obtained suspension was added EtOAc and ca. 0.1M aq. NaOH. The aqueous phase was extracted twice with EtOAc. The organic layers were washed with brine, combined and dried over Na$_2$SO$_4$. Purification by column chromatography (ISCO CombiFlash Rf, absorbed on silica gel, MeOH in CH$_2$Cl$_2$ 0-8%) afforded (S)-2-amino-3-(3-(3-((5-(difluoromethoxy)pyridin-2-yl) oxy)phenyl)-1,2,4-oxadiazol-5-yl)propan-1-ol (Example 3) as a pale yellow, clear, viscous oil (182 mg, 79%). UPLC retention time 0.69 min (Method A). $^1$H NMR (400 MHz, CDCl$_3$) δ=ppm 8.01 (d, J=2.8 Hz, 1H), 7.89 (d, J=7.8 Hz, 1H), 7.83-7.79 (m, 1H), 7.55-7.44 (m, 2H), 7.25 (dd, J=7.8, 1.6 Hz, 1H), 6.94 (d, J=8.9 Hz, 1H), 6.47 (t, J=72.9 Hz, 1H), 3.63 (dd, J=10.7, 4.4 Hz, 1H), 3.50 (dd, J=10.7, 6.1 Hz, 1H), 3.46-3.38 (m, 1H), 3.09 (dd, J=15.6, 4.7 Hz, 1H), 2.98-2.92 (m, 1H), 2.34 (s br, 3H). MS/ESI+379.2 [M+H]$^+$.

Example 4 (S)-2-amino-3-(3-(4-((5-(trifluoromethyl)pyridin-2-yl)oxy)phenyl)-1,2,4-oxadiazol-5-yl)propan-1-ol

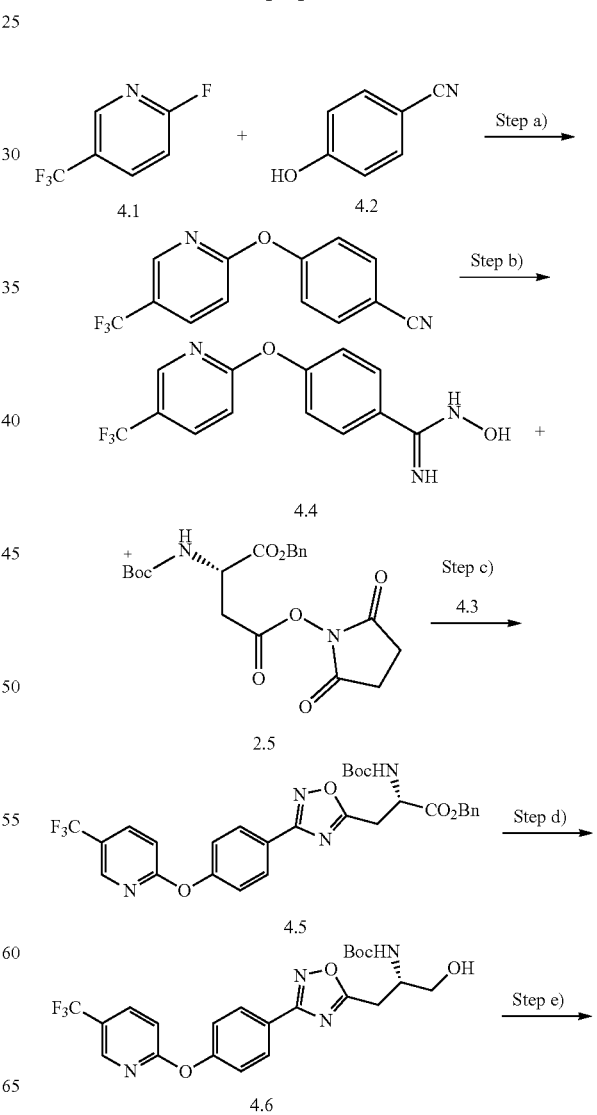

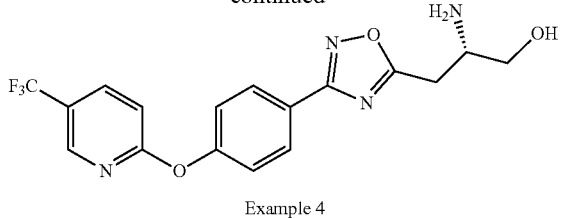

Example 4

Step a) 4-((5-(trifluoromethyl)pyridin-2-yl)oxy)benzonitrile (4.3). To a 100 mL one-necked round bottom flask equipped with a magnetic stir bar and reflux condenser was added 2 fluoro-5-(trifluoromethyl)pyridine (4.1) (0.990 g, 6.00 mmol), 4-cyanophenol (4.2) (0.786 g, 6.60 mmol), $K_2CO_3$ (2.486 g, 17.99 mmol) and DMF (30.0 ml). The reaction mixture was then stirred at 65° C. for 16 hours. Water and EtOAc were added. The aqueous phase was extracted twice with EtOAc. The organic layers were washed with brine, combined and dried over $Na_2SO_4$. Purification by column chromatography (ISCO CombiFlash Rf, absorbed on silica gel, EtOAc in cyclohexane 0-7%, fractions) afforded 4-((5-(trifluoromethyl)pyridin-2-yl)oxy)benzonitrile (4.3) (1.51 g, 95%). UPLC retention time 1.10 min (Method A). $^1$H NMR (400 MHz, CDCl$_3$) δ=ppm 8.44 (s, 1H), 7.98 (dd, J=8.6, 2.3 Hz, 1H), 7.73 (d, J=8.7 Hz, 2H), 7.28 (d, J=8.7 Hz, 2H), 7.12 (d, J=8.6 Hz, 1H). MS/ESI+ 265.3 [M+H]$^+$.

Step b) N-hydroxy-4-((5-(trifluoromethyl)pyridin-2-yl)oxy)benzimidamide (4.4). To a 50 mL one-necked pear shaped flask equipped with a magnetic stir bar and a condenser (air) was added 4-((5-(trifluoromethyl)pyridin-2-yl)oxy)benzonitrile (4.3) (0.794 g, 3.01 mmol), hydroxylamine hydrochloride (1.044 g, 15.03 mmol), NaHCO$_3$ (1.262 g, 15.03 mmol) and ethanol (15.0 ml)/Water (5.0 ml). The white suspension was stirred for 2 hours at 85° C. The reaction mixture was cooled to rt. EtOH was removed in vacuo. Water and EtOAc were added. The aqueous phase was extracted twice with EtOAc and the organic layers were washed with brine, combined and dried over $Na_2SO_4$. Purification by column chromatography (ISCO CombiFlash Rf, absorbed on silica gel, EtOAc in Cyclohexane 20-40%) afforded N-hydroxy-4-((5-(trifluoromethyl)pyridin-2-yl)oxy)benzimidamide (4.4) white crystals (828 mg, 93%). UPLC retention time 0.75 min (Method A). $^1$H NMR (400 MHz, CDCl$_2$) δ=ppm 8.47-8.43 (m, 1H), 7.93 (dd, J=8.7, 2.5 Hz, 1H), 7.73-7.68 (m, 2H), 7.23-7.17 (m, 2H), 7.05 (d, J=8.7 Hz, 1H), 4.89 (5, 2H). MS/ESI+298.2 [M+H]$^+$. Consistent with the desired product.

Step c) benzyl (S) 2-((tert-butoxycarbonyl)amino)-3-(3-(4((5-(trifluoromethyl)pyridin-2-yl)oxy)phenyl)-1,2,4-oxadiazol-5-yl)propanoate (4.5). To a 20 mL microwave vial equipped with a magnetic stir bar was added N-hydroxy-4-((5-(trifluoromethyl)pyridin-2-yl)oxy)benz-imidamide (4.4) (726 mg, 2.443 mmol), Boc-Asp(OSu)-OBzl [CAS 140171-25-1](2.5) (1130 mg, 2.69 mmol) and THF (13.0 ml). The colorless solution was stirred for 17 hours at 110° C. The solvent was removed in vacuo. Purification by column chromatography (ISCO CombiFlash Rf, absorbed on silica gel, EtOAc in Cyclohexane 0-18%) afforded benzyl (S)-2-((tert-butoxy-carbonyl)amino)-3-(3-(4-((5-(trifluoromethyl)pyridin-2-yl)oxy)phenyl)-1,2,4-oxadiazol-5-yl)propanoate (4.5) (1.41 g, 99%). UPLC retention time 1.42 min (Method A). $^1$H NMR (400 MHz, CDCl$_3$) δ=ppm 8.46 (s, 1H), 8.07 (d, J=8.7 Hz, 2H), 7.95 (dd, J=8.6, 2.4 Hz, 1H), 7.31-2.27 (m, 5H), 7.26 (d, J=8.6 Hz, 2H), 7.09 (d, J=8.6 Hz, 1H), 5.58 (d, J=7.7 Hz, 1H), 5.24-5.16 (m, 2H), 4.94-4.86 (m, 1H), 3.52 (qd, J=16.2, 4.9 Hz, 2H), 1.44 (s, 9H). MS/ESI+585.4 [M+H]$^+$.

Step d) tert-butyl (S)-(1-hydroxy-3-(3-(4-((5-(trifluoromethyl)pyridin-2-yl)oxy)phenyl)-1,2,4-oxadiazol-5-yl)propan-2-yl)carbamate (4.6). To a 25 mL two-necked round bottom flask equipped with a magnetic stir bar, gas inlet and rubber septum was added benzyl (S)-2-((tert-butoxy-carbonyl)amino)-3-(3-(4-((5-(trifluoromethyl)pyridin-2-yl)oxy)phenyl)-1,2,4-oxadiazol-5-yl)propanoate (4.5) (737 mg, 1.261 mmol). The flask was evacuated and backfilled with Ar five times. Anhydrous THF (10 mL) was then added and the colorless solution was cooled to 0° C. LiBH$_4$ (51.9 mg, 2.383 mmol) was added in one portion. The reaction mixture was stirred for 75 minutes. After 50 minutes, more LiBH$_4$ (27.5 mg, 1.26 mmol, 1.00 equiv) was added. The yellow suspension was quenched with MeOH. The mixture was stored in the freezer over the weekend. Volatiles were removed in vacuo. Purification by column chromatography (ISCO CombiFlash Rf, absorbed on silica gel, EtOAc in cyclohexane 20-40%) afforded a sticky colorless oil tort-butyl (S)-(1 hydroxy-3-(3-(4-((5-(trifluoromethyl)pyridin-2-yl)oxy)phenyl-1,2,4-oxadiazol-5-yl)propan-2-yl)carbamate (4.6) (399 mg, 65.9%). UPLC retention time 1.17 min (Method A). $^1$H NMR (400 MHz, CDCl$_3$) δ=ppm 8.45 (s, 1H), 8.14 (d, J=8.6 Hz, 2H), 7.94 (dd, J=8.6, 2.3 Hz, 1H), 7.29-7.26 (m, 2H), 7.08 (d, J=8.6 Hz, 1H), 5.23 (s, 1H), 4.20 (s, 1H), 3.80 (dq, J=11.3, 5.9, 4.7 Hz, 2H), 3.30 (d, J=5.9 Hz, 2H), 1.44 (s, 9H). 19F NMR (376 MHz, CDCl$_3$) 5-61.73. MS/ESI+481.4 [M+H]$^+$.

Step e) (S)-2-amino-3-(3-(4((5-(trifluoromethyl)pyridin-2-yl)oxy)phenyl)-1,2,4-oxadiazol-5-yl)propan-1-ol (Example 4) To a 25 mL one-necked pear shaped flask equipped with a magnetic stir bar was added tert-butyl (S)-(1-hydroxyl-3-(4-((5 (trifluoromethyl)pyridin-2-yl)oxy)phenyl)-1,2,4-oxadiazol-5-yl)propan-2-yl)carbamate (4.6) (393 mg, 0.818 mmol), dioxane (8.0 ml) and aq. HCl (8.0 ml, 16.00 mmol). The cloudy solution was stirred for 40 hours at rt. A white suspension was obtained. The solvent was removed in vacuo. 2M aq. NaOH solution (10 ml) was added. Then, EtOAc and ca. 0.2M aq. NaOH solution was added and the aqueous phase was extracted twice with EtOAc. The organic layers were washed with brine, combined and dried over $Na_2SO_4$. A pale yellow (mostly white) solid was obtained. Purification by column chromatography (ISCO CombiFlash Rf, absorbed on silica gel, MeOH in $CH_2C_{12}$ 0-10β6) afforded a white solid (S)-2-amino-3-(3-(4-((5-(trifluoromethyl)pyridin-2-yl)oxy)phenyl)-1,2,4-oxadiazol-5-yl)propan-1-ol (Example 4) (212 mg, 68.1%). UPLC retention time 0.75 min (Method A). $^1$H NMR (400 MHz, CDCl$_3$) δ=ppm 8.45 (s, 1H), 8.15 (d, J=8.7 Hz, 2H), 7.94 (dd, J=8.6, 2.3 Hz, 1H), 7.28 (d, J=8.7 Hz, 3H), 7.08 (d, J=8.6 Hz, 1H), 3.71 (dd, J=10.5, 4.3 Hz, 1H), 3.56 (dd, J=10.5, 6.3 Hz, 1H), 3.54-3.46 (m, 1H), 3.15 (dd, J=15.5, 4.7 Hz, 1H), 3.01 (dd, J=15.5, 8.1 Hz, 1H), 1.72 (s br, 3H). 19F NMR (376 MHz, CDCl$_3$) 5-61.73. MS/ESI+381.3 [M+H]$^+$.

Example 5 (S)-2-amino-3-(3 (4-((5-(difluoromethoxy)pyridin-2-yl)oxy)phenyl)-1,2,4-oxadiazol-5-yl)propan-1-01

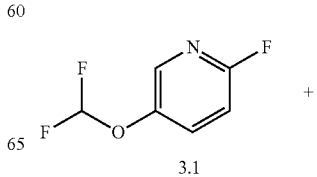

3.1

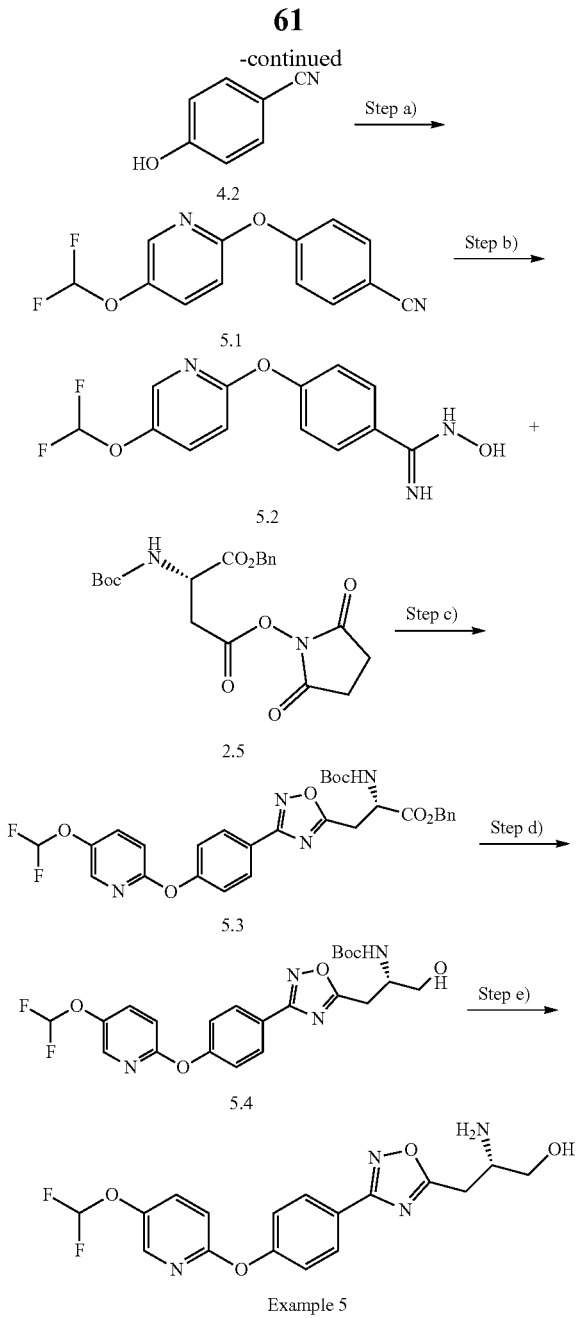

Example 5

Step a) 44(5-(difluoromethoxy)pyridin-2-yl)oxy)benzonitrile (5.1). To a 10 mL microwave vial equipped with a magnetic stir bar was added 5-(difluoromethoxy)-2-fluoropyridine (0.186 g, 1.140 mmol, Enamine Ltd.) (3.1), 4-cyanophenol (0.177 g, 1.483 mmol, Sigma-Aldrich) (4.2), $K_2CO_3$ (0.473 g, 3.42 mmol) and DMF (Volume: 4.0 ml). After sealing the vial, the white suspension was heated to 110*C and stirred for 5 days. The reaction mixture was cooled to rt. Water/EtOAc were added and the aqueous phase was extracted twice with EtOAc. The organic layers were washed with brine, combined and dried over $Na_2SO_4$. Purification by column chromatography (ISCO CombiFlash Rf, absorbed on silica gel, EtOAc in Cyclohexane 0-25%) afforded a colorless oil 4-((5-(difluoromethoxy)pyridin-2-yl)oxy)-benzonitrile (5.1) (0.25 g, 84%). UPLC retention time 1.04 min (Method A). $^1$H NMR (400 MHz, $CDCl_3$) δ=ppm 8.06 (d, J=2.8 Hz, 1H), 7.71-7.67 (m, 2H), 7.59 (dd, J=8.8, 2.9 Hz, 1H), 7.25-7.21 (m, 2H), 7.03 (d, J=8.8 Hz, 1H), 6.51 (t, J=72.6 Hz, 1H). MS/ESI+263.2 [M+H]+.

Step b) (Z)-4-((5-(difluoromethoxy)pyridin-2-yl)oxy)-N'-hydroxybenzimidamide (5.2)

To a 25 mL one-necked pear shaped flask equipped with a magnetic stir bar and a condenser (air) was added $NaHCO_3$ (400 mg, 4.77 mmol), hydroxylamine hydrochloride (331 mg, 4.77 mmol) and Water (2.0 nil). The white suspension (caution: gas formation) was stirred for 5 minutes at rt. 4-((5-(difluoromethoxy)pyridin-2-yl)oxy)-benzonitrile (5.1) (250 mg, 0.953 mmol) in EtOH (5.0 ml) was subsequently added and the reaction mixture was heated to 85'C and stirred for 80 minutes. A colorless solution was obtained within ca. 15 minutes. LC-MS after 30 minutes revealed almost full consumption of the starting material. EtOH was removed in vacuo. Water/EtOAc were added and the aqueous phase was extracted twice with EtOAc. The organic layers were washed with brine, combined and dried over $Na_2SO_4$. Purification by column chromatography (ISCO CombiFlash Rf, absorbed on silica gel, EtOAc in Cyclohexane 0-65%) afforded a cloudy oil which slowly crystallized (Z)-4-((5-(difluoromethoxy)pyridin-2-yl)oxy)-N'-hydroxybenzimidamide (0.248 g, 88%) (5.2). UPLC retention time 0.65 min (Method A). $^1$H NMR (400 MHz, $CDCl_3$) δ=ppm 8.02 (d, J=2.8 Hz, 1H), 7.67-7.60 (m, 2H), 7.53 (dd, J=8.9, 2.9 Hz, 1H), 7.17-7.11 (m, 2H), 6.94 (d, J=8.9 Hz, 1H), 6.48 (t, J=72.8 Hz, 1H)($NH_2$ and NOH peaks not observed since $CDCl_3$ (and not DMSO-d6) was used as solvent). MS/ESI+296.1 [M+H]$^+$.

Step c) benzyl (S)-2-((tert-butoxycarbonyl)amino)-3-(3-(4-((5-(difluoromethoxy)pyridin-2-yl)oxy)phenyl)-1,2,4-oxadiazol-5-yl)propanoate (5.3). To a mL microwave vial equipped with a magnetic stir bar was added (Z)-4-((5(difluoro-methoxy)pyridin-2-yl)oxy)-N'-hydroxybenzimidamide (5.2) (0.239 g, 0.810 mmol), Boc-Asp(OSu)-OBzl (2.5) (0.374 g, 0.890 mmol) and THF (3.0 ml). The colorless solution was stirred for 100 min at rt. LC-MS revealed full consumption within 90 minutes. The reaction mixture was then heated to 120*C and stirred for 3 hours. EtOAc was added to the colorless solution and the mixture was stored in the freezer over the weekend. The solvent was removed In vacuo. $CH_2Cl_2$ and silica gel were added. Purification by column chromatography (ISCO CombiFlash Rf, absorbed on silica gel, EtOAc in Cyclohexane 0-25%) to afforded benzyl (S)-2-((tert-butoxycarbonyl)amino)-3-(3-(4-((5-(difluoromethoxy)pyridin-2-yl)oxy)phenyl)-1,2,4-oxadiazol-5-yl)propanoate (0.443 g, 94%) (5.3). UPLC retention time 1.34 min (Method A). $^1$H NMR (400 MHz, $CDCl_3$) δ=ppm 8.08 (d, J=2.7 Hz, 1H), 8.04 (d, J=8.7 Hz, 2H), 7.57 (dd, J=8.9, 2.9 Hz, 1H), 7.29 (s, 5H), 7.22 (d, J=8.7 Hz, 2H), 7.00 (d, J=8.9 Hz, 1H), 6.50 (t, J=72.8 Hz, 1H), 5.58 (d, J=7.6 Hz, 1H), 5.20 (d, J=2.7 Hz, 2H), 4.93-4.85 (m, 1H), 3.51 (qd, J=16.2, 5.0 Hz, 2H), 1.44 (s, 9H). MS/ESI+583.2 [M+H]$^+$.

Step d) tert-butyl (S)-(1-(3-(4-((5-(difluoromethoxy)pyridin-2-yl)oxy)phenyl)-1,2,4-oxadiazol-5-yl)-3-hydroxypropan-2-yl)carbamate (5.4). To a 10 mL two-necked cone shaped flask equipped with a magnetic stir bar, rubber septum and gas inlet was added benzyl (S)-2-((tert-butoxycarbonyl)amino)-3-(3-(4-((5-(difluoromethoxy)-pyridin-2-yl)oxy)phenyl)-1,2,4-oxadiazol-5-yl)propanoate (5.3) (0.220 g, 0.378 mmol). The vial was evacuated and back-filled with Ar three times. Dry THF (2.0 ml) was added and the solution was cooled to 0° C. LiBH4 (0.041 g, 1.888 mmol) was then added in one portion and the suspension was stirred for 70 minutes. The reaction was quenched with MeOH. The solvents were removed in vacuo. CH₂Cl₂ and silica gel were added. Purification by column chromatography (ISCO CombiFlash Rf, absorbed on silica gel, EtOAc in Cyclohexane 0-55%) afforded tert-butyl (S)-(1-(3(4((5-(difluoromethoxy)pyridin-2-yl)oxy)phenyl)-1,2,4-oxadiazol-5-yl)-3-hydroxypropan-2-yl)carbamate (0.100 g, 55.3%) (5.4). UPLC retention time 1.07 min (Method A). ¹H NMR (400 MHz, CDCl₃) δ=ppm 8.13 (d, J=8.7 Hz, 2H), 8.10 (d, J=2.7 Hz, 1H), 7.59 (dd, J=8.9, 2.9 Hz, 1H), 7.27 (d, J=8.7 Hz, 2H), 7.02 (d, J=8.9 Hz, 1H), 6.52 (t, J=72.8 Hz, 1H), 5.24 (s, 1H), 4.22 (s, 1H), 3.84 (p, J=6.7 Hz, 2H), 3.32 (d, J=5.9 Hz, 2H), 1.46 (s, 9H). MS/ESI+479.3 [M+H]⁺.

Step e) (S)-2-amino-3-(3-(4-((5-(difluoromethoxy)pyridin-2-yl)oxy)phenyl)-1,2,4-oxadiazol-5-yl)propan-1-ol (Example 5). To a 10 mL one-necked pear shaped flask equipped with a magnetic stir bar was added tert-butyl (S)-(1-(3-(4-((5-(difluoromethoxy)pyridin-2-yl)oxy)phenyl)-1,2,4-oxadiazol-5-yl)-3-hydroxypropan-2-yl)carbamate (5.4) (0.100 g, 0.209 mmol), dichloromethane (2.0 ml) and TFA (0.081 ml, 1.045 mmol). The solution was stirred for 3 days at rt. The solvent and acid were removed in vacuo. Purification by column chromatgraphy (ISCO CombiFlash Rf, absorbed on silica gel, MeOH in CH₂Cl₂ 0-10%) to afforded (S)-2-amino-3-(3-(4 ((5-(difluoromethoxy)-pyridin-2-yl)oxy)phenyl)-1,2,4-oxadiazol-5-yl)propan-1-ol (82 mg, 99%) (Example 5) as a white (pale yellow) foam. UPLC retention time 0.70 min (Method A). ¹H NMR (400 MHz, CDCl₃) δ=ppm 8.02-7.89 (m, 3H), 7.54-7.44 (m, 1H), 7.15-7.07 (m, 2H), 6.92-6.86 (m, 1H), 6.47 (t, J=72.8 Hz, 1H), 4.01-3.72 (m, 3H), 3.42-3.20 (m, 2H). MS/ESI+379.3 [M+H]⁺.

Example 6 ethyl (S)-2-amino-3-(5-(4-((5-chloropyridin-2-yl)oxy)phenyl)-1,2,4-oxadiazol-3-yl)propanoate

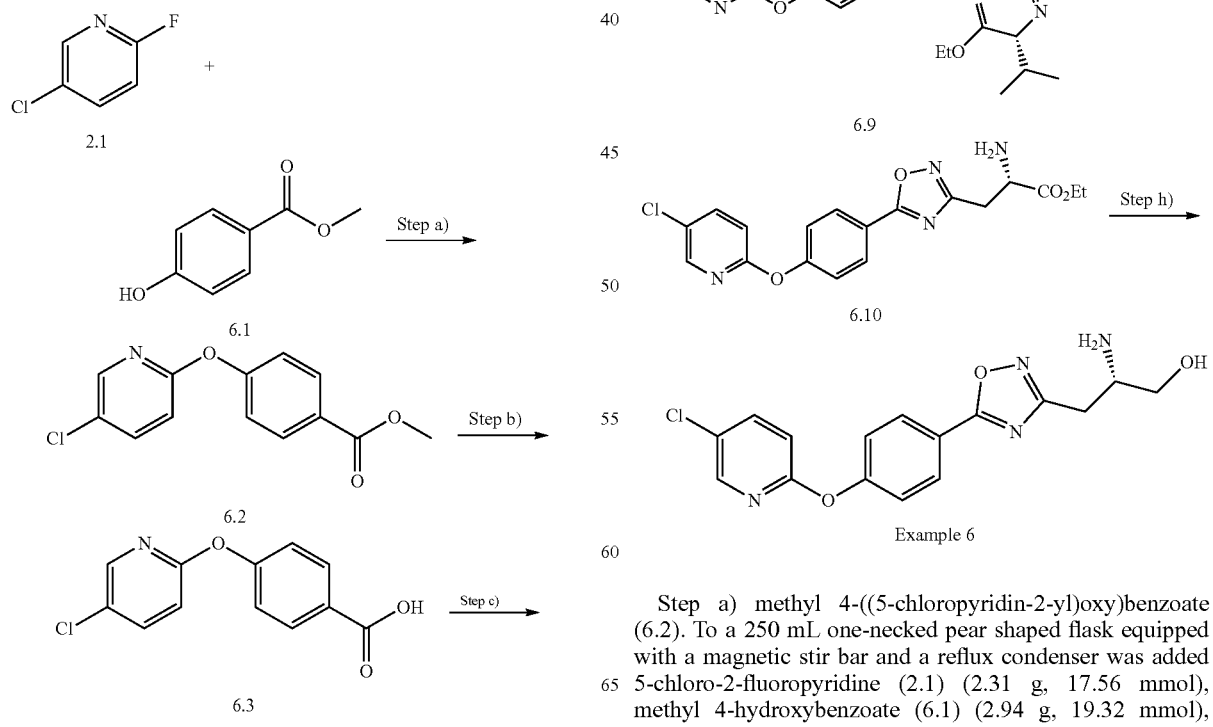

Step a) methyl 4-((5-chloropyridin-2-yl)oxy)benzoate (6.2). To a 250 mL one-necked pear shaped flask equipped with a magnetic stir bar and a reflux condenser was added 5-chloro-2-fluoropyridine (2.1) (2.31 g, 17.56 mmol), methyl 4-hydroxybenzoate (6.1) (2.94 g, 19.32 mmol), K₂CO₃ (4.85 g, 35.1 mmol) and DMF (100 ml). The white suspension was heated to 100'C and stirred for 19 hours. The reaction mixture was cooled to rt. Water and EtOAc were added. The aqueous phase was extracted twice with EtOAc. The organic layers were washed with brine, combined and dried over $Na_2SO_4$. Purification by column chromatography (ISCO CombiFlash Rf, absorbed on silica gel, EtOAc in cyclohexane 0-7%) afforded methyl 4-((5-chloropyridin-2-yl)oxy)benzoate (3.18 g, 68.7%) (6.2) as white solid crystals. UPLC retention time 1.14 min (Method A). $^1$H NMR (400 MHz, $CDCl_3$) δ=ppm 8.14 (d, J=2.5 Hz, 1H), 8.11-8.05 (m, 2H), 7.69 (dd, J=8.7, 2.7 Hz, 1H), 7.20-7.14 (m, 2H), 6.94 (d, J=8.7 Hz, 1H), 3.91 (s, 3H). MS/ESI+264.2, 266.2.

Step b) 4-((5-chloropyridin-2-yl)oxy)benzoic acid (6.3). To a 250 mL one-necked pear shaped flask equipped with a magnetic stir bar and a condenser (air) was added methyl 4-((5-chloropyridin-2-yl)oxy)benzoate (6.2) (3.09 g, 11.72 mmol), MeOH (50.0 ml)/THF (50.0 ml) and $LiOH \cdot 1H_2O$ (2.459 g, 58.6 mmol). The suspension was stirred for 2 hours at 45'C. The mixture was cooled to rt and stirred over the weekend (4 days). Volatiles were removed in vacuo. To the obtained white solid was added water, 2M aq. HCl (40 mL, 80 mmol) and EtOAc. The aqueous phase was extracted twice with EtOAc. The organic layers were washed with brine, combined and dried over $Na_2SO_4$. Concentration in vacuo afforded 4-((5-chloropyridin-2-yl)oxy)benzoic acid (2.93 g, 100%) (6.3) as a white solid. UPLC retention time 0.92 min (Method A). $^1$H NMR (400 MHz, $CDCl_3$) δ=ppm 8.10-7.88 (m, 3H), 7.64-7.53 (m, 1H), 7.09-6.97 (m, 2H), 6.89-6.78 (m, 1H). MS/ESI+250.1, 252.1.

Step c) 4-((5-chloropyridin-2-yl)oxy)benzoyl chloride (6.4). To a 50 mL two-necked round bottom flask equipped with a magnetic stir bar, rubber septum and gas inlet was added 4-((5-chloropyridin-2-yl)oxy)benzoic acid (6.3) (1.3 g, 5.21 mmol). The flask was evacuated and carefully backfilled with Ar three times. Anhydrous dichloromethane (7.0 ml) was added and the white suspension was cooled to 0° C. Oxalyl chloride (1.0 ml, 11.42 mmol) was added in one portion. After addition of 2 drops of DMF, gas formation was observed and the reaction mixture slowly turned pale yellow. It was stirred for 19.5 hours at 0° C. After 1 h 35 min: addition of more oxalyl chloride (0.50 mL, 5.71 mmol). After 19 h: addition of more oxalyl chloride (0.20 mL, 2.29 mmol) and 4 drops of DMF. Dichloromethane was added to the reaction mixture. It was filtered and the residue was washed with more dichloromethane. A white solid was obtained which was dried under high-vacuum. 4-((5-chloropyridin-2-yl)oxy)benzoyl chloride (770 mg, 55.2%) (6.4). No characterization of the intermediate acyl chloride. However, LC-MS indicated formation of methyl ester (Rt=1.15) in the presence of MeOH Step d) (E)-2-chloro-N'-((4-((5-chloropyridin-2-yl)oxy)benzoyl)oxy)acetimidamide (6.6). To a 50 mL one-necked pear shaped flask equipped with a magnetic stir bar was added 4-((5-chloropyridin-2-yl)oxy)benzoyl chloride (6.4) (1.25 g, 4.66 mmol), (Z)-2-chloro-N'-hydroxyacetimidamide (6.5) (WO2004/14370 A2 (2004); Page/Page column 44) (0.557 g, 5.13 mmol), DMAP (0.057 g, 0.466 mmol) and DCM (30 ml). The suspension was stirred for 1 hour at rt. After 30 minutes DIPEA (0.814 mL, 4.66 mmol) was added. Volatiles were removed in vacuo. EtOAc and sat. aq. $NH_4Cl$ solution was added to the residue. The aqueous phase was extracted twice with EtOAc. The organic layers were washed with brine, combined and dried over $Na_2SO_4$. Purification by column chromatography (ISCO CombiFlash Rf, absorbed on silica gel, EtOAc in Cyclohexane 23-38% to 43%) afforded (E)-2-chloro-N'-((4-((5-chloropyridin-2-yl)oxy)benzoyl)oxy)acetimidamide (1.05 g, 66.2%) (6.6) as a white solid. UPLC retention time 0.97 min (Method A). $^1$H NMR (400 MHz, $CDCl_3$) δ=ppm 8.25 (d, J=2.6 Hz, 1H), 8.19 (d, J=8.7 Hz, 2H), 8.02 (dd, J=8.7, 2.7 Hz, 1H), 7.26 (d, J=8.7 Hz, 2H), 7.20 (d, J=8.8 Hz, 1H), 6.91 (s br, 2H), 4.17 (s, 2H). MS/ESI+342.1, 340.1.

Step e) 3-(chloromethyl)-5-(4-((5-chloropyridin-2-yl)oxy)phenyl)-1,2,4-oxadiazole (6.7). To a 250 mL one-necked pear shaped flask equipped with a magnetic stir bar and a reflux condenser was added (E)-2-chloro-N'-((4-((5-chloropyridin-2-yl)oxy)benzoyl)oxy)acetimid-amide (6.6) (1.05 g, 3.09 mmol) and Toluene (50.0 ml). The solution was then stirred for 17.5 hours at 130° C. and concentrated in vacuo. Purification by column chromatography (ISCO CombiFlash Rf, absorbed on silica gel, EtOAc in Cyclohexane 0-12%) afforded 3-(chloro-methyl)-5-(4-((5-chloropyridin-2-yl)oxy)phenyl)-1,2,4-oxadiazole (463 mg, 46.6%) (6.7) as a white solid. UPLC retention time 1.23 min (Method A). $^1$H NMR (400 MHz, $CDCl_3$) δ=ppm 8.22-8.17 (m, 2H), 8.16 (d, J=2.5 Hz, 1H), 7.72 (dd, J=8.7, 2.7 Hz, 1H), 7.31-7.27 (m, 2H), 6.99 (d, J=8.7 Hz, 1H), 4.67 (s, 2H). MS/ESI+322.1, 324.1.

Step f) 5-(4-((5-chloropyridin-2-yl)oxy)phenyl)-3-(((2S, 5R)-3,6-diethoxy-5-isopropyl-2,5-dihydropyrazin-2-yl) methyl)-1,2,4-oxadiazole (6.9). A 10 mL two-necked cone shaped flask equipped with a magnetic stir bar, gas inlet and rubber septum was heated in vacuo and backfilled with Ar three times. Schöllkopf Auxiliary [CAS: 110117-71-0] (6.8) (0.50 mL, 1.369 mmol) and anhydrous THF (Volume: 5.0 mL, Ratio: 1.667) were added and the brown clear solution was cooled to −69° C. (isopropyl ether/dry ice). nBuLi in hexane (0.95 mL, 2.375 mmol) was added dropwise and the dark brown solution was stirred for 30 minutes. A dark brown solution was obtained. 3-(chloro-methyl)-5-(4-((5-chloropyridin-2-yl)oxy)phenyl)-1,2,4-oxadiazole (6.7) (441 mg, 1.369 mmol) in anhydrous THF (3.0 mL) was then added dropwise. It was stirred for 16 hours; meanwhile, it was allowed to warm to rt. A light brown solution was obtained. The reaction was quenched with a few drops of sat. aq. $NH_4Cl$ solution. More aq. sat. $NH_4Cl$ solution and EtOAc was added. The aqueous phase was extracted twice with EtOAc. The organic layers were washed with brine, combined, dried over $Na_2SO_4$ and concentrated to give a yellow oil. Purification by column chromatography (ISCO CombiFlash Rf, absorbed on silica gel, EtOAc in Cyclohexane 0-9.1%) afforded 5-(4-((5-chloropyridin-2-yl)oxy) phenyl)-3-(((2S,5R)-3,6-diethoxy-5-isopropyl-2,5-dihydropyrazin-2-yl)methyl)-1,2,4-oxadiazole (368 mg, 54%) (6.9) as a yellow oil. UPLC retention time 1.60 min (Method A). $^1$H NMR (400 MHz, $CDCl_3$) δ=ppm 8.17-8.12 (m, 3H), 7.70 (dd, J=8.7, 2.7 Hz, 1H), 7.25 (dd, J=9.0, 2.4 Hz, 2H), 6.97 (d, J=8.7 Hz, 1H), 4.48 (ddd, J=7.4, 5.0, 3.7 Hz, 1H), 4.24-3.93 (m, 4H), 3.88 (t, J=3.5 Hz, 1H), 3.37-3.28 (m, 1H), 3.12 (dd, J=14.5, 7.3 Hz, 1H), 2.24 (ddt, J=10.2, 6.8, 3.4 Hz, 1H), 1.28-1.24 (m, 3H), 1.23-1.18 (m, 3H), 1.04 (dd, J=13.7, 6.9 Hz, 3H), 0.70 (dd, J=15.4, 6.8 Hz, 3H). MS/ESI+ 498.3, 500.3.

Step g) ethyl (S)-2-amino-3-(5-(4-((5-chloropyridin-2-yl)oxy)phenyl)-1,2,4oxadiazol-3-yl)propanoate (6.10). To a 25 mL one-necked round bottom flask equipped with a magnetic stir bar was added 5-(4-((5-chloropyridin-2-yl)oxy) phenyl)-3-(((2S,5R)-3,6-diethoxy-5-isopropyl-2,5-dihydropyrazin-2-yl)methyl)-1,2,4-oxadiazole (6.9) (368 mg, 0.739 mmol) and THF (8.0 ml). After addition of aq. HCl (2.0 mL, 4.00 mmol) to the bright yellow solution, it immediately turned light orange and over time turned yellow again. The reaction mixture was stirred for 90 minutes at rt. The reaction was quenched with sat. aq. $NaHCO_3$ solution.

EtOAc was added and the aqueous phase was extracted twice with EtOAc. The organic layers were washed with brine, combined and dried over Na$_2$SO$_4$. Concentration in vacuo afforded a yellow oil. Purification by column chromatography (ISCO CombiFlash Rf, absorbed on silica gel, MeOH in CH$_2$Cl$_2$ 0 2.3%) afforded ethyl (S)-2-amino-3-(5-(4-((5-chloropyridin-2-yl)oxy)phenyl)-1,2,4-oxadiazol-3-yl)propanoate (272 mg, 95%) (6.10) as a colorless oil which slowly crystallized at rt. UPLC retention time 0.82 min (Method A). $^1$H NMR (400 MHz, CDCl$_3$) δ=ppm 8.18-8.11 (m, 3H), 7.71 (dd, J=8.7, 2.7 Hz, 1H), 7.30-7.23 (m, 2H), 6.97 (d, J=8.7 Hz, 1H), 4.22 (qq, J=7.1, 3.6 Hz, 2H), 4.01 (dd, J=8.0, 4.7 Hz, 1H), 3.28 (dd, J=15.1, 4.7 Hz, 1H), 3.13 (dd, J=15.1, 8.0 Hz, 1H), 1.86 (s, 2H), 1.28 (t, J=7.1 Hz, 3H). MS/ESI+389.2, 391.2.

Step h) ethyl (S)-2-amino-3-(5-(4-((5-chloropyridin-2-yl)oxy)phenyl)-1,2,4-oxadiazol-3-yl)propanoate (Example 6). To a 25 mL two-necked pear shaped flask equipped with a magnetic stir bar, rubber septum and gas inlet was added ethyl (S)-2-amino-3-(5-(4-((5-chloropyridin-2-yl)oxy)phenyl)-1,2,4-oxadiazol-3-yl)propanoate (6.10) (272 mg, 0.700 mmol).

The flask was evacuated and backfilled with Ar five times. Anhydrous THF (5.00 ml) was added and the solution was cooled to 0° C. After addition of LiAIH$_4$ in THF (2M) (0.350 mL, 0.700 mmol) (gas formation observed), the reaction mixture was stirred for 65 minutes at 0'C. The reaction was quenched with MeOH (still cooling at 0'C) and then water. Sat. aq. NH$_4$C$_1$ solution and EtOAc were added. The aqueous phase was extracted twice with EtOAc. The organic layers were washed with brine, combined and dried over Na$_2$SO$_4$. Purification by column chromatography (ISCO CombiFlash Rf, absorbed on silica gel, MeOH in CH$_2$Cl$_2$ 0-10β6) afforded ethyl (S)-2-amino-3-(5-(4-((5-chloropyridin-2-yl)oxy)phenyl)-1,2,4-oxadiazol-3-yl)propanoate (64.6 mg, 26.4%) (Example 6) as a pale brown solid. UPLC retention time 0.70 min (Method A). $^1$H NMR (400 MHz, CDCl$_3$) δ=ppm 8.13 (dd, J=5.9, 2.9 Hz, 3H), 7.70 (dd, J=8.7, 2.7 Hz, 1H), 7.29-7.21 (m, 2H), 6.96 (d, J=8.7 Hz, 1H), 3.68 (dd, J=10.8, 4.2 Hz, 1H), 3.52 (dd, J=10.8, 6.5 Hz, 1H), 3.40 (dq, J=11.2,4.7 Hz, 1H), 2.97 (dd, J=14.9, 4.7 Hz, 1H), 2.84 (dd, J=14.9, 8.2 Hz, 1H), 2.57 (s br, 3H). MS/ESI+347.2, 349.2.

Example 7 tert-butyl ((2S)-1-(3-(4-((3-fluoro-5-(1-(tetrahydro-2H-pyran-2-yl)-1H-pyrazol-5-yl)pyridin-2-yl)oxy)phenyl)-1,2,4-oxadiazol-5-yl)-3-hydroxypropan-2-yl)carbamate

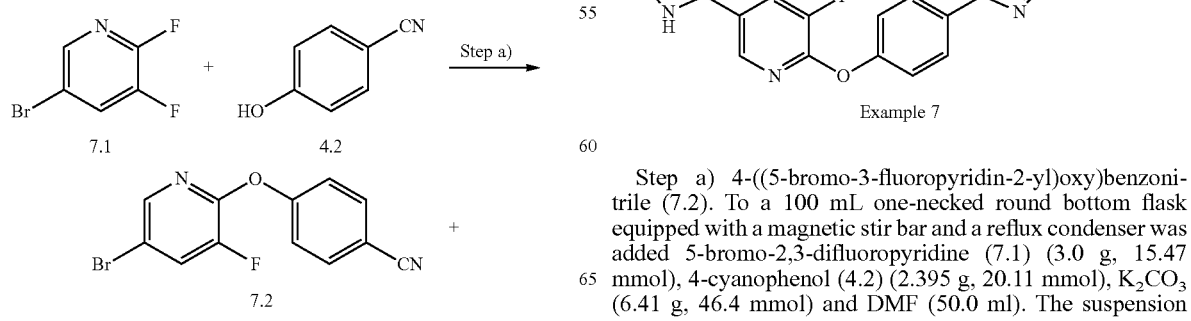

Step a) 4-((5-bromo-3-fluoropyridin-2-yl)oxy)benzonitrile (7.2). To a 100 mL one-necked round bottom flask equipped with a magnetic stir bar and a reflux condenser was added 5-bromo-2,3-difluoropyridine (7.1) (3.0 g, 15.47 mmol), 4-cyanophenol (4.2) (2.395 g, 20.11 mmol), K$_2$CO$_3$ (6.41 g, 46.4 mmol) and DMF (50.0 ml). The suspension was heated to 110'C and stirred for 17 hours. The reaction mixture was cooled to rt. Water/EtOAc were added and the yellow aqueous phase was extracted twice with EtOAc. The organic layers were washed with brine, combined and dried over $Na_2SO_4$. Concentration in vacuo afforded an intense orange oil. Purification by column chromatography (ISCO CombiFlash Rf, absorbed on silica gel, EtOAc In cyclohexane 0-10β6 then to 20%) afforded 4-((5-bromo-3-fluoropyridin-2-yl)oxy)benzonitrile (2.97 g, 64.9%) (7.2) as a white solid. UPLC retention time 1.14 min (Method A). $^1$H NMR (400 MHz, $CDCl_3$) δ=ppm 8.37 (dd, J=9.6, 2.0 Hz, 1H), 8.18 (d, J=2.0 Hz, 1H), 7.93 (d, J=8.7 Hz, 2H), 7.43 (d, J=8.7 Hz, 2H). 19F NMR (376 MHz, $CDCl_3$) 5-132.46 (d, J=8.4 Hz). MS/ESI+293.0, 295.0 (weak).

Step b) 4-((3-fluoro-5-(1-(tetrahydro-2H-pyran-2-yl)-1H-pyrazol-5-yl)pyridin-2-yl)oxy)benzonitrile (7.3). To a 50 ml two-necked round bottom flask equipped with a magnetic stir bar, gas inlet and rubber septum was added 4-((5-bromo-3-fluoropyridin-2-yloxy)benzonitrile (7.2) (0.786 g, 2.68 mmol), 1-(tetrahydro-2H-pyran-2-yl)-5-(4,4,5,5-tetramethyl-1,3,2-dioxaborolan-2-yl)-1H-pyrazole [CAS: 903550-26-5] (1.000 g, 3.49 mmol), $K_3PO_4$ (1.708 g, 8.05 mmol), [Pd(PPh_3)_4] (0.155 g, 0.134 mmol) and Toluene (15.0 ml). The flask was carefully evacuated and backfilled with Ar three times. The reaction mixture was then purged for 10 minutes with Ar. The rubber septum was removed and a reflux condenser (previously flushed with Ar) was mounted (with rubber septum and Ar baloon on top). The pale yellow suspension was then stirred for 3 hours at 110'C. The reaction mixture was cooled to rt. Water/EtOAc was added and the yellow aqueous phase was extracted twice with EtOAc. The organic layers were washed with brine, combined and dried over $Na_2SO_4$. Concentration in vacuo afforded a dark orange oil. The crude mixture was purified twice by column chromatography (ISCO CombiFlash Rf, absorbed on silica gel, EtOAc in Cyclohexane 0-30% in both cases) to afford 4-((3-fluoro-5-(1-(tetrahydro-2H-pyran-2-yl)-1H-pyrazol-5-yl)pyridin-2-yl)oxy)benzonitrile (0.628 g, 64.3%) (7.3) as a white solid. UPLC retention time 1.06 min (Method A). $^1$H NMR (400 MHz, $CDCl_3$) δ=ppm 8.10 (d, J=1.9 Hz, 1H), 7.79 (dd, J=10.3, 2.0 Hz, 1H), 7.76-7.72 (m, 2H), 7.62 (d, J=1.7 Hz, 1H), 7.37-7.32 (m, 2H), 6.39 (d, J=1.8 Hz, 1H), 5.15 (dd, J=9.9, 2.5 Hz, 1H), 4.18-4.06 (m, 1H), 3.62 (td, J=11.5, 2.3 Hz, 1H), 2.64-2.52 (m, 1H), 2.17-2.07 (m, 1H), 1.95-1.87 (m, 1H), 1.79-1.69 (m, 1H), 1.63-1.56 (m, 2H). MS/ESI+no ionization, Rf (Cyclohexane/EtOAc, 3:1)=0.26.

Step c) 4-((3-fluoro-5-(1-(tetrahydro-2H-pyran-2-yl)-1H-pyrazol-5-yl)pyridin-2-yl)oxy)-N-hydroxybenzimidamide (7.4). To a 50 mL one-necked pear shaped flask equipped with a magnetic stir bar was added hydroxylamine hydrochloride (0.599 g, 8.62 mmol), $NaHCO_3$(0.724 g, 8.62 mmol) and Water (4.0 ml). The white suspension (caution: gas formation) was stirred for 5 minutes at rt. 4-((3-fluoro-5-(1-(tetrahydro-2H-pyran-2-yl)-1H-pyrazol-5-yl)pyridin-2-yl)oxy)benzonitrile (7.3) (0.628 g, 1.724 mmol) and EtOH (10 ml) were then added and the reaction mixture was heated to 85° C. and stirred for 110 minutes. After cooling to rt, EtOH was removed in vacuo. Water/EtOAc were added and the aqueous phase was extracted twice with EtOAc. The organic layers were washed with brine, combined and dried over $Na_2SO_4$. Purification by column chromatography (ISCO CombiFlash Rf, absorbed on silica gel, EtOAc in Cyclohexane 0-66%) afforded 4-((3-fluoro-5-(1-(tetrahydro-2H-pyran-2-yl)-1H-pyrazol-5-yl)pyridin-2-yl)oxy)-N-hydroxybenzimidamide (0.570 g, 83%) (7.4) as a white foam. UPLC retention time 0.80 min (Method A). $^1$H NMR (400 MHz, $CDCl_3$) δ=ppm 8.08 (d, J=1.9 Hz, 1H), 7.77-7.70 (m, 3H), 7.62 (d, J=1.6 Hz, 1H), 7.29-7.25 (m, 2H), 6.38 (d, J=1.7 Hz, 1H), 5.15 (dd, J=10.0, 2.4 Hz, 1H), 4.87 (s br, 2H), 4.17-4.05 (m, 1H), 3.62 (td, J=11.5, 2.2 Hz, 1H), 2.66-2.49 (m, 1H), 2.15-2.06 (m, 1H), 1.90 (d, J=13.5 Hz, 1H), 1.82-1.68 (m, 1H), 1.67-1.53 (m, 2H). MS/ESI+398.3 [M+H]$^+$. lit (Cyclohexane/EtOAc, 1:2)=0.33.

Step d) benzyl (2S)-2-((tert-butoxycarbonylamino)-3-(3-(4-((3-fluoro-5-(1-(tetrahydro-2H-pyran-2-yl)-1H-pyrazol-5-yl)pyridin-2-yl)oxy)phenyl)-1,2,4-oxadiazol-5-yl)propanoate (7.5). To a 20 mL microwave vial equipped with a magnetic stir bar was added 4-((3-fluoro-5-(1-(tetrahydro-2H-pyran-2-yl)-1H-pyrazol-5-yl)pyridin-2-yl)oxy)-N-hydroxybenzimidamide (7.4) (0.563 g, 1.417 mmol), Boc-Asp (OSu)-Obzl (2.5) (0.655 g, 1.558 mmol) and THF (7.0 ml). The vial was sealed and the colorless solution was stirred for 1 hour at rt. The reaction mixture was then heated to 120'C and stirred for 140 minutes. The solution was cooled to rt. The solvent was removed In vacuo. $CH_2Cl_2$ and silica gel were added. Purification by column chromatography (ISCO CombiFlash Rf, absorbed on silica gel, EtOAc in Cyclohexane 0-35%) afforded benzyl (2S)-2-((tert-butoxycarbonyl)amino)-3-(3-(4-((3-fluoro-5-(1-(tetrahydro-2H-pyran-2-yl)-1H-pyrazol-5-yl)pyridin-2-yl)oxy)phenyl)-1,2,4-oxadiazol-5-yl)propanoate (270 mg, only 67% pure) (7.5). UPLC retention time 1.40 min (Method A). MS/ESI+685.4 [M+H]$^+$. $R_f$(Cyclohexane/EtOAc, 1:2)=0.43.

Step e) tert-butyl ((2S)-1-(3-(4-((3-fluoro-5-(1-(tetrahydro-2H-pyran-2-yl)-1H-pyrazol-5-yl)pyridin-2-yl)oxy) phenyl)-1,2,4-oxadiazol-5-yl)-3-hydroxypropan-2-yl)carbamate (7.6). To a 10 mL two-necked cone shaped flask equipped with a magnetic stir bar, rubber septum and gas inlet was added benzyl (2S)-2-((tert-butoxycarbonyl) amino)-3-(3-(4-((3-fluoro-5-(1-(tetrahydro-2H-pyran-2-yl)-1H-pyrazol-5-yl)pyridin-2-yl)oxy)phenyl)-1,2,4-oxadiazol-5-yl)propanoate (7.5) (0.134 g, 0.196 mmol) (please note: starting material not pure ca. 67% pure). The vial was evacuated and backfilled with Ar three times. THF (1 ml) was added and the colorless solution was cooled to 0'C. $LiBH_4$ (0.021 g, 0.979 mmol) was added in one portion and the suspension was stirred for 45 minutes. The reaction mixture was quenched with MeOH and the solvents removed in vacuo. Purification by column chromatography (ISCO CombiFlash Rf, absorbed on silica gel, EtOAc in cyclohexane 0-65%). Second purification by column chromatography (gradient: EtOAc in cyclohexane 20-55%) only marginally improved purity. tert-butyl ((2S)-1-(3-(4-((3-fluoro-5-(1-(tetrahydro-2H-pyran-2-yl)-1H-pyrazol-5-yl) pyridin-2-yl)oxy)phenyl)-1,2,4-oxadiazol-5-yl)-3-hydroxypropan-2-yl)carbamate (48.9 mg, 43%) (7.6).

UPLC retention time 1.16 min (Method A). MS/ESI+ 581.4 [M+H]$^+$. $R_f$(Cyclohexane/EtOAc, 1:2)=0.48.

Step e) tert-butyl ((2S)-1-(3-(4-((3-fluoro-5-(1-(tetrahydro-2H-pyran-2-yl)-1H-pyrazol-5-yl)pyridin-2-yl)oxy) phenyl)-1,2,4-oxadiazol-5-yl)-3-hydroxypropan-2-yl)carbamate (Example 7). To a 10 mL one-necked pear shaped flask equipped with a magnetic stir bar was added tert-butyl ((2S)-1-β-(4-((3-fluoro-5-(1-(tetrahydro-2H-pyran-2-yl)-1H-pyrazol-5-yl)pyridin-2-yl)oxy)phenyl)-1,2,4-oxadiazol-5-yl)-3-hydroxypropan-2-yl)carbamate (7.6). (48.9 mg, 0.084 mmol), DCM (0.800 mL) and TFA (33 μl, 0.428 mmol). The colorless solution was stirred for 5 days. LC-MS analysis revealed rapid consumption of the starting material: cleavage of THP ether was fast. However, Boc-deprotection was sluggish as expected. Equilibrium reached after 4 days. The solvent and acid were removed in vacuo. Purification by column chromatography (ISCO CombiFlash Rf, absorbed on silica gel, MeOH in CH2Cl2 0-10-15%) afforded tert-butyl ((2S)-1-(3-(4-((3-fluoro-5-(1-(tetrahydro-2H-pyran-2-yl)-1H-pyrazol-5-yl)pyridin-2-yl)oxy)phenyl)-1,2,4-oxadiazol-5-yl)-3-hydroxypropan-2-yl)carbamate (10.9 mg, 24%) (Example 7) as a cloudy oil. UPLC retention time 0.65 min (Method A). ¹H NMR (400 MHz, CDCl₃) δ=ppm 8.28 (d, J=1.8 Hz, 1H), 8.05 (d, J=8.7 Hz, 2H), 7.90 (dd, J=10.5, 1.8 Hz, 1H), 7.57 (d, J=2.1 Hz, 1H), 7.24 (d, J=8.7 Hz, 2H), 6.54 (d, J=1.9 Hz, 1H), 3.90 (dd, J=11.9, 3.3 Hz, 1H), 3.87-3.78 (m, 1H), 3.73 (dd, J=12.0, 5.7 Hz, 1H), 3.32 (dd, J=6.7, 4.5 Hz, 2H). MS/ESI+397.2 [M+H]⁺.

Example 8 (R)-2-amino-3-(3-(4-((5-chloro-3-fluoropyridin-2-yl)oxy)phenyl)-1,2,4-oxadiazol-5-yl)propan-1-ol

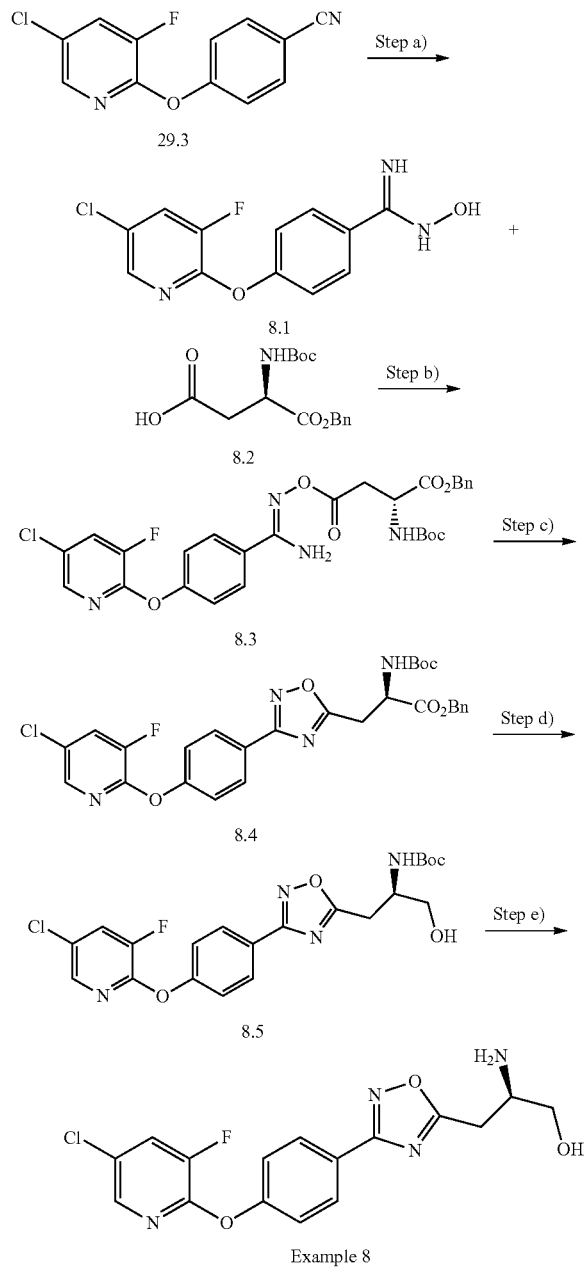

Step a) 4-((5-chloro-3-fluoropyridin-2-yl)oxy)-N-hydroxybenzimidamide (8.1). To a 100 mL one-necked pear shaped flask equipped with a magnetic stir bar and a condenser (air) was added 4-((5-chloro-3-fluoropyridin-2-yl)oxy)benzonitrile (29.3) (2.82 g, 11.34 mmol), NaHCO₃ (4.76 g, 56.7 mmol), hydroxylamine hydrochloride (3.94 g, 56.7 mmol), ethanol (40 ml) and Water (15 ml) (caution: gas formation). The white suspension was heated to 85° C. and stirred for 100 minutes. It was then cooled to rt. EtOH was removed in vacuo. Water/EtOAc were added and the aqueous phase was extracted twice with EtOAc. The organic layers were washed with brine, combined and dried over Na₂SO₄. LC-MS and 1H NMR analysis revealed high purity of the obtained white solid 4-((5-chloro-3-fluoropyridin-2-yloxy)-N-hydroxybenzimidamide (3.18 g, 97%) (8.1). Therefore, no further purification was required. UPLC retention time 0.73 min (Method A). ¹H NMR (400 MHz, DMSO-d6) δ=ppm 9.62 (s, 1H), 8.23 (dd, J=9.9, 1.9 Hz, 1H), 8.06 (d, J=2.0 Hz, 1H), 7.71 (d, J=8.7 Hz, 2H), 7.20 (d, J=8.6 Hz, 2H), 5.82 (s, 2H). MS/ESI+282.2, 284.2.

Step b) benzyl (R,Z)-4-(((amino(4-((5-chloro-3-fluoropyridin-2-yl)oxy)phenyl)methylene)-amino)oxy-2-((tert-butoxycarbonyl)amino)-4-oxobutanoate (8.3). To a 50 mL one-necked round bottom flask equipped with a magnetic stir bar was added 405-chloro-3-fluoropyridin-2-yl)oxy)-N-hydroxybenzimidamide (8.1) (0.600 g, 2.130 mmol), Boc-D-Asp-OBzl (8.2) (1.033 g, 3.20 mmol, [CAS: 92828-64-3]), HATU (1.215 g, 3.20 mmol), THF (10.0 ml) and DMF (5.0 ml). After addition of DIPEA (0.558 ml, 3.20 mmol) to the white suspension, it immediately turned yellow and the particles slowly dissolved. The yellow solution was stirred for 17.5 hours at rt. THF was removed in vacuo. Sat. aq. NaHCO₃ solution and EtOAc were added and the aqueous phase was extracted twice with EtOAc. The organic layers were washed with ca. 0.1M aq. HCl, brine, combined and dried over Na₂SO₄. Purification by column chromatography (ISCO CombiFlash Rf, absorbed on silica gel, EtOAc in cyclohexane 15-40%) afforded benzyl (R,Z)-4-(((amino(4-((5-chloro-3-fluoropyridin-2-yl)oxy)phenyl)-methylene)-amino)oxy)-2-((tert-butoxycarbonyl)amino)-4-oxobutanoate (1.35 g, 97%) (8.3) as a white solid. UPLC retention time 1.25 min (Method A). ¹H NMR (400 MHz, CDCl₃) δ=ppm 7.92 (d, J=2.1 Hz, 1H), 7.75 (d, J=8.7 Hz, 2H), 7.56 (dd, J=9.0, 2.1 Hz, 1H), 7.36 (s, 5H), 7.22 (d, J=8.7 Hz, 2H), 5.23 (d, J=2.0 Hz, 2H), 4.82-4.74 (m, 1H), 3.16 (qd, J=17.0, 4.9 Hz, 2H), 1.45 (s, 9H). MS/ESI+587.4, 589.4. R_r (cyclohexane/EtOAc, 2:1)=0.23.

Step c) benzyl (R)-2-((tert-butoxycarbonyl)amino)-3-(3-(4((5-chloro-3-fluoropyridin-2-yl)oxy)phenyl)-1,2,4-oxadiazol-5-yl)propanoate (8.4). To a 20 mL microwave vial equipped with a magnetic stir bar was added benzyl (R,Z)-4-(((amino(4-((5-chloro-3-fluoropyridin-2-yl)oxy)phenyl)-methylene-amino)oxy-2-((tert-butoxycarbonyl)amino)-4-oxobutanoate (8.3) (1.34 g, 2.055 mmol) and THF (13.0 ml). The vial was sealed and the reaction mixture was stirred for 2.5 days at 100*C. The obtained orange solution was cooled to rt and the solvent removed in vacuo. Purification by column chromatography (ISCO CombiFlash Rf, absorbed on silica gel, EtOAc in cyclohexane 0-18%) afforded benzyl (R)-2-((tert-butoxycarbonyl)amino-3-(3-(4-((5-chloro-3-fluoropyridin-2-yl)oxy)phenyl)-1,2,4-oxadiazol-5-yl)propanoate (0.806 g, 68.9%) (8.4) as a colorless, viscous oil. UPLC retention time 1.40 min (Method A). ¹H NMR (400 MHz, CDCl₃) δ=ppm 8.05 (d, J=8.7 Hz, 2H), 7.93 (d, J=2.2 Hz, 1H), 7.55 (dd, J=9.0, 2.2 Hz, 1H), 7.28 (s, 5H), 7.25 (d, J=8.4 Hz, 2H), 5.58 (d, J=7.8 Hz, 1H), 5.25-5.13 (m, 2H), 4.90 (d, J=7.3 Hz, 1H), 3.51 (qd, J=16.2, 5.0 Hz, 2H), 1.44 (s, 9H). MS/ESI+569.3, 571.3. R$_f$ (cyclohexane/EtOAc, 5:1) =0.33.

Step d) tert-butyl (R)-(1-(3-(4-((5-chloro-3-fluoropyridin-2-yl)oxy)phenyl)-1,2,4-oxadiazol-5-yl)-3-hydroxypropan-2-yl)carbamate (8.5). To a 25 mL two-necked round bottom flask equipped with a magnetic stir bar, rubber septum and gas inlet was added benzyl (R)-2-((tert-butoxycarbonylamino)-3-(3-(4-((5-chloro-3-fluoropyridin-2-yl)oxy)phenyl)-1,2,4-oxadiazol-5-yl)propanoate (8.4) (489 mg, 0.859 mmol). The flask was evacuated and backfilled with Ar four times. THF (8.0 ml) was added and the colorless solution was cooled to 0° C. After addition of LiBH4 (94 mg, 4.30 mmol), the suspension was stirred for 90 minutes at 0° C. Full conversion of the starting material within 1 hour. The reaction was quenched with MeOH. The solvents were then removed in vacuo. Purification by column chromatography (ISCO CombiFlash Rf, absorbed on silica gel, EtOAc in cyclohexane 20-46%) afforded tert-butyl (R)-(1-(3-(4-((5-chloro-3-fluoropyridin-2-yl)oxy)phenyl)-1,2,4-oxadiazol-5-yl)-3-hydroxypropan-2-yl)carbamate (0.240 g, 60.1%) (8.5) as a colorless, viscous oil. UPLC retention time 1.17 min (Method A). $^1$H NMR (400 MHz, CDCl$_3$) δ ppm 8.12 (d, J=8.8 Hz, 2H), 7.93 (d, J=2.2 Hz, 1H), 7.55 (dd, J=9.0, 2.2 Hz, 1H), 7.27 (d, J=8.7 Hz, 2H), 5.21 (s, 1H), 4.24-4.16 (s, 1H), 3.81 (hept, J=5.7, 5.1 Hz, 2H), 3.30 (d, J=5.9 Hz, 2H), 1.44 (s, 9H). MS/ESI+465.3, 467.3. R$_f$ (cyclohexane/EtOAc, 1:1)=0.43.

Step e) (R)-2-amino-3-(3-(4-((5-chloro-3-fluoropyridin-2-yl)oxy)phenyl)-1,2,4-oxadiazol-5-yl)propan-1-ol (Example 8). To a 50 mL one-necked round bottom flask equipped with a magnetic stir bar was added tert-butyl (R)-(1-(3-(4-((5-chloro-3-fluoropyridin-2-yl)oxy)phenyl)-1,2,4-oxadiazol-5-yl)-3-hydroxypropan-2-yl)carbamate (8.5) (227 mg, 0.488 mmol), dioxane (5.0 mL) and aq. HCl (5.0 ml, 10.00 mmol). The cloudy solution was stirred for 18 hours at rt. 2M aq. NaOH solution (5.0 ml, 10.0 mmol, 20.48 equiv) was added and dioxane was removed in vacuo. The obtained clear aqueous phase was basified with more 2M aq. NaOH (pH$_{final}$>10); a white solid precipitated. EtOAc was added and the aqueous phase was extracted twice with EtOAc. The organic layers were washed with brine, combined and dried over Na$_2$SO$_4$. Purification by column chromatography (ISCO CombiFlash Rf, absorbed on silica gel, MeOH in CH$_2$Cl$_2$ 0-10%) afforded (R)-2-amino-3-(3-(4-((5-chloro-3-fluoropyridin-2-yl)oxy)phenyl)-1,2,4-oxadiazol-5-yl)propan-1-ol (131 mg, 72.1%) (Example 8) as a colorless oil which crystallized in the freezer overnight. UPLC retention time 0.76 min (Method A). $^1$H NMR (400 MHz, CDCl$_3$) δ=ppm 8.13 (d, J=8.7 Hz, 2H), 7.93 (d, J=2.2 Hz, 1H), 7.55 (dd, J=9.0,2.2 Hz, 1H), 7.27 (d, J=8.6 Hz, 2H), 3.71 (dd, J=10.5, 4.3 Hz, 1H), 3.56 (dd, J=10.6, 6.2 Hz, 1H), 3.53-3.45 (m, 1H), 3.14 (dd, J=15.6, 4.7 Hz, 1H), 3.00 (dd, J=15.6, 8.1 Hz, 1H). MS/ESI+365.3, 367.3.

Example 9 tert-butyl (S)-(1-(3-(3-((5-(1H-pyrazol-5-yl)pyridin-2-yl)oxy)phenyl)-1,2,4-oxadiazol-5-yl)-3-hydroxypropan-2-yl)carbamate

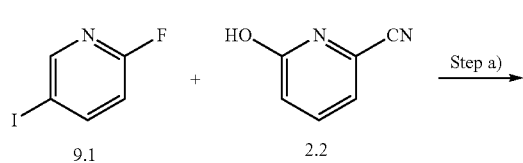

9.1    2.2

-continued

Step b)

9.3

2.5

Step c)
9.2

9.4

9.5

Step d)

9.6

Step e)

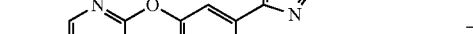

9.7

Step f)

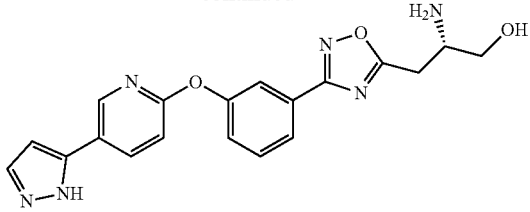

Example 9

Step a) 3-((5-iodopyridin-2-yl)oxy)benzonitrile (9.2). To a 250 mL one-necked pear shaped flask equipped with a magnetic stir bar and reflux condenser was added 2-fluoro-5-iodopyridine (9.1) (1.47 g, 6.59 mmol), 3-cyanophenol (2.2) (0.864 g, 7.25 mmol), K$_2$CO$_3$ (1.822 g, 13.18 mmol) and DMF (50.0 ml). The suspension was stirred for 15 hours at 100° C. A brown suspension was obtained. Water and EtOAc were added. The aqueous phase was extracted twice with EtOAc. The organic layers were washed with brine, combined and dried over Na$_2$SO$_4$. Concentration in vacuo afforded a light brown oil which slowly crystallized at rt. Purification by column chromatography (ISCO CombiFlash Rf, absorbed on silica gel, EtOAc in Cyclohexane 0-6% to 7.7%) yielded 3-((5-iodopyridin-2-yl)oxy)benzonitrile (1.95 g, 92%) (9.2) as a white solid. UPLC retention time 1.15 min (Method A). $^1$H NMR (400 MHz, CDCl$_3$) δ=ppm 8.35 (d, J=2.1 Hz, 1H), 7.98 (dd, J=8.6,2.3 Hz, 1H), 7.50 (d, J=5.0 Hz, 2H), 7.47-7.43 (m, 1H), 7.38 (td, J=4.7, 2.4 Hz, 1H), 6.84 (d, J=8.6 Hz, 1H). MS/ESI+323.1 [M+H]$^+$.

Step b) (Z)-N'-hydroxy-3-((5-iodopyridin-2-yl)oxy)benzimidamide (9.3). To a 50 mL one-necked pear shaped flask equipped with a magnetic stir bar was added 3-((5-iodopyridin-2-yl)oxy)benzonitrile (9.2) (1.95 g, 6.05 mmol), hydroxylamine hydrochloride (2.103 g, 30.3 mmol), NaHCO$_3$(2.54 g, 30.3 mmol) and ethanol (20.0 ml)/Water (10.0 ml). The white suspension was heated to 85° C. and stirred for 90 minutes. The reaction mixture was cooled to rt. EtOH was removed in vacuo. Water and EtOAc were added and the aqueous phase was extracted twice with EtOAc. The organic layers were washed with brine, combined and dried over Na$_2$SO$_4$. Concentration in vacuo afforded (Z)-N'-hydroxy-3-((5-iodopyridin-2-yl)oxy)benzimidamide (1.87 g, 86%) (9.3) as a white solid. UPLC retention time 0.77 min (Method A). $^1$H NMR (400 MHz, CDCl$_3$) δ=ppm 9.67 (s, 1H), 8.37 (d, J=2.2 Hz, 1H), 8.16 (dd, J=8.6, 2.4 Hz, 1H), 7.54 (d, J=7.9 Hz, 1H), 7.43-7.38 (m, 2H), 7.14 (dd, J=8.0, 1.7 Hz, 1H), 6.95 (d, J=8.6 Hz, 1H), 5.82 (s, 2H). MS/ESI+ 356.1 [M+H]$^+$.

Step c) benzyl (S)-2-((tert-butoxycarbonyl)amino)-3-(3-(3-((5-iodopyridin-2-yl)oxy)phenyl)-1,2,4-oxadiazol-5-yl) propanoate (9.4). To a 20 mL microwave vial equipped with a magnetic stir bar was added (Z)-N'-hydroxy-3-((5-iodopyridin-2-yl)oxy)benzimidamide (9.3) (0.852 g, 2.375 mmol), Boc-Asp(Su)-OBzl (2.5) (1.048 g, 2.494 mmol) and THF (13.0 ml). The colorless solution was stirred for 3 days at 100° C. Volatiles were removed in vacuo. Purification by column chromatography (ISCO CombiFlash Rf, absorbed on silica gel, EtOAc in cyclohexane 0-15.9%) afforded benzyl (S)-2-((tert-butoxycarbonyl)amino)-3-(3-(3-((5-iodopyridin-2-yl)oxy)phenyl)-1,2,4-oxadiazol-5-yl)propanoate (1.44 g, 93%) (9.4). UPLC retention time 1.44 min (Method A). $^1$H NMR (400 MHz, CDCl$_3$) δ=ppm 8.35 (d, J=2.1 Hz, 1H), 7.95 (dd, J=8.6, 2.3 Hz, 1H), 7.86 (d, J=7.8 Hz, 1H), 7.78 (s, 1H), 7.50 (t, J=8.0 Hz, 1H), 7.29-7.26 (m, 6H), 6.82 (d, J=8.6 Hz, 1H), 5.55 (d, J=7.5 Hz, 1H), 5.24-5.12 (m, 2H), 4.91-4.83 (m, 1H), 3.50 (qd, J=16.2, 5.0 Hz, 2H), 1.43 (s, 9H). MS/ESI+643.3 [M+H]$^+$.

Step d) benzyl (S)-3-(3-(3-((5-(1H-pyrazol-5-yl)pyridin-2-yl)oxy)phenyl)-1,2,4-oxadiazol-5-yl)-2-((tert-butoxycarbonyl)amino)propanoate (9.6). To a 100 mL two-necked round bottom flask equipped with a magnetic stir bar, gas inlet and rubber septum was added benzyl (S)-2-((tert-butoxycarbonyl)amino)-3-(3-(3-((5-iodopyridin-2-yl)oxy) phenyl)-1,2,4-oxadiazol-5-yl)propanoate (9.4) (1.41 g, 2.195 mmol), dioxane (20.0 ml)/Water (10.0 ml), K$_3$PO$_4$ (1.398 g, 6.58 mmol) and 4-pyrazoleboronic acid pinacol ester (9.5) (0.459 g, 2.247 mmol, [CAS: 844501-71-9]). The suspension was purged with Ar for 10 minutes. Pd(dtbpf)Cb (0.143 g, 0.219 mmol) was then added and the reaction mixture was stirred for 25 minutes at 70° C. LC-MS analysis revealed full conversion of the starting material within 25 minutes, however the product was mostly saponified. The reaction mixture was allowed to cool to rt. Volatiles were removed in vacuo. EtOAc, water and 2M aq. HCl (10 mL) was added. The aqueous phase was extracted twice with EtOAc. The organic layers were then washed with ca. 0.1 M aq. NaOH solution and brine, combined and dried over sodium sulfate. Purification by column chromatography (ISCO CombiFlash Rf, absorbed on silica gel, EtOAc in cyclohexane 20-50%) afforded benzyl (S)-3-(3 (3-((5-(1H-pyrazol-5-yl pyridin-2-yl)oxy)phenyl)-1,2,4-oxadiazol-5-yl)-2-((tert-butoxycarbonyl)amino)propanoate (325.4 mg, 25.4%) (9.6). UPLC retention time 1.22 min (Method A). $^1$H NMR (400 MHz, CDCl$_3$) δ=ppm 8.59 (d, J=2.2 Hz, 1H), 8.16 (dd, J=8.5, 2.3 Hz, 1H), 7.89-7.81 (m, 2H), 7.64 (d, J=2.3 Hz, 1H), 7.51 (t, J=8.0 Hz, 1H), 7.35-7.30 (m, 1H), 7.27 (s, 5H), 7.03 (d, J=8.5 Hz, 1H), 6.60 (d, J=2.3 Hz, 1H), 5.57 (d, J=7.8 Hz, 1H), 5.24-5.11 (m, 2H), 4.91-4.83 (m, 1H), 3.50 (qd, J=16.2, 4.7 Hz, 2H), 1.42 (s, 9H). MS/ESI+ 583.4 [M+H]$^+$.

Step e) tert-butyl (S)-(1-(3-(3-((5-(1H-pyrazol-5-yl)pyridin-2-yl)oxy)phenyl)-1,2,4-oxadiazol-5-yl)-3-hydroxypropan-2-yl)carbamate (9.7). To a 25 mL two-necked pear shaped flask equipped with a magnetic stir bar, gas inlet and rubber septum was added benzyl (S)-3-(3-(3-((5-(1H-pyrazol-5-yl)pyridin-2-yl)oxy)phenyl)-1,2,4-oxadiazol-5-yl)-2-((tert-butoxycarbonyl)amino)propanoate (9.6) (229 mg, 0.393 mmol). The flask was evacuated and backfilled with Ar five times. Anhydrous THF (4.0 mL) was added and the colorless solution was cooled to 0'C. LiBH$_4$ (42.6 mg, 1.956 mmol) was then added in one portion and the reaction mixture was stirred for 90 minutes. The ice bath was removed and the suspension was stirred for additional 30 minutes. The reaction was quenched with MeOH. The rm was stored in the freezer over night. Volatiles were removed in vacuo. Purification by column chromatography (ISCO CombiFlash Rf, absorbed on silica gel, EtOAc in cyclohexane 40-70-80-85%). Due to impurities, the product was purified again by column chromatography (ISCO CombiFlash Rf, absorbed on silica gel, EtOAc in cyclohexane 55-68-70%) to afford tert-butyl (S)-(1-(3-(3-((5 (1H-pyrazol-5-yl)pyridin-2-yl)oxy)phenyl)-1,2,4-oxadiazol-5-yl)-3-hydroxypropan-2-yl)carbamate (86.3 mg, 44.5%) (9.7) as a colorless oil. UPLC retention time 0.92 min (Method A). $^1$H NMR (400 MHz, CDCl$_3$) δ=ppm 8.58 (d, J=2.4 Hz, 1H), 8.15 (dd, J=8.5, 2.4 Hz, 1H), 7.92 (d, J=7.8 Hz, 1H), 7.87 (d, J=2.0 Hz, 1H), 7.64 (d, J=2.3 Hz, 1H), 7.52 (t, J=8.0 Hz, 1H), 7.32 (dd, J=7.8, 2.0 Hz, 1H), 7.03 (d, J=8.5 Hz, 1H), 6.60 (d, J=2.2 Hz, 1H), 5.22 (d, J=6.8 Hz, 1H), 4.22-4.15 (m, 1H), 3.84-3.74 (m, 2H), 3.28 (d, J=5.9 Hz, 2H), 1.42 (s, 9H). MS/ESI+479.4 [M+H]$^+$.

Step f) (S)-3-(3-(3-((5-(1H-pyrazol-5-yl)pyridin-2-yl)oxy)phenyl)-1,2,4-oxadiazol-5-yl)-2-aminopropan-1-ol (Example 9). To a 12 mL one-necked pear shaped flask equipped with a magnetic stir bar was added tert-butyl (S)-(1-(3-(3-((5-(1H-pyrazol-5-yl)pyridin-2-yl)oxy)phenyl)-1,2,4-oxadiazol-5-yl)-3-hydroxypropan-2-yl)carbamate (9.7) (86.3 mg, 0.180 mmol) and dioxane (2.0 ml) at rt. After addition of HCl in Dioxane (4 M solution) (0.451 mL, 1.804 mmol), the reaction mixture immediately turned into a white suspension. It was stirred for 17.5 hours at rt. The solvent was removed in vacuo. EtOAc and 2M aq. NaOH solution was added (until pH >10). The aqueous phase was extracted twice with EtOAc. The organic layers were washed with brine, combined and dried over $Na_2SO_4$. Purification by RP $C_{18}$ column chromatography (ISCO CombiFlash Rf, liquid injection, MeCN in water 10-35%, fractions 21-27). The fractions were combined and MeCN was removed in vacuo. 2M aq. NaOH solution (ca. 5 mL) was added and the aqueous phase was extracted twice with EtOAc. The organic layers were washed with brine, combined and dried over $Na_2SO_4$. Concentration in vacuo afforded (S)-3-(3-(3-((5-(1H-pyrazol-5-yl)pyridin-2-yl)oxy)phenyl)-1,2,4-oxadiazol-5-yl)-2-aminopropan-1-ol (50.1 mg, 72.7%) (Example 9) as a white foam. UPLC retention time 0.60 min (Method A). $^1$H NMR (400 MHz, $CDCl_3$) δ=ppm 8.59 (d, J=2.3 Hz, 1H), 8.14 (dd, J=8.5, 2.4 Hz, 1H), 7.93 (d, J=7.8 Hz, 1H), 7.90-7.87 (m, 1H), 7.62 (d, J=2.4 Hz, 1H), 7.52 (t, J=8.0 Hz, 1H), 7.32 (dd, J=8.1, 1.5 Hz, 1H), 7.02 (d, J=8.5 Hz, 1H), 6.59 (d, J=2.4 Hz, 1H), 3.70 (dd, J=10.6, 4.3 Hz, 1H), 3.55 (dd, J=10.6, 6.3 Hz, 1H), 3.48 (ddd, J=10.8, 7.2, 4.5 Hz, 1H), 3.13 (dd, J=15.6, 4.7 Hz, 1H), 2.99 (dd, J=15.6, 8.1 Hz, 1H). MS/ESI+379.3 [M+H]$^+$.

Example 10 (S)-2-amino-3-(3-(3-((5-(trifluoromethyl)pyridin-2-yl)oxy)phenyl)-1,2,4-oxadiazol-5-yl)propan-1-ol

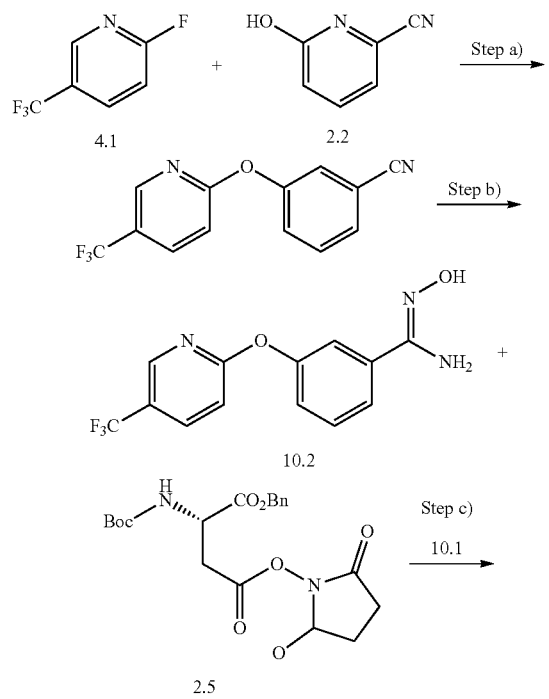

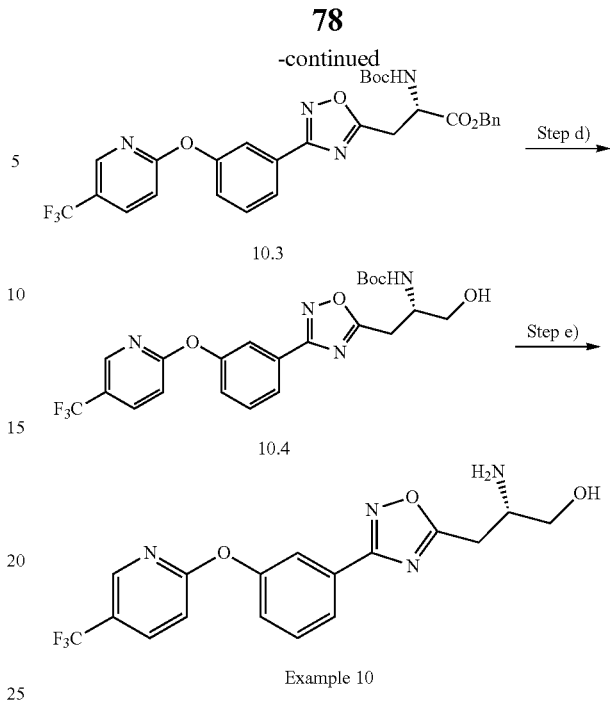

Example 10

Step a) 3-((5-(trifluoromethyl)pyridin-2-yl)oxy)benzonitrile (10.1). To a 250 mL one-necked pear shaped flask equipped with a magnetic stir bar and a condenser (air) was added 2-fluoro-5-(trifluoromethyl)pyridine (4.1) (1.30 g, 7.87 mmol), 3-cyanophenol (2.2) (1.032 g, 8.66 mmol), $K_2CO_3$ (2.177 g, 15.75 mmol) and DMF (30.0 ml). The suspension was heated to 65° C. and stirred for 19 hours. Water/EtOAc were added. The aqeuous phase was extracted twice with EtOAc. The organic layers were washed with brine, combined and dried over $Na_2SO_4$. Purification by column chromatography (ISCO CombiFlash Rf, absorbed on silica gel, EtOAc in cyclohexane 0-10β6) afforded 34(5-(trifluoromethyl)pyridin-2-yl)oxy)benzo-nitrile (1.97 g, 95%) (10.1). UPLC retention time 1.11 min (Method A). $^1$H NMR (400 MHz, $CDCl_3$) δ=ppm 8.44-8.41 (m, 1H), 7.97 (dd, J=8.6, 2.4 Hz, 1H), 7.57-7.53 (m, 2H), 7.51-7.48 (m, 1H), 7.43 (tq, J=5.4, 2.7 Hz, 1H), 7.10 (d, J=8.6 Hz, 1H). MS/ESI+265.0 [M+H]$^+$.

Step b) (Z)-N'-hydroxy-3-((5-(trifluoromethyl)pyridin-2-yl)oxy)benzimidamide (10.2). To a 100 mL one-necked pear shaped flask equipped with a magnetic stir bar and a condenser (air) was added 3-((5-(trifluoromethyl)pyridin-2-yl)oxy)benzo-nitrile (10.1) (1.93 g, 7.30 mmol), hydroxylamine hydrochloride (2.54 g, 36.5 mmol), $NaHCO_3$(3.07 g, 36.5 mmol) and ethanol (30.0 ml)/Water (10.0 ml). The white suspension was stirred for 80 minutes at 85° C. The reaction mixture was stored in the freezer over the weekend. EtOH was removed in vacuo. EtOAc and water were added. The aqeuous phase was extracted twice with EtOAc. The organic layers were washed with brine, combined and dried over $Na_2SO_4$. Concentration in vacuo and drying under high-vacuum afforded (Z)-N'-hydroxy-3-((5-(trifluoromethyl)pyridin-2-yl)oxy)benzimidamide (2.25 g, 100%) (10.2) as a brown sticky foam. UPLC retention time 0.80 min (Method A). $^1$H NMR (400 MHz, DMSO-d6) δ=ppm 9.69 (s, 1H), 8.57 (s, 1H), 8.24 (dd, J=8.7, 2.5 Hz, 1H), 7.60 (d, J=7.9 Hz, 1H), 7.50-7.41 (m, 2H), 7.26 (d, J=8.7 Hz, 1H), 7.21 (dd, J=8.0, 1.7 Hz, 1H), 5.84 (s, 2H). MS/ESI+298.2 [M+H]$^+$.

Step c) benzyl (S)-2-((tert-butoxycarbonyl)amino)-3-(3-(3-((5-(trifluoromethyl)pyridin-2-yl)oxy)phenyl)-1,2,4-oxadiazol-5-yl)propanoate (10.3). To a 20 mL microwave vial equipped with a magnetic stir bar was added (Z)-N'-hydroxy-3-((5-(trifluoromethyl)pyridin-2-yl)oxy)benzimidamide (10.2) (758 mg, 2.55 mmol), Boc Asp(Su)-OBzl (2.5) (1179 mg, 2.81 mmol) and THF (13.0 ml). The pale brown solution was stirred for 10 minutes at rt and then stirred for 17.5 hours at 110'C. The solvent was removed in vacuo. Dichloromethane and silica gel were added. Purification by column chromatography (ISCO CombiFlash Rf, absorbed on silica gel, EtOAc in cyclohexane 0-18%) afforded benzyl (S)-2-((tert-butoxycarbonyl)amino)-3-(3-(3-((5-(trifluoromethyl)pyridin-2-yl)oxy)phenyl)-1,2,4-oxadiazol-5-yl)propanoate (1.40 g, 94%) (10.3) as a colorless, highly viscous oil. UPLC retention time 1.41 min (Method A). $^1$H NMR (400 MHz, CDCl$_3$) δ=ppm 8.45-8.42 (m, 1H), 7.96-7.89 (m, 2H), 7.83-7.80 (m, 1H), 7.54 (t, J=8.0 Hz, 1H), 7.31 (ddd, J=8.2, 2.4, 0.9 Hz, 1H), 7.29-7.26 (m, 5H), 7.08 (d, J=8.7 Hz, 1H), 5.55 (d, J=7.8 Hz, 1H), 5.25-5.11 (m, 2H), 4.92-4.84 (d, J=7.3 Hz, 1H), 3.51 (qd, J=16.2, 5.0 Hz, 2H), 1.42 (s, 9H). MS/ESI+585.3 [M+H]$^+$.

Step d) tert-butyl (S)-(1-hydroxy-3-(3-(3-((5-(trifluoromethyl)pyridin-2-yl)oxy)phenyl)-1,2,4-oxadiazol-5-yl)propan-2-yl)carbamate (10.4). To a 25 mL two-necked round bottom flask equipped with a magnetic stir bar, rubber septum and gas inlet was added benzyl (S)-2-((tert-butoxycarbonyl)amino)-3-(3-(3-((5-(trifluoromethyl)pyridin-2-yl)oxy)phenyl(1,2,4-oxadiazol-5-yl)propanoate (10.3) (550 mg, 0.941 mmol). The flask was evacuated and backfilled with Ar five times. THF (6.0 ml) was added and the colorless solution was cooled to 0° C. LiBH4 (41.0 mg, 1.882 mmol) was then added and the reaction mixture was stirred for 80 minutes. More LiBH4 (20.5 mg, 0.941 mmol) was added after 50 minutes. The yellow suspension was quenched with MeOH. Volatiles were then removed in vacuo. Purification by column chromatography (ISCO CombiFlash Rf, absorbed on silica gel, EtOAc in cyclohexane 25-50%) afforded tert-butyl (S)-(1-hydroxy-3-(3-(3-((5-(trifluoromethyl)pyridin-2-yl)oxy)phenyl)-1,2,4-oxadiazol-5-yl)propan-2-yl)carbamate (298 mg, 65.9%) (10.4). a sticky, colorless oil. UPLC retention time 1.17 min (Method A). NMR (400 MHz, CDCl$_3$) δ=ppm 8.44-8.41 (m, 1H), 7.96 (d, J=7.8 Hz, 1H), 7.92 (dd, J=8.7,2.4 Hz, 1H), 7.88-7.82 (m, 1H), 7.54 (t, J=8.0 Hz, 1H), 7.30 (ddd, J=8.1, 2.3, 0.8 Hz, 1H), 7.06 (d, J=8.7 Hz, 1H), 5.28 (d, J=7.7 Hz, 1H), 4.23-4.12 (m, 1H), 3.76 (q, J=6.5, 5.2 Hz, 2H), 3.27 (d, J=5.9 Hz, 2H), 1.40 (s, 9H). MS/ESI+481.2 [M+H]$^+$.

Step e) (S)-2-amino-3-(3-(3-((5-(trifluoromethyl)pyridin-2-yl)oxy)phenyl)-1,2,4-oxadiazol-5-yl)propan-1-ol (Example 10). To a 25 mL one-necked pear shaped flask equipped with a magnetic stir bar was added tert-butyl (S)-(1-hydroxy-3-(3-(3-((5-(trifluoromethyl)pyridin-2-yl)oxy)phenyl)-1,2,4-oxadiazol-5-yl)propan-2-yl)carbamate (10.4) (297 mg, 0.618 mmol), dioxane (6.0 ml) and aq. HCl (6.0 ml, 12.00 mmol). The cloudy solution was stirred for 4 days at rt. Meanwhile, a colorless clear solution was obtained. 2M aq. NaOH solution (6.0 ml, 12.00 mmol) was added. Dioxane was removed in vacuo. EtOAc and approx. 02M aq. NaOH was added. The aqueous phase was extracted twice with EtOAc. The organic layers were washed with brine, combined and dried over Na$_2$SO$_4$. Purification by column chromatography (ISCO CombiFlash Rf, absorbed on silica gel, MeOH in CH$_2$Cl$_2$ 0-7.7%) afforded (S)-2-amino-3-(3-(3-((5-(trifluoromethyl)pyridin-2-yloxy)phenyl)-1,2,4-oxadiazol-5-yl)propan-1 of (184 mg, 78%) (Example 10) as a colorless oil which crystallized at rt to give a white solid. UPLC retention time 0.78 min (Method A). $^1$H NMR (400 MHz, CDCl$_3$) δ=ppm 8.37 (s, 1H), 7.91 (t, J=7.6 Hz, 2H), 7.81 (s, 1H), 7.51 (t, J=7.9 Hz, 1H), 7.27 (d, J=7.4 Hz, 1H), 7.03 (d. J=8.6 Hz, 1H), 3.70 (d, J=8.3 Hz, 1H), 3.59-3.45 (m, 2H), 3.16-3.09 (m, 2H). MS/ESI+381.2 [M+H]$^+$.

Example 11 (S)-2-amino-3-(3-(3-((R)-2,3-dihydro-[1,4]dioxin[2,3-b]pyridin-3-yl)phenyl)-1,2,4-oxadiazol-5-yl)propan-1-ol

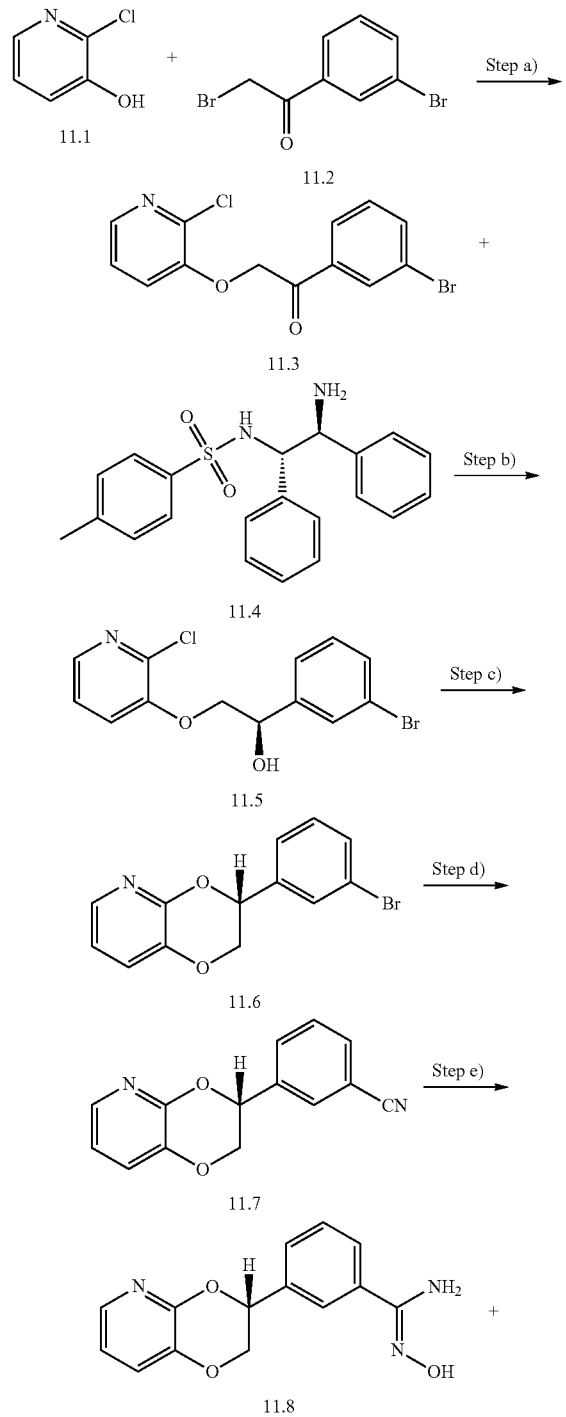

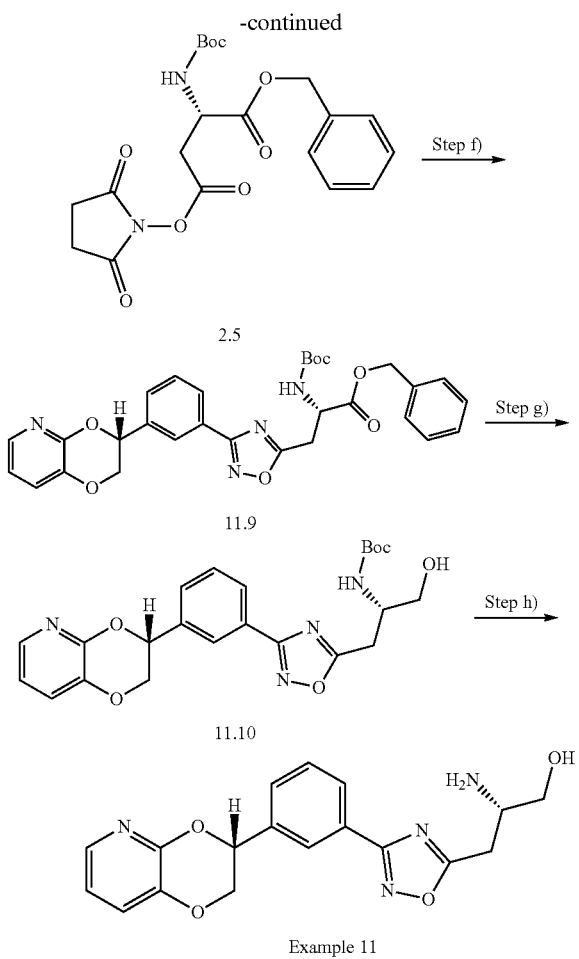

Example 11

Step a) 1-(3-bromophenyl)-2-((2-iodopyridin-3-yl)oxy)ethan-1-one (11.3). To a 1000 mL one-necked flask equipped with a magnetic stir bar was added 2-chloropyridin-3-ol (10.90 g, 82 mmol), 2-bromo-1-(3-bromophenyl)ethanone (23.38 g, 82 mmol), acetone (330 ml) and cesium carbonate (32.2 g, 99 mmol). The orange suspension was stirred for 16 hr at rt. The reaction mixture was filtered and the filter cake washed with cold acetone. The filtrate was concentrated in vacuo to give 33.31 g of crude material. This was taken up with ethyl acetate and washed with water and brine, dried over sodium sulfate, filtered and concentrated in vacuo yielding 29.8 g of a brown sticky mass. Chromatography over silicagel (cyclohexane/ethyl acetate) afforded 1-(3-bromophenyl)-2-((2-iodopyridin-3-yl)oxy)ethan-1-one (9.1 g, 23%) (11.3). UPLC retention time 1.07 min (Method A). $^1$H NMR (400 MHz, CHLOROFORM-d) δ=ppm ppm 5.34 (s, 2H) 7.14-7.21 (m, 2H), 7.41 (t, J=7.85 Hz, 1H), 7.78 (d, J=7.73 Hz, 1H), 7.95 (dt, J=7.82, 1.28 Hz, 1H), 8.07 (dd, J=4.28, 1.96 Hz, 1H), 8.16 (t, J=1.71 Hz, 1H). MS/ESI+326, 328, 330.

Step b) (R)-1-(3-bromophenyl)-2-((2-iodopyridin-3-yl)oxy)ethan-1-ol (11.5). To a 1000 mL 2-necked flask equipped with a magnetic stir bar and a thermometer was added 1-(3-bromophenyl)-2-((2-iodopyridin-3-yl)oxy)ethan-1-one (11.3) (5.22 g, 15.18 mmol) followed by DMF (67.3 ml). N-((1S,2S)-2-amino-1,2-diphenylethyl)-4-methylbenzenesulfonamide (11.4) (0.170 g, 0.456 mmol, [CAS: 167316-27-0], Strom Chemicals) and Cp°RhCl$_2$ dimer (CAS: 12354-85-7) (0.094 g, 0.152 mmol) were added. The reaction mixture was degassed with argon at 0° C. during 20 min. A formic acid-triethylamine complex 5:2 (4.66 ml, 11.16 mmol, [CAS:115077-13-1]) was added at 0° C. over 15 min. Stirring was continued at 0° C. for 50 min. The reaction mixture was then poured into water (230 ml) and extracted with ethyl acetate, washed with water and brine, dried over sodium sulfate, filtered and concentrated in vacuo affording (R)-1-(3-bromophenyl)-2-((2-iodopyridin-3-yl)oxy)ethan-1-ol (5.45 g, 100%) (11.5). This material was used in the next step without further purification. UPLC retention time 0.99 min (Method A). $^1$H NMR (400 MHz, CHLOROFORM-d) δ=ppm ppm 4.06 (dd, J=9.29, 8.31 Hz, 1H), 4.19 (dd, J=9.41, 3.42 Hz, 1H), 5.18 (dd, J=8.25, 3.36 Hz, 1H), 7.17-7.26 (m, 2H), 7.28-7.31 (m, 1H), 7.41 (d, J=7.70 Hz, 1H), 7.49 (d, J=7.95 Hz, 1H), 7.66 (s, 1H), 7.99-8.11 (m, 1H). MS/ESI+328, 330, 332.

Step c) (R)-3-(3-bromophenyl)-2,3-dihydro-[1,4]dioxino[2,3-b]pyridine (11.6). To a 500 mL 2-necked flask equipped with a magnetic stir bar and a reflux condensor was added (R)-1-(3-bromophenyl)-2-((2-iodopyridin-3-yl)oxy)ethan-1-ol (11.5) (5.45 g, 15.76 mmol) followed by DME (197 ml). KHMDS 1M in THF (15.95 ml, 15.95 mmol,[CAS: 40949-94-8]) was added dropwise at 60° C. under argon. The reaction mixture was stirred at this temperature for 1.5 hr. Additional KHMDS 1M in THF (3 ml) was added at 60° C. and stirring was continued for a further 60 min. The reaction mixture was quenched with water (100 ml) at rt and extracted with ethyl acetate, washed thoroughly with water and sat. aq. NH$_4$Cl solution and brine, dried over sodium sulfate, filtered and concentrated in vacuo. Chromatography on silicael (gradient: cyclohexane/ethyl acetate) afforded (R)-3-(3-bromophenyl)-2,3-dihydro-[1,4]dioxino[2,3-b]pyridine (2.95 g, 42.2%) (11.6). UPLC retention time 1.06 min (Method A). $^1$H NMR (400 MHz, DMSO-d$_6$) δ=ppm 4.16 (dd, J=11.62, 8.19 Hz, 1H), 4.49 (dd, J=11.55, 2.51 Hz, 1H), 5.49 (dd, J=8.01, 2.26 Hz, 1H), 7.00 (dd, J=7.82, 4.77 Hz, 1H), 7.37 (d, J=7.63 Hz, 1H), 7.42 (t, J=7.95 Hz, 1H), 7.52 (d, J=7.70 Hz, 1H), 7.61 (d, J=8.07 Hz, 1H), 7.72 (s, 1H), 7.81 (dd, J=4.77, 1.34 Hz, 1H). MS/ESI+292, 294.

Step d) (R)-3-(2,3-dihydro-[1,4]dioxino[2,3-b]pyridin-3-yl)benzonitrile (11.7). To a 100 mL 2-necked flask equipped with a magnetic stir bar and a reflux condensor was added (R)-3-(3-bromophenyl)-2,3-dihydro-[1,4]dioxino[2,3-b]pyridine (11.6) (1.158 g, 3.96 mmol) followed by DMF (21 ml). Zinc cyanide (1.862 g, 15.86 mmol), 1,1'-bus(diphenylphosphino)ferrocene (1.758 g, 3.17 mmol, [CAS: 12150-46-8]) and Pd$_2$(dba)$_3$ (0.726 g, 0.793 mmol) were added and the reaction mixture was degassed with argon. The mixture was stirred at 80° C. for 20 hr under argon. The cold reaction mixture was diluted with ethyl acetate (250 ml) and washed twice with % sodium bicarbonate solution, water and brine, dried over sodium sulfate, filtered and concentrated in vacuo. Chromatography on silicagel (gradient: cyclohexane/ethyl acetate) afforded (R)-3-(2,3-dihydro-[1,4]dioxino[2,3-b]pyridin-3-yl)benzonitrile (750 mg, 79%) (11.7). UPLC retention time 0.86 min (Method A). $^1$H NMR (400 MHz, DMSO-d$_6$) δ=ppm 4.19 (dd, J=11.55, 8.13 Hz, 1H), 4.52 (dd, J=11.55, 2.51 Hz, 1H), 5.56 (dd, J=8.07, 2.20 Hz, 1H), 7.01 (dd, J=7.82, 4.77 Hz, 1H), 7.38 (dd, J=7.89, 1.53 Hz, 1H), 7.68 (t, J=7.48 Hz, 1H), 7.81-7.91 (m, 3H), 7.98 (s, 1H). MS/ESI+239 [M+H]$^+$.

Step e) (R,Z)-3-(2,3-dihydro-[1,4]dioxino[2,3-b]pyridin-3-yl)-N'-hydroxybenzimidamide (11.8). To a 50 mL 2-necked flask equipped with a magnetic stir bar and a reflux condensor was added (R)-3-(2,3-dihydro-[1,4]dioxino[2,3-b]pyridin-3-yl)benzonitrile (11.7) (380 mg, 1.59 mmol) and ethanol (7 ml). 50% hydroxylamine solution In water (0.376 ml, 6.38 mmol) was added dropwise and the reaction mixture was refluxed for 3.5 hr to give a clear solution. The mixture was extracted twice with dichloromethane and concentrated in vacuo to yield crude (R,Z)-3-(2,3-dihydro-[1,4]dioxin[2,3-b]pyridin-3-yl)-N'-hydroxybenzimidamide (477 mg, 85%) (11.8), which was used without further purification in the next step. A small probe (51 mg) was purified via SFC to give 38 mg of a beige foam. UPLC retention time 0.54 min (Method A). $^1$H NMR (400 MHz, CHLOROFORM-d) δ=ppm 2.30 (br s, 4H), 4.02 (dd, J=11.68, 8.86 Hz, 1H), 4.41 (dd, J=11.62, 2.45 Hz, 1H), 5.09 (br s, 2H), 5.36 (dd, J=8.80, 2.20 Hz, 1H), 6.94 (dd, J=7.82, 4.77 Hz, 1H), 7.26 (br s, 1H), 7.44-7.57 (m, 2H), 7.68 (d, J=7.70 Hz, 1H), 7.78 (5, 1H), 7.90 (dd, J=4.71, 1.53 Hz, 1H). MS/ESI+272 [M+H]$^+$.

Step f) benzyl (S)-2-((tert-butoxycarbonyl)amino)-3-(3-(3-(R)-2,3-dihydro-[1,4]dioxino[2,3-b]pyridin-3-yl)phenyl)-1,2,4-oxadiazol-5-yl)propanoate (11.9). A 50 mL 2-necked flask equipped with a magnetic stir bar and a reflux condensor was charged with (R,Z)-3-(2,3-dihydro-[1,4]dioxino[2,3-b]pyridin-3-yl)-N'-hydroxybenzimidamide (11.8) (477 mg, 1.35 mmol) and 2-Me-THF (13.5 ml) followed by Boc-Asp(OSu)-OBzl (2.5) [CAS 140171-25-1] (655 mg, 1.55 mmol from Bachem). The reaction mixture was refluxed for 2 d. The solvent was evaporated on a rotavap yielding 1.30 g crude product. Chromatography over silicagel (gradient: cyclohexane/ethyl acetate) afforded benzyl (S)-2-((tert-butoxycarbonyl)-amino)-3-(3-(3-((R)-2,3-dihydro-[1,4]dioxino[2,3-b]pyridin-3-yl)phenyl)-1,2,4-oxadiazol-5-yl)propanoate (374 mg, 45.5.%) (11.9). UPLC retention time 1.27 min (Method A). $^1$H NMR (400 MHz, CHLOROFORM) δ=ppm 1.27 (s, 2H), 1.44 (s, 11H), 1.60 (br s, 3H), 3.51 (br d, J=4.89 Hz, 2H), 4.06 (dd, J=11.68, 8.86 Hz, 1H), 4.43 (dd, J=11.61, 2.32 Hz, 1H), 4.90 (br s, 1H), 5.14-5.27 (m, 3H), 5.36-5.44 (m, 1H,) 5.47-5.63 (m, 1H), 6.95 (dd, J=7.89, 4.83 Hz, 1H), 7.29 (br s, 3H), 7.35 (s, 2H), 7.55 (t, J=7.76 Hz, 1H), 7.66 (br d, J=7.70 Hz, 1H), 7.91 (dd, J=4.77, 1.34 Hz, 1H), 8.03 (d, J=7.70 Hz, 1H), 8.09 (s, 1H). MS/ESI+559 [M+H]$^+$.

Step g) tert-butyl ((S)-1-(3-(3-((R)-2,3-dihydro-[1,4]dioxino[2,3-b]pyridin-3-yl)phenyl)-1,2,4-oxadiazol-5-yl)-3-hydroxypropan-2-yl)carbamate (11.10). A 100 mL one-necked flask equipped with a magnetic stir bar was charged with benzyl (S)-2-((tert-butoxycarbonyl)-amino)-3-(3-(3-((R)-2,3-dihydro-[1,4]dioxino[2,3-b]pyridin-3-yl)phenyl)-1,2,4-oxadiazol-5-yl)propanoate (11.9) (350 mg, 0.627 mmol) and THF (8.3 ml). At 0'C lithium borohydride (54.6 mg, 2.506 mmol) was added and the cooling bath was removed after 10 min. After 7 hr stirring at rt the reaction mixture was poured into icewater and extracted twice with ethyl acetate. The organic layers were washed with brine, dried over sodium sulfate, filtered and concentrated in vacuo. Chromatography over silicagel (gradient: cyclohexane/ethyl acetate) afforded tert-butyl ((S)-1-(3-(3-((R)-2,3-dihydro-[1,4]dioxino[2,3-b]pyridin-3-yl)phenyl)-1,2,4-oxadiazol-5-yl)-3-hydroxypropan-2-yl)carbamate (63 mg, 22%) (11.10). UPLC retention time 0.96 min (Method A). $^1$H NMR (400 MHz, CHLOROFORM-d) δ=ppm 1.44 (s, 9H), 3.31 (br d, J=6.11 Hz, 2H), 3.83 (t, J=4.22 Hz, 2H), 4.07 (dd, J=11.68, 8.86 Hz, 1H), 4.21 (br s, 1H), 4.45 (dd, J=11.68, 2.51 Hz, 1H), 5.13-5.27 (m, 1H), 5.42 (dd, J=8.80, 2.32 Hz, 1H), 7.89, 4.83 Hz, 1H), 7.28-7.30 (m, 1H), 7.56 (t, J=7.76 Hz, 1H), 7.66 (d, J=7.82 Hz, 1H), 7.91 (dd, J=4.77, 1.59 Hz, 1H), 8.10 (d, J=7.70 Hz, 1H), 8.17 (s, 1H). MS/ESI+455 [M+H]$^+$.

Step h) (S)-2-amino-3-(3-(3-((R)-2,3-dihydro-[1,4]dioxin[2,3-b]pyridin-3-yl)phenyl)-1,2,4-oxadiazol-5-yl)propan-1-ol (Example 11) A 25 mL one-necked flask equipped with a magnetic stir bar was charged with tert-butyl ((S)-1-(3-(3-((R)-2,3-dihydro-[1,4]dioxino[2,3-b]pyridin-3-yl)phenyl)-1,2,4-oxadiazol-5-yl)-3-hydroxypropan-2-yl)carbamate (11.10) (46 mg, 0.101 mmol) and dioxane (1 ml). HCl in dioxane 2M (0.506 ml, 1.012 mmol) was added and the mixture was stirred at rt overnight. The reaction mixture was concentrated in vacuo and the remaining white solid was triturated twice with dichloromethane and evaporated. The crude white powder was triturated twice with ethyl ether in the ultrasound bath and decanted to give the hydro chloride salt of (S)-2-amino-3-(3-(3-((R)-2,3-dihydro-[1,4]dioxino[2,3-b]pyridin-3-yl)phenyl)-1,2,4-oxadiazol-5-yl)propan-1-ol (38 mg, 99%) (Example 11) as a white powder. UPLC retention time 0.59 min (Method A). $^1$H NMR (400 MHz, DMSO-d$_6$) δ=ppm 3.29-3.47 (m, 2H), 3.59-3.79 (m, 3H), 4.17 (dd, J=11.55, 8.25 Hz, 1H), 4.55 (br dd, J=11.61, 2.45 Hz, 2H), 5.62 (dd, J=8.13, 2.14 Hz, 1H), 7.02 (dd, J=7.82, 4.77 Hz, 1H), 7.40 (dd, J=7.82, 1.59 Hz, 1H), 7.64-7.76 (m, 2H), 7.83 (dd, J=4.77, 1.47 Hz, 1H), 8.06 (d, J=7.70 Hz, 1H), 8.18 (s, 1H), 8.29 (br s, 3H). MS/ESI+355 [M+H]$^+$.

Example 12 (S)-2-amino-3-(3-(4-((5-chloro-3-fluoropyridin-2-yl)oxy)phenyl)-1,2,4-oxadiazol-5-yl) propan-1-ol

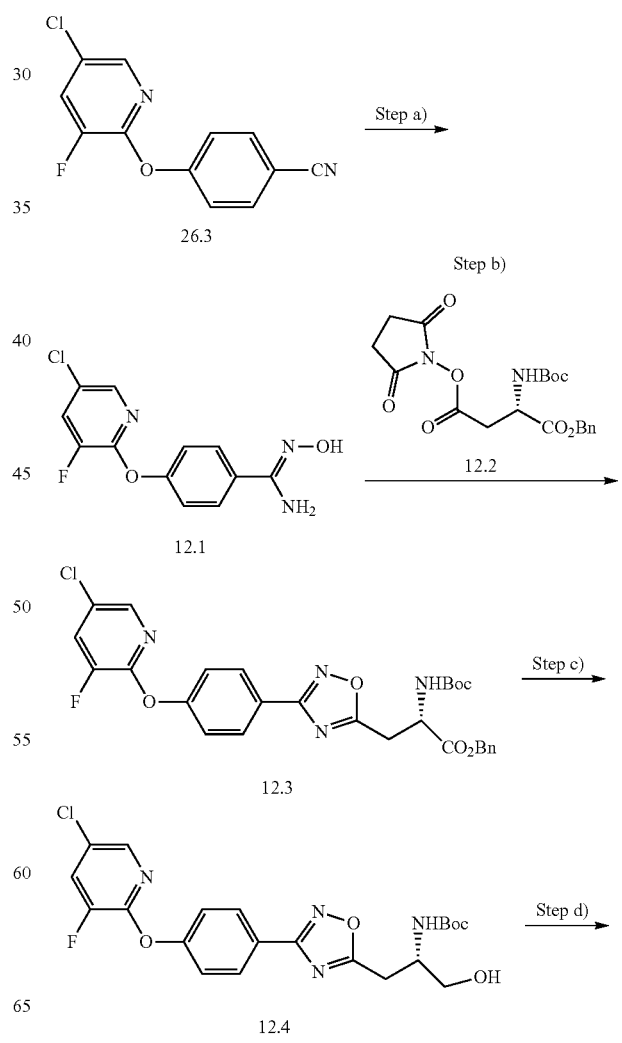

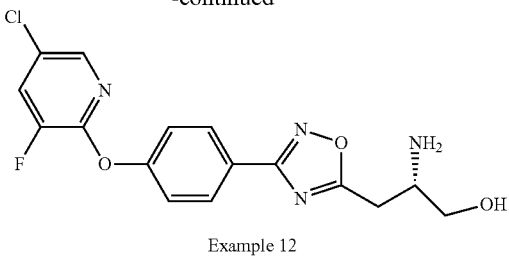

Example 12

Step a) (Z)-4-((5-Chloro-3-fluoropyridin-2-yl)oxy)-N'-hydroxybenzimidamide (12.1). To a 100 mL one-necked flask equipped with a magnetic stir bar and a condenser (air) was added 26.3 (2.82 g, 11.34 mmol), NaHCO$_3$ (4.76 g, 56.7 mmol), hydroxylamine hydrochloride (3.94 g, 56.7 mmol), ethanol (40 ml) and water (15 ml) (caution: gas formation). The white suspension was heated to 85° C. and stirred for 100 minutes. It was then cooled to 25° C. Ethanol was removed in vacuo. Water and ethyl acetate were added and the aqueous phase was extracted with ethyl acetate. The organic layers were washed with brine, dried over Na$_2$SO$_4$ and the solvent removed to give 12.1 as a colorless solid (3.18 g, 97%). UPLC retention time 0.73 min (Method A). $^1$H NMR (DMSO-d6): δ=ppm 9.62 (1H, s), 8.23 (1H, dd), 8.06 (1H, d), 7.71 (2H, d), 7.20 (2H, d), 5.82 (2H, s). MS/ESI 282.2 [M+H]$^+$.

Step b) (S)-Benzyl 2-((tert-butoxycarbonyl)amino)-3-(3-(4-((5-chloro-3-fluoropyridin-2-yl)oxy)phenyl)-1,2,4-oxadiazol-5-yl)propanoate (12.3). To a 20 mL microwave vial equipped with a magnetic stir bar was added 12.1 (0.60 g, 2.066 mmol), 12.2 (0.985 g, 2.343 mmol) and THF (13 ml). The colorless solution was stirred for 30 minutes at 25° C. It was then heated to 110° C. and stirred for 15 h. The solvent was removed in vacuo. Chromatography on silica (gradient: cyclohexane/ethyl acetate) afforded 12.3 as a colorless oil (829 mg, 71%). UPLC retention time 1.41 min (Method A). $^1$H NMR (CDCl$_3$): δ=ppm 8.05 (2H, d), 7.93 (1H, d), 7.55 (1H, dd), 7.28 (5H, s), 7.25 (2H, s), 5.58 (1H, d), 5.25-5.13 (2H, m), 4.90 (1H, d), 3.51 (2H, dq), 1.44 (9H, s). MS/ESI 569.4 [M+H]$^+$.

Step c) (S)-tert-Butyl (1-(3-(4-((5-chloro-3-fluoropyridin-2-yl)oxy)phenyl)-1,2,4-oxadiazol-5-yl)-3-hydroxypropan-2-yl)carbamate (12.4). To a 25 mL two-necked round bottom flask equipped with a magnetic stir bar, gas inlet and rubber septum was added 12.3 (474 mg, 0.833 mmol). The flask was evacuated and backfilled with argon three times. Dry THF (8.0 mL) was added and the solution was cooled to 0° C. LiBH$_4$ (91 mg, 4.17 mmol) was added in one portion and the suspension stirred for 1.5 h. The reaction mixture was quenched with methanol. The solvents were removed, the crude product dissolved in dichloromethane and adsorbed on silica. Chromatography on silica (gradient: cyclohexane/ethyl acetate) afforded 12.4 as a viscous colorless oil (229 mg, 58%). UPLC retention time 1.17 min (Method A). $^1$H NMR (400 MHz, CDCl$_3$): δ=ppm 8.12 (2H, d), 7.93 (1H, d), 7.55 (1H, dd), 7.27 (2H, d), 5.21 (1H, s), 4.24-4.16 (1H, s, br), 3.81 (2H, m), 3.30 (2H, d), 1.44 (9H, s). MS/ESI 465.3 [M+H]$^+$.

Step d) (S)-2-amino-3-(3-(4-((5-chloro-3-fluoropyridin-2-yl)oxy)phenyl)-1,2,4-oxadiazol-5-yl)propan-1-ol (Example 12). To a 25 mL pear shaped flask equipped with a magnetic stir bar was added 12.4 (225 mg, 0.484 mmol), CH$_2$Cl$_2$ (5.0 mL) and TFA (0.186 mL, 2.42 mmol). The colorless solution was stirred for 65 h at 25° C. The solvent and the acid were removed and the residue dissolved in ethyl acetate. Aqueous NaOH (0.1 M) and ethyl acetate were added and the aqueous phase was extracted with ethyl acetate. The organic layers were washed with brine, dried over Na$_2$SO$_4$, filtered and concentrated. Purification on silica (gradient: CH$_2$Cl$_2$/MeOH) afforded the product Example 12 as a colorless oil, which slowly solidified at 25° C. (64 mg, 36%). UPLC retention time 0.74 min (Method A). $^1$H NMR (CDC's): δ=ppm 8.13 (2H, d), 7.93 (1H, d), 7.55 (1H, dd), 7.27 (2H, d), 3.71 (1H, dd), 3.56 (1H, dd), 3.53-3.45 (1H, d), 3.14 (1H, dd), 3.00 (1H, dd), OH and NH$_2$ not observed. ES/ESI 365.2 [M+H]$^+$.

Example 13 (S)-3-(3-(4-((5-(1H-Pyrazol-5-yl)pyridin-2-yl)oxy)phenyl)-1,2,4-oxadiazol-5-yl)-2-aminopropan-1-ol

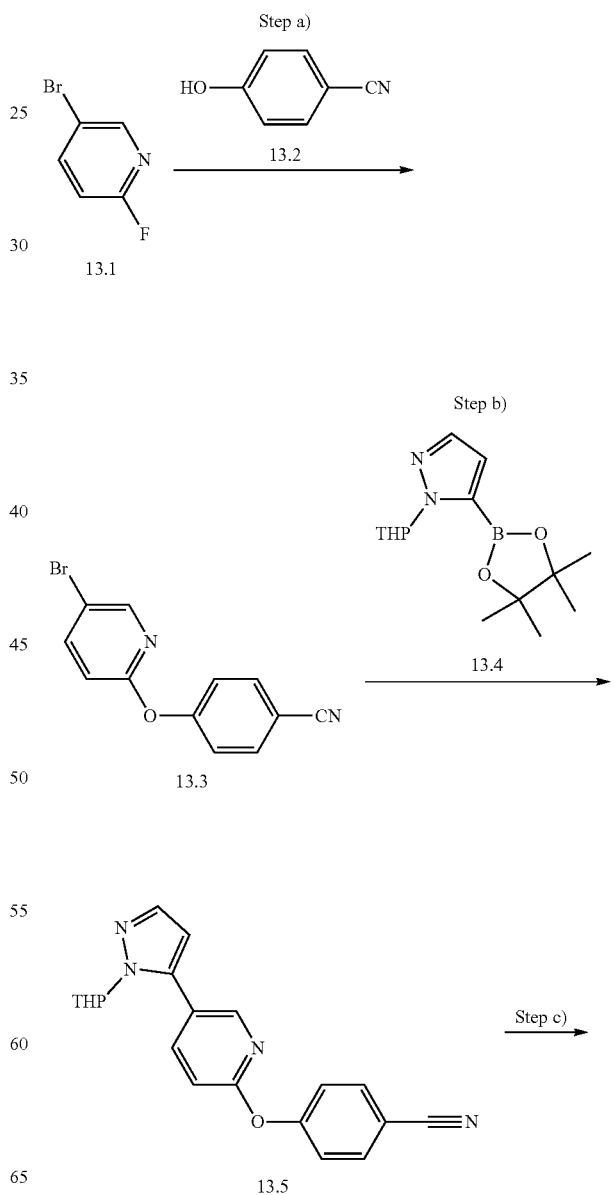

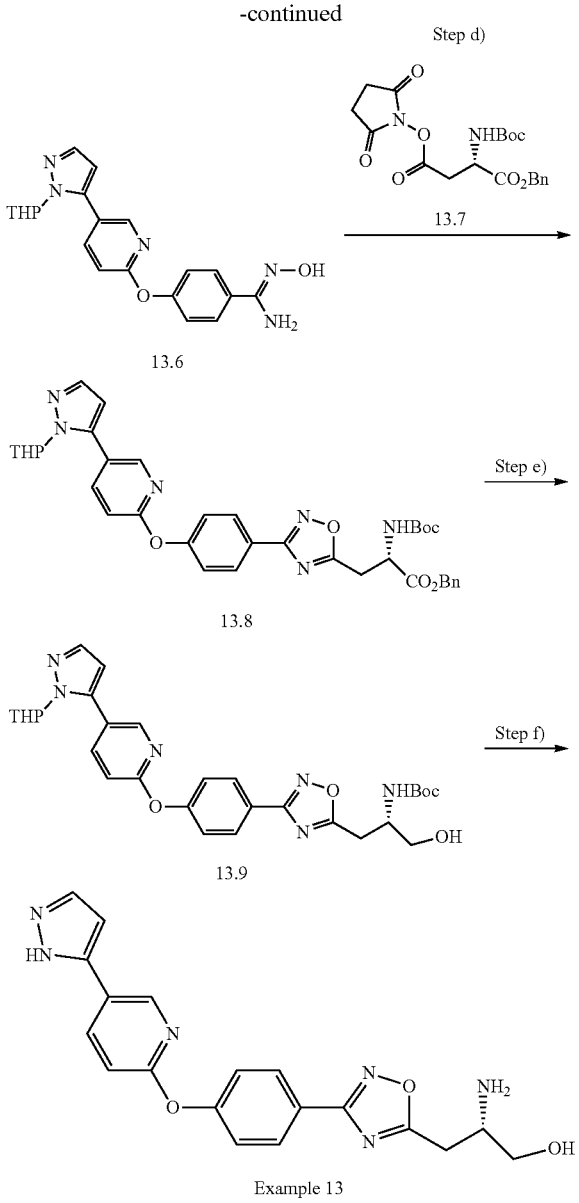

Step a) 4-((5-Bromopyridin-2-yl)oxy)benzonitrile (13.3). A suspension of 13.1 (2.5 g, 14.2 mmol), 13.2 (1.86 g, 15.6 mmol) and $K_2CO_3$ (5.9 g, 42.6 mmol) in DMF (70 mL) was heated to 110° C. for 18 h. The reaction mixture was cooled to 25° C. Water and ethyl acetate were added and the aqueous phase was extracted twice with ethyl acetate. The organic layer was washed with brine, dried over $Na_2SO_4$, filtered and the solvent removed. The residue was purified on silica (gradient: cyclohexane/ethyl acetate) to yield compound 13.3 as a colorless solid (3.30 g, 84%). UPLC retention time 1.10 min (Method A). $^1H$ NMR ($CDCl_3$): δ=ppm 8.23 (1H, d), 7.85 (1H, dd), 7.72-7.67 (2H, m), 7.25-7.20 (2H, m), 6.94 (1H, d). MS/ESI 275.1 $[M+H]^+$.

Step b) 4-((5-(1-(Tetrahydro-2H-pyran-2-yl)-1H-pyrazol-5-yl)pyridin-2-yl)oxy)benzonitrile (13.5). To a 250 mL two-necked round bottom flask equipped with a magnetic stir bar, rubber septum and gas inlet was added 13.3 (3.23 g, 11.74 mmol), $K_3PO_4$ (7.48 g, 35.2 mmol), 13.4 (3.92 g, 14.1 mmol), $Pd(PPh_3)_4$ (0.678 g, 0.587 mmol) and toluene (70 ml). The suspension was purged with argon for 15 minutes. The gas inlet was replaced by a reflux condenser and the reaction mixture was heated to 110° C. and stirred for 2 h. The suspension was cooled to 25° C. and then stored in the freezer for 16 h. Water and ethyl acetate were added and the aqueous phase was extracted twice with ethyl acetate. The organic layer was washed with brine, dried over $Na_2SO_4$, filtered and the solvent removed. Chromatography on silica (gradient: cyclohexane/ethyl acetate) and crystallization from ethyl acetate afforded compound 13.5 as a colorless solid (1.54 g, 38%). UPLC retention time 1.09 min (Method A). $^1H$ NMR ($CDCl_3$): δ =ppm 8.33 (1H, d), 7.94 (1H, dd), 7.75-7.69 (2H, m), 7.62 (1H, d), 7.34-7.28 (2H, m), 7.11 (1H, d), 6.36 (1H, d), 5.14 (1H, dd), 4.16-4.05 (1H, m), 3.59 (1H, dt), 2.58 (1H, ddt), 2.14-2.05 (1H, m), 1.95-1.85 (1H, m), 1.82-1.68 (1H, m), 1.62-1.51 (2H, m). MS/ESI 347.2 $[M+H]^+$.

Step c) (Z)-N'-Hydroxy-4-((5-(1-(tetrahydro-2H-pyran-2-yl)-1H-pyrazol-5-yl)pyridin-2-yl)oxy)benzimidamide (13.6). To a 100 mL one-necked flask equipped with a magnetic stir bar was added hydroxylamine hydrochloride (1.54 g, 22.1 mmol), $NaHCO_3$ (1.86 g, 22.1 mmol) and water (10 ml). The colorless suspension (caution: gas formation) was stirred for 5 minutes at 25° C. Compound 13.5 (1.53 g, 4.42 mmol) and ethanol (25 ml) were added and the reaction mixture was stirred for 90 minutes at 85° C. Ethanol was removed and water and ethyl acetate were added. The aqueous phase was extracted twice with ethyl acetate. The organic layer was washed with brine and dried over $Na_2SO_4$. The solvent was removed and the residue purified on silica (gradient: cyclohexane/ethyl acetate) to afford compound 13.6 as a colorless solid (1.62 g, 97%). UPLC retention time 0.71 min (Method A). $^1H$ NMR ($CDCl_3$): δ=ppm 8.33 (1H, d), 7.89 (1H, dd), 7.74-7.68 (m, 2H), 7.62 (1H, d), 7.25-7.20 (2H, m), 7.04 (1H, d), 6.35 (1H, d), 5.14 (1H, dd), 4.87 (s, 2H), 4.09 (1H, dd), 3.59 (1H, td), 2.65-2.51 (1H, m), 1.88 (1H, d), 1.82-1.68 (1H, m), 1.65-1.52 (2H, m). MS/ESI 380.4 $[M+H]^+$.

Step d) (2S)-Benzyl 2-((tert-butoxycarbonyl)amino)-3-(3-(4-((5-(1-(tetrahydro-2H-pyran-2-yl)-1H-pyrazol-5-yl)pyridin-2-yl)oxy)phenyl)-1,2,4-oxadiazol-5-yl)propanoate (13.8). To a 50 mL two-necked round bottom flask equipped with a magnetic stir bar, reflux condenser and rubber septum was added 13.6 (1.31 g, 3.45 mmol), 13.7 (1.60 g, 3.80 mmol) and THF (20 ml). The colorless solution was stirred for 30 minutes at 25° C. and then heated to 90° C. for 7 days. The solvent was removed and the residue purified on silica (gradient: cyclohexane/ethyl acetate) to afford 13.8 as a mixture of epimers (1.68 g, 73%) which was used in the next step. UPLC retention time 1.39 min (Method A). MS/ESI 667.4 $[M+H]^+$.

Step e) tert-Butyl ((2S)-1-hydroxy-3 (3-(4-((5-(1-(tetrahydro-2H-pyran-2-yl)-1H-pyrazol-5-yl)pyridin-2-yl)oxy)phenyl)-1,2,4-oxadiazol-5-yl)propan-2-yl)carbamate (13.9). To a 25 mL two-necked round bottom flask equipped with a magnetic stir bar, gas inlet and rubber septum was added 13.8 (634 mg, 0.951 mmol). The flask was evacuated and backfilled with argon three times. Dry THF (5.0 mL) was added and the colorless solution was cooled to 0° C. Lithium borohydride (104 mg, 4.75 mmol) was added and the suspension was stirred for 1 h. The reaction mixture was quenched with methanol. The solvents were removed, the crude product dissolved in dichloromethane and purified on silica (gradient: cyclohexane/ethyl acetate) to afford 13.9 (white solid) as a mixture of epimers (276 mg, 52%), which was used in the next step. UPLC retention time 1.14 min (Method A). MS/ESI 563.4 $[M+H]^+$.

Step f) (S)-3-(3-(4-((5-(1H-Pyrazol-5-yl)pyridin-2-yl)oxy)phenyl)-1,2,4-oxadiazol-5-yl)-2-aminopropan-1-ol (Example 13). To a 25 mL one-necked round bottom flask equipped with a magnetic stir bar was added 13.9 (276 mg, 0.491 mmol), dioxane (5.0 mL) and aq. HCl (5.0 mL, 10.00 mmol, 2M solution). The cloudy solution was stirred for 18 h at 25° C. Dioxane and water were removed and the residue purified by RP C18 column chromatography (ISCO CombiFlash Rf, liquid injection, MeCN in Water 10-35%). Acetonitrile was removed and the aqueous phase basified with 2M aq. NaOH. Ethyl acetate was added and the aqueous phase was extracted twice with ethyl acetate. The organic layers were washed with brine, dried over $Na_2SO_4$, filtered and concentrated to afford Example 13 as a colorless solid (112 mg, 60%). UPLC retention time 0.59 min (Method A). $^1$H NMR (DMSO-$d_6$): δ=ppm 13.00 (1H, s), 8.65 (1H, s), 8.30 (1H, d), 8.07 (2H, d), 7.83 (1H, s, br), 7.35 (2H, d), 7.20 (1H, d), 6.79 (1H, s), 4.80 (1H, m), 3.38 (2H, m), 3.22 (1H, m), 3.15 (1H, dd), 2.88 (1H, dd), 1.75 (2H, m). MS/ESI 379.4 [M+H]$^+$.

Example 14 (S)-2-amino-3-5-(3-((R)-2,3-dihydro-[1,4]dioxino[2,3-b]pyridin-3-yl)phenyl)-2H-tetrazol-2-yl)propan-1-ol

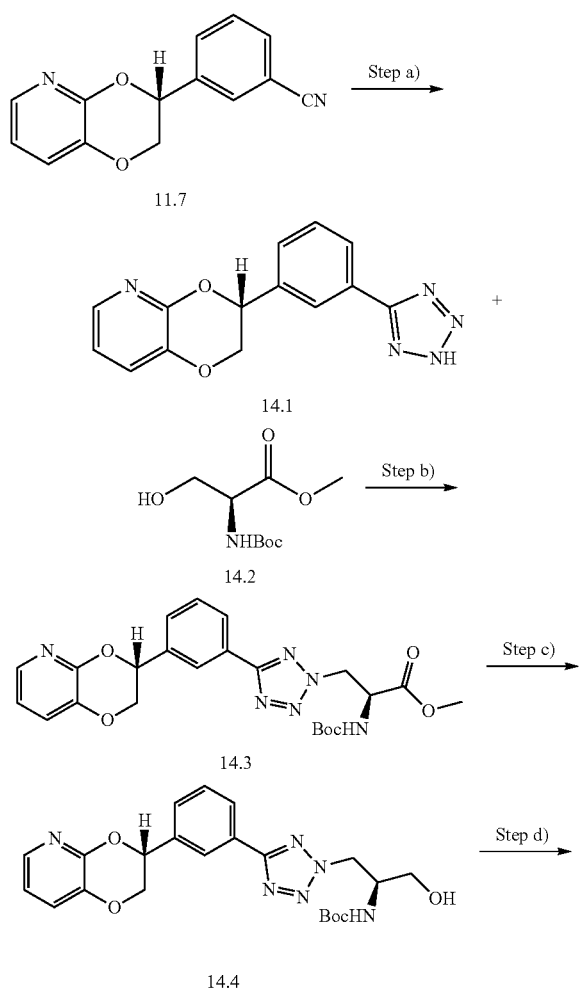

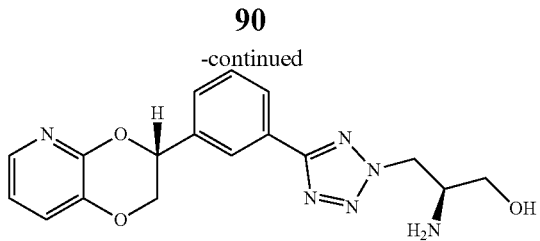

Example 14

Step a) (R)-3-(3-(2H-tetrazol-5-yl)phenyl)-2,3-dihydro-[1,4]dioxino[2,3-b]pyridine (14.1). A suspension of (R)-3-(2,3-dihydro-(1,4]dioxino[2,3-b]pyridin-3-yl)benzonitrile (11.7) (500 mg, 2.099 mmol), dibutyltinoxide (104 mg, 0.42 mmol, [CAS: 818-08-6]) and TMS-azide (509 mg, 4.2 mmol, [CAS: 4648-54-8]) in toluene (11.70 ml) was heated to 100° C. for 21.5 h. The cold reaction mixture was diluted with methanol (50 ml) and concentrated in vacuo. The crude product was triturated with diethylether/dichloromethane 1:1 plus little methanol and filtered. The solid was washed with diethylether/dichloromethane 1:1 and dried, affording (R)-3-(3-(2H-tetrazol-5-yl)phenyl)-2,3-dihydro-[1,4]dioxino[2,3-b]pyridine (386 mg, 65.4%) (14.1) as a beige powder. UPLC retention time 0.70 min (Method A). $^1$H NMR (400 MHz, DMSO-$d_6$) δ=ppm 2.99-3.66 (m, 4H), 4.17 (dd, J=11.62, 8.31 Hz, 1H), 4.55 (dd, J=11.62, 2.45 Hz, 1H), 5.61 (dd, J=8.19, 2.20 Hz, 1H), 7.02 (dd, J=7.95, 4.77 Hz, 1H), 7.39 (dd, J=7.82, 1.47 Hz, 1H), 7.64-7.76 (m, 2H), 7.84 (dd, J=4.65, 1.47 Hz, 1H), 8.06 (d, J=7.21 Hz, 1H), 8.21 (s, 1H). MS/ESI$^+$ 282 [M+H]$^+$.

Step b) methyl (S)-2-((tert-butoxycarbonyl)amino)-3-(5-(3-((R)-2,3-dihydro-[1,4]dioxino[2,3-b]pyridin-3-yl)phenyl)-2H-tetrazol-2-yl)propanoate (14.3). To a solution of (R)-3-(3-(2H-tetrazol-5-yl)phenyl)-2,3-dihydro-[1,4]dioxino[2,3-b]pyridine (14.1) (336 mg, 0.729 mmol) in THF (14.6 mL) was added under nitrogen at 0° C. DAD (419 g, 1.822 mmd), PPh$_3$ (478 mg, 1.822 mmd, 2.50) and Boc-L-Ser-OMe (14.2) (420 mg, 1.822 mmol). The resulting mixture was stirred for 4.5 h at rt. solute was added and the mixture concentrated in vacuo and the residue purified on silicagel (ethyl acetate/cyclohexane) to afford methyl (S)-2-((tert-butoxycarbonyl)amino)-3-(5-(3-((R)-2,3-dihydro-[1,4]dioxino[2,3-b]pyridin-3-yl)phenyl)-2H-tetrazol-2-yl)propanoate (490 mg, 98%) (14.3). UPLC retention time 1.09 min (Method A). $^1$H NMR (400 MHz, CHLOROFORM-d) δ=ppm 1.44 (s, 9H), 3.80 (s, 7H), 3.95 (dd, J=11.43, 3.73 Hz, 4H), 4.04-4.17 (m, 2H), 4.34-4.49 (m, 1H), 4.91 (br s, 1H), 5.05-5.22 (m, 1H), 5.27-5.50 (m, 4H), 6.95 (dd, J=7.89, 4.83 Hz, 1H), 7.28-7.32 (m, 1H), 7.52-7.65 (m, 2H), 7.91 (dd, J=4.77, 1.59 Hz, 1H), 8.15 (d, J=7.58 Hz, 1H), 8.24 (s, 1H). MS/ESI$^+$ 483 [M+H]$^+$.

Step c) tert-butyl ((S)-1-(5-(3-((R)-2,3-dihydro-[1,4]dioxino[2,3-b]pyridin-3-yl)phenyl)-2H-tetrazol-2-yl)-3-hydroxypropan-2-yl)carbamate (14.4). At 0° C. LiBH$_4$ (3.54 mL 2 molar solution in THF, 7.09 mmol) was added dropwise to a solution of methyl (S)-2-((tert-butoxycarbonyl)-amino)-3-(5-(3-((R)-2,3-dihydro-[1,4]dioxin[2,3-b]pyridin-3-yl)phenyl)-2H-tetrazol-2-yl)propanoate (14.3) (950 mg, 1.772 mmol) in THF (17.7 mL) and the mixture was stirred overnight at 0° C. The mixture was cooled to 0° C. and quenched with water and 1M hydrochloric acid to give a pH of about 7. The mixture was diluted with dichloromethane and washed with water and brine, dried over sodium sulfate, filtered and concentrated in vacuo. The residue was purified on silicagel (ethyl acetate/cyclohexane) to afford tert-butyl ((S)-1-(5-(3-((R)-2,3-dihydro-[1,4]dioxino[2,3-b]pyridin-3- yl)phenyl)-2H-tetrazol-2-yl)-3-hydroxypropan-2-yl)carbamate (264 mg, 32%) (14.4). UPLC retention time 0.94 min (Method A). $^1$H NMR (400 MHz, CHLOROFORM-d) δ=ppm 1.42 (s, 10H), 3.75 (t, J=4.95 Hz, 2H), 4.08 (dd, J=11.61, 8.80 Hz, 1H), 4.27 (br s, 1H), 4.46 (dd, J=11.62, 2.45 Hz, 1H), 4.91 (br d, J=5.87 Hz, 2H), 5.08-5.20 (m, 1H), 5.43 (dd, J=8.86, 2.26 Hz, 1H), 6.95 (dd, J=7.82, 4.77 Hz, 1H), 7.28-7.30 (m, 1H), 7.53-7.63 (m, 2H), 7.90 (dd, J=4.83, 1.53 Hz, 1H), 8.17 (d, J=7.46 Hz, 1H), 8.25 (s, 1H). MS/ESI⁻ 455 [M+H]⁺.

Step d) (S)-2-amino-3-(5-(3-((R)-2,3-dihydro-[1,4]dioxin [2,3-b]pyridin-3-yl)phenyl)-2H-tetrazol-2-yl)propan-1-ol (Example 14). To a solution of tert-butyl ((S)-1-(5-(3-((R)-2,3-dihydro-[1,4]dioxino[2,3-b]pyridin-3-yl)phenyl)-2H-tetrazol-2-yl)-3-hydroxypropan-2-yl)carbamate (14.4) (230 mg, 0.506 mmol) in dioxane (5.06 mL) hydrochloric acid in dioxane (1.265 ml, 5.06 mmol, 4 M solution) was added under nitrogen at 0° C. The reaction mixture was stirred at rt over the weekend and then concentrated in vacuo. The solid obtained was triturated thrice with diethyl ether and lyophilized from water/acetonitril to afford (S)-2-amino-3-(5-(3-((R)-2,3-dihydro-[1,4]dioxino[2,3-b]pyridin-3-yl) phenyl)-2H-tetrazol-2-yl)propan-1-ol (206 mg, 100%) (Example 14) as HCl salt. UPLC retention time 0.58 min (Method A). $^1$H NMR (400 MHz, DMSO-d6) δ=ppm 3.60-3.68 (m, 1H), 3.70-3.76 (m, 2H), 4.12-4.23 (m, 2H), 4.56 (br d, J=11.74 Hz, 1H), 4.91-5.14 (m, 2H), 5.63 (br d, J=7.95 Hz, 1H), 6.96-7.07 (m, 1H), 7.40 (br d, J=7.70 Hz, 1H), 7.64-7.74 (m, 2H), 7.83 (br d, J=3.55 Hz, 1H), 8.12 (br d, J=6.97 Hz, 1H), 8.24 (br 5, 1 H), 8.34 (br s, 3H). MS/ES⁺ 355 [M+H]⁺.

Example 15 (S)-2-amino-3-(3-(3-((R)-2,3-dihydrobenzo[b][1,4]dioxin-2-yl)phenyl)-1,2,4-oxadiazol-5-yl)propan-1-ol

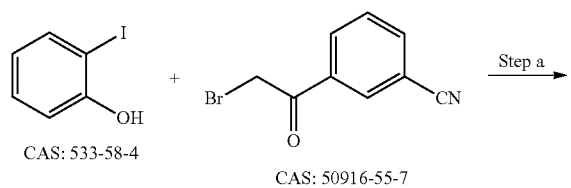

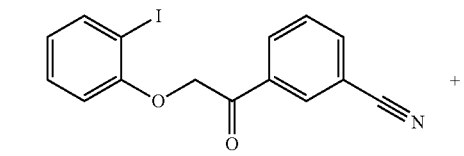

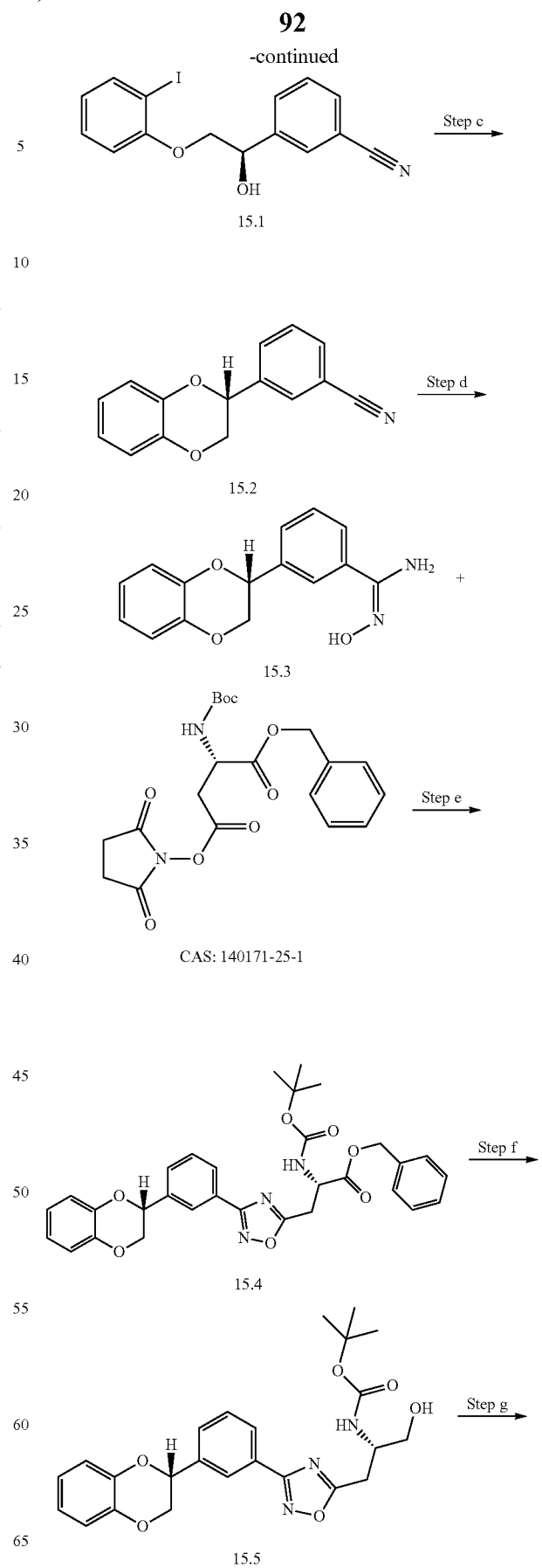

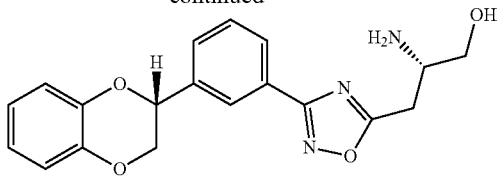

Example 15

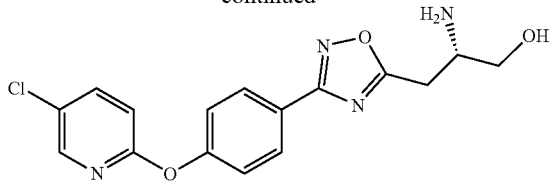

Example 16

(S)-2-amino-3-(3-(3-((R)-2,3-dihydrobenzo[b][1,4]di-oxin-2-yl)phenyl)-1,2,4-oxadiazol-5-yl)propan-1-ol (Example 15) was prepared by similar procedures used for the synthesis of Example 1 replacing the chiral sulfonamide by its S,S-enantiomer [CAS: 167316-27-7]. Example 15 was isolated as the free base. UPLC retention time 0.76 min (Method A). $^1$H NMR (400 MHz, CHLOROFORM-d) δ ppm ppm 1.82 (br. s., 3H), 3.02 (dd, J=15.59, 8.01 Hz, 1H), 3.16 (dd, J=15.53, 4.65 Hz, 1H), 3.47-3.61 (m, 2H), 3.73 (dd, J=10.45, 4.22 Hz, 1H), 4.07 (dd, J=11.49, 8.93 Hz, 1H), 4.42 (dd, J=11.49, 2.45 Hz, 1H), 5.22 (dd, J=8.86, 2.26 Hz, 1H), 6.88-7.06 (m, 4H), 7.53-7.64 (m, 2H), 8.07-8.19 (m, 2H). MS/ESI$^+$ 354 [M+H]$^+$.

Example 16 (S)-2-amino-3-(3-(4-((5-chloropyridin-2-yl)oxy)phenyl)-1,2,4-oxadiazol-5-yl)propan-1-ol

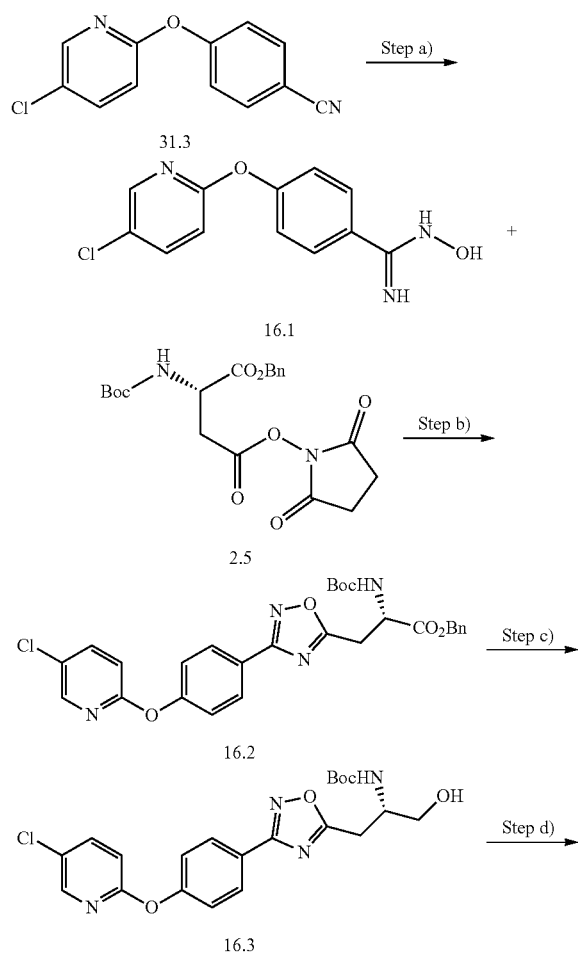

Step a) 4-((5-chloropyridin-2-yl)oxy)-N-hydroxybenzimidamide (16.1). To a 100 mL one-necked round bottom flask equipped with a magnetic stir bar and a condenser (plain air) was added hydroxylamine hydrochloride (3.89 g, 55.9 mmol), NaHCO$_3$ (4.70 g, 55.9 mmol) and Water (8 ml). The white suspension (caution: gas formation) was stirred for ca. 10 minutes. 4-((5-chloropyridin-2-yl)oxy)benzonitrile (31.3) (2.58 g, 11.19 mmol) and EtOH (30 ml) were added and the reaction mixture was heated to 85° C. and stirred for 90 minutes. LC-MS analysis revealed full conversion within 70 minutes. The reaction mixture was cooled to rt and stored in the freezer for 2 days. EtOH was removed in vacuo and water/EtOAc was added to the white solid. The aqueous phase was extracted twice with EtOAc. The organic layers were washed with brine, combined and dried over Na$_2$SO$_4$. Concentration in vacuo afforded 4-((5-chloropyridin-2-yl)oxy)-N-hydroxybenzimidamide (2.91 g, 99%) (16.1) as a white solid. UPLC retention time 0.65 min (Method A). $^1$H NMR (400 MHz, DMSO-d6) δ=9.60 (s, 1H), 8.21 (d, J=2.3 Hz, 1H), 7.97 (dd, J=8.8, 2.7 Hz, 1H), 7.70 (d, J=8.8 Hz, 2H), 7.14 (d, J=8.7 Hz, 2H), 7.12 (d, J=8.7 Hz, 1H), 5.81 (s, 2H). MS/ESI 264.1, 266.1 [M+H]$^+$.

Step b) benzyl (S)-2-((tert-butoxycarbonyl)amino)-3-(3-(4-((5-chloropyridin-2-yl)oxy)phenyl)-1,2,4-oxadiazol-5-yl)propanoate (16.2). To a 20 mL microwave vial equipped with a magnetic stir bar was added 4-((5-chloropyridin-2-yl)oxy)-N-hydroxybenzimidamide (16.1) (1.45 g, 5.50 mmol), Boc-Asp(OSu)-OBzl (2.5) (2.54 g, 6.05 mmol) and THF (15 ml). The vial was sealed and the colorless solution was stirred for 7 hours at rt. Full conversion to the ester within 6 hours. The reaction mixture was stored in the freezer over night. It was then heated to 120'C and stirred for 5 hours. The obtained yellow solution was cooled to rt and THF was removed in vacuo to give a yellow oil. Column chromatography (absorbed on silica gel, EtOAc in cyclohexane 0-25%) afforded benzyl (S)-2-((tert-butoxycarbonyl)amino)-3-(3-(4-((5-chloropyridin-2-yl)oxy)phenyl)-1,2,4-oxadiazol-5-yl)propanoate (2.94 g, 97%) (16.2) as a pale yellow, sticky foam. UPLC retention time 1.39 min (Method A). $^1$H NMR (400 MHz, CDCl$_3$) δ=8.15 (d, J=2.4 Hz, 1H), 8.04 (d, J=8.8 Hz, 2H), 7.69 (dd, J=8.7, 2.7 Hz, 1H), 7.30-7.28 (m, 5H), 7.22 (d, J=8.8 Hz, 2H), 6.95 (d, J=8.7 Hz, 1H), 5.58 (d, J=8.0 Hz, 1H), 5.20 (d, J=2.7 Hz, 2H), 4.93-4.86 (m, 1H), 3.51 (qd, J=16.2, 5.0 Hz, 2H), 1.44 (s, 9H). MS/ESI$^+$ 551.2, 553.2 [M+H]$^+$.

Step c) tert-butyl (S)-(1-(3-(4 ((5-chloropyridin-2-yl)oxy)phenyl)-1,2,4-oxadiazol-5-yl)-3-hydroxypropan-2-yl)carbamate (16.3). To a 25 mL two-necked round bottom flask equipped with a magnetic stir bar was added benzyl (S)-2-((tert-butoxycarbonyl)amino)-3 (3-(4-((5-chloropyridin-2-yl)oxy)phenyl)-1,2,4-oxadiazol-5-yl)propanoate (16.2) (0.681 g, 1.236 mmol). The flask was evacuated and refilled with Ar three times. Dry THE (5.0 ml) was added and the solution was cooled to 0'C. LiBH4 (0.081 g, 3.71 mmol) was added to the reaction mixture and it was stirred for 45 minutes. The suspension was filtered and CH$_2$Cl$_2$ was added. It was stored in the freezer overnight. Silica gel was added (caution: gas formation). Column chromatography (ISCO CombiFlash Rf, EtOAc in cyclohexane 0-50%) afforded tert-butyl (S)-(1-(3-(4-((5-chloropyridin-2-yl)oxy) phenyl)-1,2,4-oxadiazol-5-yl)-3-hydroxypropan-2-yl)carbamate (0.272 g, 49.2%) (16.3) as a white foam. UPLC retention time 1.11 min (Method A). $^1$H NMR (400 MHz, CDCl$_3$) δ=8.15 (d, J=2.6 Hz, 1H), 8.10 (d, J=8.7 Hz, 2H), 7.69 (dd, J=8.7, 2.6 Hz, 1H), 7.23 (d, J=8.7 Hz, 2H), 6.95 (d, J=8.7 Hz, 1H), 5.23 (s br, 1H), 4.23-4.15 (m, 1H), 3.80 (dq, J=11.2, 5.8, 4.7 Hz, 2H), 3.29 (d, J=5.9 Hz, 2H), 2.01 (s br, 1H), 1.43 (s, 9H). MS/ES$^+$ 447.3, 449.3 [M+H]$^+$.

Step d) (S)-2-amino-3-(3-(4-((5-chloropyridin-2-yl)oxy) phenyl)-1,2,4-oxadiazol-5-yl)propan-1-ol (Example 16). —To a 50 mL one-necked round bottom flask equipped with a magnetic stir bar was added tert-butyl (S)-(1-(3-(4-((5-chloropyridin-2-yl)oxy)phenyl)-1,2,4-oxadiazol-5-yl)-3-hydroxypropan-2-yl)carbamate (16.3) (0.270 g, 0.604 mmol), dichloromethane (8 ml) and TFA (0.233 ml, 3.02 mmol). The colorless solution was stirred for 6 days at rt. Sluggish reaction: still no full conversion within 2 days. Also, formation of side-product. Silica gel and more dichloromethane were added. The solvent was then removed in vacuo. Purification by column chromatography (ISCO CombiFlash Rf, absorbed on silica gel, MeOH in CH$_2$Cl$_2$ 0-10%) afforded (S)-2-amino-3-(3-(4-((5-chloropyridin-2-yl)oxy)phenyl)-1, 2,4-oxadiazol-5-yl)propan-1-ol (0.147 g, 70.2%) (Example 16) as a white solid. UPLC retention time 0.73 min (Method A). $^1$H NMR (400 MHz, DMSO-d6) δ=8.25 (d, J=2.5 Hz, 1H), 8.07 (d, J=8.7 Hz, 2H), 8.03 (dd, J=8.8, 2.7 Hz, 1H), 7.35 (d, J=8.7 Hz, 2H), 7.21 (d, J=8.8 Hz, 1H), 5.51 (t, J=4.7 Hz, 1H), 3.76-3.59 (dq, J=31.2, 6.0 Hz, 3H), 3.44-3.25 (m, 2H). MS/ESI$^+$ 347.1, 349.1 [M+H]$^+$.

Example 17 (S)-2-amino-3-(3-(4-(((R)-1-phenylpropan-2-yl)oxy)phenyl)-1,2,4-oxadiazol-5-yl)propan-1-ol

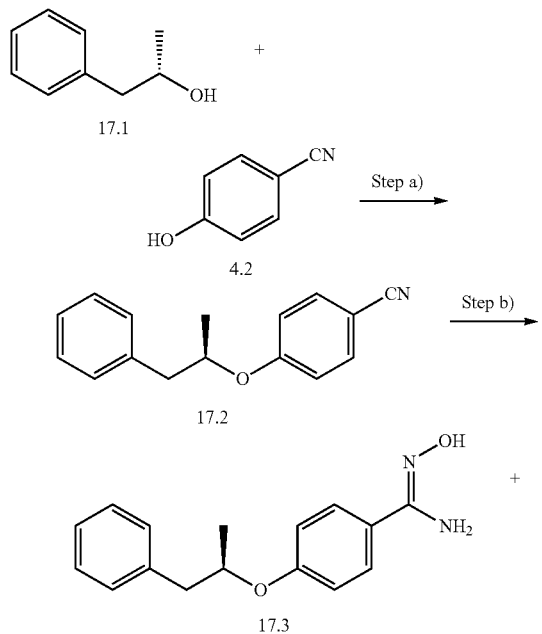

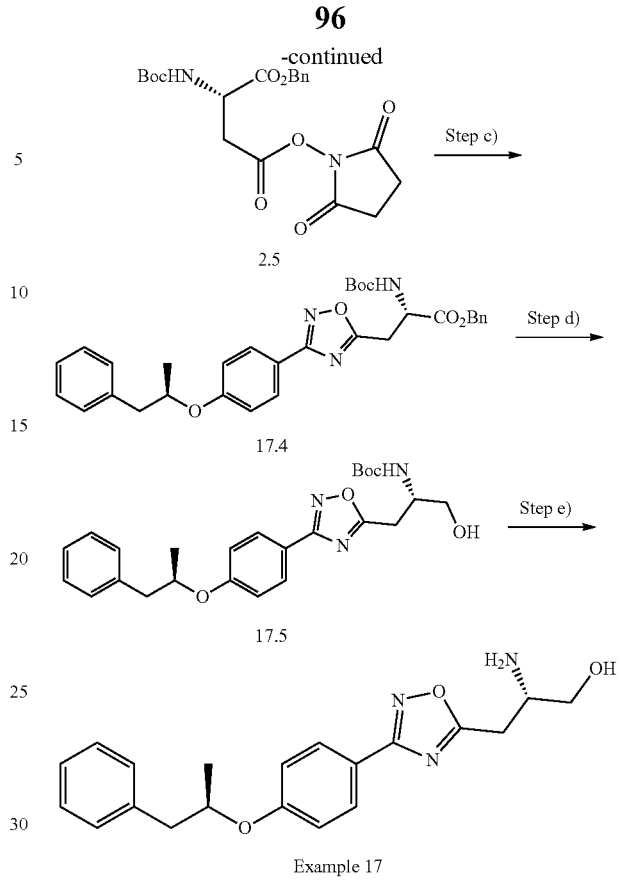

Example 17

Step a) (R)-4-((1-phenylpropan-2-yl)oxy)benzonitrile (17.2). To a 50 mL one-necked round bottom flask equipped with a magnetic stir bar was added (S)-1-phenylpropan-2-ol (17.1) (0.999 ml, 7.26 mmol, ABCR GmbH), 4-cyanophenol (4.2) (0.865 g, 7.26 mmol), PPh$_3$ (2.476 g, 9.44 mmol) and THF (25.0 ml). After complete dissolution of all solids, DIAD (1.836 ml, 9.44 mmol) was added. The yellow solution (caution: becomes very warm) was stirred for 3.5 hours at rt. It was then stored in the freezer over the weekend. The solvent was removed in vacuo. Diisopropyl ether and cyclohexane were added and the yellow solution was filtered over a silica pad (to remove some Ph$_3$PO). The solution was concentrated in vacuo to give an Intensively yellow oil. Purification by column chromatography (ISCO CombiFlash Rf, absorbed on silica gel, EtOAc in cyclohexane 0-5%, fractions) afforded (R)-4-((1-phenylpropan-2-yl)oxy)benzonitrile (0.954 g, 55.4%) (17.2). UPLC retention time 1.24 min (Method A). $^1$H NMR (400 MHz, CDCl$_3$) δ=7.57-7.52 (m, 2H), 7.32-7.27 (m, 2H), 7.25-7.20 (m, 3H), 6.93-6.88 (m, 2H), 4.65 (h, J=6.1 Hz, 1H), 3.08 (dd, J=13.8, 6.2 Hz, 1H), 2.87 (dd, J=13.8, 6.3 Hz, 1H), 1.34 (d, J=6.1 Hz, 3H). MS/ESI no ionization observed [M+H]$^+$. TLC Rf=0.32 (cyclohexane/ethyl acetate 10:1, silicagel).

Step b) (R,Z)-N'-hydroxy-4-((1-phenylpropan-2-yl)oxy) benzimidamide (17.3). To a 50 mL one-necked round bottom flask equipped with a magnetic stir bar and a condenser (air) was added hydroxylamine hydrochloride (1.397 g, 20.10 mmol), NaHCO$_3$ (1.689 g, 20.10 mmol) and Water (5.0 ml). The suspension (caution: gas formation) was stirred for 10 minutes at rt. (R)-4-((1-phenylpropan-2-yl) oxy)benzonitrile (17.2) (0.954 g, 4.02 mmol) in EtOH (15 ml) was subsequently added and the reaction mixture was heated to 85'C. It was stirred for 100 minutes. The white suspension was then stored in the freezer over night. EtOH was removed in vacuo and water/EtOAc were added. The aqueous phase was extracted twice with EtOAc. The organic layers were washed with brine, combined and dried over $Na_2SO_4$. Concentration in vacuo afforded a pale yellow oil. Purification by column chromatography (ISCO CombiFlash Rf, absorbed on silica gel, EtOAc in cyclohexane 0-50%, fractions) afforded (R,Z)-N'-hydroxy-4-((1-phenylpropan-2-yl)oxy)benzimidamide (0.976 g, 90%) (17.3) as a cloudy oil. UPLC retention time 0.81 min (Method A). $^1$H NMR (400 MHz, $CDCl_3$) δ=7.59-7.52 (m, 2H), 7.34-7.21 (m, 5H), 6.93-6.88 (m, 2H), 4.87 (s, 2H), 4.63 (h, J=6.1 Hz, 1H), 3.11 (dd, J=13.7, 5.9 Hz, 1H), 2.85 (dd, J=13.7, 6.6 Hz, 1H), 1.33 (d, J=6.1 Hz, 3H). MS/ESI$^+$ 271.2 [M+H]$^+$.

Step c) benzyl (S)-2-((tert-butoxycarbonyl)amino)-3-(3-(4-(((R)-1-phenylpropan-2-yl)oxy)phenyl)-1,2,4-oxadiazol-5-yl)propanoate (17.4). To a 20 mL microwave vial equipped with a magnetic stir bar was added (R,Z)-N'-hydroxy-4-((1-phenylpropan-2-yl)oxy)benzimidamide (17.3) (0.487 g, 1.802 mmol), Boc-Asp(OSu)-Obzl (2.5) (0.833 g, 1.982 mmol) and THF (6.0 ml). The colorless solution was stirred for 2 hours at rt. Full consumption according to LC-MS analysis within 105 minutes. The reaction mixture was then heated to 120'C and stirred for 3 hours. EtOAc was then added to the pale yellow solution and the mixture was stored in the freezer over the weekend. The solvent was removed in vacuo. Dichloromethane and silica gel were added. Purification by column chromatography (ISCO CombiFlash Rf, absorbed on silica gel, EtOAc in cyclohexane 0-15%) afforded benzyl (S)-2-((tert-butoxycarbonyl)amino)-3-(3-(4-(((R)-1-phenylpropan-2-yl)oxy)phenyl)-1,2,4-oxadiazol-5-yl)propanoate (0.814 g, 81%) (17.4) as a "grey" oil. UPLC retention time 1.48 min (Method A). $^1$H NMR (400 MHz, $CDCl_3$) δ=7.94-7.88 (m, 2H), 7.34-7.22 (m, 10H), 6.97-6.92 (m, 2H), 5.60 (d, J=8.1 Hz, 1H), 5.25-5.12 (m, 2H), 4.95-4.83 (m, 1H), 4.68 (dt, J=12.3, 6.1 Hz, 1H), 3.59-3.39 (m, 2H), 3.12 (dd, J=13.7, 5.9 Hz, 1H), 2.87 (dd, J=13.7, 6.5 Hz, 1H), 1.44 (s, 9H), 1.35 (d, J=6.1 Hz, 3H). MS/ESI$^+$ 558.4 [M+H]$^+$.

Step d) benzyl (S)-2-((tert-butoxycarbonyl)amino)-3-(3-(4-(((R)-1-phenylpropan-2-yl)oxy)phenyl)-1,2,4-oxadiazol-5-yl)propanoate (17.5). To a 10 mL two-necked cone shaped flask equipped with a magnetic stir bar, rubber septum and gas inlet was added benzyl (S)-2-((tert-butoxycarbonyl)amino)-3-(3-(4-(((R)-1-phenylpropan-2-yl)oxy)phenyl)-1,2,4-oxadiazol-5-yl)propanoate (17.4) (0.443 g, 0.794 mmol). The vial was evacuated and backfilled with Ar three times. Dry THF (3.0 ml) was added and the solution was cooled to 0'C. $LiBH_4$ (0.087 g, 3.97 mmol) was then added in one portion and the suspension was stirred for 45 minutes. The reaction was quenched with MeOH. The solvents were removed in vacuo. Dichloromethane and silica gel were added. Purified twice by column chromatography (ISCO CombiFlash Rf, absorbed on silica gel, EtOAc in cyclohexane 0-50% and 0-50%) to afford benzyl (S)-2-((tert-butoxycarbonyl)amino)-3-(3-(4-(((R)-1-phenylpropan-2-yl)oxy)phenyl)-1,2,4-oxadiazol-5-yl)propanoate (0.168 g, 46.6%) (17.5). UPLC retention time 1.24 min (Method A). $^1$H NMR (400 MHz, $CDCl_3$) δ=7.96 (d, J=8.8 Hz, 2H), 7.34-7.20 (m, 5H), 6.96 (d, J=8.8 Hz, 2H), 5.29-5.19 (m, 1H), 4.67 (h, J=6.2 Hz, 1H), 4.23-4.14 (m, 1H), 3.86-3.74 (m, 2H), 3.34-3.19 (m, 2H), 3.11 (dd, J=13.7, 5.9 Hz, 1H), 2.87 (dd, J=13.7, 6.5 Hz, 1H), 2.73 (s, 1H), 1.43 (s, 9H), 1.34 (d, J=6.1 Hz, 3H). MS/ESI$^+$ 454.3 [M+H]$^+$.

Step e) (S)-2-amino-3-(3-(4-(((R)-1-phenylpropan-2-yl)oxy)phenyl)-1,2,4-oxadiazol-5-yl)propan-1-ol (Example 17). To a 10 mL one-necked pear shaped flask equipped with a magnetic stir bar was added benzyl (S)-2-((tert-butoxycarbonyl)amino)-3-(3-(4-(((R)-1-phenylpropan-2-yl)oxy)phenyl)-1,2,4-oxadiazol-5-yl)propanoate (17.5) (0.168 g, 0.370 mmol), DCM (4.0 ml) and TFA (0.143 ml, 1.852 mmol). The colorless solution was stirred for 3 days at rt. Meanwhile, It turned orange. The solvent and acid were removed in vacuo. Purification by column chromatography (ISCO CombiFlash Rf, absorbed on silica gel, MeOH in $CH_2Cl_2$ 0 10β6). The product was again purified under identical conditions to afford (S)-2-amino-3-(3-(4-(((R)-1-phenylpropan-2-yl)oxy)phenyl-1,2,4-oxadiazol-5-yl)pro-pan-1-ol (0.108 g, 78%) (Example 17) as a colorless oil. UPLC retention time 0.84 min (Method A). $^1$H NMR (400 MHz, $CDCl_3$) δ=7.86 (d, J=8.8 Hz, 2H), 7.30-7.19 (m, 5H), 6.89 (d, J=8.9 Hz, 2H), 4.61 (h, J=6.1 Hz, 1H), 3.97 (d, J=9.1 Hz, 1H), 3.90-3.83 (m, 1H), 3.79 (dd, J=11.7, 6.5 Hz, 1H), 3.37-3.14 (m, 2H), 3.06 (dd, J=13.7, 5.9 Hz, 1H), 2.82 (dd, J=13.7, 6.5 Hz, 1H), 1.28 (d, J=6.0 Hz, 3H). MS/ES$^+$ 354.3 [M+H]$^+$.

Example 18 (3S)-3-amino-4-(3-(4-((5-bromo-3-fluoropyridin-2-yl)oxy)phenyl)-1,2,4-oxadiazol-5-yl)butan-2-ol

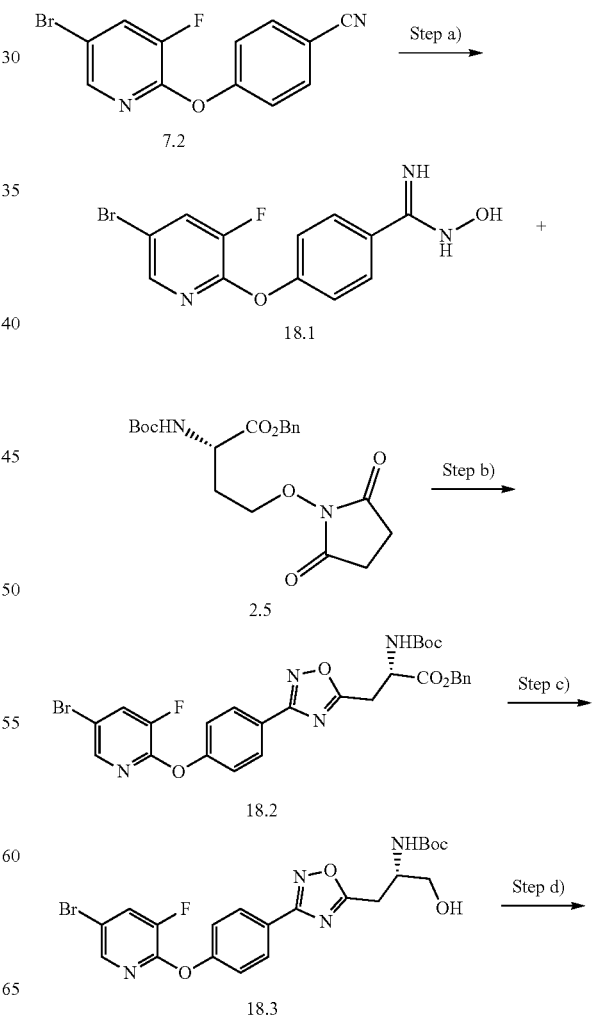

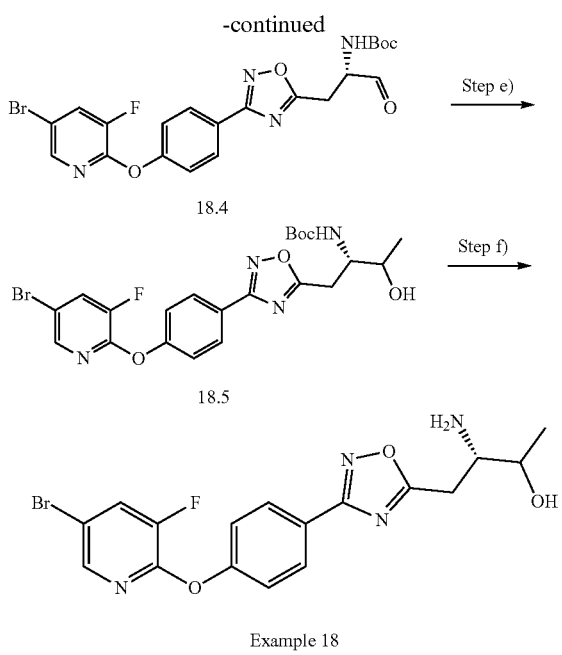

Example 18

Step a) 4-((5-bromo-3-fluoropyridin-2-yl)oxy)-N-hydroxybenzimidamide (18.1). To a 50 mL one-necked pear shaped flask equipped with a magnetic stir bar and a condenser (air) was added 4-((5-bromo-3-fluoropyridin-2-yl)oxy)benzonitrile (7.2) (763 mg, 2.60 mmol), hydroxylamine hydrochloride (905 mg, 13.02 mmol), NaHCO$_3$ (1093 mg, 13.02 mmol) and EtOH (15.0)/Water (5.0 mL). The white suspension was stirred for 80 minutes at 85° C. EtOH was removed In vacuo. Water and EtOAc were added. The aqueous phase was extracted twice with EtOAc. The organic layers were washed with brine, combined and dried over Na$_2$SO$_4$. Concentration in vacuo afforded 44(5-bromo-3-fluoropyridin-2-yl)oxy)-N-hydroxybenzimidamide (0.849 g, 98%) (18.1) as a white solid. UPLC retention time 0.75 min (Method A). MS/ES$^+$ 326.2, 328.2 [M+H]$^+$.

Step b) benzyl (S)-3-(3-(4-((5-bromo-3-fluoropyridin-2-yl)oxy)phenyl)-1,2,4-oxadiazol-5-yl)-2-((tert-butoxycarbonyl)amino)propanoate (18.2). To a 20 mL microwave vial equipped with a magnetic stir bar was added 4-((5-bromo-3-fluoropyridin-2-yl)oxy)-N-hydroxybenzimidamide (18.1) (470 mg, 1.441 mmol), Boc-Asp(OSu)-OBzl (2.5) (666 mg, 1.585 mmol) and THE (13.0 ml). The solution was stirred for 16 hours at 110° C. A suspension was obtained. Volatiles were removed in vacuo. Purification by column chromatography (ISCO CombiFlash Rf, absorbed on silica gel, EtOAc in cyclohexane 0-16%) afforded benzyl (S)-3-(3-(4-((5-bromo-3-fluoropyridin-2-yl)oxy)phenyl)-1,2,4-oxadiazol-5-yl)-2-((tert-butoxycarbonyl)amino)propanoate (433 mg, 49%) (18.2). UPLC retention time 1.44 min (Method A). $^1$H NMR (400 MHz, CDCl$_3$) δ=8.05-8.01 (m, 2H), 7.99 (d, J=2.1 Hz, 1H), 7.66 (dd, J=8.8, 2.1 Hz, 1H), 7.28-7.21 (m, 7H), 5.56 (d, J=7.7 Hz, 1H), 5.23-5.12 (m, 2H), 4.91-4.83 (m, 1H), 3.49 (qd, J=16.3, 5.1 Hz, 2H), 1.42 (s, 9H). 19F NMR (376 MHz, CDCl$_3$) δ=−132.98. MS/ESI$^+$ 613.3, 615.3 [M+H]$^+$.

Step c) tert-butyl (S)-(1-(3-(4-((5-bromo-3-fluoropyridin-2-yl)oxy)phenyl)-1,2,4-oxadiazol-5-yl)-3-hydroxypropan-2-yl)carbamate (18.3). To a 25 mL two-necked round bottom flask equipped with a magnetic stir bar, rubber septum and gas inlet was added benzyl (S)-3-(3-(4-((5-bromo-3-fluoropyridin-2-yl)oxy)phenyl)-1,2,4-oxadiazol-5-yl)-2-((tert-butoxycarbonyl)amino)propanoate (18.2) (433 mg, 0.706 mmol). The flask was evacuated and backfilled with Ar five times. Anhydrous THE (8.0 ml) was added and the clear solution was cooled to 0° C. After addition of LiBH$_4$ (61.5 mg, 2.82 mmol), the reaction mixture was stirred for 2.5 hr. Volatiles were removed in vacuo. Purification by column chromatography (ISCO CombiFlash Rf, absorbed on silica gel, EtOAc in cyclohexane 20-45%) afforded tert-butyl (S)-(1-(3-(4-((5-bromo-3-fluoropyridin-2-yl)oxy)phenyl)-1, 2,4-oxadiazol-5-yl)-3-hydroxypropan-2-yl)carbamate (217 mg, 60.4%) (18.3) as a colorless sticky oil.). UPLC retention time 1.18 min (Method A). $^1$H NMR (400 MHz, CDCl$_3$) δ=8.12 (dd, J=9.1, 2.2 Hz, 2H), 8.01 (d, J=2.1 Hz, 1H), 7.67 (dd, J=8.8, 2.1 Hz, 1H), 7.28 (d, J=1.9 Hz, 2H), 5.22 (s br, 1H), 4.24-4.15 (m, 1H), 3.86-3.76 (m, 2H), 3.29 (d, J=6.0 Hz, 2H), 1.44 (s, 9H). 19F NMR (376 MHz, CDCl$_3$) δ=132.96. MS/ESI$^+$ 509.2, 511.2 [M+H]$^+$.

Step d) tert-butyl (S)-(1-(3-(4-((5-bromo-3-fluoropyridin-2-yl)oxy)phenyl)-1,2,4-oxadiazol-5-yl)-3-oxopropan-2-yl) carbamate (18.4). To a 12 mL one-necked pear shaped flask equipped with a magnetic stir bar was added tert-butyl (S)-(1-(3-(4-((5-bromo-3-fluoropyridin-2-yl)oxy)phenyl)-1, 2,4-oxadiazol-5-yl)-3-hydroxypropan-2-yl)carbamate (18.3) (217 mg, 0.426 mmol), DCM (5.0 ml) and DMP (208 mg, 0.490 mmol). The white suspension was stirred for 28 minutes at rt. A few drops of sat. aq. NaHCO$_3$ and sat. aq. Na$_2$S$_2$O$_3$ solution were added and the biphasic system was stirred for 2 hours at rt. In the meantime, both phases became clear. Water and dichloromethane were added. The aqueous phase was extracted once with CH$_2$Cl$_2$ and once with EtOAc. The organic layers were washed with brine, combined and dried over Na$_2$SO$_4$. Purification by column chromatography (ISCO CombiFlash Rf, absorbed on silica gel, EtOAc in cyclohexane 20-26.5% to 34.3%) afforded tert-butyl (S)-(1-(3-(4-((5-bromo-3-fluoropyridin-2-yl)oxy)phenyl)-1,2,4-oxadiazol-5-yl)-3-oxopropan-2-yl)carbamate (177 mg, 82%) (18.4) as a hard white foam. UPLC retention time 1.22 min (Method A). $^1$H NMR (400 MHz, CDCl$_3$) δ=9.75 (s, 1H), 8.12-8.07 (m, 2H), 8.01 (d, J=2.1 Hz, 1H), 7.67 (dd, J=8.8, 2.1 Hz, 1H), 7.28 (d, J=2.0 Hz, 2H), 5.67 (d, J=6.9 Hz, 1H), 4.69-4.56 (m, 1H), 3.50 (d, J=5.3 Hz, 2H), 1.46 (s, 9H). MS/ESI$^+$ 507.1, 509.1 [M+H]$^+$.

Step e) tert-butyl ((2S)-1-(3-(4-((5-bromo-3-fluoropyridin-2-yl)oxy)phenyl)-1,2,4-oxadiazol-5-yl)-3-hydroxybutan-2-yl)carbamate (18.5). To a 10 mL two-necked cone shaped flask equipped with a magnetic stir bar, rubber septum and gas inlet was added tert-butyl (S)-(1-(3-(4-((5-bromo-3-fluoropyridin-2-yl)oxy)phenyl-1,2,4-oxadiazol-5-yl)-3-oxopropan-2-yl)carbamate (18.4) (91.3 mg, 0.180 mmol). The flask was evacuated and backfilled with Ar five times. Anhydrous THF (1.00 mL) was added and the colorless solution was cooled to 0'C. MeMgBr in THF (0.25 mL, 0.750 mmol) was then carefully added (gas formation during addition) and the reaction mixture was stirred for 2.5 hours (ice bath was removed after 2 hours). The reaction was quenched with a few drops of MeOH and then sat. aq. NH$_4$Cl solution. It was stored in the freezer over night. EtOAc and water were added. The aqueous phase was extracted twice with EtOAc. The organic layers were washed with brine, combined and dried over Na$_2$SO$_4$. Purification by column chromatography (ISCO CombiFlash Rf, absorbed on silica gel, EtOAc in cyclohexane 15-27.5% to 40%) afforded tert-butyl ((2S)-1-(3-(4-((5-bromo-3-fluoropyridin-2-yl)oxy)phenyl)-1,2,4-oxadiazol-5-yl)-3-hydroxybutan-2-yl)carbamate (60.2 mg, 63.9%) (18.5). UPLC retention time 1.22 min (Method A). $^1$H NMR (400 MHz, CDCl$_3$) δ=8.12 (dd, J=8.9, 2.2 Hz, 2H), 8.01 (d, J=2.0 Hz, 1H), 7.67 (dd, J=8.8, 2.0 Hz, 1H), 7.28 (d, J=1.9 Hz, 3H), 5.14 (d, J=6.7 Hz, 1H), 4.07-3.93 (m, 2H), 3.38-3.18 (m, 2H), 1.43 (s, 9H), 1.26 (d, J=2.3 Hz, 3H). 19F NMR (376 MHz, CDCl$_3$) δ=−132.99. MS/ES$^+$ 523.3, 525.3 [M+H]$^+$.

Step f) (3S)-3-amino-(3-(4-((5-bromo-3-fluoropyridin-2-yl)oxy)phenyl)-1,2,4-oxadiazol-5-yl)butan-2-ol (Example 18). To a 12 mL one-necked pear shaped flask equipped with a magnetic stir bar was added tert-butyl ((2S)-1-(3-(4-((5-bromo-3-fluoropyridin-2-yl)oxy)phenyl)-1,2,4-oxadiazol-5-yl)-3-hydroxybutan-2-yl)carbamate (18.5). (60.2 mg, 0.115 mmol), dioxane (1.00 ml) and aq. HCl (1.00 mL, 2.000 mmol). The cloudy solution was stirred for 4 days at rt. Water, 2M aq. NaOH (5.0 mL) and EtOAc were added. The aqueous phase was extracted twice with EtOAc. The organic layers were washed with brine, combined and dried over Na$_2$SO$_4$. Purification by column chromatography (ISCO CombiFlash Rf, absorbed on silica gel, MeOH in CH$_2$Cl$_2$ 0-5%) afforded (3S)-3-amino-4-(3-(4-((5-bromo-3-fluoropyridin-2-yl)oxy)phenyl)-1,2,4-oxadiazol-5-yl)butan-2-ol (33.9 mg, 67.5%) (Example 18) as a colorless oil and 78:22 diastereomeric mixture. UPLC retention time 0.79 min (Method A). $^1$H NMR (400 MHz, CDCl$_3$) δ=8.16-8.09 (m, 2H), 8.00 (d, J=2.1 Hz, 1H), 7.67 (dd, J=8.8, 2.1 Hz, 1H), 7.27 (d, J=8.8 Hz, 3H), 3.71-3.61 (m, 1H), 3.22-3.12 (m, 2H), 3.02-2.92 (m, 1H), 1.28 (d, J=6.2 Hz, 3H). MS/ES$^+$ 423.2, 425.2 [M+H]$^+$.

Example 19 (R)-3-(5-(4-((5-(1H-pyrazol-3-yl)pyridin-2-yl)oxy)phenyl)-2H-tetrazol-2-yl)-2-aminopropan-1-ol

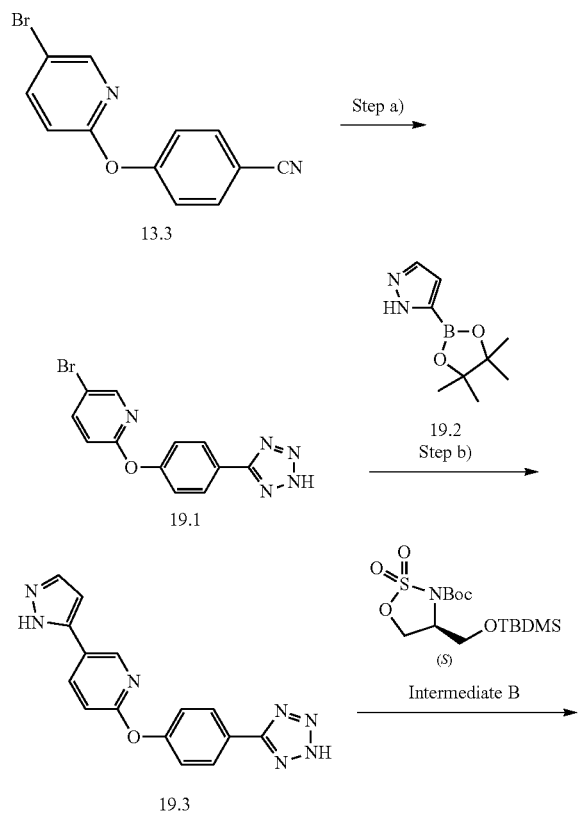

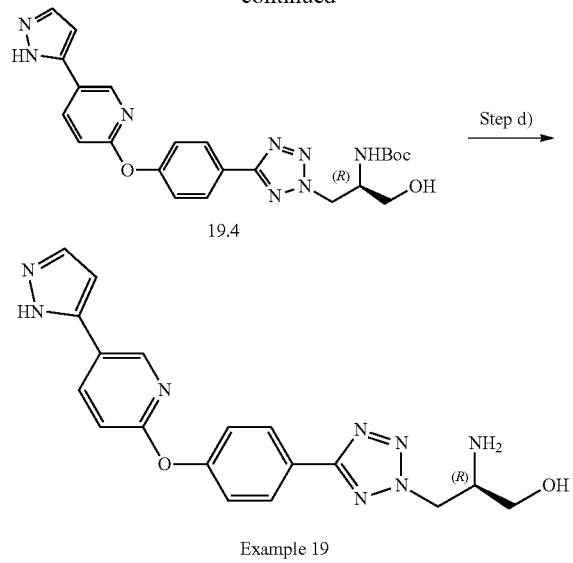

Example 19

Molecular Weight: 478.51

Step a) 2-(4-(2H-tetrazol-5-yl)phenoxy)-5-bromopyridine (19.1). At room temperature Bu$_2$SnO (0.204 g, 0.818 mmol) was added to a solution of 13.3 (1.5 g, 5.45 mmol) and trimethylsilyl azide (1.447 mL, 10.91 mmol) in toluene (20 ml). The reaction mixture (yellow solution) was stirred for 16 h at 100° C. The mixture was concentrated, the crude product triturated with diethylether and 19.1 (1.28 g, 70%) filtered off as a white solid. UPLC retention time 0.86 min (Method A). $^1$H NMR (DMSO-d6): δ=16.82 (s, br, 1H), 8.33 (d, J=2.5 Hz, 1H), 8.24-8.00 (m, 3H), 7.51-7.29 (m, 2H), 7.17 (d, J=8.7 Hz, 1H). MS/ESI 318.1 [M+H]$^+$.

Step b) 2-(4-(2H-tetrazol-5-yl)phenoxy)-5-(1H-pyrazol-3-yl)pyridine (19.3). Compounds 19.1 (1.2 g, 3.77 mmol) and 19.2 (0.732 g, 3.77 mmol) were dissolved in dioxane (15 ml) and water (15 ml). Then K$_3$PO$_4$ (2.402 g, 11.32 mmol) and PdCl$_2$(dtbpf) (0.246 g, 0.377 mmol) were added under argon and the reaction mixture was stirred for 16 h at 120° C. The reaction mixture was absorbed on (solute and dried on the RotaVap to dryness. The reaction mixture was purified on silica (gradient: ethyl acetate/MeOH) to afford compound 19.3 (1.41 g, 81% purity). UPLC retention time 0.67 min (Method A). $^1$H NMR (DMSO-d$_6$): 5=12.97 (s, br, 1H), 8.62 (s, 1H), 8.25 (m, 1H), 8.05 (m, 2H), 7.78 (s, br, 1H), 7.25 (m, 2H), 7.10 (m, 1H), 6.76 (s, 1H), tetrazole H not observed. MS/ESI 306.2 [M+H]$^+$.

Step c) tert-butyl (R)-(1-(5-(4-((5-(1H-pyrazol-5-yl)pyridin-2-yl)oxy)phenyl)-2H-tetrazol-2-yl)-3-((tert-butyldimethylsilyl)oxy)propan-2-yl)carbamate (19.4). At room temperature Intermediate B (166 mg, 0.452 mmol) was added to a mixture of 19.3 (115 mg, 0.377 mmol) and Cs$_2$CO$_3$ (368 mg, 1.13 mmol) in DMA (4 mL). The reaction mixture was stirred for 16 h at 70° C. Brine and CH$_2$Cl$_2$ were added and the mixture was extracted with CH$_2$Cl$_2$ (3x). The combined organic layers was dried with Na$_2$SO$_4$, concentrated and the residue purified on silica (gradient: ethylacetate/MeOH) to afford 19.4 as a white solid (30 mg, 83% purity). UPLC retention time 0.89 min (Method A). MS/ESI 479.4 [M+H]$^+$.

Step d) (R)-3-(5-(4-((5-(1H-pyrazol-3-ylpyridin-2-yl)oxy)phenyl)-2H-tetrazol-2-yl)-2-aminopropan-1-ol (Example 19). A 4M solution of HCl in dioxane (0.157 mL, 0.627 mmol) was added to a solution of 19.4 (30 mg, 0.063 mmol) in dioxane (0.5 ml). The resulting suspension was stirred for 1 hr at room temperature, diluted with diethylether. A colorless solid was filtered off and purified by SFC to give Example 19 as a colorless powder (10 mg, 39%). UPLC retention time 0.56 min (Method A). ¹H NMR (DMSO-d₆): δ=8.64 (1H, d), 8.31 (1H, dd), 8.13 (3H, m), 7.86 (2H, d), 7.43 (2H, d), 7.23 (1H, d), 6.78 (1H, d), 5.50 (1H, m), 4.78 (1H, dd), 4.63 (1H, dd), 3.85 (1H, m), 3.65 (1H, dd), 3.55 (1H, dd), pyrazol NH not observed. MS/ESI 379.3 [M+H]⁺.

Example 20 (S)-3-(5-(4-((5-(1H-pyrazol-3-yl)pyridin-2-yl)oxy)phenyl)-2H-tetrazol-2-yl)-2-aminopropan-1-ol

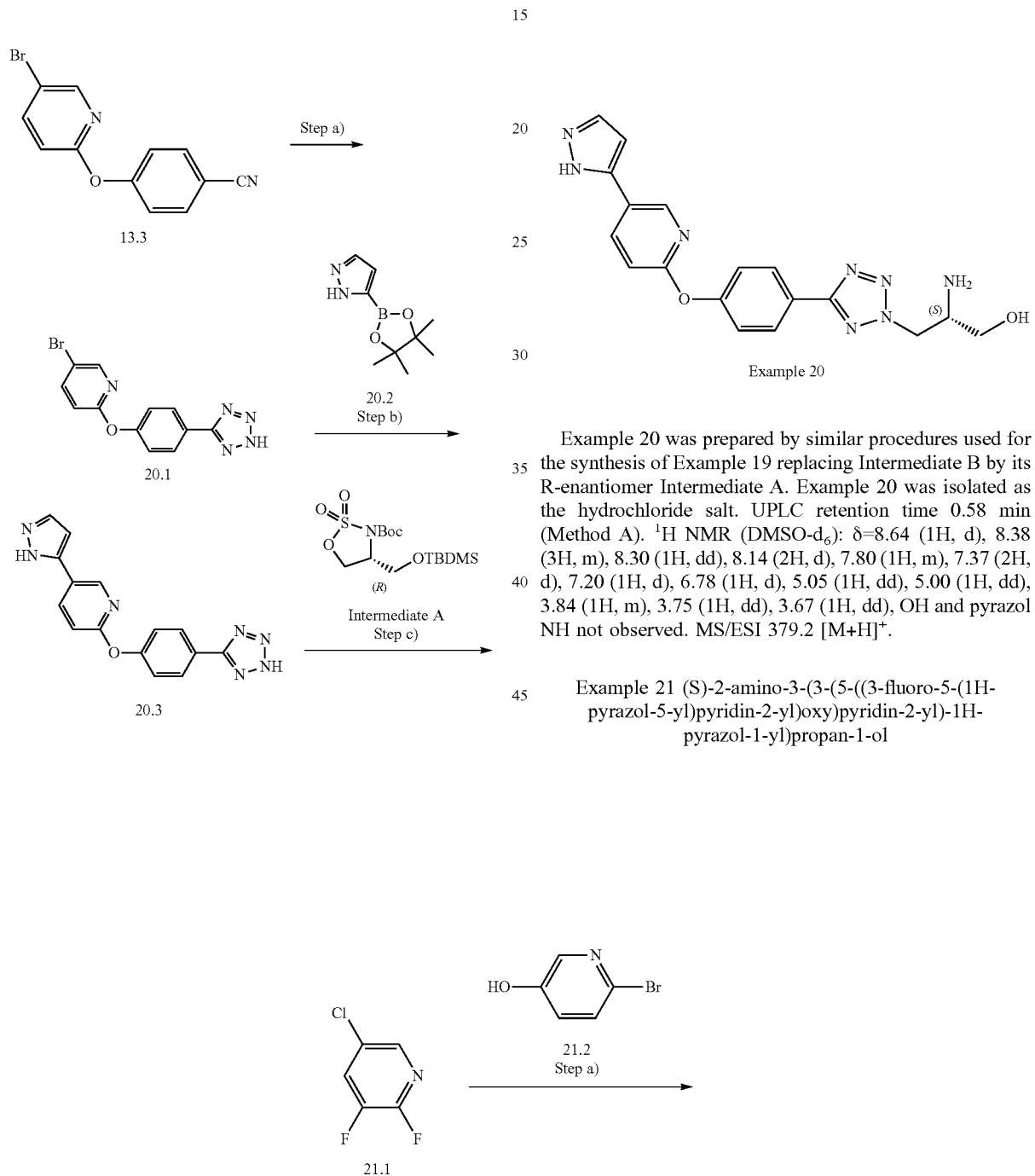

Example 20

Example 20 was prepared by similar procedures used for the synthesis of Example 19 replacing Intermediate B by its R-enantiomer Intermediate A. Example 20 was isolated as the hydrochloride salt. UPLC retention time 0.58 min (Method A). ¹H NMR (DMSO-d₆): δ=8.64 (1H, d), 8.38 (3H, m), 8.30 (1H, dd), 8.14 (2H, d), 7.80 (1H, m), 7.37 (2H, d), 7.20 (1H, d), 6.78 (1H, d), 5.05 (1H, dd), 5.00 (1H, dd), 3.84 (1H, m), 3.75 (1H, dd), 3.67 (1H, dd), OH and pyrazol NH not observed. MS/ESI 379.2 [M+H]⁺.

Example 21 (S)-2-amino-3-(3-(5-((3-fluoro-5-(1H-pyrazol-5-yl)pyridin-2-yl)oxy)pyridin-2-yl)-1H-pyrazol-1-yl)propan-1-ol -continued
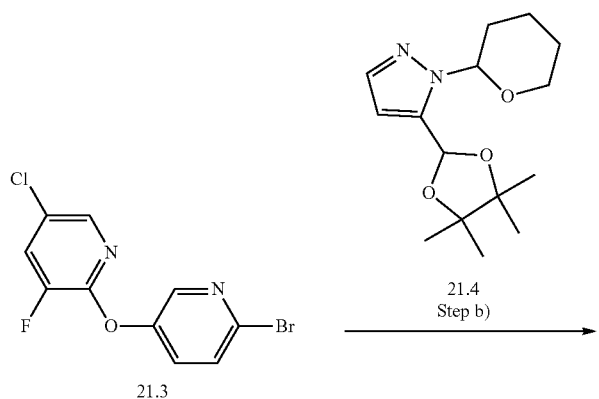
21.4
Step b)
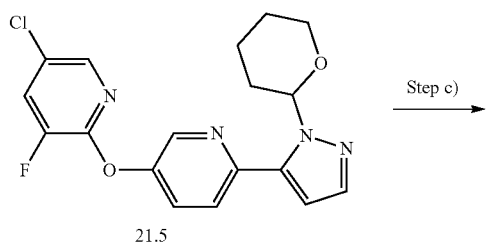
Step c)
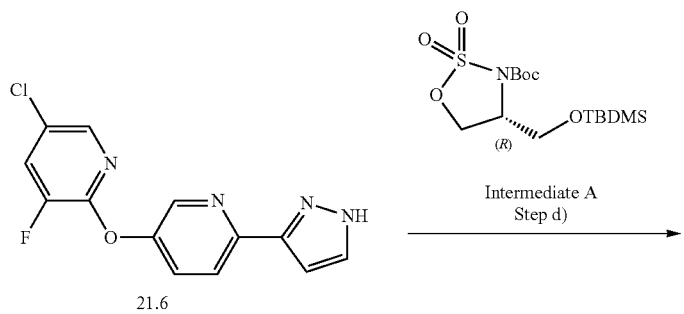
Intermediate A
Step d)
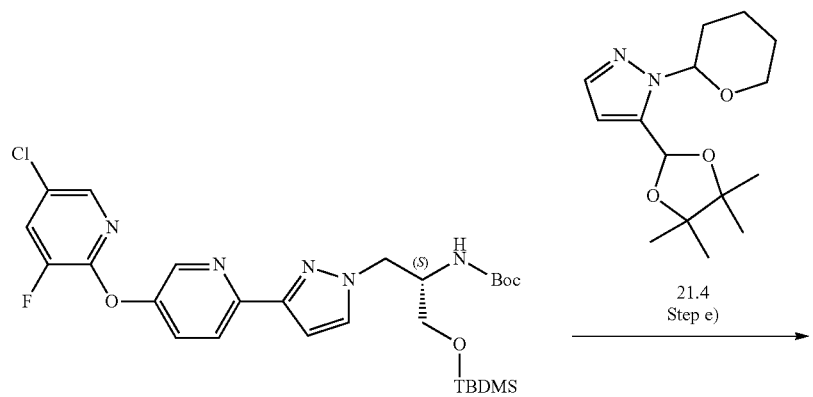
21.4
Step e)

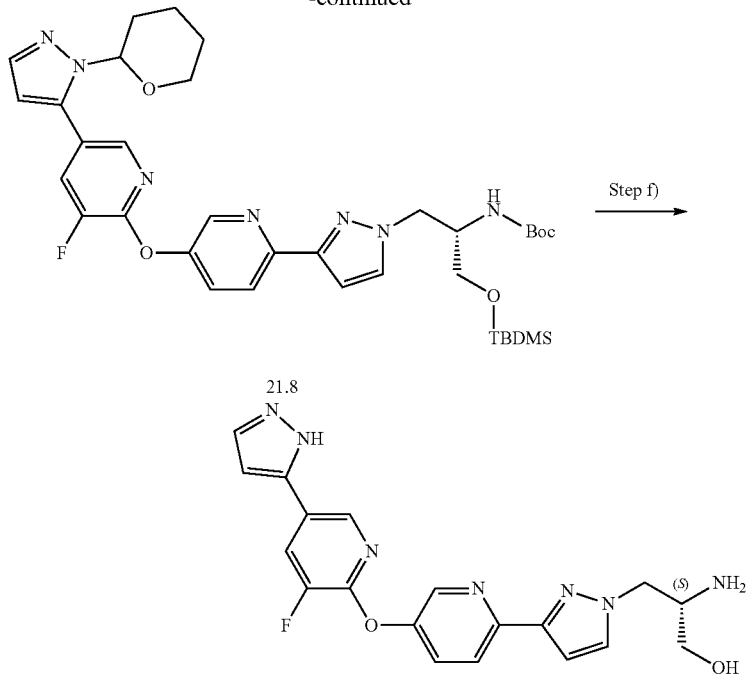

Example 21

Step a) 2-((6-bromopyridin-3-yl)oxy)-5-chloro-3-fluoropyridine (21.3). A mixture of 21.1 (189 mg, 1.264 mmol), 21.2 (200 mg, 1.149 mmol) and K$_2$CO$_3$ (318 mg, 2.299 mmol) in DMF (1.5 mL) was stirred for 5 h at 80° C. The mixture was diluted with water and extracted with ethyl acetate. The organic layer was washed with water, dried with Na$_2$SO$_4$, filtered and concentrated. The residue was purified on silica (gradient: cyclohexane/ethyl acetate) to afford 21.3 (271 mg, 73%). UPLC retention time 1.10 min (Method A). $^1$H NMR (DMSO-d$_6$): δ=8.41 (1H, s), 8.27 (1H, dd), 8.07 (1H, d), 7.75 (2H, s). MS/ESI 303.0 [M+H]$^+$.

Step b) 5-chloro-3-fluoro-2-((6-(1-(tetrahydro-2H-pyran-2-yl)-1H-pyrazol-5-yl)pyridin-3-yl)oxy)pyridine (21.5). A suspension of 21.3 (1350 mg, 4.45 mmol), 21.4 (1299 mg, 4.67 mmol), K$_3$PO$_4$ (1888 mg, 8.90 mmol) and PdCl$_2$(dtbpf) (145 mg, 0.222 mmol) in a mixture of dioxane (15 mL) and water (5 mL) was stirred under argon for 15 min at 25'C. The mixture was diluted with water and extracted with ethyl acetate. The organic layer was dried with Na$_2$SO$_4$, filtered and concentrated. The residue was purified on silica (gradient: cyclohexane/ethyl acetate) to afford 21.5 (1390 mg, 73%). UPLC retention time 1.16 min (Method A). $^1$H NMR (DMSO-d$_6$): δ=8.65 (1H, d), 8.29 (1H, dd) 8.10 (1H, d), 7.83-7.89 (2H, m), 7.60 (1H, d), 6.81 (1H, d), 6.25 (1H, dd), 3.86 (1H, d), 3.46-3.56 (1H, m), 2.33-2.46 (1H, m), 1.88-2.06 (2H, m), 1.48-1.71 (3H, m). MS/ESI 375.1 [M+H]$^+$.

Step c) 2-((6-(1H-pyrazol-3-yl)pyridin-3-yl)oxy)-5-chloro-3-fluoropyridine (21.6). To a solution of 21.5 (1380 mg, 3.68 mmol) in methanol (12 mL) was added 2N HCl (11.05 mL, 22.1 mmol) and the mixture stirred for 1 h at 25° C. A suspension formed. Filtration afforded a colorless solid, which was dissolved in CH$_2$Cl$_2$ (20 mL). Water was added and the pH adjusted to 10 by addition of 2N K$_2$CO$_3$. The layers were separated and the aqueous layer extracted with CH$_2$C$_{12}$. The combined organic layers were dried with Na$_2$CO$_3$, filtered and concentrated to afford 21.6 (960 mg, 89%). UPLC retention time 0.89 min (Method A). $^1$H NMR (DMSO-d$_6$): δ=13.50 and 13.05 (1H, 2s), 8.52 (1H, s br), 8.27 (1H, dd), 7.95-8.10 (2H, m), 7.83 (1H, s br), 7.71-7.80 (1H, m), 6.83 (1H, s br), mixture of tautomers. MS/ESI 291.1 [M+H]$^+$.

Step d) (S)-tert-butyl (1-((tert-butyldimethylsilyl)oxy)-3-(3-(5-((5-chloro-3-fluoropyridin-2-yl)oxy)pyridin-2-yl)-1H-pyrazol-1-yl)propan-2-yl)carbamate (21.7). A mixture of 21.6 (900 mg, 3.10 mmol), Intermediate A (1366 mg, 3.72 mmol) and K$_2$CO$_3$ (1284 mg, 9.29 mmol) in DMF (11 mL) was stirred under argon for 70 h at 25° C. The mixture was diluted with water and extracted with ethyl acetate. Brine was added and the layers separated. The aqueous layer was extracted with ethyl acetate, the combined organic layers dried with Na$_2$SO$_4$, filtered and concentrated. The residue was purified on silica (gradient: cyclohexane/ethyl acetate) to afford 21.7 (518 mg, 28%). UPLC retention time 1.54 min (Method A). $^1$H NMR (DMSO-d$_6$): δ=8.50 (1H, d), 8.26 (1H, dd), 8.06 (1H, d), 7.97 (1H, d), 7.74 (1H, dd), 7.71 (1H, d), 6.83 (1H, d br), 6.77 (1H, d), 4.30 (1H, dd), 4.13 (1H, dd br), 3.93 (1H, d br), 3.46-3.62 (2H, m), 1.32 (9H, s), 0.85-0.89 (9H, m), 0.02-0.06 (6H, m). MS/ESI 578.3 [M+H]$^+$.

Step e) tert-butyl ((2S)-1-((tert-butyldimethylsilyl)oxy)-3-(3-(5-((3-fluoro-5-(1-(tetrahydro-2H-pyran-2-yl)-1H-pyrazol-5-yl)pyridin-2-yl)oxy)pyridin-2-yl)-1H-pyrazol-1-yl)propan-2-yl)carbamate (21.8). A suspension of 21.7 (250 mg, 0.432 mmol), 21.4 (241 mg, 0.865 mmol), K$_3$PO$_4$ (275 mg, 1.297 mmol) and PdCl$_2$(dtbpf) (145 mg, 0.222 mmol) in a mixture of dioxane (2.5 mL) and water (1 mL) was stirred under argon for 15 min at 90° C. The mixture was diluted with water and extracted with ethyl acetate. The organic layer was dried with Na$_2$SO$_4$, filtered and concentrated. The residue was purified on silica (gradient: cyclohexane/ethyl acetate) to afford 21.8 (180 mg, 60β6). UPLC retention time 1.55 min (Method A). $^1$H NMR (DMSO-d$_6$): 5=8.55 (1H, d), 8.10 (1H, s), 8.02-8.08 (1H, m), 8.00 (1H, d), 7.79 (1H, dd), 7.73 (1H, d), 7.61 (1H, s), 6.84 (1H, d br), 6.79 (1H, d), 6.59 (1H, d), 5.29 (1H, dd), 4.31 (1H, dd), 4.14 (1H, dd br), 3.94 (2H, d br), 3.53-3.59 (3H, m), 2.28-2.44 (1H, m), 1.90-2.02 (1H, m), 1.77-1.88 (1H, m), 1.50-1.55 (3H, m), 1.33 (9H, s), 0.89 (9H, s), 0.05 (6H, s). MS/ESI 694.5 [M+H]$^+$.

Step f) (S)-2-amino-3-(3-(5-((3-fluoro-5-(1H-pyrazol-5-yl)pyridin-2-yl)oxy)pyridin-2-yl)-1H-pyrazol-1-yl)propan-1-ol (Example 21). A 4M solution of HCl in dioxane (0.612 mL, 2.45 mmol) was added to a solution of 21.8 (170 mg, 0.245 mmol) in acetone (2.5 ml). The resulting suspension was stirred for 16 hr at room temperature. A colorless solid was filtered off, washed with acetone and purified by SFC and chromatography on silica (gradient: CH$_2$Cl$_2$/MeOH) to give Example 21 as a colorless powder (12 mg, 12%). UPLC retention time 0.55 min (Method A). $^1$H NMR (DMSO-d$_6$): δ=13.07 (1H, s br), 8.52 (1H, d), 8.41 (1H, s), 8.25 (1H, d br), 7.98 (1H, d), 7.76-7.85 (2H, m), 7.74 (1H, dd), 6.81 (2H, dd), 4.71 (1H, t), 4.22 (1H, dd), 3.99 (1H, dd), 3.25-3.30 (2H, m), 3.08-3.16 (1H, m), 1.58 (2H, s br). MS/ESI 396.2 [M+H]$^+$.

Example 22 (S)-2-amino-3-(5-(5-((3-fluoro-5-(1H-pyrazol-5-yl)pyridin-2-yl)oxy)pyridin-2-yl)-2H-tetrazol-2-yl)propan-1-ol

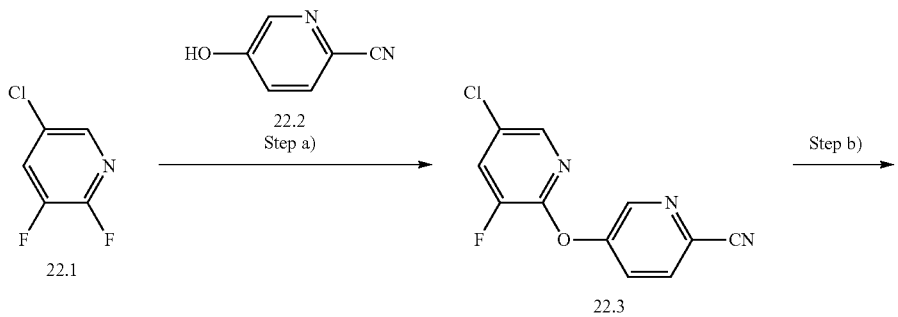

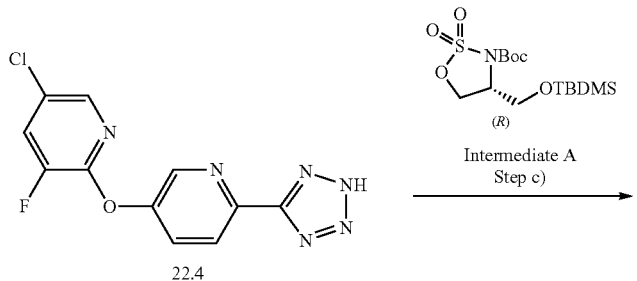

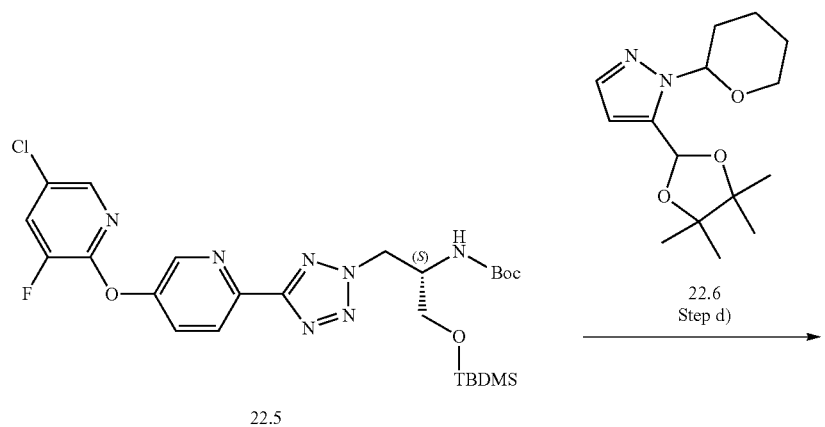

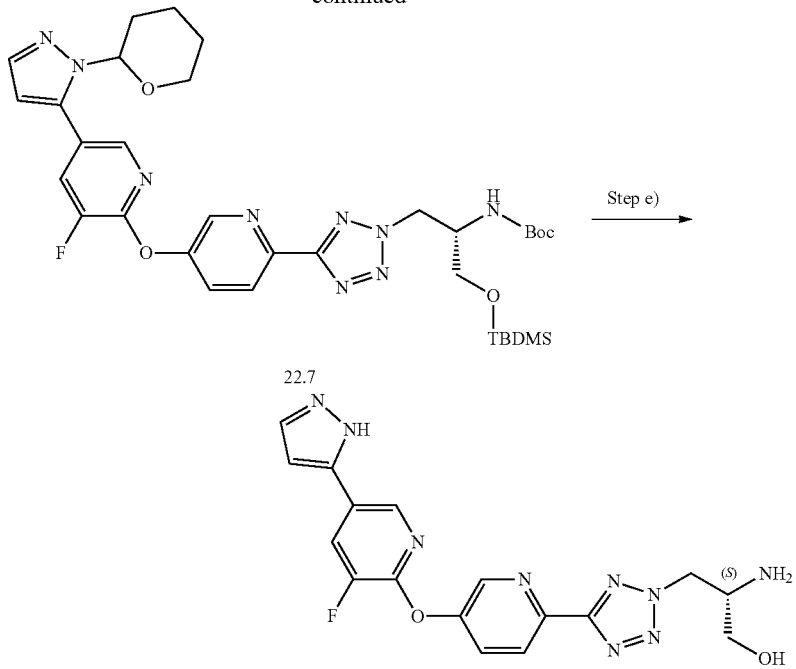

Example 22

Step a) 5-((5-chloro-3-fluoropyridin-2-yl)oxy)picolinonitrile (22.3). A mixture of 22.1 (1245 mg, 8.33 mmol), 22.2 (1000 mg, 8.33 mmol) and K$_2$CO$_3$ (2301 mg, 16.65 mmol) in DMF (10 mL) was stirred under argon for 16 h at 80° C. The mixture was diluted with water and extracted with ethyl acetate. The organic layer was washed with water, dried with Na$_2$SO$_4$, filtered and concentrated. The residue was purified on silica (gradient CH$_2$Cl$_2$/MeOH) to afford 22.3 (1181 mg, 54%). UPLC retention time 1.01 min (Method A). $^1$H NMR (DMSO-d$_6$): δ=8.77 (1H, d), 8.34 (1H, dd), 8.18 (1H, d), 8.13 (1H, s), 8.03 (1H, dd). MS/ESI 250.1 [M+H]$^+$.

Step b) 2-((6-(2H-tetrazol-5-yl)pyridin-3-yl)oxy)-5-chloro-3-fluoropyridine (22.4). Under argon a solution of 22.3 (1120 mg, 4.49 mmol), Bu$_2$SnO (112 mg, 0.449 mmol) and TMSN$_3$ (1034 mg, 8.97 mmol) in dry toluene (8 mL) was heated in a sealed tube at 90° C. for 18 h on a heating block. Additional Bu$_2$SnO and TMSN$_3$ were added and heating continued for 3 h. After cooling down to room temperature MeOH (2 mL) was added and the mixture concentrated. The residue was purified on silica (gradient: cyclohexane/ethyl acetate, then CH$_2$Cl$_2$/MeOH) to afford 29.4 as a colorless powder (960 mg, 73%). UPLC retention time 0.85 min (Method A). $^1$H NMR (DMSO-d$_6$): δ=8.79 (1H, d), 8.28-8.35 (2H, m), 8.11 (1H, d), 8.02 (1H, dd), tetrazole NH not observed. MS/ESI 293.1 [M+H]$^+$.

Step c) (5)-tert-butyl (1-((tert-butyldimethylsilyl)oxy-3-(5-(5-((5-chloro-3-fluoropyridin-2-yl)oxy)pyridin-2-y)-2H-tetrazol-2-yl)propan-2-yl)carbamate (22.5). A mixture of 22.4 (950 mg, 2.60 mmol), Intermediate A (1145 mg, 3.12 mmol) and K$_2$CO$_3$ (1077 mg, 7.79 mmol) in DMF (17 mL) was stirred under argon for 1.5 h at 25° C. The mixture was diluted with water and extracted with cyclohexane/ethyl acetate. The organic layer was dried with Na$_2$SO$_4$, filtered and concentrated. The residue was purified on silica (gradient cyclohexane/ethyl acetate) to afford 22.5 (773 mg, 51%). UPLC retention time 1.50 min (Method A). $^1$H NMR (DMSO-d$_6$): δ=8.69 (1H, d), 8.32-8.36 (2H, m), 8.11 (1H, d), 8.04 (1H, dd), 6.83 (1H, d), 5.08-5.23 (1H, m), 4.61-4.75 (1H, m), 3.90-4.01 (1H, m), 3.62-3.68 (2H, m), 1.21 (9H, s), 0.84 (9H, s), 0.02-0.06 (6H, m). MS/ESI 580.2 [M+H]$^+$.

Step d) tert-butyl ((2S)-1-((tert-butyldimethylsilyl)oxy)-3-(5-(5-((3-fluoro-5-(1-(tetrahydro-2H-pyran-2-yl)-1H-pyrazol-5-yl)pyridin-2-yl)oxy)pyridin-2-yl)-2H-tetrazol-2-yl)propan-2-yl)carbamate (22.7). A suspension of 22.5 (330 mg, 0.569 mmol), 22.6 (264 mg, 0.948 mmol), K$_3$PO$_4$ (302 mg, 1.423 mmol) and PdCl$_2$(dtbpf) (30.9 mg, 0.047 mmol) in a mixture of dioxane (3.5 mL) and water (1.17 mL) was stirred under argon for 1.25 h at 90'C. The mixture was diluted with water and extracted with CH$_2$Cl$_2$. The organic layer was dried with Na$_2$SO$_4$, filtered and concentrated. The residue was purified on silica (gradient: cyclohexane/ethyl acetate) to afford 22.7 (118 mg, 30%). UPLC retention time 1.52 min (Method A). $^1$H NMR (DMSO-d$_6$): δ=8.76 (1H, d), 8.23 (1H, d), 8.13 (1H, s), 8.09 (1H, d), 7.99 (1H, dd), 7.60-7.68 (m, 1H, m), 6.96 (1H, d br), 6.61 (1H, d), 5.30 (1H, dd), 4.91 (1H, dd), 4.70 (1H, dd br), 3.91-4.12 (2H, m), 3.53-3.70 (3H, m), 2.26-2.48 (1H, m), 1.92-2.01 (1H, m), 1.77-1.89 (1H, m), 1.50-1.68 (3H, m), 1.02-1.28 (9H, m), 0.88 (9H, s), 0.07 (6H, s). MS/ESI 696.3 [M+H]$^+$.

Step e) (S)-2-amino-3-(5-(5-((3-fluoro-5-(1H-pyrazol-5-yl)pyridin-2-yl)oxy)pyridin-2-yl)-2H-tetrazol-2-yl)propan-1-ol (Example 22). A 4M solution of HCl in dioxane (0.284 mL, 1.15 mmol) was added to a solution of 22.7 (80 mg, 0.115 mmol) in acetone (1 ml). The resulting suspension was stirred for 4 hr at room temperature. The mixture was concentrated, the residue dissolved in water, and CH$_2$Cl$_2$ was added. The pH was adjusted to 9 by with a saturated NaHCO$_3$solution and the aqueous layer extracted with CH$_2$C$_{12}$/isopropanol (3:1). The combined organic layers were dried with Na$_2$SO$_4$, filtered and concentrated. The residue was purified on silica (gradient: CH$_2$Cl$_2$/MeOH) to afford Example 22 (15 mg, 31%) as a colorless solid. UPLC retention time 0.52 min (Method A). $^1$H NMR (DMSO-d$_6$): δ=13.09 (1H, s br), 8.72 (1H, s br), 8.45 (1H, s br), 8.28 (1H, d br), 8.23 (1H, d br), 7.94 (1H, d br) 7.85 (1H, s br), 6.84 (1H, s br), 4.86 (1H, s br), 4.71-4.83 (1H, m), 4.50-4.71 (1H, m), 3.39 (2H, m), 3.35 (1H, m), 1.70 (2H, s br). MS/ESI 398.1 [M+H]$^+$.

Example 23 (S)-2-amino-3-(3-(5-((5-chloro-3-fluoropyridin-2-yl)oxy)pyridin-2-yl)-1H-pyrazol-1-yl)propan-1-ol

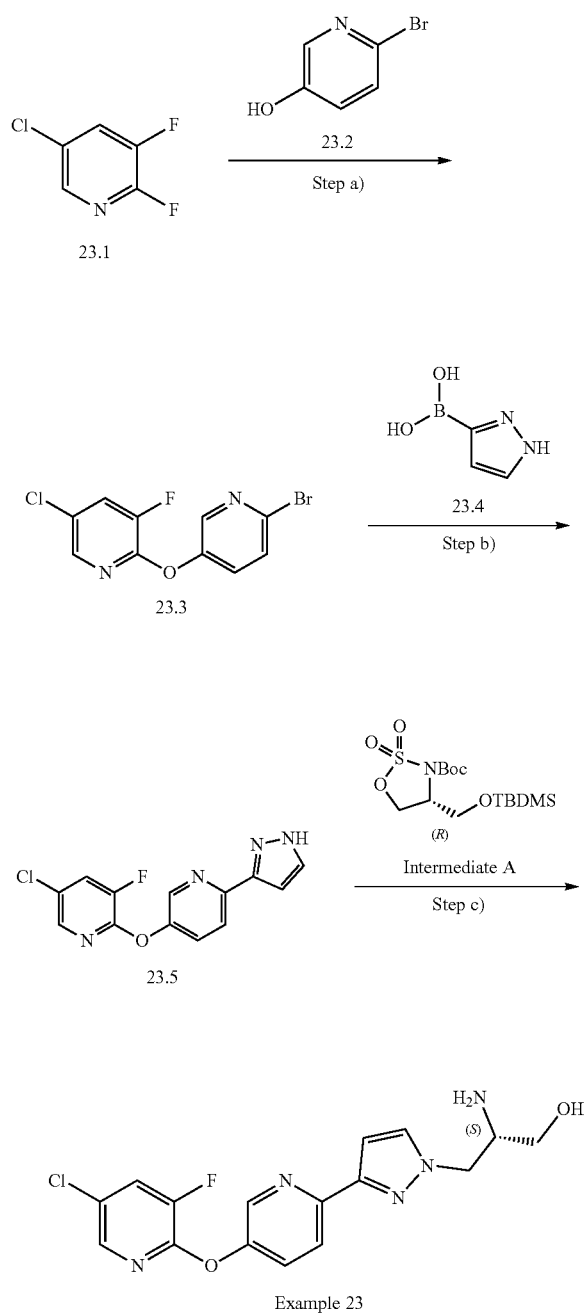

Step a) 2-((6-Bromopyridin-3-yl)oxy)-5-chloro-3-fluoropyridine (23.3). Under argon potassium carbonate (1.33 g, 9.63 mmol) was added to a solution of 23.1 (1.00 g, 6.42 mmol) and 23.2 (1.11 g, 6.42 mmol) in DMA (5 mL). The resulting suspension was stirred for 18 h at 80° C. After cooling the reaction mixture was poured into water (40 mL) and MTBE (20 ml) and vigorously stirred for 10 min. Then, the aqueous layer was extracted twice with MTBE. The combined organic phases were washed with H$_2$O and dried over Na$_2$SO$_4$. Evaporation gave the crude product as a yellow al. Crystallization from cyclohexane (4 mL) afforded compound 23.3 as an off white solid (1.57 g, 81%). UPLC retention time 1.15 min (Method A). $^1$H NMR (DMSO-de): δ=8.42 (1H, s), 8.29 (1H, dd), 8.08 (1H, d), 7.76 (2H, s). MS/ESI: m/z=303.0 [M+H]$^+$.

Step b) 2-((6-(1H-pyrazol-3-yl)pyridin-3-yl)oxy)-5-chloro-3-fluoropyridine (23.5). To a suspension of 23.3 (686 mg, 2.26 mmol) and 23.4 (582 mg, 5.20 mmol) in dioxane (22.6 mL) was added 2 M aqueous Na$_2$CO$_3$ (2.26 mL, 4.52 mmol) and tetrakis(triphenylphosphine)-palladium(0) (313 mg, 0.271 mmol). After purging with argon, the reaction mixture was stirred for 20 h at 85'C in a sealed tube. After cooling, the suspension was distributed between ethyl acetate (50 mL) and water (75 mL). The aqueous layer was extracted twice with ethyl acetate. The combined organic layers were washed with 1 M aqueous Na$_2$CO$_3$ and half-saturated brine. Drying over Na$_2$SO$_4$ and evaporation gave a yellow oil. Flash-chromatography (gradient: cyclohexane/ethyl acetate) to a light yellow oil. The residue was crystallized from EtOH/Et$_2$O give the pure compound 23.5 as a white solid (353 mg, 48%). UPLC retention time 0.95 min (Method A). $^1$H NMR (DMSO-d$_6$): 5 10.61 (br s), 8.57 (d, 1H), 8.29 (d, 1H), 8.08 (s), 8.07 (d), 7.86 (dd, 1H), 7.80 (s, 1H), 6.89 (s, 1H). MS/ESI: m/z=291.1 [M+H]$^+$.

Step c) (S)-2-amino-(3-(5-((5-chloro-3-fluoropyridin-2-yl)oxy)pyridin-2-yl)-1H-pyrazol-1-yl)propan-1-ol (23.6, Example 23). To a solution of 23.5 (117 mg, 0.40 mmol) and Intermediate A (177 mg, 0.482 mmol) in DMA (4.5 mL) was added Cs$_2$CO$_3$ (392 mg, 1.204 mmol). The suspension was stirred for 1.5 h at 0° C. under argon and another 2 h at rt followed by over-night stirring at 45° C. The reaction mixture was poured into a mixture of ethyl acetate (50 mL) and water (25 mL). The aqueous layer was extracted twice with ethyl acetate. The combined organic phases were washed four times with brine and dried over Na$_2$SO$_4$. Evaporation of the solvent gave a yellow oil. Separation by flash-chromatography (gradient: CH$_2$Cl$_2$/MeOH/NH$_3$) gave the pure compound Example 23 as colorless oil (89 mg, 55%). UPLC retention time 0.71 min (Method A). $^1$H NMR (DMSO-d$_6$): δ=8.55 (1H, d), 8.29 (1H, d), 8.21 (3H, br s), 8.08 (1H, d), 8.05 (1H, dm), 7.90 (1H, d), 7.80 (1H, d), 6.87 (1H, d), 4.52-4.37 (2H, m), 3.68-3.55 (2H, m), 3.54-3.45 (1H, m). MS/ESI: m/z=364.1 [M+H]$^+$.

The material was converted in its hydrochloride salt by treating a solution in acetone (5 mL) with 1.25 M HCl in MeOH (0.6 mL), followed by evaporation and trituration with Et$_2$O. The precipitate formed was filtered off and vacuum dried at 80'C to afford the product as colorless crystalline solid (81.2 mg). Additionally the regioisomeric product (S)-2-amino-3-(5-(5-((5-chloro-3-fluoropyridin-2-yl)oxy)pyridin-2-yl)-1H-pyrazol-1-yl)propan-1-ol 23' could be isolated. Recrystallization from Et$_2$O provided a colorless crystalline solid (17.2 mg, 12%). UPLC retention time 0.67 min (Method A). $^1$H NMR (DMSO-d$_6$): δ=8.63 (1H, d), 8.29 (1H, dd), 8.11 (1H, d), 7.92-7.82 (2H, m), 7.54 (1H, d), 6.78 (1H, d), 4.62-4.51 (2H, m), 4.43 (1H, dd), 3.29-3.07 (3H, m), 1.50 (2H, br s). MS/ESI: m/z=364.2 [M+H]$^+$.

Example 24 (S)-2-amino-3-(3-(3-((5-chloro-3-fluoropyridin-2-yl)oxy)phenyl)-1H-pyrazol-1-yl)propan-1-ol

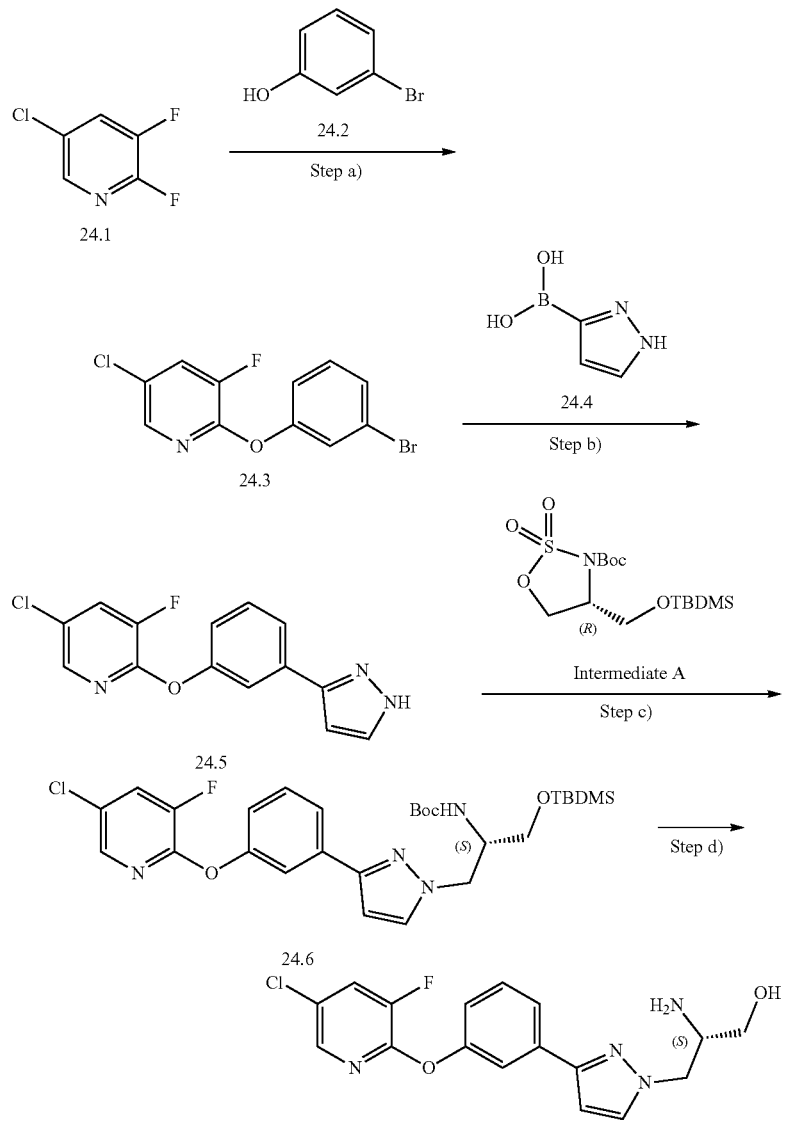

Example 24

Step a) 2-(3-Bromophenoxy)-5-chloro-3-fluoropyridine (24.3). Under argon potassium carbonate (3.99 g, 28.9 mmol) was added to a solution of 24.1 (3.00 g, 19.26 mmol) and 24.2 (3.33 g, 19.26 mmol) in DMA (10 mL). The resulting suspension was stirred for 18 h at 80° C. After cooling the reaction mixture was poured into water (120 mL) and MTBE (60 ml). The aqueous layer was extracted twice with MTBE. The combined organic phases were washed with 10% $K_2CO_3$, $H_2O$ and brine. The organic phases were dried over $Na_2SO_4$. Evaporation gave the crude product as a yellow oil. The residue was purified by flash chromatography (cyclohexane/DCM) to give compound 24.3 as a colourless oil (5.06 g, 87%). UPLC retention time 1.31 min (Method A). $^1$H NMR (DMSO-$d_6$): δ=8.25 (1H, dd), 8.09 (1H, d), 7.52 (1H, s), 7.47 (1H, d), 7.41 (1H, "t"), 7.25 (1H, dd). MS/ESI: m/z=302.0 [M+H]$^+$.

Step b) 2-(3-(1H-pyrazol-3-yl)phenoxy)-5-chloro-3-fluoropyridinedine (24.5). To a suspension of 24.3 (1.5 g, 4.96 mmol) and 24.4 (1.11 g, 9.92 mmol) in DMA (15 mL) was added $KHCO_3$ (0.993 g, 9.91 mmol) and tetrakis(triphenylphosphine)-palladium(0) (286 mg, 0.248 mmol). After purging with argon, the reaction mixture was stirred for 24 h at 93° C. in a sealed tube. After cooling, the suspension was distributed between ethyl acetate (60 mL) and water (60 mL). The aqueous layer was extracted twice with ethyl acetate. The combined organic layers were washed with 1 M aqueous $Na_2CO_3$ and half-saturated brine. Drying over $Na_2SO_4$ and evaporation gave a yellow oil. Flash-chromatography (gradient: cyclohexane/ethyl acetate) gave the pure compound 24.5 as a colorless oil (547 mg, 38%). UPLC retention time 1.04 min (Method A). $^1$H NMR (DMSO-$d_6$):

δ 12.96 (1H, br 5), 8.24 (1H, s), 8.23 (1H, dd), 8.07 (1H, d), 7.95 (1H, br s), 7.51 (1H, d), 7.47 (1H, s), 7.40 (1H, "t"), 7.00 (dd, 1H). MS/ESI: m/z=290.1 [M+H]$^+$.

Step c) tert-butyl (S)-(1-((tert-butyldimethylsilyl)oxy)-3-(3-(3-((5-chloro-3-fluoropyridin-2-yl)oxy)phenyl)-1H-pyrazol-1-yl)propan-2-yl)carbamate (24.6). To a solution of 24.5 (523 mg, 1.805 mmol) and Intermediate A (796 mg, 2.166 mmol) in DMA (12 mL) was added Cs$_2$CO$_3$ (1.765 g, 5.42 mmol). The suspension was stirred for 4 h at rt. The RM was poured into a mixture of ethyl acetate (60 mL) and water (30 mL). The aqueous layer was extracted twice with ethyl acetate. The combined organic phases were washed four times with brine and dried over Na$_2$SO$_4$. Evaporation of the solvent gave a yellow oil. Separation by flash-chromatography (gradient: CH$_2$CL$_2$/EtOAc) to give the pure compound 24.6 colourless oil (917 mg, 88%). UPLC retention time 1.63 min (Method A). $^1$H NMR (DMSO-d$_6$): δ 8.23 (1H, dd), 8.07 (1H, d), 7.68 (1H, s), 7.67 (1H, d), 7.58 (1H, br s), 7.46 (1H, "t"), 7.12 (1H, dd), 6.78 (1H, d), 6.72 (1H, d), 4.26 (1H, dd), 4.16-4.05 (1H, m), 3.94-3.82 (1H, m), 3.61-3.45 (2H, m), 1.32 (9H, s), 0.87 (s, 9H), 0.04 (s, 6H). MS/ESI: m/z=577.3 [M+H]$^+$.

Step d) (S)-2-amino-3-(3-(3-((5-chloro-3-fluoropyridin-2-yl)oxy)phenyl)-1H-pyrazol-1-yl)propan-1-ol (Example 24). Compound 24.6 (917 mg, 1.589 mmol) was dissolved in acetone (10 mL) and 4 M HCl in dioxane (3.97 mL, 15.89 mmol) was added. Immediately a gas evolution could be observed and a thick suspension formed within 15 min. The mixture was stirred at 25° C. for 16 h. The reaction was evaporated leaving a tacky residue. The compound was purified by flash-chromatography (gradient: CH$_2$Cl$_2$/MeOH-32% aq. NH$_3$) to afford Example 24 as colorless oil which crystallized upon standing (531 mg, 92%). UPLC retention time 0.76 min (Method A). $^1$H NMR (DMSO-d$_6$): δ 8.23 (1H, dd), 8.06 (1H, d), 7.76 (1H, d), 7.68 (1H, d), 7.59 (1H, "r"), 7.45 (1H, 1"), 7.11 (1H, dd), 6.73 (1H, d), 4.67 (1H, t), 4.17 (1H, dd), 3.94 (1H, dd), 3.31-3.21 (2H, m), 3.14-3.02 (1H, m), 1.48 (2H, br s). MS/ESI: m/z=363.1 [M+H]$^+$.

Example 25 S)-2-amino-3-(4-(4-((5-chloro-3-fluoropyridin-2-yl)oxy)phenyl)-1H-pyrazol-1-yl)propan-1-ol

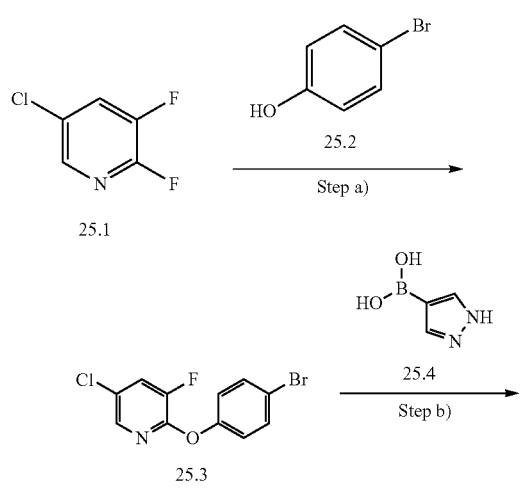

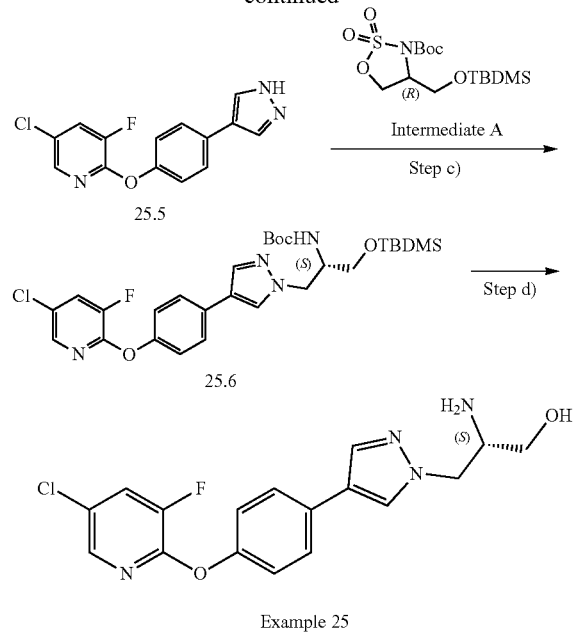

Example 25

Step a) 2-(4-bromophenoxy)-5-chloro-3-fluoropyridine (25.3). Under argon potassium carbonate (3.99 g, 28.9 mmol) was added to a solution of 25.1 (3.00 g, 19.26 mmol) and 25.2 (3.33 g, 19.26 mmol) in DMA (10 mL). The resulting suspension was stirred for 18 h at 80° C.

After cooling the reaction mixture was poured into water (120 mL) and MTBE (60 mL). The aqueous layer was extracted twice with MTBE. The combined organic phases were washed with 10% K$_2$CO$_3$, H$_2$O and brine. The organic phases were dried over Na$_2$SO$_4$. Evaporation gave the crude product as a yellow oil. The residue was purified by flash chromatography (cyclohexane/DCM) to give compound 25.3 as a colorless oil (5.16 g, 89%). UPLC retention time 1.31 min (Method A). $^1$H NMR (DMSO-d$_6$): δ=8.24 (1H, dd), 8.07 (1H, d), 7.62 (2H, "d"), 7.21 (2H, "d"). MS/ESI: m/z=301.9 [M+H]$^+$.

Step b) 2-(4-(1H-pyrazol-4-yl)phenoxy)-5-chloro-3-fluoropyridine (25.5). To a suspension of 25.3 (1.5 g, 4.96 mmol) and 25.4 (1.11 g, 9.92 mmol) in DMA (15 mL) was added KHCO$_3$ (0.993 g, 9.91 mmol) and tetrakis(triphenylphosphine)-palladium(0) (286 mg, 0.248 mmol). After purging with argon, the reaction mixture was stirred for 48 h at 90'C in a sealed tube. After cooling, the suspension was distributed between ethyl acetate (100 mL) and water (100 mL). The aqueous layer was extracted twice with ethyl acetate. The combined organic layers were washed with 1 M aqueous Na$_2$CO$_3$ and half-saturated brine. Drying over Na$_2$SO. and evaporation gave a yellow oil. Flash-chromatography (gradient: cyclohexane/ethyl acetate) to give a sticky oil. The residue was crystallized with cyclohexane/Et$_2$O 2:1 to give the pure compound 25.5 as a white solid (472 mg, 27%). UPLC retention time 0.99 min (Method A). $^1$H NMR (DMSO-d$_6$): δ 12.93 (1H, br s), 8.21 (1H, dd), 8.18 (1H, br s), 8.06 (1H, d), 7.92 (1H, br s), 7.65 (2H, "d"), 7.19 (2H, "d"). MS/ESI: m/z=290.1 [M+H]$^+$.

Step c) tert-butyl (S)-(1-((tert-butyldimethylsilyl)oxy)-3-(4-(4-((5-chloro-3-fluoropyridin-2-yl)oxy)phenyl)-1H-pyrazol-1-yl)propan-2-yl)carbamate (25.6). To a solution of 25.5 (196 mg, 0.676 mmol) and Intermediate A (323 mg, 0.878 mmol) in DMA (5.5 mL) was added Cs$_2$CO$_3$ (660 mg, 2.027 mmol). The suspension was stirred for 28 h at rt. The RM was poured into a mixture of ethyl acetate (60 mL) and water (30 mL). The aqueous layer was extracted twice with ethyl acetate. The combined organic phases were washed four times with brine and dried over Na$_2$SO$_4$. Evaporation of the solvent gave a yellow oil. Separation by flash-chromatography (gradient: CH$_2$CL$_2$/EtOAc) to give the pure compound 25.6 colourless oil which crystallized upon standing (399 mg, 86%). UPLC retention time 1.60 min (Method A). $^1$H NMR (DMSO-d$_6$): δ 8.22 (1H, dd), 8.09-8.01 (2H, m), 7.89 (1H, s), 7.59 (2H, "d"), 7.20 (2H, "d"), 6.78 (1H, br d), 4.25 (1H, dd), 4.15-4.06 (1H, m), 3.98-3.86 (1H, m)), 3.60-3.46 (2H, m), 1.33 (9H, s), 0.89 (9H, s), 0.05 (6H, s). MS/ESI: m/z=577.4 [M+H]$^+$.

Step d) (S)-2-amino-3-(4-(4-((5-chloro-3-fluoropyridin-2-yl)oxy)phenyl)-1H-pyrazol-1-yl)propan-1-ol (Example 25). Compound 25.6 (388 mg, 0.672 mmol) was dissolved in acetone (5 ml) and 4 M HCl in dioxane (1.68 mL, 6.72 mmol) was added. Immediately a gas evolution could be observed and a thick suspension formed within 15 min. The mixture was stirred at 40° C. for 2.5 h. Then additional 4 M HCl in dioxane (0.84 mL, 3.36 mmol) was added and stirring was continued for 4 h at 40° C. The clear solution was evaporated leaving a tacky residue. The compound was purified by flash-chromatography (gradient: CH$_2$Cl$_2$/MeOH-32% aq. NH$_3$) to afford a solid. Trituration with isopropanol gave Example 25 as a white solid after vacuum drying at 60° C. (157 mg, 64%). UPLC retention time 0.76 min (Method A). $^1$H NMR (DMSO-d$_6$): δ 8.21 (1H, dd), 8.14 (1H, s), 8.06 (1H, d), 7.88 (1H, s), 7.62 (2H, "d"), 7.19 (2H, "d"), 4.68 (1H, t) 4.17 (1H, dd), 3.94 (1H, dd), 3.33-3.21 (2H, m), 3.15-3.03 (1H, m), 1.49 (2H, br s). MS/ESI: m/z=363.1 [M+H]$^+$.

Example 26 (S)-2-Amino-3-(3-(4-((5-chloro-3-fluoropyridin-2-yl)oxy)phenyl)-1H-pyrazol-1-yl)propan-1-ol

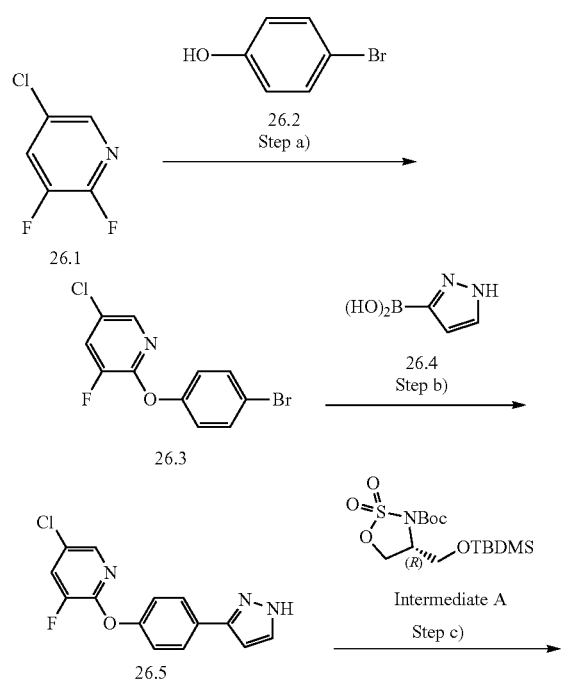

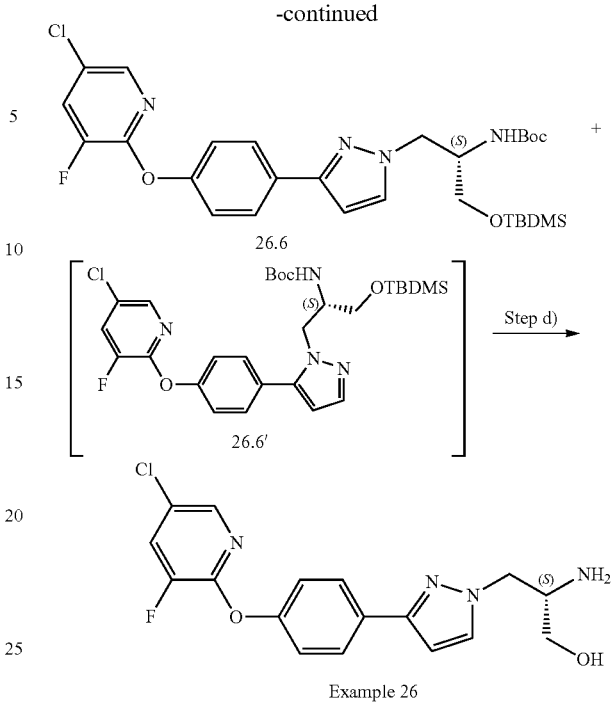

Example 26

Step a) 2-(4-Bromophenoxy)-5-chloro-3-fluoropyridine (26.3). Under argon potassium carbonate (1.33 g, 9.63 mmol) was added to a solution of 26.1 (1.00 g, 6.42 mmol) and 26.2 (1.11 g, 6.42 mmol) in DMA (5 mL). The resulting suspension was stirred for 18 h at 80° C. After cooling the reaction mixture was poured into water (40 mL) and MTBE (20 ml) and vigorously stirred for 10 min. Then, the aqueous layer was extracted twice with MTBE. The combined organic phases were washed with 10% aq. K$_2$CO$_3$, half-saturated brine, and dried over Na$_2$SO$_4$. Evaporation gave the crude product as a colorless oil. Flash-chromatography on silica (gradient: cyclohexane/CH$_2$Cl$_2$) furnished compound 26.3 as a colorless solid (1.75 g, 90%). UPLC retention time 1.31 min (Method A). TLC: R$_f$=0.25 (CH$_2$Cl$_2$/cyclohexane 1:4), $^1$H NMR (DMSO-de): δ=8.24 (1H, dd), 8.06 (1H, s), 7.62 (2H, d), 7.21 (2H, d). MS/ESI: m/z=302.0 [M+H]$^+$.

Step b) 2-(4-(1H-Pyrazol-3-yl)phenoxy)-5-chloro-3-fluoropyridine (26.5). To a suspension of 26.3 (1.00 g, 3.31 mmol) and 26.4 (1.11 g, 9.92 mmol) in dioxane (14 mL) was added 2 M aqueous Na$_2$CO$_3$ (1.65 mL, 3.30 mmol) and tetrakis(triphenylphosphine)-palladium(0) (0.31 g, 0.2 mmol). After purging with argon, the reaction mixture was stirred for 40 h at 75° C. in a sealed tube. After cooling, the suspension was distributed between ethyl acetate (50 mL) and water (75 mL). The aqueous layer was extracted twice with ethyl acetate. The combined organic layers were washed with 1 M aqueous Na$_2$CO$_3$ and half-saturated brine. Drying over Na$_2$SO$_4$ and evaporation gave a yellow oil. Flash-chromatography (gradient: cyclohexane/ethyl acetate) afforded pure compound 26.5 as a colorless oil (0.27 g, 28%). UPLC retention time 1.01 min (Method A). TLC: R$_f$=0.35 (Ethyl acetate/cyclohexane 1:1), $^1$H NMR (DMSO-d$_6$): δ=8.24 (1H, dd), 8.08 (1H, d), 7.86 (2H, d), 7.79 (1H, d), 7.22 (2H, d), 6.72 (1H, d). MS/ESI: m/z=290.1 [M+H]$^+$.

Step c) tert-Butyl (S)-(1-(((tert-butyldimethylsilyl)oxy)-3-(3-(4-((5-chloro-3-fluoropyridin-2-yl)oxy)phenyl)-1H-pyrazol-1-yl)propan-2-yl)carbamate (26.6). To a solution of 26.5 (261 mg, 0.90 mmol) and Intermediate A (398 mg, 1.08 mmol) in DMA (10 mL) was added Cs$_2$CO$_3$ (880 mg, 2.70 mmol). The colorless suspension was stirred for 2.5 h at 25° C. under argon and then poured into a mixture of ethyl acetate (75 mL) and water (30 mL). The aqueous layer was extracted twice with ethyl acetate. The combined organic phases were washed four times with brine and dried over Na$_2$SO$_4$. Evaporation of the solvent gave a colorless oil containing the two possible regioisomeric alkylation products in a ratio of 14:1 (UPLC, UV 215 nm). Separation by flash-chromatography (gradient: CH$_2$CL$_2$/ethyl acetate) afforded the desired regioisomer 26.6 as a colorless oil (370 mg, 71%). UPLC retention time 7.63 min (Method B). TLC: R$_f$=0.64 (ethyl acetate/CH$_2$Cl$_2$ 1:1), $^1$H NMR (DMSO-d$_6$): δ=8.23 (1H, dd), 8.08 (1H, d), 7.82 (2H, d), 7.68 (1H, d), 7.22 (2H, d), 6.80 (1H, br d), 6.69 (1H, d), 4.39 (1H, dd), 4.11 (1H, dd), 3.94 (1H, m), 3.55 (2H, m), 1.38 (9H, 5), 0.89 (9H, s), 0.02 (3H, s), 0.02 (3H, s). MS/ESI: m/z=577.4 [M+H]$^+$. The undesired pyrazol regioisomer 26.6' was also obtained as a colorless oil (42 mg, 8%). UPLC retention time 7.53 min (Method B). TLC: R$_f$=0.27 (ethyl acetate/CH$_2$CL$_2$ 1:1), $^1$H NMR (DMSO-d$_6$): δ=8.26 (1H, dd), 8.09 (1H, d), 7.54 (2H, d), 7.53 (1H, d), 7.30 (2H, d), 6.57 (1H, br d), 6.49 (1H, d), 4.29 (1H, dd), 4.10 (1H, dd), 3.94 (1H, m), 3.40 (2H, m), 1.33 (9H, s), 0.79 (9H, s), −0.04 (3H, s), −0.05 (3H, s). MS/ESI: m/z=577.4 [M+H]$^+$.

Step d) (S)-2-Amino-3-(3-(4-((5-chloro-3-fluoropyridin-2-yl)oxy)phenyl)-1H-pyrazol-1-yl)propan-1-ol (Example 26). Compound 26.6 (362 mg, 0.627 mmol) was dissolved in 4 M HCl in dioxane (1.5 mL). Immediately an effervescence could be observed and a thick suspension formed within 15 min. Acetone (4.5 mL) was added and stirring at 25° C. was continued for further 1.5 h. The reaction was evaporated leaving a tacky residue. Flash-chromatography (gradient: CH$_2$Cl$_2$/MeOH-32% aq. NH$_3$) and recrystallization from ethyl ether/n-pentane afforded Example 26 as colorless powder (166 mg, 73%). UPLC retention time 0.76 min (Method A). TLC: R$_f$=0.19 (CH$_2$CL$_2$/MeOH/25% aq. NH$_3$ 90:9:1), $^1$H NMR (DMSO-d$_6$): δ=8.23 (1H, dd), 8.07 (1H, d), 7.84 (2H, d), 7.76 (1H, d), 7.22 (2H, d), 6.69 (1H, d), 4.68 (1H, t, OH), 4.19 (1H, dd), 3.96 (1H, dd), 3.32-3.25 (3H, m), 3.11 (1H, m), 1.51 (2H, br s, NH$_2$). MS/ESI: m/z=363.2[M+H]$^+$.

Example 27 (S)-2-Amino-3-(5-(4-(4-chlorophenoxy)phenyl)-2H-tetrazol-2-yl)propan-1-ol

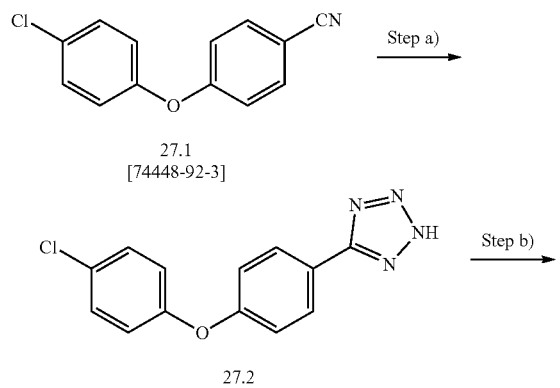

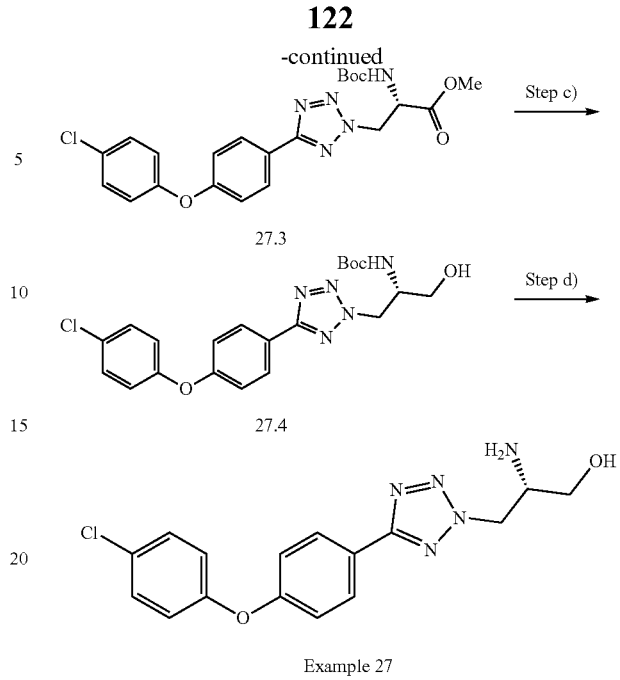

Example 27

Step a) 5-(4-(4-Chlorophenoxy)phenyl)-2H-tetrazole (26.3). To a solution of nitrite 27.1 (1.43 g, 6.23 mmol) in dry toluene (9 mL) were added dibutylstannanone (155 mg, 0.623 mmol) and azidotrimethylsilane (1.7 mL, 12.4 mmol). The reaction mixture was heated in a sealed vial to 100° C. for 17 h. After cooling to room temperature, all volatiles were removed I. vac. and the crude was triturated with MeOH (6 mL) and concentrated again. The material was suspended in MeCN (6 mL) and filtered. The solids were washed with MeCN (2×3 mL) and dried i. vac. to afford tetrazole 27.2 as a colorless powder (1.49 g, 86%). UPLC retention time 0.99 min (Method A). $^1$H NMR (400 MHz, DMSO-d$_6$): δ=16.82 (s, br, 1H), 8.09-8.02 (m, 2H), 7.55-7.46 (m, 2H), 7.27-7.12 (m, 4H). MS/ESI: m/z=273.0 [M+H]$^+$.

Step b) Methyl (S)-2-((tert-butoxycarbonyl)amino)-3-(5-(4-(4-chlorophenoxy)phenyl)-2H-tetrazol-2-yl)propanoate (27.3). To a solution of 27.2 (1.2 g, 4.40 mmol) and PPh$_3$ (2.89 g, 11.0 mmol) in THF (60 mL) were added di-tert-butyl azodicarboxylate (2.53 g, 11.00 mmol) and Boc-Ser-OMe (2.41 g, 11.0 mmol) in THF (20 mL). After stirring at room temperature for 19 h, all volatiles were removed i. vac. and the crude was adsorbed on isolute™. Purification by flash column chromatography (80 g SiO$_2$, Heptane to EtOAc) afforded a colorless solid (4.1 g) containing the title compound 27.3 and significant amounts of BocNH-NHBoc. The material was carried forward without additional purification. UPLC retention time 1.34 min (Method A). $^1$H NMR (400 MHz, DMSO-4): δ=8.15-8.07 (m, 2H), 7.40-7.31 (m, 2H), 7.31 (s, 1H), 7.14-7.06 (m, 2H), 7.06-6.98 (m, 2H), 5.14 (qd, 2H), 4.90 (dt, 1H), 3.85 (s, 3H), 1.45 (s, 9H). MS/ESI: m/z=474.0[M+H]$^+$.

Step c) tert-Butyl (S)-(1-(5-(4-(4-chlorophenoxy)phenyl)-2H-tetrazol-2-yl)-3-hydroxypropan-2-yl)carbamate (27.4). A solution of 27.3 (414 mg, 0.874 mmol) in THF (10 mL) was treated with 2N LiBH$_4$ in THF (1.75 mL, 3.5 mmol) at 0° C. After 30 min, the reaction mixture was adsorbed on isolute™ and dried i.vac. Flash column chromatography (43 g RP18 silica, 0.1% TFA in water:MeCN from 19:1 to 0:1) afforded the alcohol 27.4 (173 mg, 44%) as a colorless solid. UPLC retention time 1.22 min (Method A). $^1$H NMR (400

MHz, DMSO-d$_6$): δ=8.09-8.02 (m, 2H), 7.54-7.45 (m, 2H), 7.23-7.11 (m, 4H), 6.88 (d, 1H, —NH), 5.03 (t, 1H, —OH), 4.89 (dd, 1H), 4.61 (dd, 1H), 3.99 (s, br, 1H), 3.48 (d, br, 2H), 1.25 (s, 9H). MS (ESI+): m/z=446.1 [M+H]$^+$.

Step d) (S)-2-Amino-3-(5-(4-(4-chlorophenoxy)phenyl)-2H-tetrazol-2-yl)propan-1-ol (Example 27). A solution of 27.4 (88 mg, 0.197 mmol) in DCM (4 mL) was treated with TFA (2 mL) and kept at room temperature for 1 h. The reaction mixture was concentrated I. vac. and adsorbed on isolute™. Flash column chromatography (43 g RP18 silica, 0.1% TFA in water:MeCN from 19:1 to 0:1), followed by lyophilization from HCl containing aqueous solution afforded the hydrochloride of Example 27 (71 mg, 92%) as a colorless powder. UPLC retention time 0.81 min (Method A). $^1$H NMR (400 MHz, DMSO-d$_6$): δ=8.24 (s, br, 3H, —NH$_3$), 8.12-8.06 (m, 2H), 7.55-7.47 (m, 2H), 7.25-7.12 (m, 4H), 5.56 (t, 1H, —OH), 5.04 (dd, 1H), 4.96 (dd, 1H), 3.81 (dq, 1H), 3.72 (dt, 1H), 3.63 (dt, 1H). MS (ESI+): m/z=346.0 [M+H]$^+$.

Example 28 (S)-2-Amino-3-(5-(4-((5-cyclopropylpyridin-2-yl)oxy)phenyl)-2H-tetrazol-2-yl)propan-1-ol

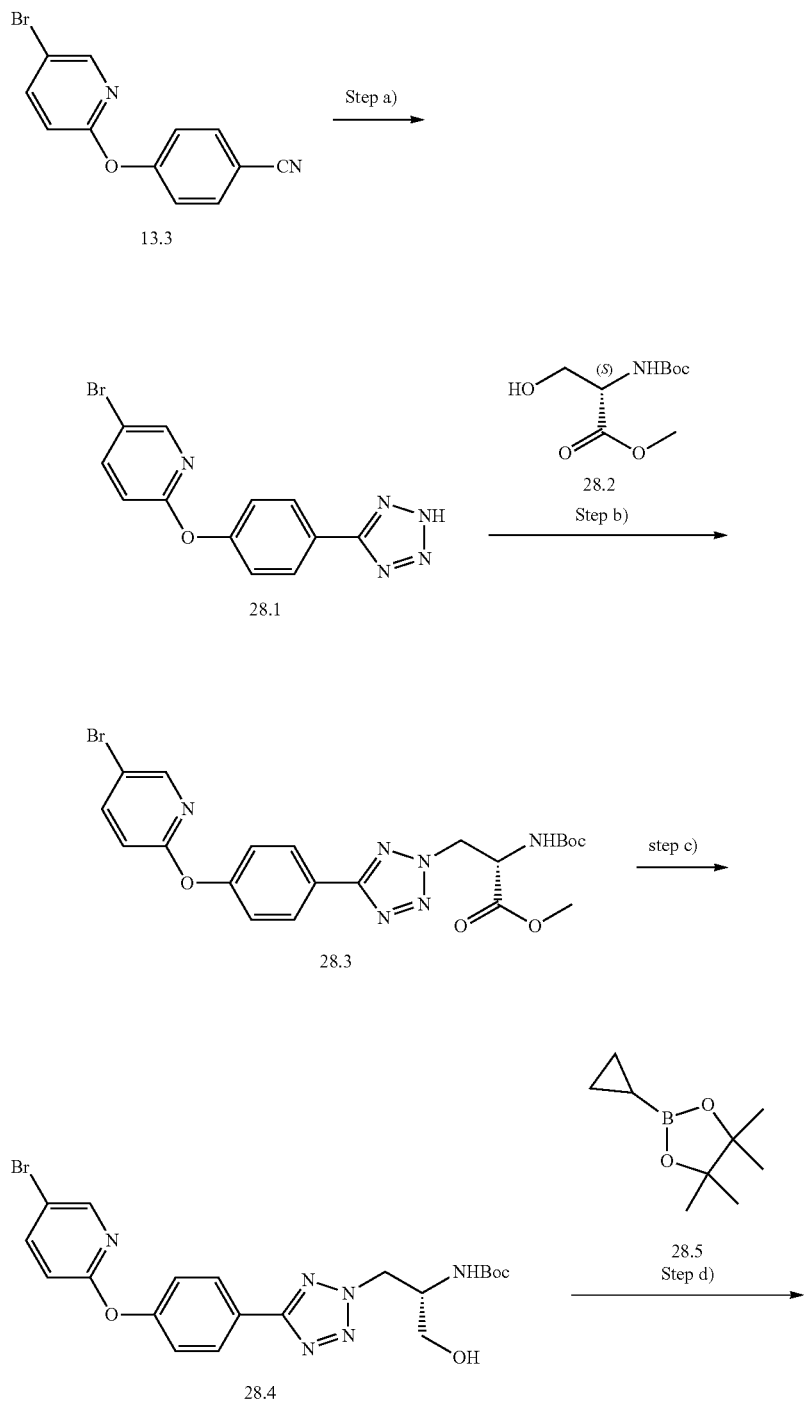

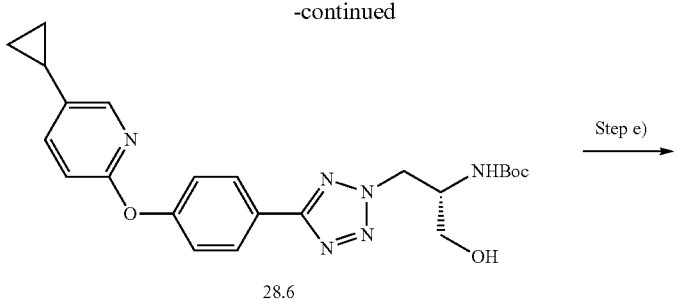

28.6

Step e) →

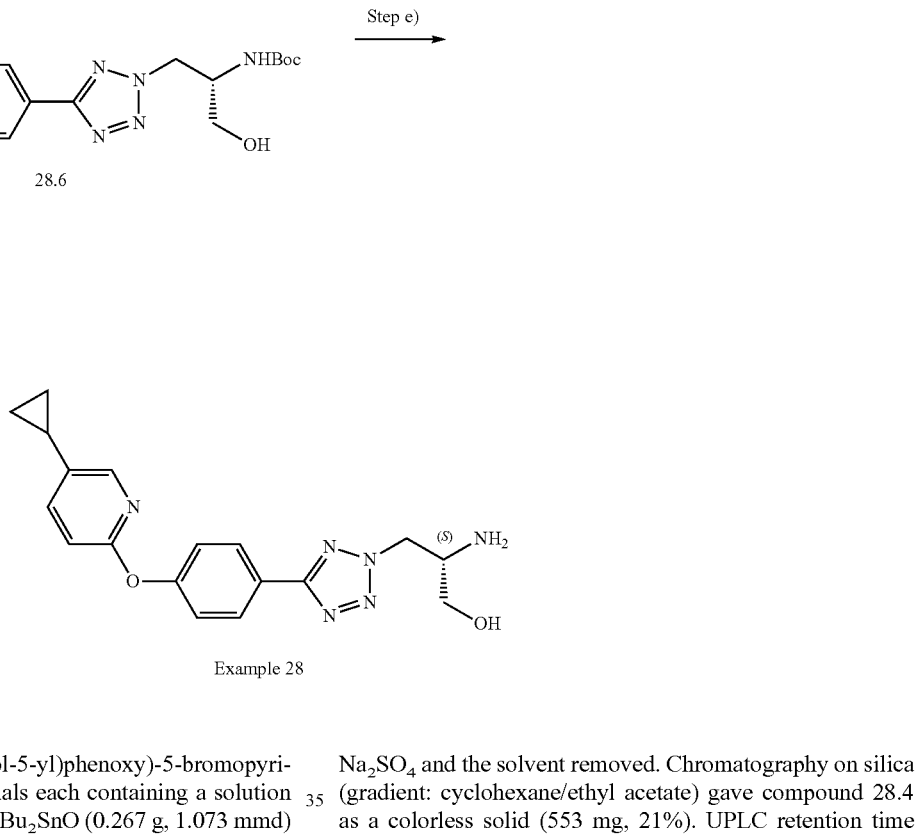

Example 28

Step a) 2-(4-(2H-Tetrazol-5-yl)phenoxy)-5-bromopyridine (28.1). Under argon 2 vials each containing a solution of 13.3 (2.95 g, 10.72 mmol), Bu$_2$SnO (0.267 g, 1.073 mmd) and TMSN$_3$ (2.47 g, 21.45 mmol) in dry toluene (10.5 mL) were sealed and stirred at 100° C. for 8 h on a heating block. The heterogeneous mixtures were combined, treated with MeOH and concentrated under reduced pressure. The solid residue was crystallized from MeOH to afford 28.1 as a colorless solid (2.60 g, 42%). UPLC retention time 0.86 min (Method A). $^1$H NMR (DMSO-d$_6$): δ=16.5 (1H, s, br), 8.32 (1H, d), 8.11 (1H, dd), 8.04-8.09 (2H, m), 7.35-7.40 (2H, m), 7.14 (1H, d). MS/ESI 318.1 [M+H]$^+$.

Step b) (S)-Methyl 3-(5-(4-((5-bromopyridin-2-yl)oxy)phenyl)-2H-tetrazol-2-yl)-2-((tert-butoxycarbonyl)amino)propanoate (28.3). A solution of 28.1 (2.60 g, 8.17 mmd), triphenylphosphine (3.22 g, 12.26 mmol), DIAD (2.82 g, 12.26 mmd) and 28.2 (2.69 g, 12.26 mmol) in THF (60 ml) was stirred for 1.5 h at 25° C. solute was added and the mixture dried in vacuo. Chromatography on silica (gradient: cyclohexane/ethyl acetate) afforded 28.3 (5.65 g) containing ca 10% triphenylphosphine oxide as a colorless solid, which was used in the next step. A small portion was further purified by SFC to afford an analytical sample. UPLC retention time 1.25 min (Method A). $^1$H NMR (DMSO-d$_6$): δ=8.33 (1H, d), 8.12 (1H, dd), 8.08 (2H, d), 7.49 (1H, d), 7.34 (2H, d), 5.11 (1H, dd), 5.01 (1H, dd), 4.71 (1H, m), 3.70 (3H, s), 1.32 (9H, s). MS/ESI 519.1 [M+H]$^+$.

Step c) (S)-tert-Butyl (1-hydroxy-3-(5-(4-hydroxyphenyl)-2H-tetrazol-2-yl)propan-2-yl)carbamate (28.4). At 0° C. LiBH$_4$ (2N solution in THF, 10.28 mL, 20.56 mmol) was added dropwise to a solution of 28.3 (2.67 g, 5.14 mmol) in THF (50 mL) and the mixture stirred for 45 min at 0° C. The mixture was neutralized with HCl (1 N aqueous solution), CH$_2$Cl$_2$ added, the organic layer separated, dried with Na$_2$SO$_4$ and the solvent removed. Chromatography on silica (gradient: cyclohexane/ethyl acetate) gave compound 28.4 as a colorless solid (553 mg, 21%). UPLC retention time 1.11 min (Method A). $^1$H NMR (DMSO-d$_6$): δ=8.33 (1H, d), 8.12 (1H, dd), 8.08 (2H, d), 7.34 (2H, d), 7.24 (1H, d), 6.88 (1H, d), 5.03 (1H, t, br), 4.91 (1H, dd), 4.63 (1H, dd), 4.02 (1H, m), 3.48 (2H, m), 1.27 (9H, s). MS/ESI 491.2 [M+H]$^+$.

Step d) (S)-tart-Butyl (1-(5-(4-((5-cyclopropylpyridin-2-yl)oxy)phenyl)-2H-tetrazol-2-yl)-3-hydroxypropan-2-yl)carbamate (28.6). A suspension of 28.4 (400 mg, 0.814 mmol), 28.5 (164 mg, 0.977 mmol), K$_3$PO$_4$ (518 mg, 2.442 mmol) and PdCl$_2$(dtbpf) (53.1 mg, 0.081 mmol) in a mixture of dioxane (7.5 mL) and water (3.75 mL) was stirred under argon for 2 h at 85'C. The mixture was concentrated and the residue purified on silica (gradient: cyclohexane/ethyl acetate) to afford 28.6 (80 mg, 21%). UPLC retention time 1.11 min (Method A). $^1$H NMR (DMSO-d$_6$): δ=8.05 (3H, m), 7.57 (1H, dd), 7.25 (2H, d), 7.02 (1H, d), 6.88 (1H, d), 5.02 (1H, t, br), 4.90 (1H, dd), 4.62 (1H, dd), 4.02 (1H, m), 3.47 (2H, m), 1.95 (1H, m), 1.25 (9H, s), 0.96 (2H, m), 0.71 (2H, m). MS/ESI 453.4 [M+H]$^+$.

Step e) (S)-2-Amino-3-(5-(4-((5-cyclopropylpyridin-2-yl)oxy)phenyl)-2H-tetrazol-2-yl)propan-1-el (Example 28). To a solution of 28.6 (77 mg, 0.170 mmol) in CH$_2$Cl$_2$ (1.7 mL) was added HCl (4N solution in dioxane, 0.638 mL, 2.55 mmol) and the mixture stirred for 1.5 h at 25° C. Filtration gave the hydrochloride of Example 28 as a colorless solid (60 mg, 89%). UPLC retention time 0.72 min (Method A). $^1$H NMR (DMSO-d$_6$): δ=8.42 (3H, s br), 8.12 (2H, d), 8.04 (1H, d), 7.57 (1H, dd), 7.28 (2H, d), 7.02 (1H, d), 5.56 (1H, s, br), 5.08-4.94 (2H, m), 3.81 (1H, m), 3.72 (1H, dd), 3.65 (1H, dd), 1.95 (1H, m), 0.96 (2H, m), 0.71 (2H, m). MS/ESI 353.3 [M+H]$^+$.

Example 29 (S)-2-Amino-3-(5-(4-((5-chloro-3-fluoropyridin-2-yl)oxy)phenyl)-2H-tetrazol-2-yl)propan-1-ol

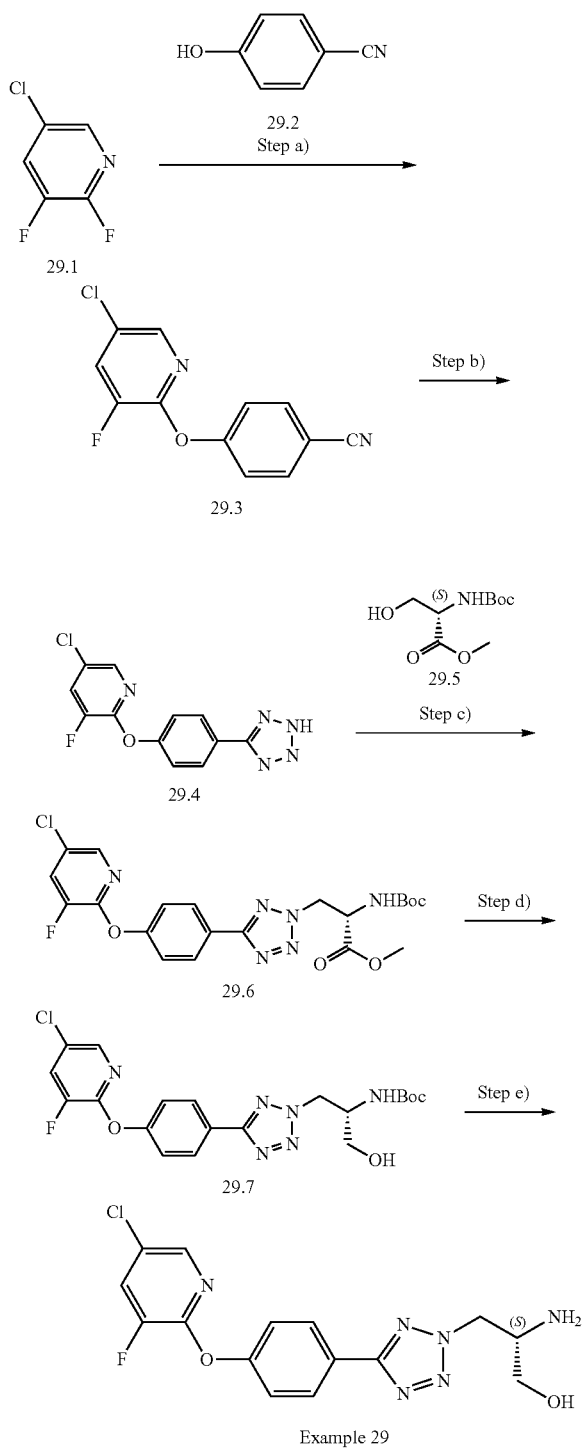

Step a) 44(5-Chloro-3-fluoropyridin-2-yl)oxy)benzonitrile (29.3). A suspension of 29.1 (23.6 g, 158 mmol), 29.2 (17.9 g, 150 mmol), and $K_2CO_3$ (24.9 g, 180 mmol) in DMF (40 mL) was heated to 100° C. for 3 h. The reaction mixture was partitioned between heptane-ethyl acetate (2:1, 500 mL) and water (250 mL). The organic layer was washed with $Na_2CO_3$ and brine, dried over $Na_2SO_4$, filtered and concentrated to afford crude product, which was recrystallized form hexane/ethyl acetate. Pure product 29.3 was obtained as a colorless solid (20.5 g, 53%). UPLC retention time 1.10 min (Method A). $^1$H NMR (DMSO-$d_6$): δ=8.30 (1H, dd), 8.13 (1H, dd), 7.93 (2H, d), 7.43 (2H, d). MS/ESI 249.0 [M+H]$^+$.

Step b) 2-(4-(2H-Tetrazol-5-yl)phenoxy)-5-chloro-3-fluoropyridine (29.4). Under argon 9 vials each containing a solution of 29.3 (2.24 g, 9.00 mmol), $Bu_2SnO$ (0.224 g, 0.900 mmol) and $TMSN_3$ (2.39 mL, 18.0 mmol) in dry toluene (9 mL) were sealed and stirred at 90° C. for 18 h on a heating block. The heterogeneous mixtures were concentrated, the combined crudes treated with MOOH (100 mL) and concentrated once more under reduced pressure affording a pale brown-orange solid. The solid residue was suspended in MeOH (100 mL), stirred for 20 min and filtered. The solid was washed with heptane and dried to give the compound 29.4 as a colorless powder (18.5 g, 77%). UPLC retention time 0.89 min (Method A). $^1$H NMR (DMSO-$d_6$): δ=16.8 (1H, s, br), 8.28 (1H, dd), 8.08-8.13 (3H, m), 7.43 (2H, d). MS/ESI 292.1 [M+H]$^+$.

Step c) (S)-Methyl 2-((tert-butoxycarbonyl)amino)-3-(5-(4-((5-chloro-3-fluoropyridin-2-yl)oxy)phenyl)-2H-tetrazol-2-yl)propanoate (29.6). At 0° C. $PPh_3$ (29.5 g, 112.5 mmol), DIAD (25.9 g, 112.5 mmol) and 29.5 (24.6 g, 112.5 mmol) were added to a solution of 29.4 (13.1 g, 45.0 mmol) in THF (150 ml). The resulting mixture was stirred for 4 h at 25° C. The reaction mixture was diluted with water and extracted with ethyl acetate. The organic layer was washed with water, brine, dried over $Na_2SO_4$, filtered and evaporated. Chromatography on silica (15% ethyl acetate in petrol ether) gave the compound 29.6 as a colorless solid (13.7 g, 62%). UPLC retention time 1.26 min (Method A). $^1$H NMR (DMSO-$d_6$): δ=8.28 (1H, dd), 8.10 (3H, m), 7.49 (1H, d), 7.41 (2H, d), 5.13 (1H, dd), 5.01 (1H, dd), 4.72 (1H, m), 3.70 (3H, s), 1.31 (9H, s). MS/ESI 493.3 [M+H]$^+$.

Step d) (S)-tert-Butyl (1-(5-(4-((5-chloro-3-fluoropyridin-2-yl)oxy)phenyl)-2H-tetrazol-2-yl)-3-hydroxypropan-2-yl)carbamate (29.7). At 0° C. LiBH4 (2N solution in THF, 2.94 mL, 5.88 mmol) was added dropwise to a solution of 29.6 (724 mg, 1.47 mmol) in THF (15 mL) and the mixture stirred for 1 h at 0° C. The mixture was neutralized with HCl (1 N aqueous solution), $CH_2Cl_2$ added, the organic layer separated, dried with $Na_2SO_4$ and the solvent removed. Chromatography on silica (gradient: cyclohexane/ethyl acetate) gave compound 29.7 as a colorless oil (555 mg, 72%). UPLC retention time 1.13 min (Method A). $^1$H NMR (DMSO-$d_6$): δ=8.28 (1H, dd), 8.10 (3H, m), 7.40 (2H, d), 6.88 (1H, d), 5.03 (1H, t, br), 4.91 (1H, dd), 4.63 (1H, dd), 4.01 (1H, m), 3.48 (2H, m), 1.25 (9H, s). MS/ESI 465.3 [M+H]$^+$.

Step e) (S)-2-Amino-3-(5-(4-((5-chloro-3-fluoropyridin-2-yl)oxy)phenyl)-2H-tetrazol-2-yl)propan-1-ol (Example 29). To a solution of 29.7 (172 mg, 0.37 mmol) in $CH_2Cl_2$ (3 mL) was added HCl (4N solution in dioxane, 1.4 mL, 5.6 mmol) and the mixture stirred for 1 h at 25° C. Filtration gave the hydrochloride of Example 29 as a colorless solid (93 mg, 62%). UPLC retention time 0.74 min (Method A). NMR (DMSO-$d_6$): δ=8.42 (3H, s, br), 8.29 (1H, dd), 8.15 (2H, d), 8.11 (1H, d), 7.42 (2H, d), 5.56 (1H, s, br), 5.08-4.94 (2H, m), 3.81 (1H, m), 3.77-3.60 (2H, m). MS/ESI 365.2 [M+H]$^+$.

Example 30 (R)-2-Amino-3-(5-(4-((5-chloro-3-fluoropyridin-2-yl)oxy)phenyl)-2H-tetrazol-2-yl)propan-1-ol

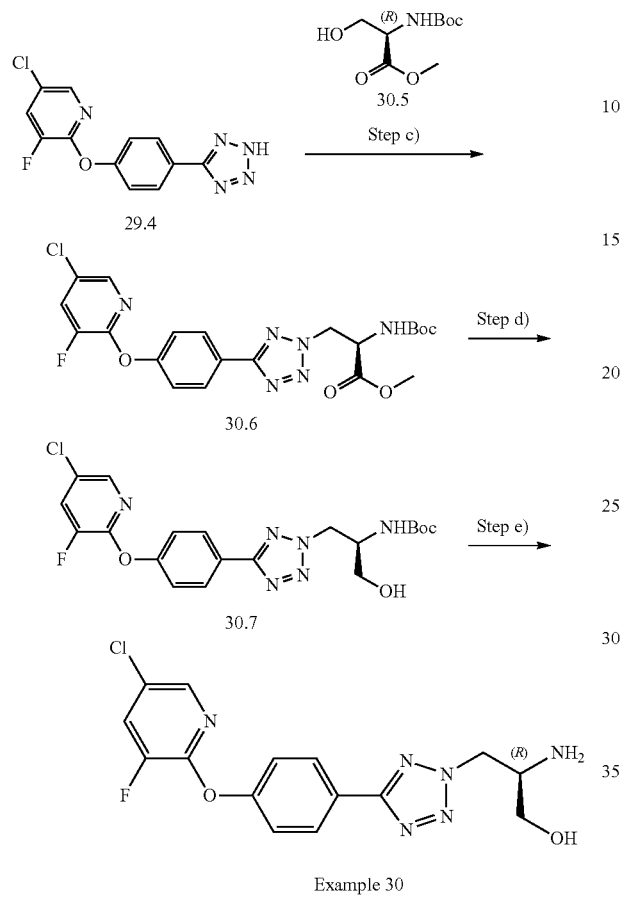

Example 30

The hydrochloride of (R)-2-Amino-3-(5-(4-((5-chloro-3-fluoropyridin-2-yl)oxy)phenyl)-2H-tetrazol-2-yl)propan-1-ol (Example 30) was prepared by similar procedures used for the synthesis of Example 29 replacing 29.5 by Its R-enantiomer 30.5. UPLC retention time 0.74 min (Method A). $^1$H NMR (DMSO-d$_6$): δ=8.37 (3H, s, br), 8.29 (1H, dd), 8.15 (2H, m), 8.11 (1H, d), 7.42 (2H, m), 5.57 (1H, t), 5.08-4.94 (2H, m), 3.82 (1H, m), 3.77-3.62 (2H, m). MS/ESI 365.2 [M+H]$^+$.

Example 31 (R)-2-Amino-3-(5-(4-((5-chloropyridin-2-yl)oxy)phenyl)-2H-tetrazol-2-yl)propan-1-ol

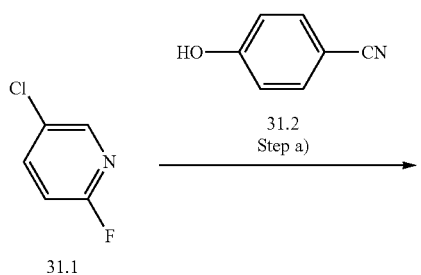

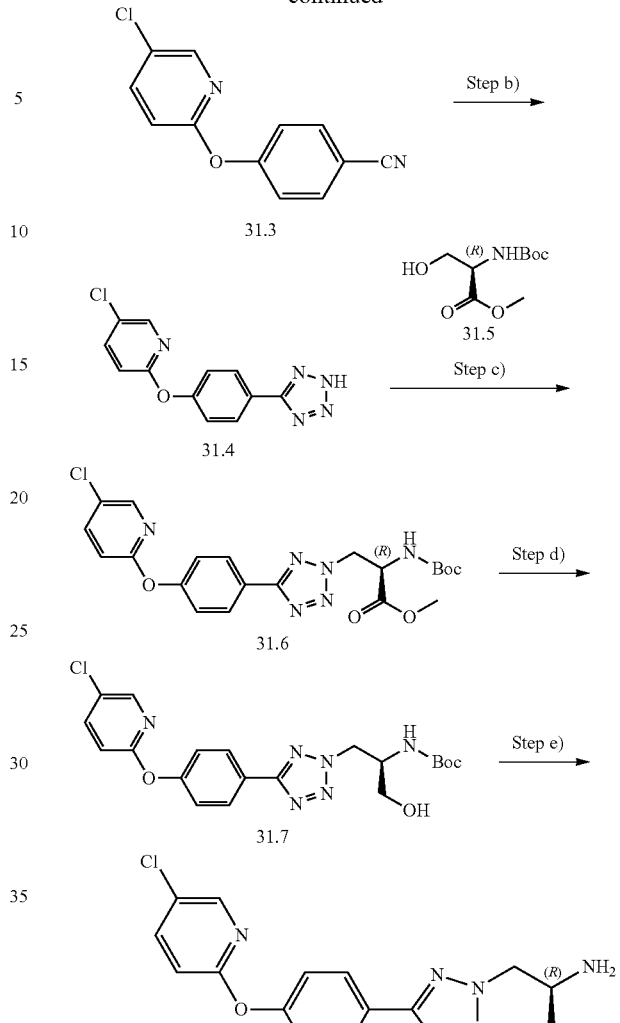

Example 31

Step a) 4-((5-Chloropyridin-2-yl)oxy)benzonitrile (31.3). Compound 31.1 (19.7 g, 150 mmol) was added dropwise at room temperature to a suspension of 31.2 (16.99 g, 143 mmol) and powdered K$_2$CO$_3$ (23.66 g, 171 mmol) in DMF (Volume: 30 mL). The reaction mixture remained a suspension, no temperature change was observed. The mixture was heated to 140° C. for 24 h. The RM was cooled to ca. 80° C. resulting in a very thick yellow suspension. Ethyl acetate (100 mL) and water (100 mL) were added resulting in two clear layers. Cooling to room temperature initiated crystallization of the product in the upper organic layer. The colorless fine needles were collected by filtration, washed with MeOH (3×30 mL), and dried in a stream of air affording 31.3 (17.5 g, 52% yield). The filtrate was diluted with additional water (200 ml) and ethyl acetate/heptane (1:2) (300 ml). The phases were separated and the organic layer was washed with water (2×100 ml), NaHCO$_3$(100 mL), and brine (100 mL). The combined organic extracts were dried over Na$_2$SO$_4$, filtered and concentrated in vacuo to afford a colorless solid, which was suspended in MeOH (ca. 50 mL). A second batch of 31.3 was collected by filtration, washed with MeOH (2×30 mL) and dried in a stream of air affording (11.4 g, 34% yield). UPLC retention time 1.06 min (Method A). $^1$H NMR (DMSO-d$_6$): δ=8.27 (1H, d), 8.04 (1H, dd), 7.91 (2H, m), 7.36 (2H, m), 7.24, (1H, d). MS/ESI 230.9 [M+H]$^+$.

Step b) 2-(4-(2H-Tetrazol-5-yl)phenoxy)-5-chloropyridine (31.4). Five solutions of 31.3 (1.442 g, 6.25 mmol), Bu$_2$SnO (0.156 g, 0.625 mmol) and TMS-Azide (1.659 mL, 12.50 mmol) in dry toluene (9 mL) were prepared under argon. The vials were sealed and the mixtures stirred at 100° C. for 65 h on a heating block. The mixtures were combined and treated with MeOH (50 mL), turning the RM into a suspension. All solvents were removed under reduced pressure. The solid residue was suspended in MeCN (70 mL) and filtered. The colorless powder was washed with MeCN (2×25 mL) and pentane, and dried to give 31.4 (7.66 g, 88% yield) as a colorless powder. UPLC retention time 2.81 min (Method B). $^1$H NMR (DMSO-d$_6$): δ=16.7 (1H, s br), 8.27 (1H, d), 8.04 (1H, dd), 7.91 (2H, m), 7.36 (2H, m), 7.24, (1H, d). MS/ESI 274.0 [M+H]$^+$.

Step c) (R)-Methyl 2-((tert-butoxycarbonyl)amino)-3-(5-(4-((5-chloropyridin-2-yl)oxy)phenyl)-2H-tetrazol-2-yl) propanoate (31.6). A mixture of triphenylphosphine (2.396 g, 9.13 mmol), DIAD (2.103 g, 9.13 mmol) and 31.4 (1.00 g, 3.65 mmol) and 31.5 (2.003 g, 9.13 mmol) in THF (65 ml) was stirred for 1 h at 25° C. (solute was added and the mixture dried in vacuo. Chromatography on silica (gradient: cyclohexane/ethyl acetate) afforded 31.6 (1.57 g, 89%) as a colorless solid. UPLC retention time 1.33 min (Method A). $^1$H NMR (DMSO-d$_6$): δ=8.25 (1H, d), 8.09 (2H, d), 8.01 (1H, d), 7.49 (1H, d), 7.34 (2H, d), 7.20 (1H, d), 5.11 (1H, dd), 5.01 (1H, dd), 4.72 (1H, m), 3.71 (3H, s), 1.25-1.40 (9H, m). MS/ESI 475.3 [M+H]$^+$.

Step d) (R)-tert-Butyl (1-(5-(4-((5-chloropyridin-2-yl) oxy)phenyl)-2H-tetrazol-2-yl)-3-hydroxypropan-2-yl)carbamate (31.7). At 0° C. LiBH4 (2N solution in THF, 2.106 mL, 4.21 mmol) was added dropwise to a solution of 31.6 (500 mg, 1.053 mmol) in THF (10 mL) and the mixture stirred for 1 h at 0° C. The mixture was neutralized with HCl (1 N aqueous solution), CH$_2$Cl$_2$ added, the organic layer separated, dried with Na$_2$SO$_4$ and the solvent removed. Chromatography on silica (gradient: cyclohexane/ethyl acetate) gave compound 31.7 as a colorless oil (555 mg, 72%). UPLC retention time 1.10 min (Method A). $^1$H NMR (DMSO-d$_6$): δ=8.27 (1H, dd), 8.09 (2H, d), 8.03, (1H, d), 7.34 (2H, d), 7.20 (1H, d), 6.88 (1H, d), 5.03 (1H, t, br), 4.91 (1H, dd), 4.63 (2H, dd), 4.00 (1H, m), 3.40-3.51 (2H, m), 1.25 (9H, s). MS/ESI 447.2 [M+H]$^+$.

Step d) (R)-2-Amino-3-(5-(4-((5-chloropyridin-2-yl)oxy) phenyl)-2H-tetrazol-2-yl)propan-1-ol (Example 31). To a solution of 31.7 (275 mg, 0.615 mmol) in CH$_2$Cl$_2$ (6 mL) was added HCl (4N solution in dioxane, 2.308 mL, 9.23 mmol) and the mixture stirred for 2 h at 25° C. Filtration gave a first batch of the hydrochloride of Example 31 as a colorless solid (40 mg, 18%). The filtrate was concentrated and the residue purified by preparative HPLC. The TFA salt was converted into the free base, which was further purified on silica (gradient: CH$_2$Cl$_2$/MeOH) to afford Example 31 (37 mg, 15%). UPLC retention time 0.70 min (Method A). $^1$H NMR (DMSO-d$_6$): δ=8.26 (1H, d), 8.10 (2H, d), 8.02 (1H, dd), 7.34 (2H, d), 7.00, (1H, d), 4.85 (1H, t, br), 4.77 (1H, dd), 4.55 (1H, dd), 3.33-3.45 (2H, m), 3.25-3.30 (1H, m), 1.60 (2H, s br). MS/ESI 347.1 [M+H]$^+$.

Example 32 (S)-2-Amino-3-(5-(4-((3-fluor-5-(1H-pyrazol-5-yl)pyridin-2-yl)oxy)phenyl)-2H-tetrazol-2-yl)propan-1-ol

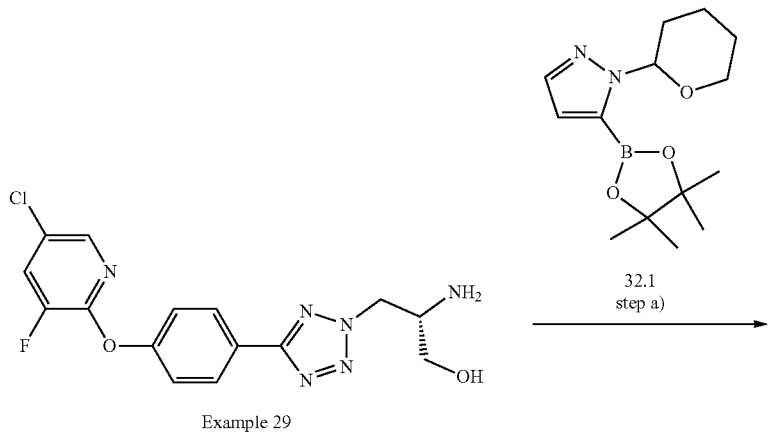

Example 29

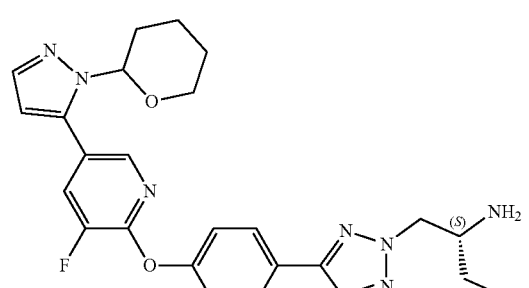

32.2

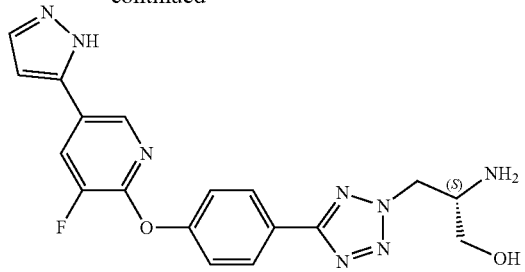

Example 32

Step a) (2S)-2-Amino-3-(5-(4-((3-fluoro-5-(1-(tetrahydro-2H-pyran-2-yl)-1H-pyrazol-5-yl)pyridin-2-yl)oxy)phenyl)-2H-tetrazol-2-yl)propan-1-ol (32.2). A suspension of Example 29 (2000 mg, 5.48 mmol), 32.1 (2050 mg, 10.97 mmol), 1βPO$_4$ (2328 mg, 10.97 mmol) and PdCl$_2$(dtbpf) (357 mg, 0.548 mmol) in a mixture of dioxane (20 mL) and water (6.3 mL) was stirred under argon for 1.5 min at 120° C. A solution of additional 32.1 and PdCl$_2$(dtbpf) in dioxane (5 mL) was added heating at 120° C. continued for 1 h. The mixture was diluted with water and extracted with ethyl acetate. The organic layer was dried with Na$_2$SO$_4$, filtered and concentrated. The residue was purified on silica (gradient: CH$_2$Cl$_2$/MeOH) to afford 32.2 (1127 mg, 42%). The material was dissolved in THF (70 mL), SiliaMetS DMT was added and this mixture stirred for 16 h at 50° C. The scavenger was filtered off, the residue washed with THF and concentrated to afford a solid, which was used in the next step. UPLC retention time 0.78 min (Method A). $^1$H NMR (DMSO-d$_6$): δ=8.12-8.17 (3H, m), 8.06 (1H, d), 7.62 (1H, d), 7.45 (2H, d), 6.61 (1H, d), 5.31 (1H, dd), 4.83-4.91 (1H, m), 4.77 (1H, dd), 4.56 (1H, dd), 3.95 (1H, d br), 3.53-3.62 (1H, m), 3.25-3.45 (3H, m), 2.33-2.44 (1H, m), 1.92-2.01 (1H, m), 1.85 (1H, d br), 1.49-1.72 (m, 5H). MS/ESI 481.2 [M+H]$^+$.

Step b) (S)-2-Amino-3-(5-(4-((3-fluoro-5-(1H-pyrazol-5-yl)pyridin-2-yl)oxy)phenyl)-2H-tetrazol-2-yl)propan-1-ol (Example 32). To a solution of 32.2 (1125 mg, 2.341 mmol) in THF (15 mL) was added 2N HCl (2.0 mL) and the mixture stirred for 1.5 h at 25° C. The mixture was concentrated and the residue purified on silica (gradient: CH$_2$Cl$_2$/MeOH) to afford Example 32 (421 mg, 41%). UPLC retention time 0.63 min (Method A). $^1$H NMR (DMSO-d$_6$): δ=8.54 (3H, s br), 8.48 (1H, d), 8.28 (1H, dd), 8.15 (2H, d), 7.83 (1H, d), 7.41 (2H, d), 6.85 (1H, d), 5.00-5.10 (2H, m), 3.75-3.85 (2H, m), 3.67-3.76 (2H, m), OH and pyrazol NH not observed. MS/ESI 397.2 [M+H]$^+$.

Example 33 (S)-2-Amino-3-(5-(4-((5-bromopyridin-2-yl)oxy)phenyl)-2H-tetrazol-2-yl)propan-1-ol

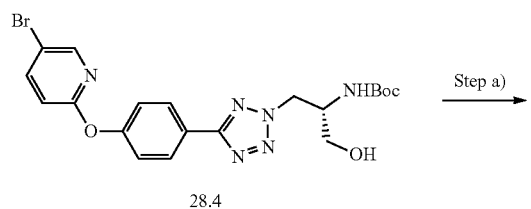

28.4

Step a)

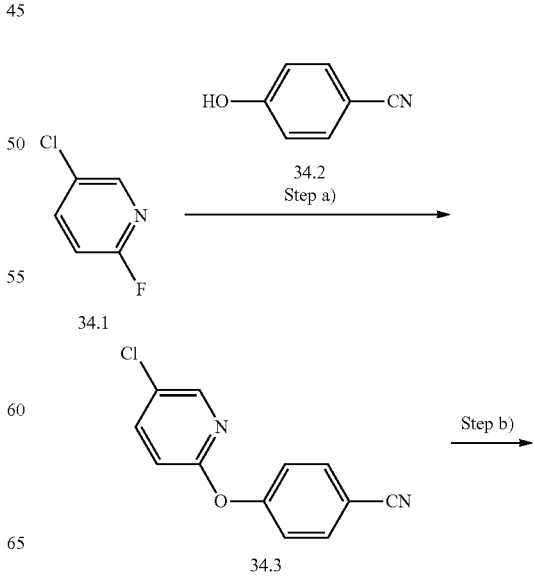

Example 33

Step a) (S)-2-Amino-3-(5-(4-((5-bromopyridin-2-yl)oxy)phenyl)-2H-tetrazol-2-yl)propan-1-ol (Example 33). To a solution of 28.4 (139 mg, 0.283 mmol) in CH$_2$Cl$_{1-2}$ (2.8 mL) was added HCl (4N solution in dioxane, 1.061 mL, 4.24 mmol) and the mixture stirred for 2 h at 25° C. Filtration gave the hydrochloride of Example 33 as a colorless solid (100 mg, 83%). UPLC retention time 0.73 min (Method A). $^1$H NMR (DMSO-d$_6$): δ=8.41 (2H, s br), 8.33 (1H, d), 8.10-8.17 (3H, m), 7.37 (2H, d), 7.17 (1H, d), 4.95-5.10 (2H, m), 3.82 (1H, m), 3.72 (1H, dd), 3.65 (1H, dd). MS/ESI 391.1 [M+H]$^+$.

Example 34 (S)-2-Amino-3-(5-(4-((5-chloropyridin-2-yl)oxy)phenyl)-2H-tetrazol-2-yl)propan-1-ol

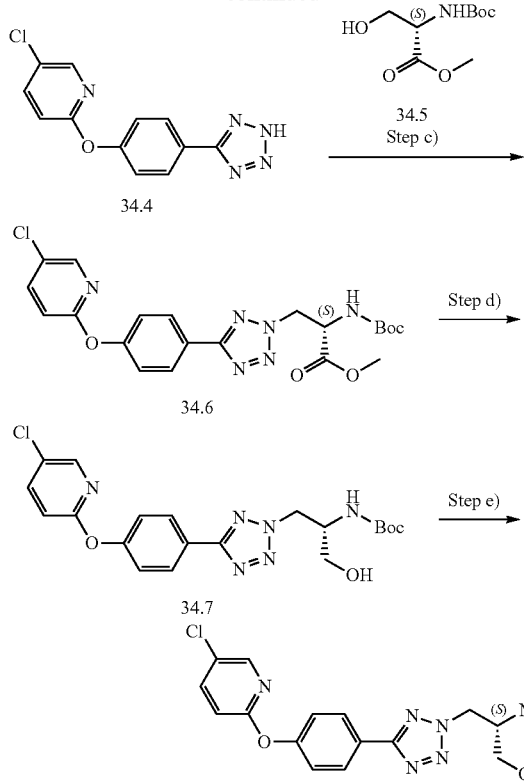

Example 34

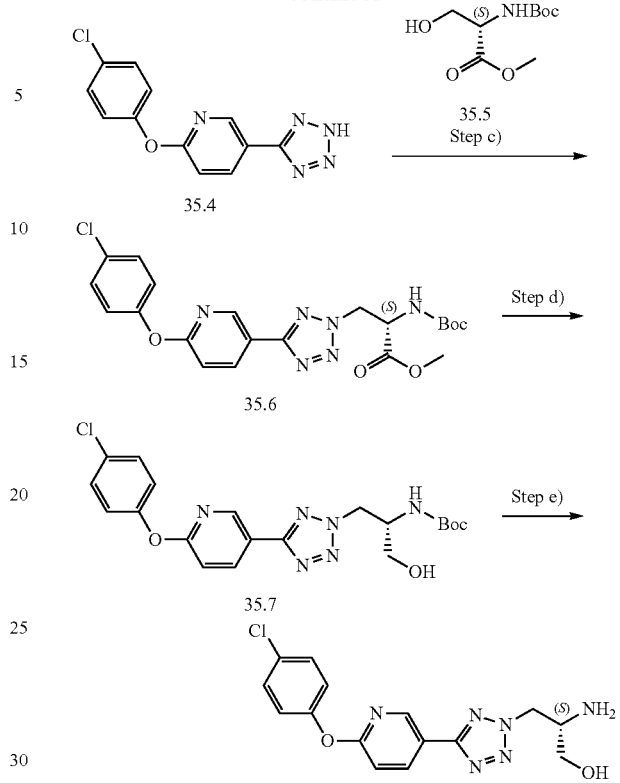

Example 35

(S)-2-Amino-3-(5 (4-((5-chloropyridin-2-yl)oxy)phenyl)-2H-tetrazol-2-yl)propan-1-ol (Example 34) was prepared as hydrochloride by similar procedures used for the synthesis of Example 31 replacing 31.5 by its S-enantiomer 34.5. UPLC retention time 0.68 min (Method A). $^1$H NMR (DMSO-$d_6$): δ=8.43 (3H, s br), 8.27 (1H, d), 8.14 (2H, m), 8.03 (1H, dd), 7.36 (2H, m), 7.21 (1H, d 5.57 (1H, t), 4.95-5.10 (2H, m), 3.82 (1H, m), 3.73 (1H, dd), 3.65 (1H, dd), OH not observed. MS/ESI 347.2 [M+H]$^+$.

Example 35 S)-2-Amino-3-(5-(6-(4-chlorophenoxy)pyridin-3-yl)-2H-tetrazol-2-yl)propan-1-ol

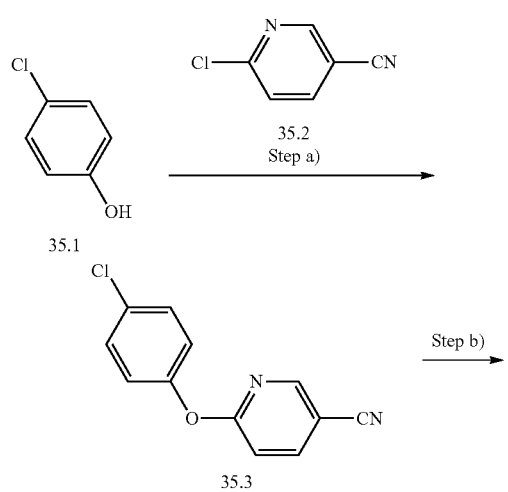

Step a) 6-(4-Chlorophenoxy)nicotinonitrile (35.3). A mixture of 35.1 (1.948 g, 15.16 mmol), 35.2 6-chloronicotinonitrile (2 g, 14.43 mmol) and $K_2CO_3$ (2.394 g, 17.32 mmol) in DMF (6 mL) was stirred at 120'C for 3 hr. The reaction was quenched by pouring the mixture in water (100 ml) and diluting with ethyl acetate/heptane (1:1) (150 ml). The phases were separated and the organic phase was washed with water (100 ml) and brine (50 mL). The combined organic extracts were dried over $Na_2SO_4$, filtered and concentrated in vacuo to ca. 40 mL, which initiated crystallization. The solid was collected by filtration, washed with heptane (3×10 mL) and dried in a stream of air. Compound 35.3 (2.15 g, 9.14 mmol, 63.3% yield) was obtained as a colorless powder. UPLC retention time 1.10 min (Method A). $^1$H NMR (DMSO-$d_6$): δ=8.65 (1H, d), 8.34 (1H, dd), 7.49-7.53 (2H, m), 7.26-7.29 (3H, m). MS/ESI 231.0 [M+H]$^+$.

Step b) 2-(4-Chlorophenoxy)-5-(2H-tetrazol-5-yl)pyridine (35.4). To a mixture of 35.3 (1.50 g, 6.50 mmol) and $Bu_2SnO$ (0.162 g, 0.650 mmol) in toluene (8 mL) was added $TMSN_3$ (1.726 mL, 13.01 mmol) under Ar. The RM was heated to 100'C for 16 h. After cooling back to RT, the resulting suspension was dissolved in MeOH (50 mL) and concentrated in vacuo. The residue was suspended in MeCN (30 mL), filtered and washed with several portions of MeCN (3×10 mL) and heptane (3×20 mL). The product was dried in a stream of air yielding 35.4 (990 mg, 3.29 mmol, 50.5% yield) as a colorless solid. UPLC retention time 0.86 min (Method A). $^1$H NMR (DMSO-$d_6$): δ=17.1 (1H, s br), 8.77 (1H, d), 8.43 (1H, dd), 7.49-7.53 (2H, m), 7.29 (1H, d), 7.24-7.28 (2H, m). MS/ESI 274.2 [M+H]$^+$.

Step c) (S)-Methyl 2-((tert-butoxycarbonyl)amino)-3-(5-(6-(4-chlorophenoxy)pyridin-3-yl)-2H-tetrazol-2-yl)propanoate (35.6). A mixture of triphenylphosphine (575 mg, 2.192 mmol), DIAD (505 mg, 2.192 mmol) and 35.4 (400 mg, 1.462 mmol) and 35.5 (481 mg, 2.192 mmol) in THF (25 ml) was stirred for 1.5 h at 25° C. (solute was added and the mixture dried in vacuo. Chromatography on silica (gradient: cyclohexane/ethyl acetate) afforded 35.6 (1.57 g, 89%) as a colorless solid. UPLC retention time 1.25 min (Method A). $^1$H NMR (DMSO-d$_6$): δ=8.79 (1H, d), 8.43 (1H, dd), 7.47-7.54 (3H, m), 7.44-7.30 (3H, m), 5.12 (1H, dd), 5.02 (1H, dd), 4.72 (1H, m), 3.71 (3H, s), 1.30 (9H, s). MS/ESI 475.1 [M+H]$^+$.

Step d) (S)-tert-Butyl (1-(5-(6-(4-chlorophenoxy)pyridin-3-yl)-2H-tetrazol-2-yl)-3-hydroxypropan-2-yl)carbamate (35.7). At 0'C LiBH4 (2N solution in THF, 1.722 mL, 3.44 mmol) was added dropwise to a solution of 35.6 (409 mg, 0.861 mmol) in THF (5 mL) and the mixture stirred for 1 h at 0° C. The mixture was neutralized with HCl (1 N aqueous solution), CH$_2$C1$_2$ added, the organic layer separated, dried with Na$_2$SO$_4$ and the solvent removed. Chromatography on silica (gradient: cyclohexane/ethyl acetate) gave compound 35.7 as a colorless solid (197 mg, 51%). UPLC retention time 1.13 min (Method A). $^1$H NMR (DMSO-d$_6$): δ=8.79 (1H, d), 8.43 (1H, dd), 7.48-7.54 (2H, m), 7.25-7.29 (3H, m), 6.88 (1H, d), 5.03 (1H, t), 4.93 (1H, dd), 4.53 (1H, dd), 4.00 (1H, m), 3.43-3.54 (2H, m), 1.25 (9H, s). MS/ESI 447.1 [M+H]$^+$.

Step d) (S)-2-Amino-3-(5-(6-(4-chlorophenoxy)pyridin-3-yl)-2H-tetrazol-2-yl)propan-1-01 (Example 35). To a solution of 35.7 (182 mg, 0.407 mmol) in CH$_2$Cl$_2$ (4 mL) was added HCl (4N solution in dioxane, 1.527 mL, 6.11 mmol) and the mixture stirred for 2 h at 25'C. Filtration gave the hydrochloride of Example 35 as a colorless solid (151 mg, 97%). UPLC retention time 0.72 min (Method A). $^1$H NMR (DMSO-d$_6$): δ=8.83 (1H, d), 8.48 (1H, dd), 8.42 (3H, s br), 7.50-7.54 (2H, m), 7.25-7.30 (3H, m), 4.97-5.11 (2H, m), 3.80 (1H, m), 3.72 (1H, dd), 3.65 (1H, dd), OH not observed. MS/ESI 347.1 [M+H]$^+$.

Example 36 (S)-3-(3-(4-((5-(1H-pyrazol-5-yl)pyridin-2-yloxy)phenyl)-1H-pyrazol-1-yl)-2-aminopropan-1-ol

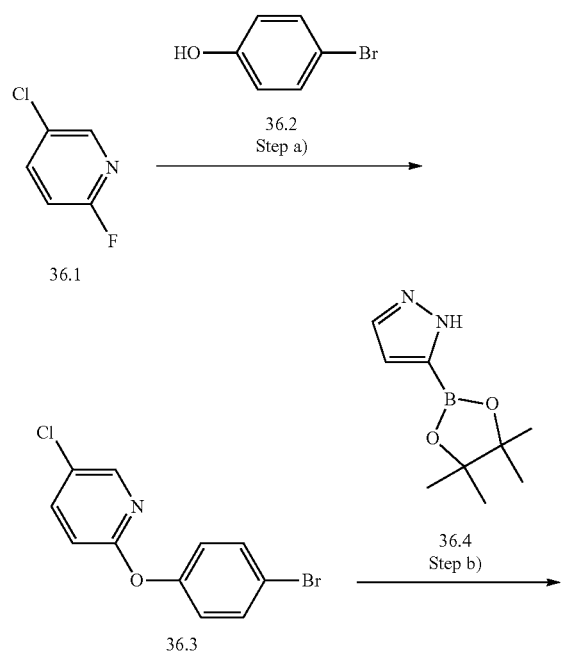

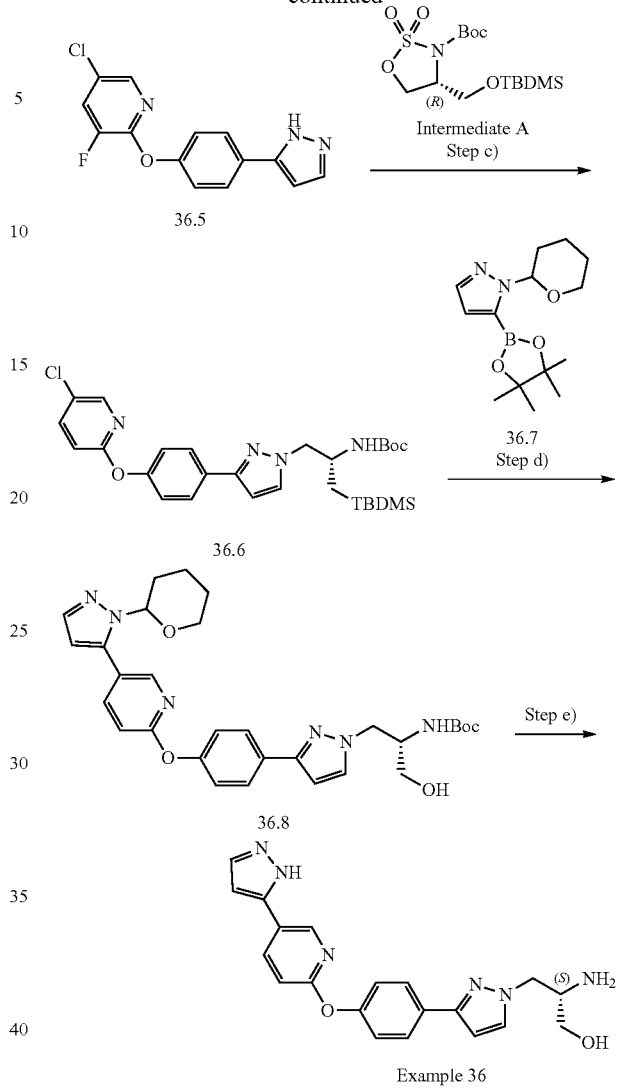

Step a) 2-(4-Bromophenoxy)-5-chloro-3-fluoropyridine (36.3). A mixture of compound 36.1 (5.00 g, 33.4 mmol), 36.2 (6.36 g, 36.8 mmol), K$_2$CO$_3$ (6.93 g, 50.2 mmol) in DMF (50 mL) was degassed and purged with N$_2$ for 3 times, and then the mixture was stirred at 80° C. for 4 h under N$_2$ atmosphere. The mixture was diluted with ethyl acetate (100 mL) and then washed with brine (3×100 mL) and H$_2$O (100 mL). The organic layer was dried and concentrated to give a residue. The residue was purified on silica (gradient petroleum ether/ethyl acetate) to affor compound 36.3 (8.20 g, 80%) as a white solid. $^1$H NMR (CDCl$_3$): δ=7.81 (1H, d), 7.45 (3H, m), 6.92-7.06 (2H, m). MS/ESI 301.9 [M+H]$^+$.

Step b) 2-(4-(1H-pyrazol-3-yl)phenoxy)-5-chloro-3-fluoropyridine (36.5). A mixture of 36.3 (7.0 g, 23.1 mmol), compound 36.4 (13.5 g, 69.4 mmol), Pd(PPh$_3$)$_4$ (1.34 g, 1.16 mmol), Na$_2$CO$_3$ (3.84 g, 36.2 mmol) in H$_2$O (20 mL) and dioxane (100 mL) was degassed and purged with N$_2$ for 3 times, and then the mixture was stirred at 75° C. for 24 h under N$_2$ atmosphere. The mixture was diluted with H$_2$O (100 mL) and then extracted with ethyl acetate (3×100 mL). The organic layer was dried over Na$_2$SO$_4$, filtered and concentrated to give a residue, which was purified on silica (gradient petroleum ether/ethyl acetate) to afford 36.5 (3.0 g, 10.2 mmol, 44%) as a white solid. $^1$H NMR (DMSO-$d_6$): δ=12.90 (1H, s br), 8.24 (br d, J=9.8 Hz, 1H), 8.08 (s, 1H), 7.69-7.95 (m, 3H), 7.17-7.34 (m, 2H), 6.75-6.85 (m, 1H), mixture of tautomers. MS/ESI 289.9 [M+H]$^+$.

Step c) tert-butyl (S)-(1-((tert-butyldimethylsilyl)oxy)-3-(3-(4-((5-chloro-3-fluoropyridin-2-yl)oxy)phenyl)-1H-pyrazol-1-yl)propan-2-yl)carbamate (36.6). A mixture of 36.5 (2.5 g, 8.53 mmol), Intermediate A (3.76 g, 10.2 mmol), Cs$_2$CO$_3$ (8.34 g, 25.6 mmol) in DMF (40 mL) was degassed and purged with N$_2$ for 3 times, and then the mixture was stirred at 20° C. for 2 h under N$_2$ atmosphere. The mixture was poured into ethyl acetate (100 mL) and water (50 mL). The aqueous layer was extracted twice with ethyl acetate. The combined organic phases were washed four times with brine and dried over Na$_2$SO$_4$. Evaporation of the solvent gave a residue, which was purified on silica (gradient petroleum ether/ethyl acetate) to afford 36.6 (2.3 g, 38%) as colorless gum. $^1$H NMR (DMSO-$d_6$): δ=8.23 (1H, dd), 8.06 (1H, d), 7.82 (2H, d), 7.68 (1H, d), 7.16-7.28 (2H, m), 6.84 (1H, d), 6.68 (1H, d), 4.26 (1H, dd), 4.01-4.13 (m, 1H), 3.88-3.95 (1H, m), 3.50-3.63 (2H, m), 1.20-1.35 (m, 9H), 0.88 (9H, s), 0.04 (s, 6H). MS/ESI 577.2 [M+H]$^+$.

Step d) tert-Butyl ((2S)-1-(3-(4-((3-fluoro-5-(1-(tetrahydro-2H-pyran-2-yl)-1H-pyrazol-5-ylpyridin-2-yl)oxy) phenyl)-1H-pyrazol-1-yl)-3-hydroxypropan-2-yl)carbamate (36.8). A mixture of 36.6 (1.01 g, 1.65 mmol), 36.7 (682 mg, 2.47 mmol), PdCl$_2$ (29.2 mg, 0.165 mmol), P(c-C$_6$H$_{11}$)$_3$ (138 mg, 0.494 mmol) and CsF (500 mg, 3.29 mmol) in NMP (10 mL) and H$_2$O (1 mL) was degassed and purged with N$_2$, and then the mixture was stirred at 100° C. for 12 h under N$_2$ atmosphere. The mixture was diluted with ethyl acetate (50 mL) and washed with H$_2$O (3×30 mL) and brine (30 mL). The organics was dried over Na$_2$SO$_4$, filtered and concentrated to give 36.8 (1.1 g, crude) as light yellow gum, which was used for step e) without further purification. MS/ESI 579.1 [M+H]$^+$.

Step e) (S)-2-Amino-3-(3-(4-((3-fluoro-5-(1H-pyrazol-5-yl)pyridin-2-yl)oxy)phenyl)-1H-pyrazol-1-yl)propan-1-ol (Example 36). A mixture of 36.8 (1.1 g crude from step d) in HCl/ethyl acetate (20 mL, 4M) was stirred at 20° C. for 0.5 h under N$_2$ atmosphere. The mixture was concentrated and the residue purified by prep-HPLC (column: Phenomenex luna C18 250×50 mm, 10 μm; mobile phase: [water (0.05% HCl)-ACN]; B %: 5 ACN %-35 ACN %, 35 min, 80% min) to afford the hydrochloride of Example 36 (317 mg, 44%) as a light yellow solid. UPLC retention time 0.52 min (Method C). $^1$H NMR (CD$_3$OD): δ=8.75 (1H, s br), 8.47-8.54 (1H, m), 7.03-7.08 (1H, m), 7.99 (2H, d), 7.78 (1H, m), 7.32 (2H, d), 7.23 (1H, d), 6.98-7.02 (1H, m), 6.78 (1H, d), 4.42-4.60 (2H, m), 3.63-3.70 (2H, m), 3.55-3.61 (1H, m). $^1$H NMR (DMSO-$d_6$): δ=8.60 (1H, d), 8.28 (3H, s br), 8.25 (1H, dd), 7.84-7.89 (3H, m), 7.77 (1H, d), 7.16-7.21 (2H, m), 7.10 (1H, d), 6.76 (1H, m), 4.35-4.46 (2H, m), 3.56-3.68 (2H, m), 3.45-3.52 (1H, m), pyrazol-NH and OH not observed. MS/ESI 377.3 [M+H]$^+$.

Example 37 (S)-2-amino-3-(3-(4-((3-fluoro-5-(1H-pyrazol-5-yl)pyridin-2-yl)oxy)phenyl)-1H-pyrazol-1-yl)propan-1-ol

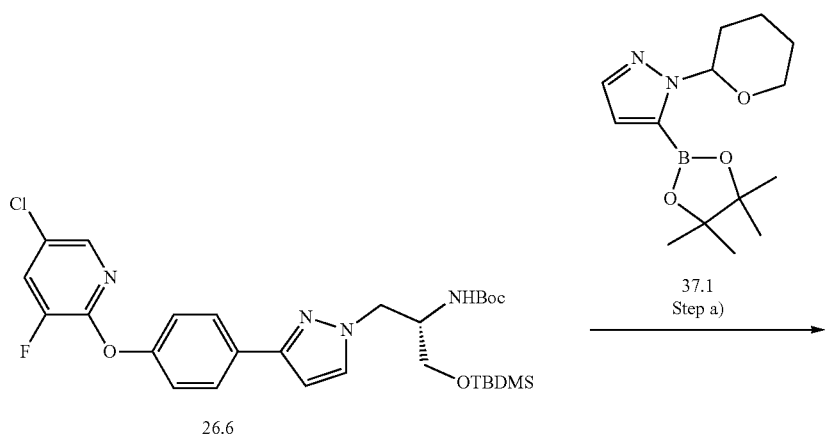

26.6

37.1
Step a)

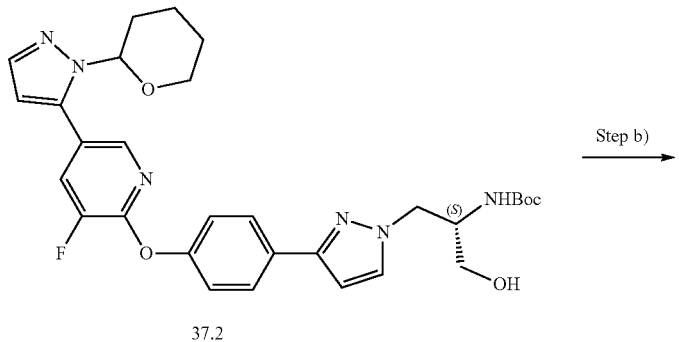

Step b)

37.2

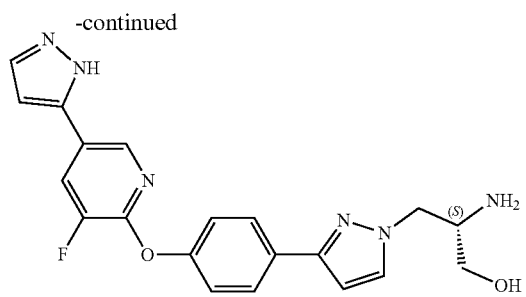

Example 37

Step a) tert-Butyl ((2S)-1-(3-(4-((3-fluoro-5-(1-(tetrahydro-2H-pyran-2-yl)-1H-pyrazol-5-yl)pyridin-2-yl)oxy)phenyl)-1H-pyrazol-1-yl)-3-hydroxypropan-2-yl)carbamate (37.2). A mixture of 26.6 (1.01 g, 1.65 mmol), 37.1 (682 mg, 2.47 mmol), PdCl$_2$ (29.2 mg, 0.165 mmol), P(c-C$_6$H$_{11}$)$_3$ (138 mg, 0.494 mmol) and CsF (500 mg, 3.29 mmol) in NMP (10 mL) and H$_2$O (1 mL) was degassed and stirred under nitrogen at 100° C. for 12 h. The mixture was diluted with ethyl acetate (50 mL) and washed with brine (3×30 mL) and H$_2$O (30 mL). The organic layer was dried over Na$_2$SO$_4$, filtered and concentrated to give 37.2 (1.1 g, crude) as light yellow gum, which was used for step b) without further purification. MS/ESI 579.1 [M+H]$^+$.

Step b) (S)-2-amino-3-(3-(4-((3-fluoro-5-(1H-pyrazol-5-yl)pyridin-2-yl)oxy)phenyl)-1H-pyrazol-1-yl)propan-1-ol (Example 37). A mixture of compound 37.2 (1.1 g) in HCl/ethyl acetate (20 mL, 4M) was degassed and stirred at 20'C for 0.5 h under nitrogen. The mixture was concentrated and the residue purified by prep-HPLC (column: Phenomenex luna C18 250×50 mm×10 μm; mobile phase: [water (0.05% HCl)-ACN]; B %: 5 ACN %-35 ACN %, 35 min, 80% min) to afford the hydrochloride of Example 37 (317 mg, 44% over 2 steps) as a light yellow solid. UPLC retention time 0.60 min (Method C). $^1$H NMR (CD$_3$OD): δ=8.38 (1H, d), 8.13 (1H, dd), 7.90-7.95 (2H, m), 7.84-7.87 (1H, m), 7.74 (1H, d), 7.22-7.26 (2H, m), 6.83-6.86 (1H, m), 6.75 (1H, d), 4.43-4.56 (2H, m), 3.78-3.85 (2H, m), 3.65-3.71 (1H, m). $^1$H NMR (DMSO-d$_6$): δ=8.42 (1H, d), 8.16-8.28 (4H, m), 7.84-7.89 (3H, m), 7.80 (1H, d), 7.22-7.26 (2H, m), 6.82 (1H, d), 6.77 (1H, d), 4.35-4.48 (2H, m), 3.56-3.68 (2H, m), 3.45-3.52 (1H, m), pyrazol-NH and OH not observed. MS/ESI 395.4 [M+H]$^+$.

Example 38 (2S)-2-amino-3-[5-(4-[[3-fluoro-5-(1,3-oxazol-2-yl)pyridin-2-yl]oxy]phenyl)-2H-1,2,3,4-tetrazol-2-yl]propan-1-ol

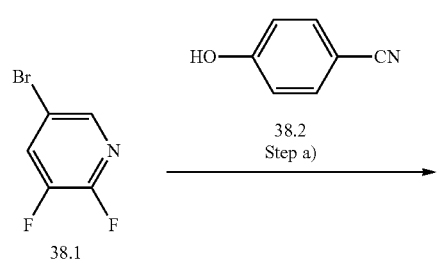

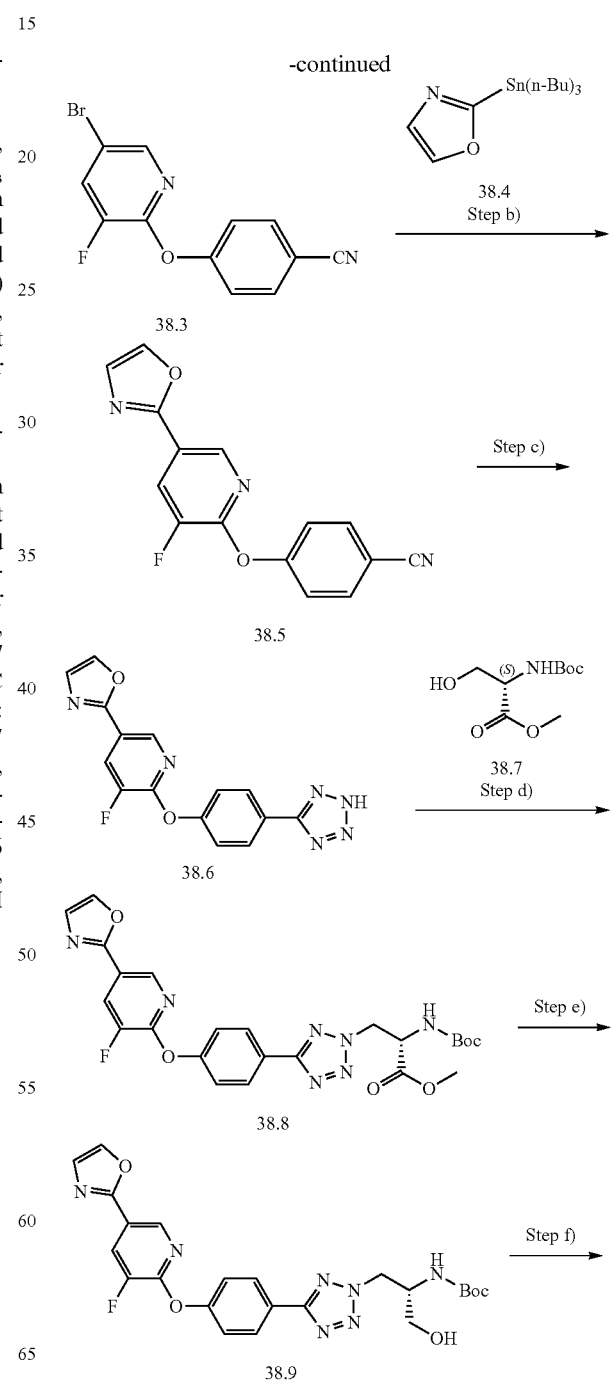

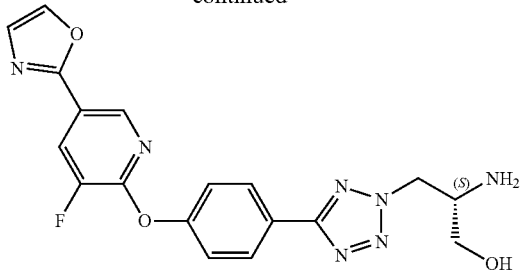

Example 38

Step a) 4-[(5-Bromo-3-fluoropyridin-2-yl)oxy]benzonitrile (38.3). A mixture of 38.1 (8 g, 41.24 mmol), 4-hydroxybenzonitrile (5.43 g, 45.58 mmol) and $K_2CO_3$ (6.3 g, 45.25 mmol) in DMF (80 mL) was stirred under argon at 120° C. for 16 h. The mixture was cooled to room temperature, diluted with $H_2O$ (300 mL) and extracted with ethyl acetate (3×100 mL). The combined organic layers were washed with of brine (100 mL), dried over $Na_2SO_4$, filtered and concentrated. The residue was purified on silica (ethyl acetate/petroleum ether; 12:88) to afford 38.3 (7.00 g, 58%) of as a colorless solid.

Step b) 4-[[3-Fluoro-5-(1,3-oxazol-2-yl]pyridin-2-yl)oxy]benzonitrile (38.5). Under nitrogen mixture of 38.3 (5.00 g, 17.06 mmol), 38.4 (18.33 g, 51.19 mmol) and $Pd(PPh_3)_4$ (2.00 g, 1.73 mmol) in $CH_3CN$ (150 mL) was heated under reflux for 16 h. The mixture was cooled to room temperature and concentrated under vacuum. The residue was purified on silica (ethyl acetate/petroleum ether, 25:75) affording 38.5 (4.00 g, 83%) as a colorless solid. MS/ESI 282.0 $[M+H]^+$.

Step c) 3-Fluoro-5-(1,3-oxazol-2-yl)-2-[4-(2H-1,2,3,4-tetrazol-5-yl)phenoxy]pyridine (38.6). Under nitrogen a mixture of 38.5 (4.00 g, 14.22 mmol), $Bu_2SnO$ (350 mg, 1.41) and $TMSN_3$ (5.00 g, 43.40 mmol) in toluene (40 mL) was heated under reflux for 3 h. The mixture was concentrated under vacuum and the residue purified on silica (ethyl acetate/petroleum ether, 70:30) to afford 38.6 (3.5 g, 76%) as a colorless solid.

Step d) Methyl (S)-2-((tert-butoxycarbonyl)amino)-3-(5-(4-((3-fluoro-5-(oxazol-2-yl)pyridin-2-yl)oxy)phenyl)-2H-tetrazol-2-yl)propanoate (38.8). To a solution of 38.6 (3.50 g, 10.79 mmol) in THF (100 mL) was added under nitrogen at 0° C. DIAD (6.20 g, 26.96 mmol), $PPh_3$ (7.10 g, 27.07 mmol, 2.50) and 38.7 (6.00 g, 27.37 mmol). The resulting mixture was stirred for 16 h at room temperature, concentrated and the residue purified on silica (ethyl acetate/petroleum ether; 45:55) to afford 38.8 (3.20 g, 56%) as a colorless solid. MS/ESI 526.1 $[M+H]^+$.

Step e). tert-butyl N-[(2S)-1-[5-(4-[[3-fluoro-5-(1,3-oxazol-2-yl)pyridin-2-yl]oxy]phenyl)-2H-1,2,3,4-tetrazol-2-yl]-3-hydroxypropan-2-yl]carbamate (38.9). At 0'C LiBH4 (7.6 mL 2 molar solution in THF) was added dropwise to a solution of 38.8 in THF (40 mL) and the mixture was stirred for 2 h at 0-10° C. The mixture was cooled to 0° C. and AcOH (920 mg, 15.6 mmol) was added. The mixture was diluted with $H_2O$ (150 mL) and extracted with ethyl acetate (3×50 mL). The organic layer was washed with brine (50 mL), dried over $Na_2SO_4$, filtered and concentrated. The residue was purified on silica (ethyl acetate/petroleum ether: 60/40) to afford 38.9 (800 mg, 42%) as a colorless solid. MS/ESI 498.1 $[M+H]^+$.

Step f) (2S)-2-amino-3-[5-(4-[[3-fluoro-5-(1,3-oxazol-2-yl)pyridin-2-yl]oxy]phenyl)-2H-1,2,3,4-tetrazol-2-yl]propan-1-ol (Example 38). To a solution of 38.9 (800 mg, 1.61 mmol) in $CH_2Cl_2$ (50 mL) and MeOH (10 mL) was added under nitrogen at 0° C. HCl (8 mL 4 M in dioxane) and the mixture stirred for 16 h at room temperature. The solution was diluted with ether (50 mL) and the solid collected by filtration. The crude product was purified by prep-HPLC to afford Example 38 (280 mg, 44) as a colorless solid. $^1$H NMR (DMSO-$d_6$): δ=8.57 (1H, d), 8.38 (1H, dd), 8.30 (1H, s), 8.14 (2H, d), 7.41-7.50 (3H, m), 4.85 (1H, s br), 4.78 (1H, dd), 4.56 (1H, dd), 3.35-3.50 (3H, m), 1.75 (2H, s br). MS/ESI 398.1 $[M+H]^+$.

Example 39 2-Amino-3-(2-(4-((5-chloro-3-fluoropyridin-2-yl)oxy) phenyl)-2H-tetrazol-5-yl)propan-1-ol

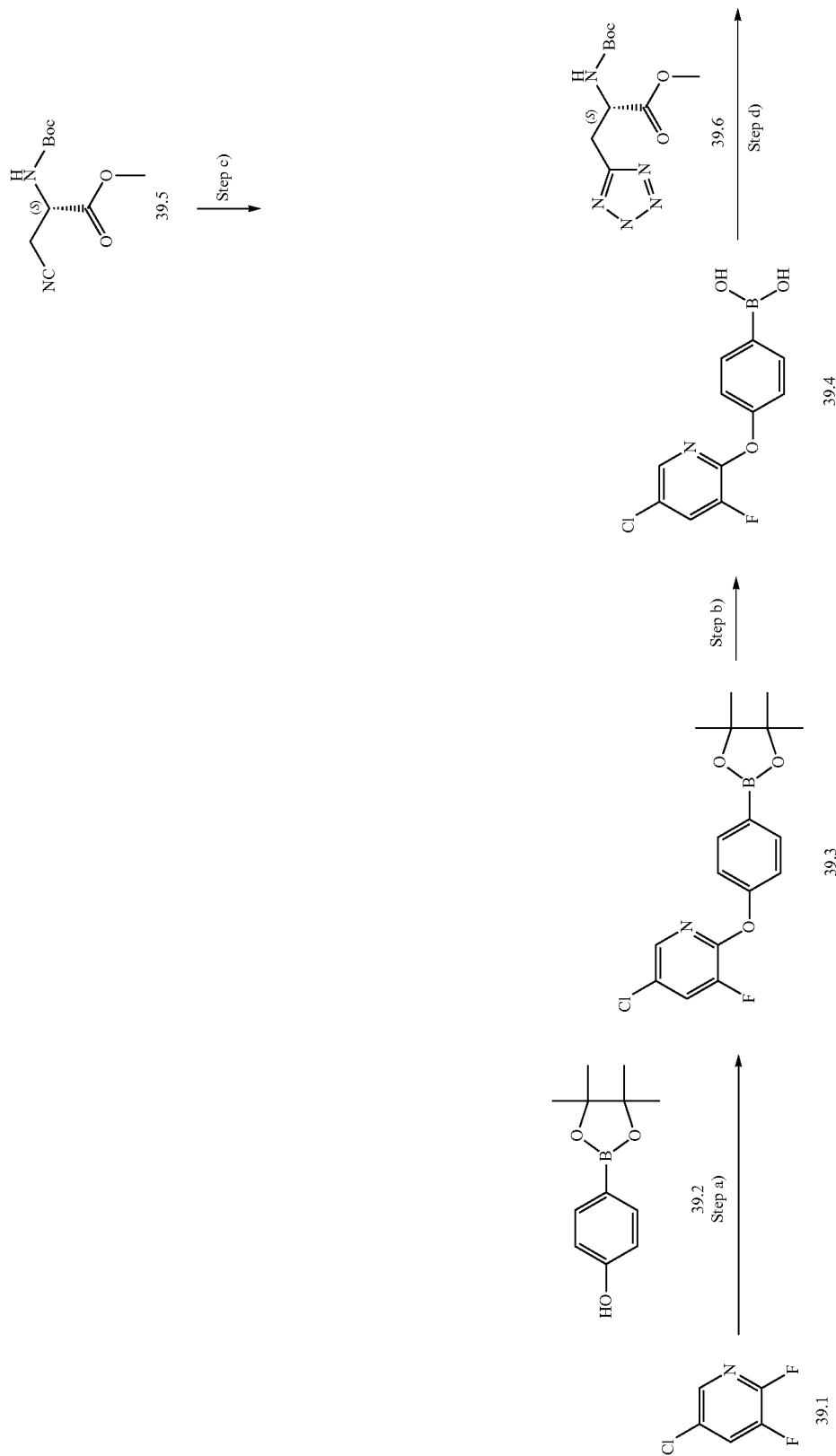

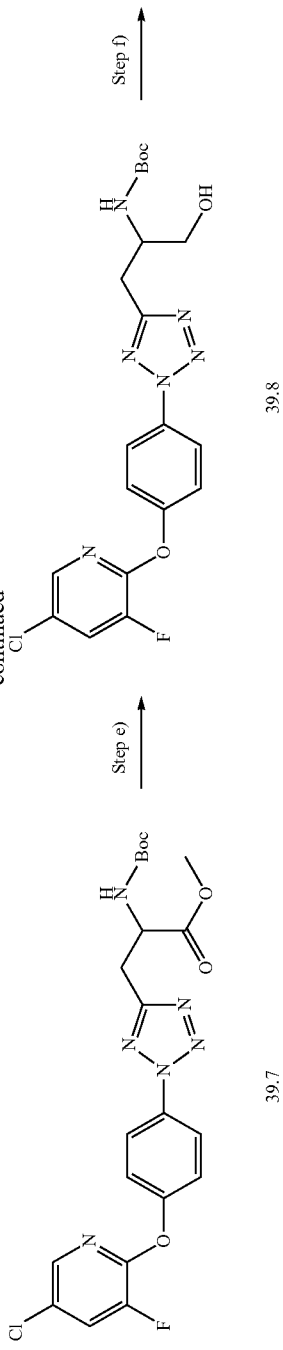
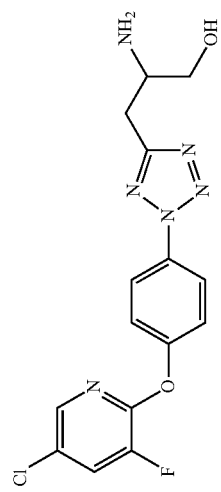
Example 39

Step a) 5-Chloro-3-fluoro-2-(4-(4,4,5,5-tetramethyl-1,3,2-dioxaborolan-2-yl)phenoxy)pyridine (39.3). A solution of 39.1 (6.73 g, 45.0 mmol), 39.2 (9.00 g, 40.9 mmol) and $K_2CO_3$ (11.30 g, 82.0 mmol) in DMF (45 mL) was stirred at 80'C for 5 h. The mixture was diluted with ethyl acetate and washed with water. The organic layer was separated and the remaining aqueous layer was extracted with ethyl acetate. The combined organic extracts were dried over $Na_2SO_4$, filtered and evaporated. The residue was purified on silica to afford 39.3 (11.23 g, 76%). UPLC retention time 1.47 min (Method A). $^1$H NMR (DMSO-$d_6$): δ=8.24 (1H, dd), 8.08 (1H, s), 7.73 (2H, d), 7.19 (2H, d), 1.31 (12H, s). MS/ESI 350.2 [M+H]$^+$.

Step b) (4-((5-chloro-3-fluoropyridin-2-yl)oxy)phenyl) boronic acid (39.4). To a solution of 39.3 (11.20 g, 32.0 mmol) in THE (90 mL) and water (90 mL) was added $Na_1O_3$ (20.56 g, 96 mmol) and the mixture was stirred at 25° C. for 72 h. HCl (1N, 22.43 mL) was added and stirring continued for 1 h. The mixture was diluted with ethyl acetate and washed with water. The aqueous layer was extracted with ethyl acetate, the combined organic layers dried over $Na_2SO_4$, filtered and concentrated. the residue was triturated with cyclohexane, the resulting solid was filtered off and washed with cyclohexane and dried in vacuo to afford 39.4 (7.02 g, 78%) as a solid. UPLC retention time 0.91 min (Method A). $^1$H NMR (DMSO-$d_6$): δ=8.22 (1H, dd), 8.04-8.09 (3H, m), 7.84 (2H, d), 7.14 (2H, d). MS/ESI 268.2 [M+H]$^+$.

Step c) (S)-Methyl 2-((tert-butoxycarbonyl)amino)-3-(2H-tetrazol-5-yl)propanoate (39.6). To a solution of 39.5 (900 mg, 3.94 mmol) in DMF (9 mL) was added $NaN_3$ (769 mg, 11.83 mmol) and $NEt_3$ x HCl (1628 mg, 11.83 mmol) and the mixture heated in a microwave oven at 130° C. for 2 h. The mixture was filtered and the residue washed with ethyl acetate. The organic layer was washed with aqueous HCl (pH 1), dried over $Na_2SO_4$, filtered and concentrated. The residue was purified on silica (gradient: cyclohexane/ethyl acetate) to afford 39.6 (480 mg, 44%). $^1$H NMR (DMSO-$d_6$): δ=16.13 (1H, s br), 7.39 (1H, d br), 4.46-4.54 (1H, m), 3.62 (3H, s), 3.39-3.18 (2H, m), 1.35 (9H, s). MS/ESI 272.1 [M+H]$^+$.

Step d) Methyl 2-((tert-butoxycarbonyl)amino)-3-(2-(4-((5-chloro-3-fluoropyridin-2-yl)oxy)phenyl)-2H-tetrazol-5-yl)propanoate (39.7). To a solution of 35.6 (400 mg, 1.475 mmol) in $CH_2Cl_2$ (8 mL) was added at 25° C. under argon 39.4 (631 mg, 2.359 mmol) $K_2CO_3$ (224 mg, 1.622 mmol) and [Cu(OH)(TMEDA)]$_2$Cl$_2$(82 mg, 0.177 mmol). The blue mixture was stirred for at 25° C. for 72 h under an atmosphere of oxygen (balloon). The mixture was filtered through hyflo, the residue washed with $CH_2Cl_2$ and the combined solutions concentrated. The residue was purified on silica (gradient: cyclohexane/ethyl acetate) to afford 39.7 (375 mg, 48%). The material was further purified by SFC. UPLC retention time 1.28 min (Method A). $^1$H NMR (DMSO-$d_6$): δ=8.29 (1H, dd), 8.08-8.14 (3H, m), 7.52 (2H, d), 7.27-7.49 (1H, m), 4.58 (1H, m), 3.67 (3H, s), 3.33-3.55 (2H, m), 1.34 (9H, s). MS/ESI 493.3 [M+H]$^+$.

Step e) tert-Butyl (1-(2-(4-((5-chloro-3-fluoropyridin-2-yl)oxy)phenyl)-2H-tetrazol-5-yl)-3-hydroxypropan-2-yl) carbamate (39.8). At 0° C. LiBH4 (2N solution in THF, 0.651 mL, 1.302 mmol) was added dropwise to a solution of 39.7 (107 mg, 0.217 mmol) in THF (2 mL) and the mixture stirred for 2 h at 0° C. The mixture was neutralized with HCl (1 N aqueous solution), $CH_2Cl_2$ added, the organic layer separated, dried with $Na_2SO_4$ and the solvent removed. Chromatography on silica (gradient: cyclohexane/ethyl acetate) gave compound 39.8 (63 mg, 63%). UPLC retention time 1.13 min (Method A). $^1$H NMR (DMSO-$d_6$): δ=8.29 (1H, dd), 8.00-8.21 (3H, m), 7.37-7.61 (2H, m), 6.71 (1H, d br), 4.84 (1H, t br), 3.79-3.96 (1H, m), 3.33-3.51 (2H, m), 3.28 (1H, dd), 2.95 (1H, dd), 1.12-1.31 (m, 9H). MS/ESI 465.3 [M+H]$^+$.

Step f) 2 Amino-3-(2-(4-((5-chloro-3-fluoropyridin-2-yl)oxy)phenyl)-2H-tetrazol-5-yl)propan-1-ol (Example 39). To a solution of 39.8 (63 mg, 0.137 mmol) in $CH_2Cl_2$ (1.5 mL) was added HCl (4N solution in dioxane, 0.515 mL, 2.059 mmol) and the mixture stirred for 2 h at 25° C. The suspension was partially concentrated in a stream of argon. Filtration gave the hydrochloride of Example 39 as a colorless solid (50 mg, 92%). UPLC retention time 0.76 min (Method A). $^1$H NMR (DMSO-$d_6$): δ=8.30 (1H, dd), 8.12-8.23 (6H, m), 7.54 (2H, d), 5.47 (1H, t br), 3.65-3.78 (1H, m), 3.50-3.64 (2H, m), 3.25-3.33 (2H, m). MS/ESI 365.1 [M+H]$^+$.

Example 39 was found to be a racemic mixture of Example 39R (retention time: 9.98 min) and Example 39S (retention time: 11.48 min) (Chiralpak IA KL034, 5 μm, 250×4.6 mm; heptane/ehtyl acetate/MeOH/diethyl amine 40:30:30:0.05, 1 ml/min, 254 nm). (S) 2-Amino-3-(2-(4-((5-chloro-3-fluoropyridin-2-yl)oxy)phenyl)-2H-tetrazol-5-yl) propan-1-ol (Example 39S) was obtained from the racemate by chiral SFC (AD, 5 μm, 250×50 mm; mobile phase: 0.1% $NH_3$ x $H_2O$ in EtOH, 40%).

Example 40 (2S)-2-amino-3-(2-(4-((3-fluoro-5-(1-(tetrahydro-2H-pyran-2 yl)-1H-pyrazol-5-yl)pyridin-2yl)oxy)phenyl)-2H-tetrazol-5-/l)propan-1-01 (hydrochloride salt)

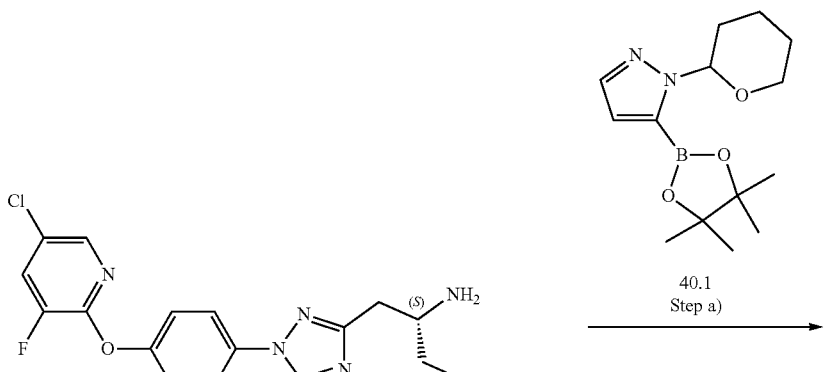

Example 39S

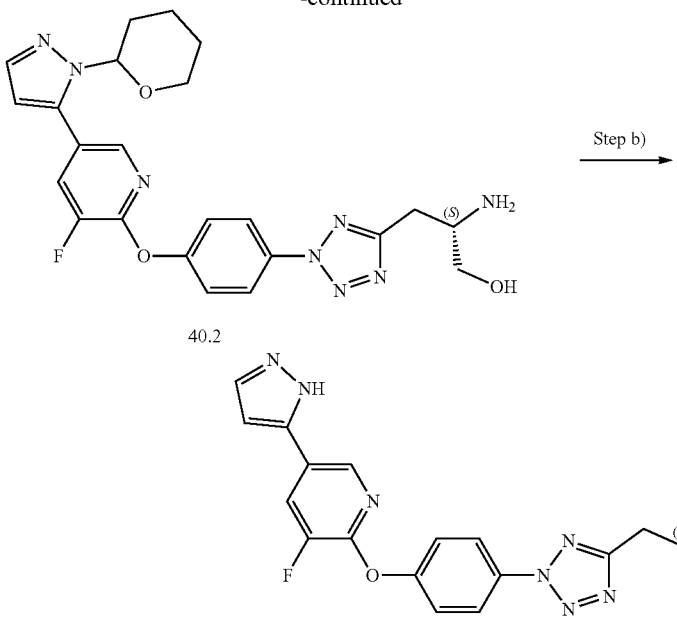

40.2

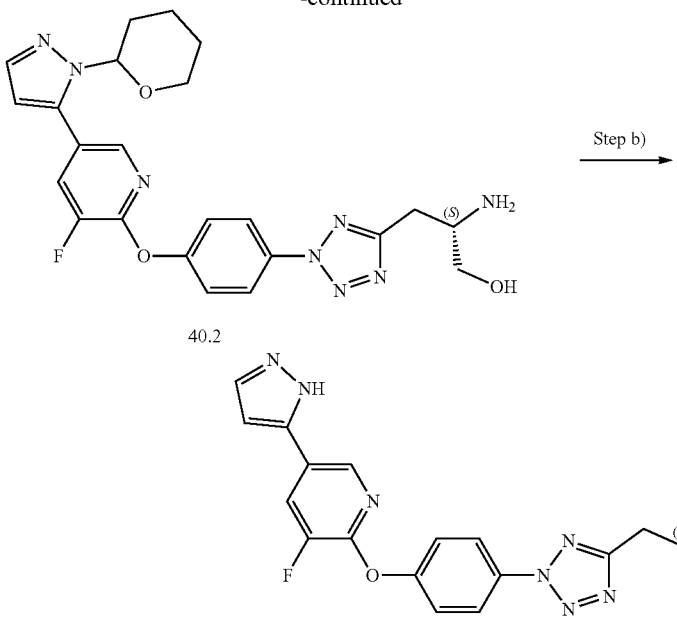

Example 40

Step a) (2S)-2-amino-3-(2-(4-((3-fluoro-5-(1-(tetrahydro-2H-pyran-2-yl)-1H-pyrazol-5-yl)pyridin-2-yl)oxy)phenyl)-2H-tetrazol-5-yl)propan-1-ol (Example 40). A suspension of Example 39S (950 mg, 2.60 mmol), 40.1 (1449 mg, 5.21 mmol), $K_3PO_4$ (1106 mg, 5.21 mmol) and $PdCl_2$(dtbpf) (136 mg, 0.208 mmol) in a mixture of dioxane (9.5 mL) and water (3.166 mL) was stirred under argon for 1.5 h at 90° C. Additional 40.1 and $PdCl_2$(dtbpf) were added and heating continued for 1 h. The mixture was diluted with water and extracted with $CH_2Cl_2$. The organic layer was dried with $Na_2SO_4$, filtered and concentrated. The residue was purified on silica (gradient: cyclohexane/ethyl acetate) to afford 40.2 (518 mg, 49%). The material was dissolved in DMF (20 mL), SiliaMetS DMT was added and this mixture stirred for 16 h at 50° C. The scavenger was filtered off, the residue washed with $CH_2Cl_2$/MeOH and concentrated to afford a solid, which was used in the next step. UPLC retention time 0.78 min (Method A). $^1$H NMR (DMSO-$d_6$): δ=8.10-8.20 (3H, m), 8.07 (1H, dd), 7.62 (1H, d), 7.56 (2H, d), 6.61 (1H, d), 5.31 (1H, dd), 4.73 (1H, s br), 3.95 (1H, d br), 3.50-3.66 (1H, m), 3.37 (2H, m), 3.08-3.35 (2H) 2.83 (1H, dd), 2.25-2.45 (1H, m), 1.95-2.05 (1H, m), 1.83-1.93 (1H, m), 1.50-1.72 (5H, m). MS/ESI 481.3 [M+H]$^+$.

Step b) (S)-2-amino-(2-(4-((3-fluoro-5-(1H-pyrazol-5-yl)pyridin-2-yl)oxy)phenyl)-2H-tetrazol-5-yl)propan-1-ol (Example 40). To a solution of 40.2 (510 mg, 1.061 mmol) in THF (7 mL) was added HCl (2 mL 2N) and the mixture stirred at 25° C. for 1.5 h. The mixture was concentrated and the residue purified on silica (gradient: $CH_2Cl_2$/MeOH) to afford the hydrochloride of Example 40 (289 mg, 61%). UPLC retention time 0.65 min (Method A). $^1$H NMR (DMSO-$d_6$): δ=8.47 (1H, d), 8.23-8.33 (4H, m), 8.07-8.23 (2H, m), 7.82 (1H, d), 7.47-7.59 (2H, m), 6.85 (1H, d), 5.82 (1H, m), 3.59-3.76 (3H, m), 3.26-3.43 (2H, m). MS/ESI 397.2 [M+H]$^+$.

Example 41: Free base type-1 Form C of (S)-2-amino-3-(3-(4-((3-fluoro-i-(1H-pyrazol-5-yl)pyridin-2yl)oxy)phenyl)-1H-pyrazol-1 yl)propan-1-ol/(S)-2-amino-3-(3-(4 ((3 fluoro-5-(1H-pyrazol-3-yl)pyridin-2-yl)oxy)phenyl)-1H-pyrazol-1 yl)propan-1-01

Step-1: Synthesis of 2-(4-bromophenoxy)-5-chloro-3fluoropyridine

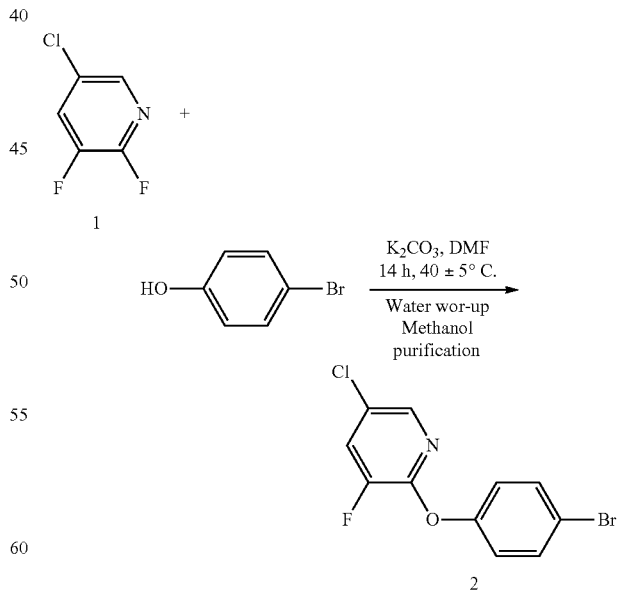

Synthetic Procedure:

To a cleaned round bottom (RB) flask DMF, potassium carbonate (69.32 g, 0.5016 moles, 1.50 eq.), 2,3-Difluoro-5-chloropyridine (50 g, 0.3344 moles, 1.0 eq.), 4-Bromophenol (57.85 g, 0.3344 moles, 1.0 eq.) were charged and mixture was stirred at 40±5'C temperature. Cooled the reaction mass and slowly charged Purified water. Filtered the product and washed with purified water followed by Dry the material to give 2-(4-bromophenoxy)-5-chloro-3-fluoro-pyridine.

$^1$H NMR (DMSO-d6, 400 MHz): δ=7.20 (dd, J=5.2, 3.2Hz, 2H), 7.62 (dd, J=5.6, 3.2 Hz, 2H), 8.06 (d, J=2.4 Hz 1H), 8.25 (dd, J=10, 2.4 HZ 1H), HPLC purity: >98% area, RT:21.73 minute

| Details | Chemical purity | |
|---|---|---|
| System | HPLC | |
| Mobile phase | A: 0.1% v/v Perchloric acid in water | |
| | B: Methanol | |

| | Time (min) | % of Mobile phase A | % of Mobile phase B |
|---|---|---|---|
| Gradient | 0 | 80 | 20 |
| | 5 | 50 | 50 |
| | 10 | 40 | 60 |
| | 15 | 20 | 80 |
| | 25 | 20 | 80 |
| | 30 | 10 | 90 |
| | 40 | 10 | 90 |
| | 40.1 | 80 | 20 |
| | 45 | 80 | 20 |

| Column | Eclipse XDB C18(150 × 4.6) mm, 3.5 μm |
|---|---|
| Retention time | 2,3-Difluoro-5-Chloropyridine: 16.8 min |
| | 4-Bromophenol: 19.1 min |
| | Rt: 21.7 min |

Step-2 and Step-3: Synthesis of 2-(4-(1H-pyrazol-3-yl)phenoxy)-5-chloro-3-fluoropyridine Reaction scheme

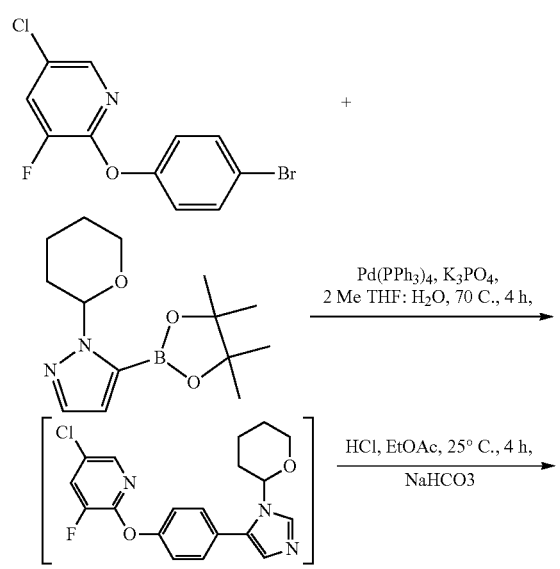

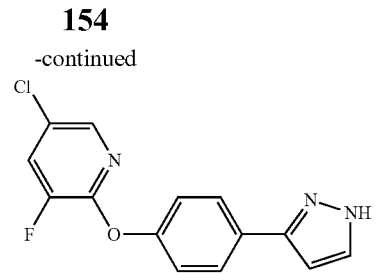

Experimental Procedure for A1:

To a round bottom flask, 2-Methyl tetrahydrofuran-com, purified water, 1H-Pyrazole, 1-(tetrahydro-2H-pyran-2-yl)-5-(4,4,5,5-tetramethyl-1,3,2-dioxaborolan-2-yl)-(119.52 g, 0.4 mole, 1.30 eq), Potassium phosphate tribasic (210.50 g, 1 moles, 3 eq), A1-2(100 g, 0.3 moles, 1.0 eq) were charged. Purged the reaction mass under nitrogen. Charged triphenylphosphine palladium (0) (19.09 g, 0.016 moles, 5 mole %) under purging. Heated the mass temperature to 70±5'C for 3 h. Cooled the mass temperature and charge dPurified water. Extracted the product in Ethylacetate. Back extracted the aqueous layer with Ethyl Acetate. To the combined organic layer washed with Purified water followed by brine solution. Organic layer dried with Sodium Sulfate-Com and concentrate the organic layer below 45° C. under vacuum until approximately −5.0 w/v. Charged the Hydrochloric acid 4 M in ethyl acetate reaction mass and stir for 3 h at 25±5° C. Filter the product and wash with ethyl acetate. Charged purified water and wet material into RB flask ethyl acetate. Adjust the pH to 7-8 using sat. sodium bicarbonate solution. Separated the organic layer and wash the organic layer with brine solution, followed by dried over sodium sulfate. Concentrated the organic layer and crystallized with n-Heptane to give 2 (4-(1H-pyrazol-3-yl)phenoxy)-5-chloro-3-fluoropyridine.

$^1$H NMR (DMSO-d6, 400 MHz): δ=6.72 (dd, J=5.2, 3.2 Hz, 1H), 7.22 (m, 2H), 7.79 (m, 1H), 7.86 (m, 2H), 8.07 (d, J=2 Hz, 1H), 8.23 (dd, J=4.8 Hz, 2.4 Hz, 1H), 13.08 (bs, 1H), HPLC purity: >97 & area, HPLC RT: 17.27 minute, MS/ESI+ 290.20. HPLC RT: 17.27 minute

| Parameters | Chemical purity | |
|---|---|---|
| System | HPLC | |
| Mobile phase | Mobile Phase A: 10 mM Ammonium bicarbonate in water | |
| | Mobile Phase B: Methanol | |

| | Time (min) | % of Mobile phase A | % of Mobile phase B |
|---|---|---|---|
| Gradient | 0 | 80 | 20 |
| | 5 | 50 | 50 |
| | 10 | 40 | 60 |
| | 15 | 20 | 80 |
| | 25 | 20 | 80 |
| | 30 | 10 | 90 |
| | 40 | 10 | 90 |
| | 40.1 | 80 | 20 |
| | 45 | 80 | 20 |

| Column | Eclipse XDB C18(150 × 4.6) mm, 3.5 μm |
|---|---|

Step-4: Synthesis of tert-butyl (S)-(1-((tert-butyldimethylsllyl)oxy)-3-(3-(4-((5-chloro-3-fluoropyridin-2-yl)oxy)phenyl)-1H-pyrazol-1-yl)propan-2-yl)carbamate (A3)

Reaction scheme

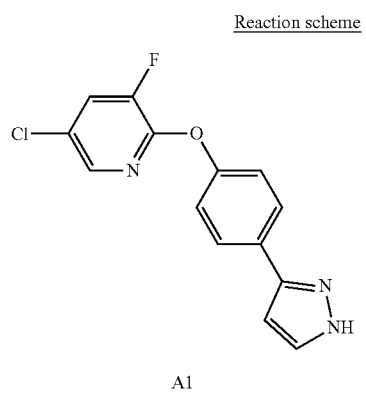

A1

+

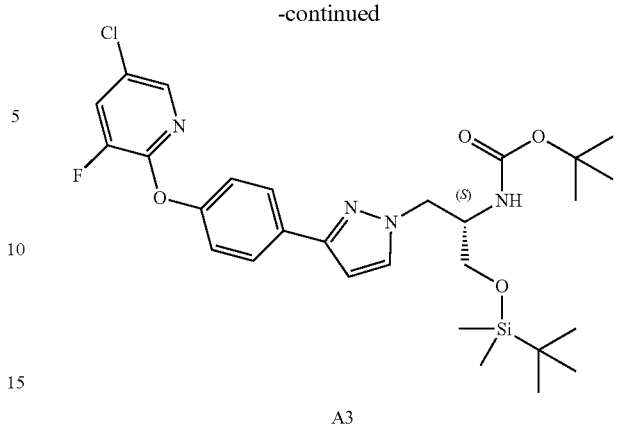

A3

Experimental Procedure:

To a cleaned RB flask DMF, A1 (50 g, 0.1725 moles, 1.0 eq.) and cesium carbonate (112.4 g, 0.345 moles, and 2.0 eq.) were charged. A separate vessel prepared A2 (69.80 g, 0.1898 moles, and 1.10 eq.) in DMF. Slowly add the A2 solution into the reaction mass containing A1, and maintained the reaction mass for 4 hours. Cooled the reaction mass and slow add purified water. Separated the organic layer and re-extracted the aqueous layer with ethyl acetate. To that combined organic layer, charged purified water and adjust the pH using a 1% citric acid solution, followed by washing the organic layer with sat. Sodium bicarbonate solution, purified water and brine solution. Dry the organic layer with sodium sulphate and concentrate the organic layer below 50° C. under vacuum. Purify the crude product with column chromatography using 0-40% ethyl acetate in n-heptane. Collect pure fraction and concentrate under vacuum to get the tert-butyl (S)-(1-((tert-butyldimethylsilyl)oxy)-3-(3-(4-((5-chloro-3-fluoropyridin-2-yl)oxy)phenyl)-1H-pyrazol-1-yl)propan-2-yl)carbamate as viscous syrup.

$^1$H NMR (DMSO-d6, 400 MHz): δ=0.046 (S, 6H), 0.0850 (s, 9H), 1.1372 (s, 9H), 3.54 (m, 2H), 3.943-3.909 (m, 1H), 4.38 (m, 1H), 4.28 (m, 1H), 6.68 (d, J=2.4 Hz, 1H), 6.82 (d, J=8.4 Hz, 1H), 7.22 (d, J=8 Hz, 2H), 7.68 (d, J=2 Hz, 1H), 7.82 (d, J=8.8, 2H), 8.06 (d, J=2 Hz, 1H), 8.22 (dd, J=10 Hz, 2.4 Hz, 1H) and having additional reagents and solvents signal observed, HPLC purity: >95% area

Chromatographic Conditions:

| Parameter | Chemical purity | | | Chiral purity |
|---|---|---|---|---|
| System | HPLC | | | HPLC |
| Mobile phase | A: Water B: Acetonitrile and Methanol in the ratio of 70:30 | | | n-Hexane and IPA in the ratio of 90:10 |
| | Time (min) | % of Mobile phase A | % of Mobile phase B | |
| Gradient | 0 | 80 | 20 | Isocratic, Flow rate: 1.0 mL/min |
| | 5 | 50 | 50 | |
| | 10 | 40 | 60 | |
| | 15 | 20 | 80 | |
| | 20 | 20 | 80 | |
| | 30 | 10 | 90 | |
| | 50 | 10 | 90 | |
| | 50.1 | 80 | 20 | |
| | 55 | 80 | 20 | |

-continued

| Column | ACE 3 C18-PFP (150 × 4.6) mm, 3.0 μm | CHIRALPAK AD-H (250 * 4.6) mm * 5.0 μm |
|---|---|---|
| Retention time | A1: 14.03 min<br>A3 Regio isomer: 25.05 min<br>A3: 26.57 min | A3 (S-enantiomer): 6.226 min<br>A3 (R-enantiomer): 7.312 min |

Step-5: Synthesis of tert-butyl ((2S)-1-((tert-butyldimethylsilyl)oxy)₃-(3-(4-((3-fluoro-5-(1-(tetrahydro-2H-pyran-2-yl)-1H-pyrazol-5-yl)pyridin-2-yl)oxy)phenyl)-1H-pyrazol-1-yl)propan-2-yl)carbamate (AS)

Reaction scheme

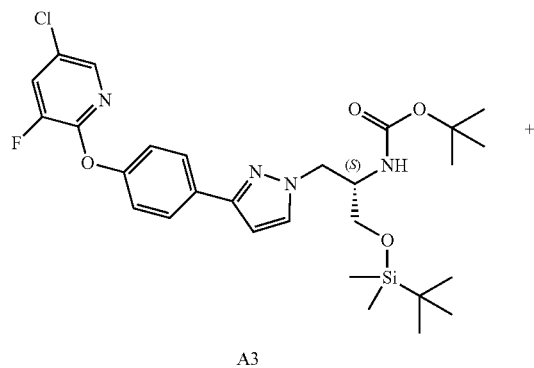

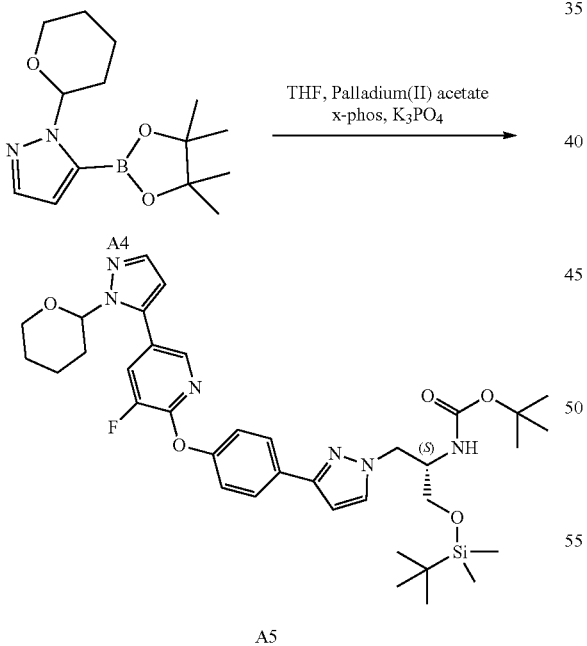

Experimental Procedure:

To a RB flask, THF, A3 (90 g, 0.1559 moles, 1.0 eq), K₃PO₄ (99.26 g, 0.4676 moles, 3.0 eq), XPHOS (4.45 g, 0.009 moles, 0.06 eq) and followed by purified water were charged. Purged the reaction mass with nitrogen. In-parallel, prepared the solution A4 in THF. Charged Pd(OAc)z (2.09 g, 0.009 moles, 0.06 eq) and heated the reaction mass to 50±5° C. Slowly added the A4 solution at 50±5° C. After completion of addition, maintained the reaction mass for 2-3 hrs at 50+5° C. Cooled the reaction mass and slowly added purified water) followed by ethyl acetate. Filter the reaction mass through celite bed and wash the celite bed with ethyl acetate. Separated the layers and back extract the aqueous layer with ethyl acetate. Wash the combined organic layer with 10% brine solution, dry over sodium sulfate, and concentrate the organic layer under vacuum. Purified the crude product by column chromatography using silica gel, EtOAc (10%), and n-Heptane(90%) as an eluent.

$^1$H NMR (DMSO-d6, 400 MHz): δ=0.04 (s, 6H), 0.09 (s, 9H), 1.134 (s, 9H), 1.53 (m, 4H), 1.87 (m. 4H), 2.51 (m, 1H), 3.56 (m, 4H), 3.94 (m, 3H), 4.07 (m, 2H), 4.25 (m, 1H), 5.29 (m, 1H), 6.59 (d, J=2 Hz, 1H), 6.70 (d, J=2 Hz, 1H), 6.83 (d, J=8.8 Hz, 1H). 7.27 (m, 2H), 7.61 (d, J=1.6 Hz, 1H), 7.69 (d, J=2.4 Hz, 1H), 7.85 (m, 2H), 8.02 (dd, J=11.2 Hz, 2.0 Hz, 1H), 8.10 (d, J=2 Hz, 1H), HPLC purity: >97% area Note: NMR signals having additional reagents and solvents signal observed.

| Parameters | Chemical purity | |
|---|---|---|
| System | HPLC | |
| Mobile phase | A: Water | |
| | B: Acetonitrile and Methanol in the ratio of 70:30 | |

| | Time (min) | % of Mobile phase A | % of Mobile phase B |
|---|---|---|---|
| Gradient | 0 | 80 | 20 |
| | 5 | 50 | 50 |
| | 10 | 40 | 60 |
| | 15 | 20 | 80 |
| | 20 | 20 | 80 |
| | 30 | 10 | 90 |
| | 50 | 10 | 90 |
| | 50.1 | 80 | 20 |
| | 55 | 80 | 20 |

| Column | ACE 3 C18-PFP (150 × 4.6) mm, 3.0 μm |
|---|---|
| Retention time | A1: 14.03 min<br>A5 Regio isomer: 24.13 min<br>A3 Regio isomer: 25.05 min<br>A5: 25.68 min<br>A3: 26.57 min |

Step-6 Synthesis of (S)-2-amino-3-(3-(4-((3-fluoro-5-(1H-pyrazol-5-yl)pyridin-2-yl)oxy)phenyl)-1H-pyrazol-1-yl)propan-1-ol (A6)

Reaction scheme

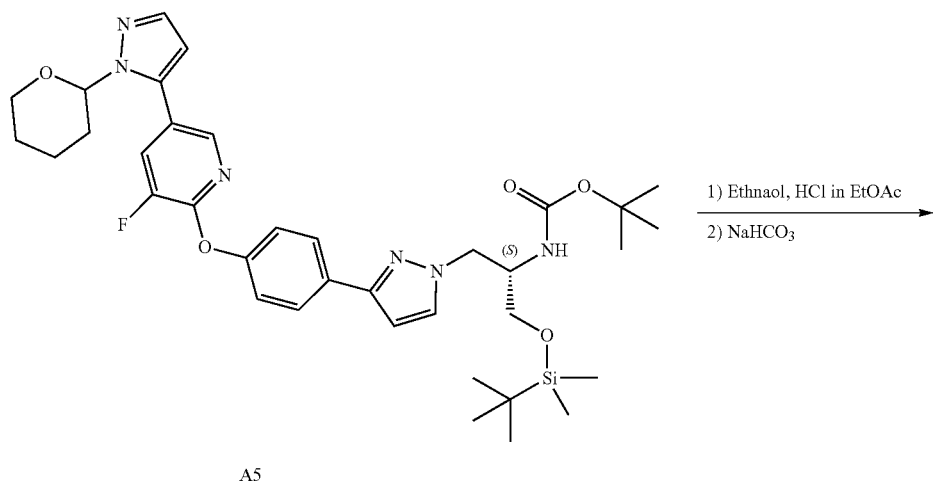

A5

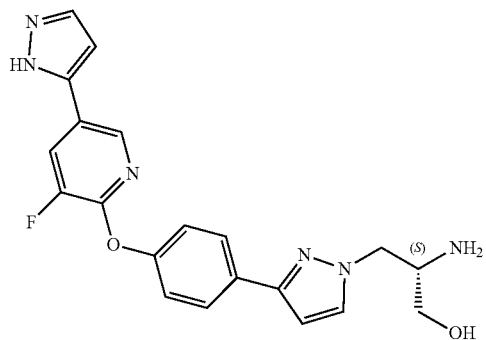

A6

Experimental Procedure:

To a cleaned RB flask, A5 and absolute alcohol was charged. Cool to 0-5° C. and slowly add 4M HCl in EtOAc. Increased the reaction mass temperature to 25 t 5° C. for 12 hrs. Concentrated the reaction mass under vacuum below 50° C. up to 1-2 vol. Charged absolute alcohol and increased the reaction mass temperature to 50+5° C. and maintained for 1 hr. Cooled the reaction mass and filtered the mass. Washed with absolute alcohol; basify the material with sat. NaHCO₃ and filtered the product and washed. Slur the product in purified water at 60±5° C. for 1 hr. Cool the mass and filter the product Dried the material into the VTD for 8 hrs at 55+5° C. under vacuum. Dissolved the material in THF and treated with silia bond thiol to remove the residual metal. Concentrated the THF and dissolved the product in methanol and filtered to the (S)-2-amino-3-(3-(4((3-fluoro-5-(1H-pyrazol-5-yl)pyridin-2-yl)oxy)phenyl)-1H-pyrazol-1-yl)propan-1-ol (A6).

¹H NMR (DMSO-d6, 400 MHz): δ=1.55 (bs, 2H), 3.10 (m, 1H), 3.28 (m, 2H), 3.96 (m, 1H),

| | Chemical purity | | |
|---|---|---|---|
| System | UPLC | | |
| Mobile phase | A: Mobile Phase-A (0.1% Trifluroacetic acid in water) B: Acetonitrile:THF:Mobile phase A (850:100:50) | | |
| | Time (min) | % of Mobile phase A | % of Mobile phase B |
| Gradient | 0 | 95 | 5 |
| | 1 | 95 | 5 |
| | 17 | 70 | 30 |
| | 27 | 50 | 50 |
| | 29 | 10 | 90 |
| | 39 | 10 | 90 |
| | 39.1 | 95 | 5 |
| | 45 | 95 | 5 |
| Column | ACQUITY UPLC BEH Shield RP18 C18 (100 × 2.1) mm, 1.7 μm | | |
| Retention time | A6: 16.810 min Regioisomer A6: 17.103 min A5: 31.890 min | | |

4.18 (m, 1H), 4.71 (t, 1H), 6.69 (d, J=2 Hz, 1H), 6.82 (d, J=2.4 Hz, 2H), 7.22 (d, J=8.8 Hz, 1H), 7.76 (d, J=2 Hz, 2H), 7.83 (d, J=8.4 Hz, 2H), 8.22 (dd, J=11.2 Hz, 1.6 Hz, 1H), 8.42 (d, J=1.6 Hz, 1H) HPLC purity: >99% area, HPLC RT: 10.03 minute, MS/ESI+ 395.10

The isolated material was characterized by various methods to determine its physicochemical characteristics. The isolated material was a highly crystalline powder consisting of acicular and plate like particles. The isolated material was analyzed by XRPD, DSC and TGA (FIGS. 1A, 1B and 1C respectively). The material was of high purity and showed dehydration endotherm at about 45° C. with an enthalpy of 19 J/g followed by a small melting endotherm and an immediate exothermic recrystallization event at about 110° C. FinaNy a melting point at about 146° C. with an enthalpy of 121 J/g can be seen. The loss on drying was determined to 1.4% by TGA that was corroborated by Kart Fischer titration.

TABLE 1

XRPD peaks Example 41 (free base Type 1 Form C)

| Angle | d Value | Net Intensity | Rel. Intensity |
|---|---|---|---|
| 11.4 | 7.787 | 12564 | 100% |
| 15.2 | 5.824 | 11252 | 90% |
| 15.9 | 5.567 | 1379 | 11% |
| 16.2 | 5.483 | 786 | 6% |
| 16.9 | 5.257 | 916 | 7% |
| 17.4 | 5.079 | 441 | 4% |
| 18.3 | 4.846 | 1135 | 9% |
| 21.1 | 4.210 | 744 | 6% |
| 21.6 | 4.103 | 779 | 6% |
| 22.8 | 3.897 | 3981 | 32% |
| 24.6 | 3.616 | 808 | 6% |
| 27.8 | 3.211 | 355 | 3% |
| 28.6 | 3.118 | 3532 | 28% |
| 37.0 | 2.425 | 476 | 4% |
| 40.7 | 2.215 | 325 | 3% |

Example 42: Free base type-2 Form D of (S)-2-amino-3-(3-(4-((3-fluoro-i-(1H-pyrazol-5-yl)pyridin-2-yl)oxy)phenyl)-1H-pyrazol-1-yl)propan-1-ol/(S)-2-amino-3-(3-(4-((3-fluoro-5-(1H-pyrazol-3-yl)pyridin-2-yl)oxy)phenyl)-1H-pyrazol-1-yl)propan-1-ol In a vial, 300 mg of example 41 were added to 5 mL of ethanol. The sample was stirred at 50'C with 500 rpm. The suspension was vortexed periodically to disrupt lumps that formed with time. After 4 h the suspension was stirred at room temperature overnight with 500 rpm. The solid was recovered by centrifugal filtration and vacuum dried at 50° C. The isolated material was analyzed by XRPD, DSC and TGA (FIGS. 2A, 2B and 2C respectively).

The crystalline form free base Type 2 (Form D) melted at about 146° C. and showed a glass transition at 52° C. after reheating a melted sample The crystalline form free base Type 2 (Form D) gave a loss on drying of about 0.15% by TGA The crystalline form free base Type 2 (Form D) was shown to be hygroscopic by DVS, reversibly absorbing 3% moisture above 70% RH transforming into a hydrated form.

TABLE 2

XRPD peak-example 42

| Angle | d Value | Net Intensity | Rel. Intensity |
|---|---|---|---|
| 11.3 | 7.809 | 5736 | 55% |
| 15.2 | 5.836 | 10359 | 100% |
| 17.8 | 4.977 | 634 | 6% |
| 18.3 | 4.857 | 2919 | 28% |
| 19.2 | 4.627 | 1106 | 11% |
| 20.3 | 4.373 | 1194 | 12% |
| 21.6 | 4.109 | 1329 | 13% |
| 22.8 | 3.902 | 3875 | 37% |
| 23.6 | 3.764 | 555 | 5% |
| 24.2 | 3.668 | 1351 | 13% |
| 26.3 | 3.391 | 568 | 5% |
| 28.6 | 3.122 | 1512 | 15% |
| 29.3 | 3.042 | 789 | 8% |

TABLE 3

Characterization of Example 42

| Parameter | Method | Result |
|---|---|---|
| Melting onset (° C.) | DSC, 10 K/min | 146.7 |
| Crystallinity | XRPD, 2-40° (2 theta) | Highly crystalline |
| Loss on drying (% @ ° C.) | TGA, 10 K/min | 0.15 @ 140 |
| Water content (%) | Karl Fischer titration | Not performed |
| Hygroscopicity (% @ % RH) | DVS | 2.97 @ 95 |
| Morphology | SEM | Plate-like particles |

Example 43: hydrochloric acid salt (Form E) of (S)-2-amino-3-(3-(4-((3-fluoro-5-(1H-pyrazol-5-yl)pyridin-2-yl)oxy)phenyl)-1H-pyrazol-1-yl)propan-1-ol/(S)-2-amino-3-(3-4-((3-fluoro-5-(1H-pyrazol-3-yl)pyridin-2-yl)oxy)phenyl)-1H-pyrazol-1-yl)propan-1-ol In a vial, 300 mg of example 41 were added to a mixture of 70 μL of 12 N hydrochloric acid and 3 mL ethanol. The sample was stirred at 50° C. with 500 rpm. An additional 2 mL of ethanol was added to dilute the suspension and the mixture was stirred for 3 h. Afterwards, the suspension was stirred at room temperature overnight at 300 rpm. Solids were isolated by centrifugal filtration and vacuum dried at 50'C overnight. The isolated material was analyzed by XRPD, DSC and TGA (FIGS. 3A, 3B and 3C respectively).

The hydrochloride salt (Form E) melted at about 236'C with corresponding glass transitions of 91° C.

The hydrochloride salt (Form E) showed a loss on drying of about 0.5% by TGA.

The hydrochloride salt (Form E) was slightly hygroscopic absorbing only 0.6% of water vapor at 95% RH.

TABLE 4

XRPD peaks: example 43

| Angle | d Value | Net Intensity | Rel. Intensity |
|---|---|---|---|
| 15.8 | 5.601 | 1711 | 43% |
| 16.4 | 5.385 | 2495 | 63% |
| 17.5 | 5.056 | 455 | 12% |

TABLE 4-continued

XRPD peaks: example 43

| Angle | d Value | Net Intensity | Rel. Intensity |
|---|---|---|---|
| 18.3 | 4.836 | 884 | 22% |
| 19.3 | 4.592 | 817 | 21% |
| 21.0 | 4.236 | 1911 | 48% |
| 22.0 | 4.039 | 3955 | 100% |
| 22.4 | 3.959 | 3001 | 76% |
| 23.8 | 3.740 | 712 | 18% |
| 24.9 | 3.576 | 489 | 12% |
| 25.2 | 3.532 | 437 | 11% |
| 26.2 | 3.395 | 756 | 19% |
| 27.6 | 3.231 | 1364 | 34% |
| 29.6 | 3.019 | 400 | 10% |
| 33.6 | 2.668 | 338 | 9% |

Example 44: (S)-2-amino-3-(3-(4-((3-fluoro-5-(1H-pyrazol-3-yl)pyridin-2-yl)oxy)phenyl)-1H-pyrazol-1-yl)propan-1-ol hippurate salt (Form B)

300 mg of example 41, 150 mg hippuric acid and 3 mL ethanol were added into a vial. The sample was stirred at 50° C. with 500 rpm. An additional 2 mL of ethanol was added to dilute the suspension and the mixture was briefly sonicated. After 3 h, the suspension was stirred at room temperature overnight at 300 rpm. Solids were isolated by centrifugal filtration for characterization. The isolated material was characterized by XRPD, DSC and TGA (FIGS. 4A, 4B and 4C respectively). The hippuric acid salt (Form B) is a highly crystalline form with a melting point of approximately 180° C. and an enthalpy of fusion of 134 J/g. It showed about 0.3% weight loss by TGA at 170 T. Modification B is only slightly hygroscopic, absorbing about 0.3% of moisture at 95% RH.

Alternative Synthesis to (S)-2-amino-3-(3-(4-((3-fluoro-5-(1H-pyrazol-5-yl)pyridin-2-yl)oxy)phenyl)-1H-pyrazol-1-yl)propan-1-ol-Hippurate salt) (A7-Form B)

Reaction scheme

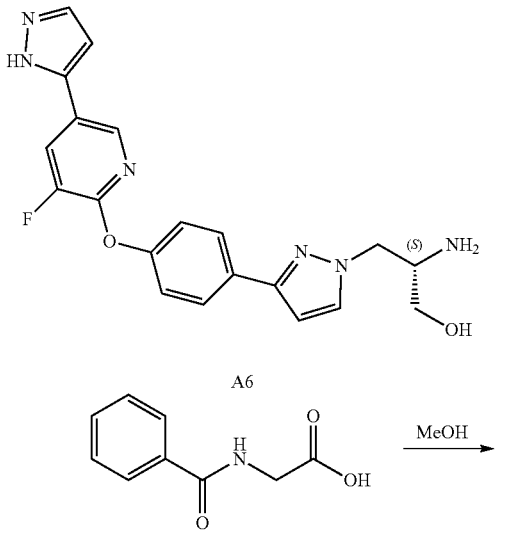

A6

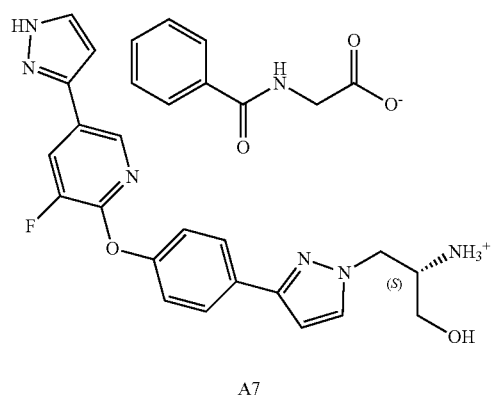

A7

Experimental Procedure:

To cleaned RB flask, methanol and A6 (Example 41) (80 g, 0.202 moles, 1.0 eq) were charged Heat the reaction mass to 55±5° C. to get dear solution. Slowly added pre-dissolved hippuric acid in methanol (40 g, 0.2244 moles, 1.1 eq). Added the 0.08 wt % of A7 seed material at 55±5° C. and maintain for 6 hrs. Concentrate the mass up to stirrable volume and filter. Filtered the product and wash the product with methanol to get the (S)-2-amino-3-(3-(4-((3-fluoro-5-(1H-pyrazol-5-yl)pyridin-2-yl)oxy)phenyl-1H-pyrazol-1-yl)propan-1-ol.Hippurate salt) (A7)

$^1$H NMR (DMSO-d6, 400 MHz): δ=3.31 (m, 4H), 3.84 (d, J=6 Hz, 2H), 4.06 (m, 1H), 4.25 (m, 1H), 6.72 (d, J=2.4 Hz, 1H), 6.83 (d, J=2.4 Hz, 1H), 7.24 (m, 2H), 7.51 (m, 3H), 7.83 (m, 6H), 8.23 (dd, J=11.2 Hz, 1.6 Hz, 1H), 8.43 (d, J=2 Hz, 1H), 8.61 (t, 1H), HPLC chemical purity: >99%, chiral purity: >99% area.

| Parameters | Chemical purity | Chiral purity |
|---|---|---|
| System | UPLC | HPLC |
| Mobile phase | A: 0.1% Trifluroacetic acid in water B: Acetonitrile:THF:Mobile phase A(850:100:50) | 0.05% DEA in n-Hexane: Ethanol and Methanol in the ratio of 30:50:20 |
| Gradient | Time (min) | % of Mobile phase A | % of Mobile phase B |
|  | 0 | 95 | 5 |
|  | 1 | 95 | 5 |
|  | 17 | 70 | 30 |
|  | 27 | 50 | 50 |
|  | 29 | 10 | 90 |
|  | 39 | 10 | 90 |
|  | 39.1 | 95 | 5 |
|  | 45 | 95 | 5 |
| Column | ACQUITY UPLC BEH Shield RP18 C18 (100 × 2.1) mm, 1.7 μm | CHIRALPAK IA3 (150 × 4.6) mm ×3.0 μm |
| Retention time | Hippuric acid: 3.903 min A7 Regioisomer: 16.810 min A7: 17.103 min A5: 31.890 | A7 S-isomer: 6.181 min A7 R-isomer: 9.488 min |

TABLE 5

XRPD peak: Ex 44:
Hippurate, Mod B)

| Angle | d Value | Net Intensity | Rel. Intensity |
|---|---|---|---|
| 6.8 | 12.986 | 415 | 3% |
| 9.3 | 9.475 | 1010 | 8% |
| 11.1 | 7.983 | 1089 | 8% |
| 13.0 | 6.819 | 1505 | 11% |
| 15.0 | 5.907 | 713 | 5% |
| 17.1 | 5.196 | 4803 | 36% |
| 18.0 | 4.919 | 13263 | 100% |
| 18.8 | 4.728 | 1950 | 15% |
| 23.5 | 3.779 | 1844 | 14% |
| 24.2 | 3.677 | 741 | 6% |
| 25.7 | 3.462 | 528 | 4% |
| 28.0 | 3.189 | 726 | 5% |

TABLE 6

Basic characterization of Example 44 modification B

| Parameter | Method | Results |
|---|---|---|
| Purity | HPLC | 99.65% |
| DSC melting onset | DSC, 10 K/min | 180.3° C. |
| X-ray diffraction | 2-40° (2 theta) | High crystallinity (Modification B) |
| Thermogravimetry | TGA, 10 K/min | 0.34% @ 170° C. |
| Water content | Karl Fischer titration | 0.33% |
| Hygroscopicity | DVS | 0.32% @ 95% RH |
| Morphology | SEM | acicular |

Example 45: Hippuric acid salt Form A of (S)-2-amino-3-(3-(4-((3-fluoro-5-(1H-pyrazol-5-yl)pyridin-2-yl)oxy)phenyl)-1H-pyrazol-1.yl)propan-1-ol/(S)-2-amino-3-(3-(4-((3-fluoro-5-(1H-pyrazol-3-yl)pyridin-2-yl)oxy)phenyl)-1H-pyrazol-1 yl)propan-1-ol The hippurate salt (Form A) was obtained through reverse antisolvent precipitation from tetrahydrofuran/water (95:5) into ethyl acetate. The isolated material was characterized by XRPD, DSC and TGA (FIGS. 5A, 5B and 5C respectively). It showed a melting point of approximately 172° C. with an enthalpy of fusion of about 106 J/g. Modification A was also only slightly hygroscopic absorbing about 0.5% of moisture at 95% RH. The hippurate salt (Form A) melted at about 172° C., respectively with corresponding glass transitions of 77° C. The hipurrate salt (Form A) showed a loss on drying of 0.2% by TGA. The hippurate salt (Form A) was slightly hygroscopic absorbing only 0.5% of water vapor at 95% RH.

TABLE 7

XRPD peak of example 45
(Hippurate, Mod A)

| Angle | d Value | Net Intensity | Rel. Intensity |
|---|---|---|---|
| 8.1 | 10.854 | 728 | 21% |
| 11.2 | 7.905 | 424 | 12% |
| 12.2 | 7.238 | 396 | 12% |
| 16.2 | 5.459 | 3242 | 95% |
| 16.3 | 5.431 | 3403 | 100% |
| 17.8 | 4.969 | 244 | 7% |
| 18.2 | 4.874 | 210 | 6% |
| 18.4 | 4.806 | 326 | 10% |
| 18.8 | 4.728 | 429 | 13% |
| 19.7 | 4.511 | 483 | 14% |
| 20.4 | 4.341 | 3323 | 98% |
| 21.0 | 4.224 | 1154 | 34% |
| 21.6 | 4.115 | 208 | 6% |
| 22.3 | 3.983 | 428 | 13% |
| 22.6 | 3.934 | 459 | 13% |
| 23.1 | 3.855 | 827 | 24% |
| 25.4 | 3.501 | 353 | 10% |
| 26.5 | 3.362 | 311 | 9% |

Example 46: L-tartaric acid salt (Form F) of (S)-2-amino-3-(3-(4-((3fluoro-5-(1H-pyrazol-5-yl)pyridin-2-yl)oxy)phenyl)-1H-pyrazol-1-yl)propan-1-ol/(S)-2-amino-3-(3-(4-((3-fluoro-5-(1H-pyrazol-3-yl)pyridin-2-yl)oxy)phenyl)-1H-pyrazol-1-yl)propan-1-ol (2:1 ratio tartric acid:compound)

300 mg of example 41, 57 mg L-tartaric acid and 5 mL of ethanol were added into a vial. The mixture was stirred at 50° C. with 500 rpm for 4 h with periodic vortexing to disrupt lumps that formed with time. Afterwards, the suspension was stirred at room temperature overnight at 500 rpm. Solids were isolated by centrifugal filtration and vacuum dried at 50° C. The isolated material was characterized by XRPD, DSC and TGA (FIGS. 6A, 6B and 6C respectively). The (2:1) L-tartrate melted at 215° C. with decomposition.

TABLE 8

XRPD peaks example 46 (Tartrate)

| Angle | d Value | Net Intensity | Rel. Intensity |
|---|---|---|---|
| 5.3 | 16.745 | 573 | 46% |
| 12.4 | 7.151 | 119 | 10% |
| 15.9 | 5.556 | 1080 | 87% |
| 16.8 | 5.266 | 842 | 68% |
| 17.2 | 5.141 | 238 | 19% |
| 17.7 | 5.004 | 798 | 64% |
| 18.0 | 4.927 | 318 | 26% |
| 21.0 | 4.221 | 1243 | 100% |
| 21.3 | 4.175 | 870 | 70% |
| 22.3 | 3.989 | 841 | 68% |
| 23.7 | 3.752 | 543 | 44% |
| 26.8 | 3.324 | 244 | 20% |

Summary of Method Used for Crystalline Form Characterization:
Powder X-Ray Diffraction X-ray powder diffraction (XRPD) patterns were obtained using a Bruker D8 Advance in reflection geometry. Powders were analyzed using a zero background Si-wafer sample holder. The radiation was Cu Kα (I=1.5406 Å). Patterns were measured between 3° and 45° 2 theta DSC: Differential scanning calorimetry was conducted for each crystalline form using a TA Instruments (Q2000). For each analysis, 0.5-2 mg of sample was placed in an aluminum pan (TI20608). The heating rate was 10° C. per minute in the temperature range between 30 and 300'C. Temperatures are reported in degrees Celsius (° C.) and enthalpies are reported in Joules per gram (J/g). Plots are showing endothermic peaks as down. The endothermic melt peak (melting point) was evaluated for extrapolated onset temperature. The accuracy of the measured sample temperature with this method is within about ±1° C., and the heat of fusion can be measured within a relative error of about ±5%.

Thermogravimetric Analysis (TGA):

TGA curves were obtained using a TA-instrument Q5000. 0.5-2 mg of sample was placed into an open aluminum pan. The TGA curve was measured at 10° C./min between 30-300° C. The LoD (Loss of drying) was calculated between 30° C. and 100° C. or 150° C. The weight loss is plotted against the measured sample temperature. Temperatures are reported in degrees Celsius (° C.) and weight loss in %.

TABLE 9

Summary of Morphic properties of forms D, B, E and F

| Parameter | Physical Form | | | |
|---|---|---|---|---|
| | Ex 42 | Ex 43 | Ex 44 | Ex 46 |
| Identity by XRPD | | | | |
| Crystallinity of form | High | Medium | Medium | Medium |
| Melting point by DSC (heating rate 10 K/min) | | | | |
| Onset & enthalpy (° C., J/g) | 146.7, 120 | 235.7, 128 | 171.7, 106 | 215.3 (Decomposition) |
| Glass transition by DSC after heating and cooling | | | | |
| $T_g$ & $\Delta c_p$ (° C., J/g/K) | 52, 0.47 | 91, 0.45 | 77, 0.61 | |
| Loss on drying by TGA (heating rate 10 K/min) | | | | |
| As is (% @ ° C.) | 0.15 @ 140 | 0.53 @ 230 | 0.24 @ 170 | 0.37 @ 195 |
| After 1 day at 92 % RH (% @ ° C.) | 2.46 @ 100 | 0.30 @ 230 | 0.21 @ 170 | 0.96 @ 195 |

The invention claimed is:

1. A compound of Formula (I):

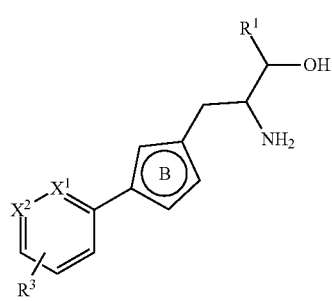

(I)

or a pharmaceutically acceptable salt thereof, wherein:

Ring B is a 5-membered ring heteroaryl;

$R^1$ is H or $C_{1-4}$alkyl;

$X^1$ is N or CH;

$X^2$ is N or $CR^2$, wherein $R^2$ is H or $C_{1-4}$alkyl;

$R^3$ is:

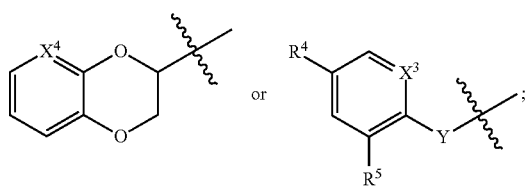

$X^3$ is N or CH;

$X^4$ is N or CH;

Y is O, $NR^a$ or $CH_2$; and $R^1$ is H or $C_{1-4}$alkyl;

$R^4$ is selected from the group consisting of is halo, halo$C_{1-4}$alkoxy, $C_{1-4}$alkoxy, halo$C_{1-4}$alkyl, $C_{1-4}$alkyl, 5-membered heteroaryl and $C_{1-5}$cycloalkyl; and $R^5$ is H or halo.

2. The compound according to claim 1 having Formula (IA):

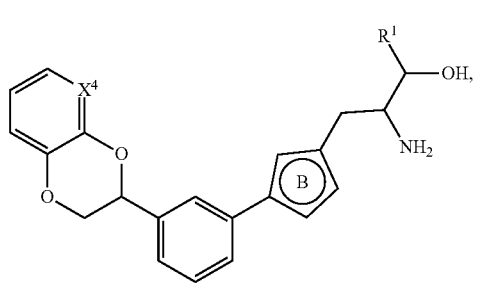

(IA)

or a pharmaceutically acceptable salt thereof.

3. The compound according to claim 1 having Formula (IB):

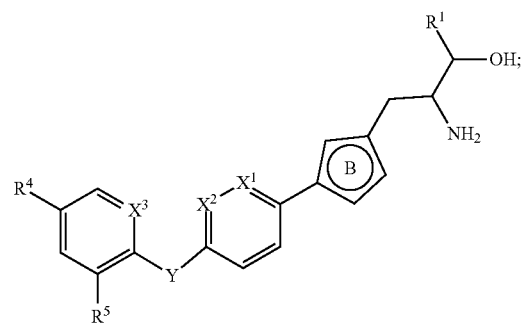

(IB)

or a pharmaceutically acceptable salt thereof.

4. The compound according to claim 1 having Formula (IC):

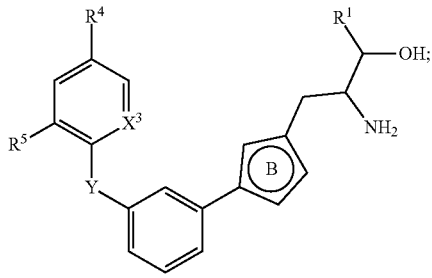

(IC)

or a pharmaceutically acceptable salt thereof.

5. The compound according to claim 1 having Formula (II):

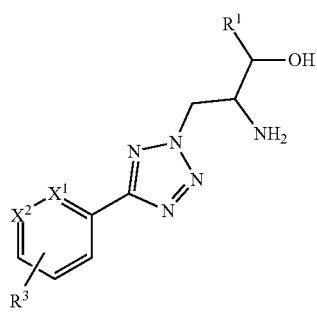

(II)

or a pharmaceutically acceptable salt thereof.

6. The compound according to claim 1 having Formula (III):

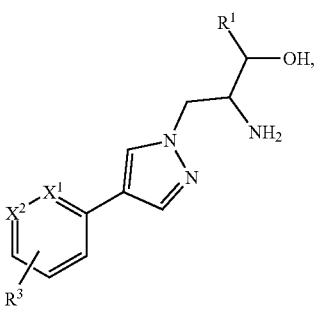

(III)

or a pharmaceutically acceptable salt thereof.

7. The compound according to claim 1 having Formula (IV):

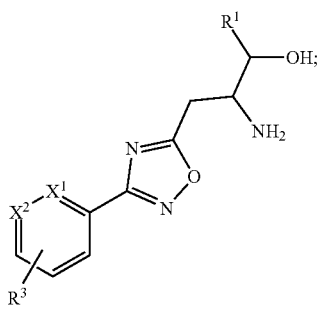

(IV)

or a pharmaceutically acceptable salt thereof.

8. The compound according to claim 1 having Formula (V):

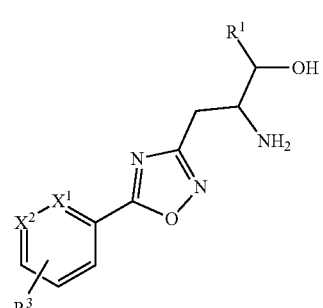

(V)

or a pharmaceutically acceptable salt thereof.

9. The compound according to claim 1 having Formula (VI):

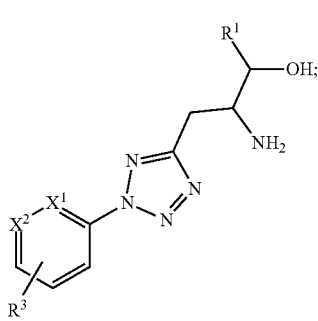

(VI)

or a pharmaceutically acceptable salt thereof.

10. The compound according to claim 1 wherein $X^1$ is CH; or a pharmaceutically acceptable salt thereof.

11. The compound according to claim 1 wherein $R^1$ is H; or a pharmaceutically acceptable salt thereof.

12. The compound according to claim 1 wherein $X^3$ is N and Y is O; or a pharmaceutically acceptable salt thereof.

13. The compound according to claim 1 wherein $R^5$ is H or halo and $R^4$ is selected from halo, haloC$_{1-4}$alkoxy, C$_{1-4}$alkoxy, haloC$_{1-4}$alkyl, C$_{1-4}$alkyl, 5-membered heteroaryl and C$_{3-5}$cycloalkyl; or a pharmaceutically acceptable salt thereof.

14. The compound according to claim 13 wherein R⁴ is selected from cyclopropyl, Cl, Br, —OCH₃, —OCHF₂, CF₃, pyrazolyl, oxazolyl, and R⁵ is H or F; or a pharmaceutically acceptable salt thereof.

15. The compound according to claim 1 wherein the compound is selected from:
- (S)-2-amino-3-(3-(3-((S)-2,3-dihydrobenzo[b][1,4]dioxin-2-yl)phenyl)-1,2,4-oxadiazol-5-yl)propan-1-ol;
- (S)-2-amino-3-(3-(3-((5-chloropyridin-2-yl)oxy)phenyl)-1,2,4-oxadiazol-5-yl)propan-1-ol;
- (S)-2-amino-3-(3-(3-((5-(difluoromethoxy)pyridin-2-yl)oxy)phenyl)-1,2,4-oxadiazol-5-yl)propan-1-ol;
- (S)-2-amino-3-(3-(4-((5-(trifluoromethyl)pyridin-2-yl)oxy)phenyl)-1,2,4-oxadiazol-5-yl)propan-1-ol;
- (S)-2-amino-3-(3-(4-((5-(difluoromethoxy)pyridin-2-yl)oxy)phenyl)-1,2,4-oxadiazol-5-yl)propan-1-ol;
- Ethyl (S)-2-amino-3-(5-(4-((5-chloropyridin-2-yl)oxy)phenyl)-1,2,4-oxadiazol-3-yl)propanoate;
- tert-butyl ((2S)-1-(3-(4-((3-fluoro-5-(1-(tetrahydro-2H-pyran-2-yl)-1H-pyrazol-5-yl)pyridin-2-yl)oxy)phenyl)-1,2,4-oxadiazol-5-yl)-3-hydroxypropan-2-yl)carbamate;
- (R)-2-amino-3-(3-(4-((5-chloro-3-fluoropyridin-2-yl)oxy)phenyl)-1,2,4-oxadiazol-5-yl)propan-1-ol;
- tert-butyl (S)-(1-(3-(3-((5-(1H-pyrazol-5-yl)pyridin-2-yl)oxy)phenyl)-1,2,4-oxadiazol-5-yl)-3-hydroxypropan-2-yl)carbamate;
- (S)-2-amino-3-(3-(3-((5-(trifluoromethylpyridin-2-yl)oxy)phenyl)-1,2,4-oxadiazol-5-yl)propan-1-ol;
- (S)-2-amino-3-(3-(3-((R)-2,3-dihydro-[1,4]dioxino[2,3-b]pyridin-3-yl)phenyl)-1,2,4-oxadiazol-5-yl)propan-1-ol;
- (S)-2-amino-3-(3-(4-((5-chloro-3-fluoropyridin-2-yl)oxy)phenyl)-1,2,4-oxadiazol-5-yl)propan-1-ol;
- (S)-3-(3-(4-((5-(1H-Pyrazol-5-yl)pyridin-2-yl)oxy)phenyl)-1,2,4-oxadiazol-5-yl)-2-aminopropan-1-ol;
- (S)-2-amino-3-(5-(3-((R)-2,3-dihydro-[1,4]dioxino[2,3-b]pyridin-3-yl)phenyl)-2H-tetrazol-2-yl)propan-1-ol;
- (S)-2-amino-3-(3-(3-((R)-2,3-dihydrobenzo[b][1,4]dioxin-2-yl)phenyl)-1,2,4-oxadiazol-5-yl)propan-1-ol;
- (S)-2-amino-3-(3-(4-((5-chloropyridin-2-yl)oxy)phenyl)-1,2,4-oxadiazol-5-yl)propan-1-ol;
- (S)-2-amino-3-(3-(4-(((R)-1-phenylpropan-2-yl)oxy)phenyl)-1,2,4-oxadiazol-5-yl)propan-1-ol;
- (3S)-3-amino-4-(3-(4-((5-bromo-3-fluoropyridin-2-yl)oxy)phenyl)-1,2,4-oxadiazol-5-yl)butan-2-ol;
- (R)-3-(5-(4-((5-(1H-pyrazol-3-yl)pyridin-2-yl)oxy)phenyl)-2H-tetrazol-2-yl)-2-aminopropan-1-ol;
- (R)-3-(5-(4-((5-(1H-pyrazol-3-yl)pyridin-2-yl)oxy)phenyl)-2H-tetrazol-2-yl)-2-aminopropan-1-ol;
- (S)-2-amino-3-(3-(5-((3-fluoro-5-(1H-pyrazol-5-yl)pyridin-2-yl)oxy)pyridin-2-yl)-1H-pyrazol-1-yl)propan-1-ol;
- (S)-2-amino-3-(5-(5-((3-fluoro-5-(1H-pyrazol-5-yl)pyridin-2-yl)oxy)pyridin-2-yl)-2H-tetrazol-2-yl)propan-1-ol;
- (S)-2-amino-3-(3-(5-((5-chloro-3-fluoropyridin-2-yl)oxy)pyridin-2-yl)-1H-pyrazol-1-yl)propan-1-ol; (S)-2-amino-3-(3-(3-((5-chloro-3-fluoropyridin-2-yl)oxy)phenyl)-1H-pyrazol-1-yl)propan-1-ol;
- (S)-2-amino-3-(4-(4-((5-chloro-3-fluoropyridin-2-yl)oxy)phenyl)-1H-pyrazol-1-yl)propan-1-ol;
- (S)-2-Amino-3-(3-(4-((5-chloro-3-fluoropyridin-2-yl)oxy)phenyl)-1H-pyrazol-1-yl)propan-1-ol;
- (S)-2-Amino-3-(5-(4-(4-chlorophenoxy)phenyl)-2H-tetrazol-2-yl)propan-1-ol;
- (S)-2-Amino-3-(5-(4-((5-cyclopropylpyridin-2-yl)oxy)phenyl)-2H-tetrazol-2-yl)propan-1-ol;
- (S)-2-Amino-3-(5-(4-((5-chloro-3-fluoropyridin-2-yl)oxy)phenyl)-2H-tetrazol-2-yl)propan-1-ol;
- (R)-2-Amino-3-(5-(4((5-chloro-3-fluoropyridin-2-yl)oxy)phenyl)-2H-tetrazol-2-yl)propan-1-ol;
- (R)-2-Amino-3-(5-(4((5-chloropyridin-2-yl)oxy)phenyl)-2H-tetrazol-2-yl)propan-1-ol;
- (S)-2-Amino-3-(5-(4-((3-fluoro-5-(1H-pyrazol-5-yl)pyridin-2-yl)oxy)phenyl)-2H-tetrazol-2-yl)propan-1-ol;
- (S)-2-Amino-3-(5-(4-((5-bromopyridin-2-yl)oxy)phenyl)-2H-tetrazol-2-yl)propan-1-ol;
- (S)-2-Amino-3-(5-(4-((5-chloropyridin-2-yl)oxy)phenyl)-2H-tetrazol-2-yl)propan-1-ol;
- (S)-2-Amino-3-(5-(6-(4-chlorophenoxy)pyridin-3-yl)-2H-tetrazol-2-yl)propan-1-ol;
- (S)-3-(3-(4((5-(1H-pyrazol-5-yl)pyridin-2-yl)oxy)phenyl)-1H-pyrazol-1-yl)-2-aminopropan-1-ol;
- (S)-2-amino-3-(3-(4((3-fluoro-5-(1H-pyrazol-3-yl)pyridin-2-yl)oxy)phenyl)-1H-pyrazol-1-yl)propan-1-ol;
- (2S)-2-amino-3-[5-(4-[[3-fluoro-5-(1,3-oxazol-2-yl)pyridin-2-yl]oxy]phenyl)-2H-1,2,3,4 tetrazol-2-yl] propan-1-ol;
- (S)-2-Amino-3-(2-(4-((5-chloro-3-fluoropyridin-2-yl)oxy)phenyl)-2H-tetrazol-5-yl)propan-1-ol;
- (R)-2-Amino-3-(2-(4((5-chloro-3-fluoropyridin-2-yl)oxy)phenyl)-2H-tetrazol-5-yl)propan-1-ol; and
- (2S)-2-amino-3-(2-(4((3-fluoro-5-(1-(tetrahydro-2H-pyran-2-yl)-1H-pyrazol-5-yl)pyridin-2-yl)oxy)phenyl)-2H-tetrazol-5-yl)propan-1-ol; or a pharmaceutically acceptable salt thereof.

16. A pharmaceutical composition comprising a therapeutically effective amount of a compound according to claim 1 and one or more pharmaceutically acceptable carriers.

17. A combination comprising a therapeutically effective amount of a compound according to claim 1 or a pharmaceutically acceptable salt thereof and one or more therapeutically active co-agents selected from a croup consisting of a COX inhibitor, a Cysteinyl-Leukotriene Receptor antagonist, a leukotriene C4 synthase (LTC4S) inhibitor, a NLRP3 inhibitor, a statin, sulfasalazine, Mesalamine, a calcineurin inhibitor, a mTOR inhibitor, an ascomycin having immunosuppressive properties, corticosteroids, cyclophosphamide; azathioprene; methotrexate; leflunomide; mizoribine; mycophenolic acid or salt; mycophenolate mofetil and IL-1beta inhibitor.

18. A method of treatment of a disease and/or disorder mediated by LTA4H activity in a subject, wherein the method comprises administering to said subject a therapeutically effective amount of the compound according to claim 1 or a pharmaceutically acceptable salt thereof, wherein the disease and/or disorder is selected from: acute or chronic inflammation, anaphylactic reactions, allergic reactions, atopic dermatitis, psoriasis, acute respiratory distress syndrome, immune complex-mediated pulmonary injury and chronic obstructive pulmonary disease, inflammatory bowel diseases, gastrointestinal ulcers, non-alcoholic fatty liver disease (NAFLD), non-alcoholic steatohepatitis (NASH), neutrophilic dermatoses, immune-complex-mediated glomerulonephritis, Hidradenitis suppurativa, autoimmune diseases, vasculitides, cardiovascular disorders, sepsis, inflammatory and neuropathic pain, periodontal disease, ear infections, migraine, benign prostatic hyperplasia, Sjogren-Larsson Syndrome and cancers.

19. A compound which is (S)-2-amino-3-(3-(4-((3-fluoro-5-(1H-pyrazol-5-yl)pyridin-2-yl)oxy)phenyl)-1H-pyrazol-1-yl)propan-1-ol having formula:

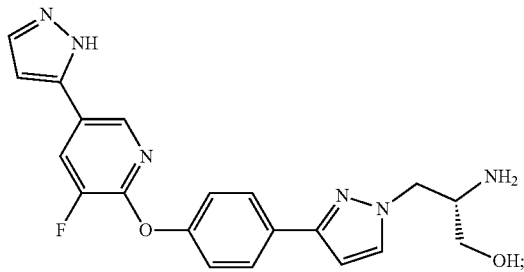 [SMILES: N[C@H](CO)Cn1ccc(-c2ccc(Oc3ncc(-c4ccn[nH]4)cc3F)cc2)n1]

or its tautomeric form ((S)-2-amino-3-(3-(4-((3-fluoro-5-(1H-pyrazol-3-yl)pyridin-2-yl)oxy)phenyl)-1H-pyrazol-1-yl)propan-1-ol) of Formula:

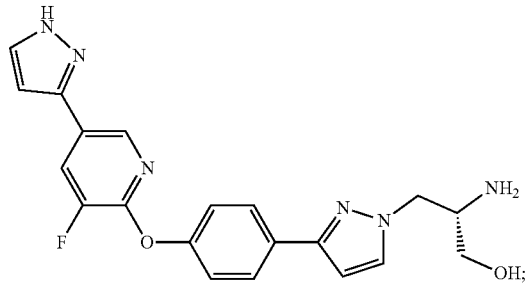 [SMILES: N[C@H](CO)Cn1ccc(-c2ccc(Oc3ncc(-c4cc[nH]n4)cc3F)cc2)n1]

or a pharmaceutical salt thereof.

20. A pharmaceutical composition comprising a therapeutically effective amount of a compound according to claim 19 and one or more pharmaceutically acceptable carriers.

* * * * *